(12) United States Patent
Koeris et al.

(10) Patent No.: US 9,828,625 B2
(45) Date of Patent: *Nov. 28, 2017

(54) PHAGE-BASED BACTERIAL DETECTION ASSAY

(71) Applicant: Sample6 Technologies, Inc., Boston, MA (US)

(72) Inventors: Michael Sandor Koeris, Natick, MA (US); Julie Thomason, Reading, MA (US); Michael Cappillino, Reading, MA (US); Robert Patrick Shivers, Watertown, MA (US); Daniel Robert Brownell, Arlington, MA (US); Jayson L. Bowers, Cambridge, MA (US); Timothy Kuan Ta Lu, Charlestown, MA (US); Edyta Krzymanska-Olejnik, Brookline, MA (US)

(73) Assignee: Phage Diagnostics, Inc., Lake Forest Park, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/309,389

(22) Filed: Jun. 19, 2014

(65) Prior Publication Data

US 2015/0004595 A1 Jan. 1, 2015

Related U.S. Application Data

(60) Provisional application No. 61/837,152, filed on Jun. 19, 2013, provisional application No. 61/844,399, filed on Jul. 9, 2013, provisional application No. 61/879,640, filed on Sep. 18, 2013, provisional application No. 61/884,931, filed on Sep. 30, 2013, provisional application No. 61/884,935, filed on Sep. 30, 2013, provisional application No. 61/884,935, filed on Sep. 30, 2013, provisional application No. 61/884,946, filed on Sep. 30, 2013.

(51) Int. Cl.
*C12Q 1/66* (2006.01)
*C12Q 1/10* (2006.01)
*C12N 7/00* (2006.01)
*G01N 33/82* (2006.01)

(52) U.S. Cl.
CPC ............ *C12Q 1/66* (2013.01); *C12N 7/00* (2013.01); *C12Q 1/10* (2013.01); *G01N 33/82* (2013.01); *G01N 2333/245* (2013.01); *G01N 2333/255* (2013.01)

(58) Field of Classification Search
None
See application file for complete search history.

(56) References Cited

U.S. PATENT DOCUMENTS

| | | |
|---|---|---|
| 4,868,105 A | 9/1989 | Urdea et al. |
| 5,118,801 A | 6/1992 | Lizardi et al. |
| 5,124,246 A | 6/1992 | Urdea et al. |
| 5,130,238 A | 7/1992 | Malek et al. |
| 5,283,174 A | 2/1994 | Arnold, Jr. et al. |
| 5,312,728 A | 5/1994 | Lizardi et al. |
| 5,399,491 A | 3/1995 | Kacian et al. |
| 5,437,990 A | 8/1995 | Burg et al. |
| 5,480,784 A | 1/1996 | Kacian et al. |
| 5,554,516 A | 9/1996 | Kacian et al. |
| 5,639,604 A | 6/1997 | Arnold, Jr. et al. |
| 5,824,468 A | 10/1998 | Scherer et al. |
| 5,925,517 A | 7/1999 | Tyagi et al. |
| 6,361,945 B1 | 3/2002 | Becker et al. |
| 6,534,274 B2 | 3/2003 | Becker et al. |
| 6,835,542 B2 | 12/2004 | Becker et al. |
| 6,849,412 B2 | 2/2005 | Becker et al. |
| 7,374,885 B2 | 5/2008 | Becker et al. |
| 8,178,087 B2 | 5/2012 | Krisch et al. |
| 8,338,144 B2 | 12/2012 | Berry et al. |
| 8,557,970 B2 | 10/2013 | Encell et al. |
| 8,669,103 B2 | 3/2014 | Binkowski et al. |
| 9,234,227 B2 | 1/2016 | Lu et al. |
| 2004/0197833 A1* | 10/2004 | Loessner .......... C12N 1/02 435/7.2 |
| 2005/0175594 A1 | 8/2005 | Loessner et al. |

(Continued)

FOREIGN PATENT DOCUMENTS

CN 101955916 * 7/2010
EP 0495960 B1 3/1997

(Continued)

OTHER PUBLICATIONS

GenBank Accession No. P08659 (Apr. 24, 1993).*
GenBank Accession No. AFI79290 (May 6, 2012).*
Ceglarek et al., Scientific Reports, 2013, 3:1-6.*
PALCAM Broth (7670) (Nov. 2010).*
Klumpp and Loessner. 2014. "Detection of Bacteria with Bioluminescent Reporter Bacteriophage". *Bioluminescence: Fundamentals and Applications in Biotechnology* vol. 1, Advances in Biochemical Engineering/Biotechnology 144 pp. 155-171.
Casjens S, Gilcrease EB (2009), "Determining dna packaging stragety by analysis of the termini of the chromosomes in tailed-bacteriophage virions", in: Clokie MRJ, Kropinski A (eds) *Bacteriophages—Methods and protocols. vol. 2: molecular and applied aspects.* Humana Press, New York, pp. 91-11.
Klumpp J, Dorscht J, Lurz R, Bielmann R, Wieland M, Zimmer M, Calendar R, Loessner MJ (2008), "The terminally redundant, nonpermuted genome of Listeria bacteriophage A511: a Model for the SPO1-like myoviruses of gram-positive bacteria", *J. Bacteriol.* 190:5753-5765.
Nightingale et al., "Combine sigB allelic typing and multiplex PCR provide improved discriminatory power and reliability for Listeria monocytogenes molecular serotyping", *J. Microbiol. Methods*, Aug. 2, 2006.

(Continued)

Primary Examiner — Nicole Kinsey White
(74) Attorney, Agent, or Firm — Barry L. Davison; Davis Wright Tremaine LLP

(57) ABSTRACT

Methods of detecting target bacteria are provided. In some embodiments the methods comprise exposing the sample to a phage capable of infecting a set of target bacteria and comprising a heterologous nucleic acid sequence encoding a marker. In some embodiments the target bacteria comprise *Listeria*. In some embodiments the target bacteria are all *Listeria*. Recombinant *Listeria* phage comprising a heterologous nucleic acid sequence encoding a marker are also provided as are useful combinations of such phage and articles of manufacture comprising such phage, among other things.

22 Claims, No Drawings

(56) References Cited

U.S. PATENT DOCUMENTS

| | | | |
|---|---|---|---|
| 2005/0202518 A1* | 9/2005 | Vedrine | C12Q 1/04 435/7.32 |
| 2006/0046265 A1 | 3/2006 | Becker et al. | |
| 2007/0072174 A1 | 3/2007 | Sayler et al. | |
| 2008/0241819 A1* | 10/2008 | Smith | C12Q 1/025 435/5 |
| 2010/0075398 A1* | 3/2010 | Mathers | A61K 35/76 435/235.1 |
| 2010/0281552 A1 | 11/2010 | Encell et al. | |
| 2010/0285460 A1 | 11/2010 | Schofield | |
| 2011/0076672 A1 | 3/2011 | Schofield | |
| 2012/0009574 A1 | 1/2012 | Petrauskene et al. | |
| 2012/0040441 A1* | 2/2012 | Fujii | C07K 14/195 435/252.33 |
| 2012/0064210 A1* | 3/2012 | Stiles | A01N 63/00 426/335 |
| 2012/0174242 A1 | 7/2012 | Binkowski et al. | |
| 2014/0302487 A1* | 10/2014 | Koeris | C12N 7/00 435/5 |
| 2016/0040215 A1* | 2/2016 | Henn | C12Q 1/689 506/2 |

FOREIGN PATENT DOCUMENTS

| | | |
|---|---|---|
| WO | WO-88/01302 A1 | 2/1988 |
| WO | WO 95/03430 A1 | 2/1995 |
| WO | WO-88/10315 A1 | 12/1998 |
| WO | WO-2004/041156 A2 | 5/2004 |
| WO | WO-2010010192 A1 | 1/2010 |
| WO | WO-2012061529 | 5/2012 |
| WO | WO 2013/049121 A2 | 4/2013 |

OTHER PUBLICATIONS

Ho et al., "Longitudinal monitoring of Listeria monocytogenes contamination patterns in a farmstead dairy processing facility", *J. Dairy Sci.*, May 1, 2007, vol. 90, No. 5, pp. 2517-2524.
Dorscht et aL, "Comparative genome analysis of Listeria bacteriophages reveals extensive mosaicism, programmed translational frameshifting, and a novel prophage insertion site", *J. Bacteriol.*, Sep. 25, 2009, vol. 191, No. 23, pp. 7206-7215.
Liu, D. Molecular Detection of Human Bacterial Pathogens. CRC Press. 2011; Boca Raton, FL; p. 985, right column, third paragraph.
Kalantri S. et al. Bacteriophage-Based Tests for the Detection of *Mycobacterium tuberculosis* in Clinical Specimens: A Systematic Review and Meta-Analysis. BMC Infectious Disease. Jul. 16, 2005; vol. 5, No. 59; abstract; p. 2, left column, third paragraph; Table 2. D01:10.1186/1471-2334-5-59.
Gu, Y. et al. Eliminating the Interference of Oxygen for Sensing Hydrogen Peroxide With the Polyaniline Modified Electrode. Sensors. Dec. 12, 2008; vol. 8, No. 12; pp. 8237-8247; abstract. DOI: 10.3390/s8128237.
International Search Report issued for PCT/US2014/043190, mailed Dec. 31, 2014.
Loessner M.J. et al. "Construction of luciferase reporter bacteriophage A511::luxAB for rapid and sensitive detection of viable Listeria cells", *Appl Enviorn Microbiol*, 1996, 62(4), pp. 1133-1140.
Williams S.K. et al. "Molecular ecology of Listeria monocytogenes and other Listeria species in small and very small ready-to-eat meat processing plants", *J Food Prot.*, 2011, 47(1), pp. 63-77.
Sauders B.D. et al. "Diversity of Listeria species in urban and natural environments", *Appl Enviorn Microbiol.*, 2012, 78(12), pp. 4420-4433.
Shaw D.R. et al. "Use of UV-irradiated bacteriophage T6 to kill extracellular bacteria in tissue culture infectivity assays", *J Immunol Methods.*, 1983, 56(1): 75-83.
Altschul et al., "Basic Local Alignment Search Tool", J. Mol. Biol. 215:403-410 (1990).
Altschul et al., "Gapped BLAST and PSI-BLAST: a new generation of protein database search program", Nucleic Acids Research, vol. 25, No. 17, p. 3389-3402 (1997).
Busch and Donnelly, "Development of a Repair-Enrichment Broth for Resuscitation of Heat-Injured Listeria monocytogenes and Listeria innocua," 1992, Applied and Environmental Microbiology, vol. 58, No. 1, pp. 14-20, (1992).
Gish and States, "Identification of protein coding regions by database similarity search", Nature Genetics, vol. 3, p. 266-272 (1993).
Loessner M. et al. "Construction of Luciferase Reporter Bacteriophage A511::luxAB for Rapid and Sensitive Detection of Viable Listeria Cells", Applied and Environmental Microbiology, vol. 62, No. 4, p. 1133-1140. (1996).
Madden et al., "Applications of Network BLAST Server", Methods in Enzymology, vol. 266, p. 131-141 (1996).
Pearson, W. "Using the FASTA Program to Search Protein and DNA Sequence Databases", 1994, Methods in Molecular Biology, vol. 24, p. 307-331.
Pearson, W. "Using the FASTA Program to Search Protein and DNA Sequence Databases", 1994, Methods in Molecular Biology, vol. 25, p. 365-368.
Pearson, "Rapid and Sensitive Sequence Comparison with FASTP and FASTA", Methods in Enzymology, vol. 183, p. 63-98 (1990).
Sambrook and Russell, Molecular Cloning, vol. 1, 3rd edition 2001. Protocol 6, Precipitation of Bacteriophage Lambda Particles from Large-scale Lysates, p. 2.43-2.44.
Sambrook and Russell, Molecular Cloning, vol. 1, 3rd edition 2001. Protocol 8, Purification of Bacteriophage Lambda Particles by Isopycnic Centrifugation through CsCl Gradients, at p. 2.47-2.51.
Sutcliffe, J.G. "Nucleotide sequence of the ampicillin resistance gene of *Escherichia coli* plasmid pBR322", Proc Natl Acad Sci USA, Aug. 1978, vol. 75, No. 8, p. 3737-3741.
Zhang and Madden, "PowerBLAST: A New Network BLAST Application for Interactive or Automated Sequence Analysis and Annotation", Genome Methods, vol. 7, p. 649-656 (1997).
den Bakker et al., "*Listeria floridensis* sp. nov., *Listeria aquatica* sp. nov., *Listeria cornellensis* sp. nov., *Listeria riparia* sp. nov. and *Listeria grandensis* sp. nov., from agricultural and natural environments", Int. J. of Systematic and Evolutionary Microbiology. 64: 1-8 (2014).
NCBI Accession No. (NC_003298), genomic sequence of T3.
ATCC Accession No. PTA-4608, "Phage in the *Myoviridae* targeting numerous strains of *Listeria monocytogenes*, A511" (2008) (retrieved on Jun. 27, 2017).
Genbank (NC_009811), Listeria phage A511, complete genome (Mar. 18, 2013).
Genbank (DQ004855), Listeria bacteriophage P100, complete genome (Nov. 3, 2009).
Lu T. K. et al. "Dispersing biofilms with engineered enzymatic bacteriophage," *Proceedings of the National Academy of Sciences*, vol. 104, No. 27, pp. 11197-11202, (2007).
Pritchard et al. "Combined Secondary Enrichment of Primary Enrichment Broths Increases *Listeria* Detection," *Journal of Food Protection*, vol. 62, No. 5, pp. 532-535 (1999).

\* cited by examiner

SEQUENCE LISTING

<160> NUMBER OF SEQ ID NOS: 91

<210> SEQ ID NO 1
<211> LENGTH: 1653
<212> TYPE: DNA
<213> ORGANISM: Photinus pyralis

<400> SEQUENCE: 1

```
atggaagacg ccaaaaacat aaagaaaggc ccggcgccat tctatcctct agaggatgga      60
accgctggag agcaactgca taaggctatg aagagatacg ccctggttcc tggaacaatt     120
gcttttacag atgcacatat cgaggtgaac atcacgtacg cggaatactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgaacatt     360
tcgcagccta ccgtagtgtt tgtttccaaa aagggggttgc aaaaaatttt gaacgtgcaa     420
```

```
aaaaaattac caataatcca gaaaattatt atcatggatt ctaaaacgga ttaccaggga    480
tttcagtcga tgtacacgtt cgtcacatct catctacctc ccggttttaa tgaatacgat    540
tttgtaccag agtcctttga tcgtgacaaa acaattgcac tgataatgaa ttcctctgga    600
tctactgggt tacctaaggg tgtggccctt ccgcatagaa ctgcctgcgt cagattctcg    660
catgccagag atcctatttt tggcaatcaa atcattccgg atactgcgat tttaagtgtt    720
gttccattcc atcacggttt tggaatgttt actacactcg atatttgat atgtggattt     780
cgagtcgtct taatgtatag atttgaagaa gagctgtttt tacgatccct tcaggattac    840
aaaattcaaa gtgcgttgct agtaccaacc ctattttcat tcttcgccaa aagcactctg    900
attgacaaat acgatttatc taatttacac gaaattgctt ctggggggcgc acctctttcg   960
aaagaagtcg gggaagcggt tgcaaaacgc ttccatcttc cagggatacg acaaggatat   1020
gggctcactg agactacatc agctattctg attacacccg aggggatga taaaccgggc    1080
gcggtcggta agttgttcc attttttgaa gcgaaggttg tggatctgga taccgggaaa    1140
acgctgggcg ttaatcagag aggcgaatta tgtgtcagag acctatgat tatgtccggt    1200
tatgtaaaca atccggaagc gaccaacgcc ttgattgaca aggatggatg ctacattct    1260
ggagacatag cttactggga cgaagacgaa cacttcttca tagttgaccg cttgaagtct   1320
ttaattaaat acaaaggata tcaggtggcc cccgctgaat tggaatcgat attgttacaa   1380
caccccaaca tcttcgacgc gggcgtggca ggtcttcccg acgatgacgc cggtgaactt   1440
cccgccgccg ttgttgtttt ggagcacgga aagacgatga cggaaaaaga gatcgtggat   1500
tacgtcgcca gtcaagtaac aaccgcgaaa aagttgcgcg gaggagttgt gtttgtggac   1560
gaagtaccga aggtcttac cggaaaactc gacgcaagaa aaatcagaga gatcctcata    1620
aaggccaaga agggcggaaa gtccaaattg taa                                 1653
```

<210> SEQ ID NO 2  
<211> LENGTH: 550  
<212> TYPE: PRT  
<213> ORGANISM: Photinus pyralis

<400> SEQUENCE: 2

```
Met Glu Asp Ala Lys Asn Ile Lys Lys Gly Pro Ala Pro Phe Tyr Pro
1               5                   10                  15

Leu Glu Asp Gly Thr Ala Gly Glu Gln Leu His Lys Ala Met Lys Arg
                20                  25                  30

Tyr Ala Leu Val Pro Gly Thr Ile Ala Phe Thr Asp Ala His Ile Glu
            35                  40                  45

Val Asn Ile Thr Tyr Ala Glu Tyr Phe Glu Met Ser Val Arg Leu Ala
        50                  55                  60

Glu Ala Met Lys Arg Tyr Gly Leu Asn Thr Asn His Arg Ile Val Val
65                  70                  75                  80

Cys Ser Glu Asn Ser Leu Gln Phe Phe Met Pro Val Leu Gly Ala Leu
                85                  90                  95

Phe Ile Gly Val Ala Val Ala Pro Ala Asn Asp Ile Tyr Asn Glu Arg
            100                 105                 110

Glu Leu Leu Asn Ser Met Asn Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
```

Phe Gln Ser Met Tyr Thr Phe Val Thr Ser His Leu Pro Pro Gly Phe
145                 150                 155                 160

Asn Glu Tyr Asp Phe Val Pro Glu Ser Phe Asp Arg Asp Lys Thr Ile
            165                 170                 175

Ala Leu Ile Met Asn Ser Ser Gly Ser Thr Gly Leu Pro Lys Gly Val
        180                 185                 190

Ala Leu Pro His Arg Thr Ala Cys Val Arg Phe Ser His Ala Arg Asp
    195                 200                 205

Pro Ile Phe Gly Asn Gln Ile Ile Pro Asp Thr Ala Ile Leu Ser Val
210                 215                 220

Val Pro Phe His His Gly Phe Gly Met Phe Thr Thr Leu Gly Tyr Leu
225                 230                 235                 240

Ile Cys Gly Phe Arg Val Val Leu Met Tyr Arg Phe Glu Glu Glu Leu
            245                 250                 255

Phe Leu Arg Ser Leu Gln Asp Tyr Lys Ile Gln Ser Ala Leu Leu Val
        260                 265                 270

Pro Thr Leu Phe Ser Phe Phe Ala Lys Ser Thr Leu Ile Asp Lys Tyr
    275                 280                 285

Asp Leu Ser Asn Leu His Glu Ile Ala Ser Gly Gly Ala Pro Leu Ser
290                 295                 300

Lys Glu Val Gly Glu Ala Val Ala Lys Arg Phe His Leu Pro Gly Ile
305                 310                 315                 320

Arg Gln Gly Tyr Gly Leu Thr Glu Thr Thr Ser Ala Ile Leu Ile Thr
            325                 330                 335

Pro Glu Gly Asp Asp Lys Pro Gly Ala Val Gly Lys Val Val Pro Phe
        340                 345                 350

Phe Glu Ala Lys Val Val Asp Leu Asp Thr Gly Lys Thr Leu Gly Val
    355                 360                 365

Asn Gln Arg Gly Glu Leu Cys Val Arg Gly Pro Met Ile Met Ser Gly
370                 375                 380

Tyr Val Asn Asn Pro Glu Ala Thr Asn Ala Leu Ile Asp Lys Asp Gly
385                 390                 395                 400

Trp Leu His Ser Gly Asp Ile Ala Tyr Trp Asp Glu Asp Glu His Phe
            405                 410                 415

Phe Ile Val Asp Arg Leu Lys Ser Leu Ile Lys Tyr Lys Gly Tyr Gln
        420                 425                 430

Val Ala Pro Ala Glu Leu Glu Ser Ile Leu Leu Gln His Pro Asn Ile
    435                 440                 445

Phe Asp Ala Gly Val Ala Gly Leu Pro Asp Asp Asp Ala Gly Glu Leu
450                 455                 460

Pro Ala Ala Val Val Val Leu Glu His Gly Lys Thr Met Thr Glu Lys
465                 470                 475                 480

Glu Ile Val Asp Tyr Val Ala Ser Gln Val Thr Thr Ala Lys Lys Leu
            485                 490                 495

Arg Gly Gly Val Val Phe Val Asp Glu Val Pro Lys Gly Leu Thr Gly
        500                 505                 510

Lys Leu Asp Ala Arg Lys Ile Arg Glu Ile Leu Ile Lys Ala Lys Lys
    515                 520                 525

Gly Gly Lys Ser Lys Leu
530                 535                 540

545                 550

<210> SEQ ID NO 3

<211> LENGTH: 516
<212> TYPE: DNA
<213> ORGANISM: Artificial Sequence
<220> FEATURE:
<223> OTHER INFORMATION: Synthetic Oligonucleotide

<400> SEQUENCE: 3

```
atggtcttca cactcgaaga tttcgttggg gactggcgac agacagccgg ctacaacctg    60
gaccaagtcc ttgaacaggg aggtgtgtcc agtttgtttc agaatctcgg ggtgtccgta   120
actccgatcc aaaggattgt cctgagcggt gaaaatgggc tgaagatcga catccatgtc   180
atcatcccgt atgaaggtct gagcggcgac caaatgggcc agatcgaaaa aatttttaag   240
gtggtgtacc ctgtggatga tcatcacttt aaggtgatcc tgcactatgg cacactggta   300
atcgacgggg ttacgccgaa catgatcgac tatttcggac ggccgtatga aggcatcgcc   360
gtgttcgacg gcaaaaagat cactgtaaca gggaccctgt ggaacggcaa caaaattatc   420
gacgagcgcc tgatcaaccc cgacggctcc ctgctgttcc gagtaaccat caacggagtg   480
accggctggc ggctgtgcga acgcattctg gcgtaa                             516
```

<210> SEQ ID NO 4
<211> LENGTH: 171
<212> TYPE: PRT
<213> ORGANISM: Artificial Sequence
<220> FEATURE:
<223> OTHER INFORMATION: Synthetic Polypeptide

<400> SEQUENCE: 4

```
Met Val Phe Thr Leu Glu Asp Phe Val Gly Asp Trp Arg Gln Thr Ala
1               5                   10                  15

Gly Tyr Asn Leu Asp Gln Val Leu Glu Gln Gly Gly Val Ser Ser Leu
            20                  25                  30

Phe Gln Asn Leu Gly Val Ser Val Thr Pro Ile Gln Arg Ile Val Leu
        35                  40                  45

Ser Gly Glu Asn Gly Leu Lys Ile Asp Ile His Val Ile Ile Pro Tyr
    50                  55                  60

Glu Gly Leu Ser Gly Asp Gln Met Gly Gln Ile Glu Lys Ile Phe Lys
65                  70                  75                  80

Val Val Tyr Pro Val Asp Asp His His Phe Lys Val Ile Leu His Tyr
                85                  90                  95

Gly Thr Leu Val Ile Asp Gly Val Thr Pro Asn Met Ile Asp Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Asn Pro Asp Gly Ser Leu Leu Phe Arg Val Thr Ile Asn Gly Val
145                 150                 155                 160

Thr Gly Trp Arg Leu Cys Glu Arg Ile Leu Ala
                165                 170
```

<210> SEQ ID NO 5
<211> LENGTH: 1407
<212> TYPE: DNA
<213> ORGANISM: Artificial Sequence
<220> FEATURE:
<223> OTHER INFORMATION: Synthetic Oligonucleotide

<400> SEQUENCE: 5

| | | |
|---|---|---|
| atgccaaaaa ataacaaaga agaagaagtt aaagaagtaa accttaattc agtacaagag | 60 |
| gatgcgttaa agtcctttac aactggttat ggtatcacac ctgatacaca aacagatgca | 120 |
| ggggcactaa gacgtgagtt cctagacgac caaatctcaa tgcttacttg gacagaaaat | 180 |
| gatttaacat tctacaaaga catcgctaaa aaaccagcta catctacagt agcaaaatac | 240 |
| gatgtgtaca tgcaacacgg taaagtaggt catactagat ttactcgtga gattggggta | 300 |
| gcaccagtaa gtgaccctaa catccgtcaa aaaacagtaa acatgaaatt tgcttctgat | 360 |
| actaaaaata ttagtatcgc agcaggtcta gtaaacaaca ttcaagaccc tatgcaaatt | 420 |
| ttgactgatg atgctatcgt aaatatcgct aaaacaattg agtgggcttc attctttgga | 480 |
| gattctgact tatcagatag cccagaacca caagcaggat tagaatttga tggcttggct | 540 |
| aaacttatta accaagataa cgttcatgat gctcgtggag ctagcttgac tgaaagcttg | 600 |
| ttaaaccaag cagcagtaat gattagtaaa ggttatggta cacctacaga tgcttacatg | 660 |
| ccagtagggg ttcaagcaga ctttgttaac caacaacttt ctaaacaaac acaacttgtt | 720 |
| cgcgataacg gaaacaacgt aagcgttggt ttcaacatcc aaggtttcca ttcagctcgt | 780 |
| ggatttatca aacttcacgg ttctacagta atggaaaacg aacaaatctt agatgaacgt | 840 |
| attcttgctt taccaacagc tccacaacca gctaaggtaa ctgcaacaca gaagcaggt | 900 |
| aaaaaaggac aatttagagc agaagattta gcagcacatg aatataaagt tgttgtaagt | 960 |
| tctgacgatg cagagtctat tgcaagtgaa gtggctacag ctacagttac tgcaaaagat | 1020 |
| gacggcgtta aactagaaat cgaattagct ccaatgtata gctctcgtcc acaattcgtt | 1080 |
| tcaatctata gaaaaggtgc agaaacaggt ttattctacc taatcgctcg tgtacctgct | 1140 |
| agcaaagcag agaacaacgt aatcactttc tacgacttaa acgactctat tcctgaaaca | 1200 |
| gtagacgtat tcgttggtga atgtcggct aacgtagtac acttgtttga attactacca | 1260 |
| atgatgagat tacctctagc tcaaattaac gcatctgtta catttgcagt tttatggtat | 1320 |
| ggcgcattag ctctaagagc acctaagaaa tgggtacgta ttagaaacgt taaatatatt | 1380 |
| cctgtaaaaa acgttcatag caactaa | 1407 |

<210> SEQ ID NO 6
<211> LENGTH: 468
<212> TYPE: PRT
<213> ORGANISM: Artificial Sequence
<220> FEATURE:
<223> OTHER INFORMATION: Synthetic Polypeptide

<400> SEQUENCE: 6

Met Pro Lys Asn Asn Lys Glu Glu Val Lys Glu Val Asn Leu Asn
1               5                   10                  15

Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110

Val Asn Met Lys Phe Ala Ser Asp Thr Lys Asn Ile Ser Ile Ala Ala
            115                 120                 125

Gly Leu Val Asn Asn Ile Gln Asp Pro Met Gln Ile Leu Thr Asp Asp
130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
    210                 215                 220

Gln Ala Asp Phe Val Asn Gln Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
    290                 295                 300

Phe Arg Ala Glu Asp Leu Ala Ala His Glu Tyr Lys Val Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
    370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
        435                 440                 445

Lys Lys Trp Val Arg Ile Arg Asn Val Lys Tyr Ile Pro Val Lys Asn
    450                 455                 460

Val His Ser Asn
465

<210> SEQ ID NO 7
<211> LENGTH: 1407
<212> TYPE: DNA
<213> ORGANISM: Artificial Sequence
<220> FEATURE:
<223> OTHER INFORMATION: Synthetic Oligonucleotide

<400> SEQUENCE: 7

```
atgccaaaaa ataacaaaga agaagaagtt aaagaagtaa accttaattc agtacaagag      60
gacgcgttaa agtcctttac aactggttat ggtatcacac ctgatacaca aacagatgca     120
ggagcattaa gacgtgagtt cctagacgac caaatctcaa tgcttacttg gacagagaat     180
gatttaacat tctataaaga catcgctaaa aaaccagcta catctacagt agcaaaatac     240
gatgtataca tgcaacatgg taaggtaggt catactagat ttactcgtga gattggggta     300
gcaccagtaa gtgaccctaa catccgtcaa aaaacagtaa acatgaaatt tgcttccgat     360
actaaaaaca tcagtatcgc agcaggtcta gtaaacaaca ttcaagaccc aatgcaaatt     420
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
ccagtagggg ttcaagcaga ctttgttaac caacaacttt ctaaacaaac acaacttgtt     720
cgcgataacg gaaacaacgt aagcgttggt ttcaacatcc aaggtttcca ttcagctcgt     780
ggatttatca aacttcacgg ttctacagta atggaaaacg aacaaatctt agatgaacgt     840
attcttgctt taccaacagc tccacaacca gctaaggtaa ctgcaacaca agaagcaggt     900
aaaaaaggac aatttagagc agaagattta gcagcacatg aatataaagt tgttgtaagt     960
tctgacgatg cagagtctat tgcaagtgaa gtggctacag ctacagttac tgcaaaagat    1020
gacggcgtta aactagaaat cgaattagct ccaatgtata gctctcgtcc acaattcgtt    1080
tcaatctata gaaaaggtgc agaaacaggt ttattctacc taatcgctcg tgtacctgct    1140
agcaaagcag agaacaacgt aatcactttc tacgacttaa cgactctat tcctgaaaca    1200
gtagacgtat cgttggtga atgtcggct aacgtagtac acttgtttga attactacca    1260
atgatgagat acctctagc tcaaattaac gcatctgtta catttgcagt tttatggtat    1320
ggcgcattag ctctaagagc acctaagaaa tgggtacgta ttagaaacgt taaatatatt    1380
cctgtaaaaa acgttcatag caactaa                                        1407
```

<210> SEQ ID NO 8
<211> LENGTH: 468
<212> TYPE: PRT
<213> ORGANISM: Artificial Sequence
<220> FEATURE:
<223> OTHER INFORMATION: Synthetic Polypeptide

<400> SEQUENCE: 8

```
Met Pro Lys Asn Asn Lys Glu Glu Val Lys Glu Val Asn Leu Asn
1               5                   10                  15

Ser Val Gln Glu Asp Ala Leu Lys Ser Phe Thr Thr Gly Tyr Gly Ile
                20                  25                  30

Thr Pro Asp Thr Gln Thr Asp Ala Gly Ala Leu Arg Arg Glu Phe Leu
            35                  40                  45

Asp Asp Gln Ile Ser Met Leu Thr Trp Thr Glu Asn Asp Leu Thr Phe
        50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110
```

```
Val Asn Met Lys Phe Ala Ser Asp Thr Lys Asn Ile Ser Ile Ala Ala
        115                 120                 125

Gly Leu Val Asn Asn Ile Gln Asp Pro Met Gln Ile Leu Thr Asp Asp
130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
    210                 215                 220

Gln Ala Asp Phe Val Asn Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
    290                 295                 300

Phe Arg Ala Glu Asp Leu Ala Ala His Glu Tyr Lys Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
    370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
        435                 440                 445

Lys Lys Trp Val Arg Ile Arg Asn Val Lys Tyr Ile Pro Val Lys Asn
    450                 455                 460

Val His Ser Asn
465

<210> SEQ ID NO 9
<211> LENGTH: 1407
<212> TYPE: DNA
<213> ORGANISM: Artificial Sequence
<220> FEATURE:
<223> OTHER INFORMATION: Synthetic Oligonucleotide

<400> SEQUENCE: 9
```

-continued

| | |
|---|---:|
| atgccaaaaa ataacaaaga agaagaagtt aaagaagtaa accttaattc agtacaagag | 60 |
| gacgcgttaa agtcctttac aactggttat ggtatcacac ctgatacaca aacagatgca | 120 |
| ggagcattaa gacgtgagtt cctagacgac caaatctcaa tgcttacttg gacagagaat | 180 |
| gatttaacat tctataaaga catcgctaaa aaaccagcta catctacagt agcaaaatac | 240 |
| gatgtataca tgcaacatgg taaggtaggt catactagat ttactcgtga gattggggta | 300 |
| gcaccagtaa gtgaccctaa catccgtcaa aaaacagtaa acatgaaatt tgcttccgat | 360 |
| actaaaaaca tcagtatcgc agcaggtcta gtaaacaaca ttcaagaccc aatgcaaatt | 420 |
| ttgactgacg atgctatcgt aaatattgct aaaacaattg agtgggcttc attctttgga | 480 |
| gattctgact tatcagatag cccagaacca caagcaggac tagaatttga cggcttggct | 540 |
| aaacttatta accaagataa cgttcatgat gctcgtggag ctagcttgac tgaaagcttg | 600 |
| ttaaaccaag cagcagtaat gattagtaaa ggttatggta cacctacaga tgcttacatg | 660 |
| ccagtagggg ttcaagcaga ctttgttaac caacaacttt ctaaacaaac acaacttgtt | 720 |
| cgcgataacg gaaacaacgt aagcgttggt ttcaacatcc aaggtttcca ttcagctcgt | 780 |
| ggatttatca aacttcacgg ttctacagta atggaaaacg aacaaatctt agatgaacgt | 840 |
| attcttgctt taccaacagc tccacaacca gctaaggtaa ctgcaacaca agaagcaggt | 900 |
| aaaaaaggac aatttagagc agaagattta gcagcacatg aatataaagt tgttgtaagt | 960 |
| tctgacgatg cagagtctat tgcaagtgaa gtggctacag ctacagttac tgcaaaagat | 1020 |
| gacggcgtta aactagaaat cgaattagct ccaatgtata gctctcgtcc acaattcgtt | 1080 |
| tcaatctata gaaaggtgc agaaacaggt ttattctacc taatcgctcg tgtacctgct | 1140 |
| agcaaagcag agaacaacgt aatcactttc tacgacttaa acgactctat tcctgaaaca | 1200 |
| gtagacgtat tcgttggtga atgtcggct aacgtagtac acttgtttga attactacca | 1260 |
| atgatgagat tacctctagc tcaaattaac gcatctgtta catttgcagt tttatggtat | 1320 |
| ggcgcattag ctctaagagc acctaagaaa tgggtacgta ttagaaacgt taaatatatt | 1380 |
| cctgtaaaaa acgttcatag caactaa | 1407 |

<210> SEQ ID NO 10
<211> LENGTH: 468
<212> TYPE: PRT
<213> ORGANISM: Artificial Sequence
<220> FEATURE:
<223> OTHER INFORMATION: Synthetic Polypeptide

<400> SEQUENCE: 10

Met Pro Lys Asn Asn Lys Glu Glu Glu Val Lys Glu Val Asn Leu Asn
1               5                   10                  15

Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110

Val Asn Met Lys Phe Ala Ser Asp Thr Lys Asn Ile Ser Ile Ala Ala
            115                 120                 125

Gly Leu Val Asn Asn Ile Gln Asp Pro Met Gln Ile Leu Thr Asp Asp
130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
            165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
            195                 200                 205

Ser Lys Gly Tyr Gly Thr Pro Thr Asp Ala Tyr Met Pro Val Gly Val
            210                 215                 220

Gln Ala Asp Phe Val Asn Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
            275                 280                 285

Gln Pro Ala Lys Val Thr Ala Thr Gln Glu Ala Gly Lys Lys Gly Gln
290                 295                 300

Phe Arg Ala Glu Asp Leu Ala Ala His Glu Tyr Lys Val Val Ser
305                 310                 315                 320

Ser Asp Asp Ala Glu Ser Ile Ala Ser Glu Val Ala Thr Ala Thr Val
            325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
            355                 360                 365

Thr Gly Leu Phe Tyr Leu Ile Ala Arg Val Pro Ala Ser Lys Ala Glu
            370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
            435                 440                 445

Lys Lys Trp Val Arg Ile Arg Asn Val Lys Tyr Ile Pro Val Lys Asn
450                 455                 460

Val His Ser Asn
465

<210> SEQ ID NO 11
<211> LENGTH: 1407
<212> TYPE: DNA
<213> ORGANISM: Artificial Sequence
<220> FEATURE:
<223> OTHER INFORMATION: Synthetic Oligonucleotide

<400> SEQUENCE: 11

| | |
|---|---|
| atgccaaaaa ataacaaaga agaagaagtt aaagaagtaa accttaattc agtacaagag | 60 |
| gacgcgttaa agtcctttac aactggttat ggtatcacac ctgatacaca aacagatgca | 120 |
| ggagcattaa gacgtgagtt cctagacgac caaatctcaa tgcttacttg gacagagaat | 180 |
| gatttaacat tctataaaga catcgctaaa aaaccagcta catctacagt agcaaaatac | 240 |
| gatgtataca tgcaacatgg taaggtaggt catactagat ttactcgtga gattggggta | 300 |
| gcaccagtaa gtgaccctaa catccgtcaa aaaacagtaa acatgaaatt tgcttccgat | 360 |
| actaaaaaca tcagtatcgc agcaggtcta gtaaacaaca ttcaagaccc aatgcaaatt | 420 |
| ttgactgacg atgctatcgt aaatattgct aaaacaattg agtgggcttc attctttgga | 480 |
| gattctgact tatcagatag cccagaacca caagcaggac tagaatttga cggcttggct | 540 |
| aaacttatta accaagataa cgttcatgat gctcgtggag ctagcttgac tgaaagcttg | 600 |
| ttaaaccaag cagcagtaat gattagtaaa ggttatggta cacctacaga tgcttacatg | 660 |
| ccagtagggg ttcaagcaga ctttgttaac caacaacttt ctaaacaaac acaacttgtt | 720 |
| cgcgataacg gaaacaacgt aagcgttggt ttcaacatcc aaggtttcca ttcagctcgt | 780 |
| ggatttatca aacttcacgg ttctacagta atggaaaacg aacaaatctt agatgaacgt | 840 |
| attcttgctt taccaacagc tccacaacca gctaaggtaa ctgcaacaca agaagcaggt | 900 |
| aaaaaaggac aatttagagc agaagattta gcagcacatg aatataaagt tgttgtaagt | 960 |
| tctgacgatg cagagtctat tgcaagtgaa gtggctacag ctacagttac tgcaaaagat | 1020 |
| gacggcgtta aactagaaat cgaattagct ccaatgtata gctctcgtcc acaattcgtt | 1080 |
| tcaatctata gaaaggtgc agaaacaggt ttattctacc taatcgctcg tgtacctgct | 1140 |
| agcaaagcag agaacaacgt aatcactttc tacgacttaa cgactctat tcctgaaaca | 1200 |
| gtagacgtat tcgttggtga atgtcggct aacgtagtac acttgtttga attactacca | 1260 |
| atgatgagat tacctctagc tcaaattaac gcatctgtta catttgcagt tttatggtat | 1320 |
| ggcgcattag ctctaagagc acctaagaaa tgggtacgta ttagaaacgt taaatatatt | 1380 |
| cctgtaaaaa acgttcatag caactaa | 1407 |

<210> SEQ ID NO 12
<211> LENGTH: 468
<212> TYPE: PRT
<213> ORGANISM: Artificial Sequence
<220> FEATURE:
<223> OTHER INFORMATION: Synthetic Polypeptide

<400> SEQUENCE: 12

Met Pro Lys Asn Asn Lys Glu Glu Val Lys Glu Val Asn Leu Asn
1               5                   10                  15

Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110

```
Val Asn Met Lys Phe Ala Ser Asp Thr Lys Asn Ile Ser Ile Ala Ala
        115                 120                 125

Gly Leu Val Asn Asn Ile Gln Asp Pro Met Gln Ile Leu Thr Asp Asp
130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
        195                 200                 205

Ser Lys Gly Tyr Gly Thr Pro Thr Asp Ala Tyr Met Pro Val Gly Val
    210                 215                 220

Gln Ala Asp Phe Val Asn Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
        275                 280                 285

Gln Pro Ala Lys Val Thr Ala Thr Gln Glu Ala Gly Lys Lys Gly Gln
    290                 295                 300

Phe Arg Ala Glu Asp Leu Ala Ala His Glu Tyr Lys Val Val Ser
305                 310                 315                 320

Ser Asp Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
        355                 360                 365

Thr Gly Leu Phe Tyr Leu Ile Ala Arg Val Pro Ala Ser Lys Ala Glu
    370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
        435                 440                 445

Lys Lys Trp Val Arg Ile Arg Asn Val Lys Tyr Ile Pro Val Lys Asn
    450                 455                 460

Val His Ser Asn
465

<210> SEQ ID NO 13
<211> LENGTH: 1407
<212> TYPE: DNA
<213> ORGANISM: Artificial Sequence
<220> FEATURE:
<223> OTHER INFORMATION: Synthetic Oligonucleotide

<400> SEQUENCE: 13
```

```
atgccaaaaa ataacaaaga agaagaagtt aaagaagtaa accttaattc agtacaagag      60
gacgcgttaa agtcctttac aactggttat ggtatcacac ctgatacaca aacagatgca     120
ggagcattaa gacgtgagtt cctagacgac caaatctcaa tgcttacttg gacagagaat     180
gatttaacat tctataaaga catcgctaaa aaaccagcta catctacagt agcaaaatac     240
gatgtataca tgcaacatgg taaggtaggt catactagat ttactcgtga gattggggta     300
gcaccagtaa gtgaccctaa catccgtcaa aaaacagtaa acatgaaatt tgcttccgat     360
actaaaaaca tcagtatcgc agcaggtcta gtaaacaaca ttcaagaccc aatgcaaatt     420
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
ccagtagggg ttcaagcaga ctttgttaac caacaacttt ctaaacaaac acaacttgtt     720
cgcgataacg gaaacaacgt aagcgttggt ttcaacatcc aaggtttcca ttcagctcgt     780
ggatttatca aacttcacgg ttctacagta atggaaaacg aacaaatctt agatgaacgt     840
attcttgctt taccaacagc tccacaacca gctaaggtaa ctgcaacaca agaagcaggt     900
aaaaaaggac aatttagagc agaagattta gcagcacatg aatataaagt tgttgtaagt     960
tctgacgatg cagagtctat tgcaagtgaa gtggctacag ctacagttac tgcaaaagat    1020
gacggcgtta aactagaaat cgaattagct ccaatgtata gctctcgtcc acaattcgtt    1080
tcaatctata gaaaaggtgc agaaacaggt ttattctacc taatcgctcg tgtacctgct    1140
agcaaagcag agaacaacgt aatcactttc tacgacttaa acgactctat tcctgaaaca    1200
gtagacgtat cgttggtga atgtcggct aacgtagtac acttgtttga attactacca    1260
atgatgagat acctctagc tcaaattaac gcatctgtta catttgcagt tttatggtat    1320
ggcgcattag ctctaagagc acctaagaaa tgggtacgta ttagaaacgt taaatatatt    1380
cctgtaaaaa acgttcatag caactaa                                       1407
```

<210> SEQ ID NO 14
<211> LENGTH: 468
<212> TYPE: PRT
<213> ORGANISM: Artificial Sequence
<220> FEATURE:
<223> OTHER INFORMATION: Synthetic Polypeptide

<400> SEQUENCE: 14

```
Met Pro Lys Asn Asn Lys Glu Glu Glu Val Lys Glu Val Asn Leu Asn
1               5                   10                  15

Ser Val Gln Glu Asp Ala Leu Lys Ser Phe Thr Thr Gly Tyr Gly Ile
                20                  25                  30

Thr Pro Asp Thr Gln Thr Asp Ala Gly Ala Leu Arg Arg Glu Phe Leu
            35                  40                  45

Asp Asp Gln Ile Ser Met Leu Thr Trp Thr Glu Asn Asp Leu Thr Phe
        50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110
```

Val Asn Met Lys Phe Ala Ser Asp Thr Lys Asn Ile Ser Ile Ala Ala
            115                 120                 125

Gly Leu Val Asn Asn Ile Gln Asp Pro Met Gln Ile Leu Thr Asp Asp
130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
            165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
            195                 200                 205

Ser Lys Gly Tyr Gly Thr Pro Thr Asp Ala Tyr Met Pro Val Gly Val
            210                 215                 220

Gln Ala Asp Phe Val Asn Gln Leu Ser Lys Gln Thr Gln Leu Val
225                 230                 235                 240

Arg Asp Asn Gly Asn Asn Val Ser Val Gly Phe Asn Ile Gln Gly Phe
            245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
            275                 280                 285

Gln Pro Ala Lys Val Thr Ala Thr Gln Glu Ala Gly Lys Lys Gly Gln
            290                 295                 300

Phe Arg Ala Glu Asp Leu Ala Ala His Glu Tyr Lys Val Val Ser
305                 310                 315                 320

Ser Asp Asp Ala Glu Ser Ile Ala Ser Glu Val Ala Thr Ala Thr Val
            325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
            355                 360                 365

Thr Gly Leu Phe Tyr Leu Ile Ala Arg Val Pro Ala Ser Lys Ala Glu
            370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val Val His Leu Phe
            405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
            435                 440                 445

Lys Lys Trp Val Arg Ile Arg Asn Val Lys Tyr Ile Pro Val Lys Asn
            450                 455                 460

Val His Ser Asn
465

<210> SEQ ID NO 15
<211> LENGTH: 1407
<212> TYPE: DNA
<213> ORGANISM: Artificial Sequence
<220> FEATURE:
<223> OTHER INFORMATION: Synthetic Oligonucleotide

<400> SEQUENCE: 15

```
atgccaaaaa ataacaaaga agaagaagtt aaagaagtaa accttaattc agtacaagag      60
gacgcgttaa agtcctttac aactggttat ggtatcacac ctgatacaca aacagatgca     120
ggagcattaa gacgtgagtt cctagacgac caaatctcaa tgcttacttg gacagagaat     180
gatttaacat tctataaaga catcgctaaa aaaccagcta catctacagt agcaaaatac     240
gatgtataca tgcaacatgg taaggtaggt catactagat ttactcgtga gattggggta     300
gcaccagtaa gtgaccctaa catccgtcaa aaaacagtaa acatgaaatt tgcttccgat     360
actaaaaaca tcagtatcgc agcaggtcta gtaaacaaca ttcaagaccc aatgcaaatt     420
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
ccagtagggg ttcaagcaga ctttgttaac caacaacttt ctaaacaaac acaacttgtt     720
cgtgataacg gaaacaacgt aagcgttggt ttcaacatcc aaggtttcca ttcagctcgt     780
ggatttatca aacttcacgg ttctacagta atggaaaacg aacaaatctt agatgaacgt     840
attcttgctt taccaacagc tccacaacca gctaaggtaa ctgcaacaca agaagcaggt     900
aaaaaaggac aatttagagc agaagattta gcagcacatg aatataaagt tgttgtaagt     960
tctgacgatg cagagtctat tgcaagtgaa gtggctacag ctacagttac tgcaaaagat    1020
gacggcgtta aactagaaat cgaattagct ccaatgtata gctctcgtcc acaattcgtt    1080
tcaatctata gaaaaggtgc agaaacaggt ttattctacc taatcgctcg tgtacctgct    1140
agcaaagcag agaacaacgt aatcactttc tacgacttaa cgactctat tcctgaaaca     1200
gtagacgtat tcgttggtga atgtcggct aacgtagtac acttgtttga attactacca    1260
atgatgagat tacctctagc tcaaattaac gcatctgtta catttgcagt tttatggtat    1320
ggcgcattag ctctaagagc acctaagaaa tgggtacgta ttagaaacgt taaatatatt    1380
cctgtaaaaa acgttcatag caactaa                                        1407
```

<210> SEQ ID NO 16
<211> LENGTH: 468
<212> TYPE: PRT
<213> ORGANISM: Artificial Sequence
<220> FEATURE:
<223> OTHER INFORMATION: Synthetic Polypeptide

<400> SEQUENCE: 16

```
Met Pro Lys Asn Asn Lys Glu Glu Glu Val Lys Glu Val Asn Leu Asn
1               5                   10                  15

Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110
```

```
Val Asn Met Lys Phe Ala Ser Asp Thr Lys Asn Ile Ser Ile Ala Ala
            115                 120                 125
Gly Leu Val Asn Asn Ile Gln Asp Pro Met Gln Ile Leu Thr Asp Asp
130                 135                 140
Ala Ile Val Asn Ile Ala Lys Thr Ile Glu Trp Ala Ser Phe Phe Gly
145                 150                 155                 160
Asp Ser Asp Leu Ser Asp Ser Pro Glu Pro Gln Ala Gly Leu Glu Phe
                165                 170                 175
Asp Gly Leu Ala Lys Leu Ile Asn Gln Asp Asn Val His Asp Ala Arg
            180                 185                 190
Gly Ala Ser Leu Thr Glu Ser Leu Leu Asn Gln Ala Ala Val Met Ile
        195                 200                 205
Ser Lys Gly Tyr Gly Thr Pro Thr Asp Ala Tyr Met Pro Val Gly Val
    210                 215                 220
Gln Ala Asp Phe Val Asn Gln Leu Ser Lys Gln Thr Gln Leu Val
225                 230                 235                 240
Arg Asp Asn Gly Asn Asn Val Ser Val Gly Phe Asn Ile Gln Gly Phe
                245                 250                 255
His Ser Ala Arg Gly Phe Ile Lys Leu His Gly Ser Thr Val Met Glu
            260                 265                 270
Asn Glu Gln Ile Leu Asp Glu Arg Ile Leu Ala Leu Pro Thr Ala Pro
        275                 280                 285
Gln Pro Ala Lys Val Thr Ala Thr Gln Glu Ala Gly Lys Lys Gly Gln
    290                 295                 300
Phe Arg Ala Glu Asp Leu Ala Ala His Glu Tyr Lys Val Val Ser
305                 310                 315                 320
Ser Asp Asp Ala Glu Ser Ile Ala Ser Glu Val Ala Thr Ala Thr Val
                325                 330                 335
Thr Ala Lys Asp Asp Gly Val Lys Leu Glu Ile Glu Leu Ala Pro Met
            340                 345                 350
Tyr Ser Ser Arg Pro Gln Phe Val Ser Ile Tyr Arg Lys Gly Ala Glu
        355                 360                 365
Thr Gly Leu Phe Tyr Leu Ile Ala Arg Val Pro Ala Ser Lys Ala Glu
    370                 375                 380
Asn Asn Val Ile Thr Phe Tyr Asp Leu Asn Asp Ser Ile Pro Glu Thr
385                 390                 395                 400
Val Asp Val Phe Val Gly Glu Met Ser Ala Asn Val Val His Leu Phe
                405                 410                 415
Glu Leu Leu Pro Met Met Arg Leu Pro Leu Ala Gln Ile Asn Ala Ser
            420                 425                 430
Val Thr Phe Ala Val Leu Trp Tyr Gly Ala Leu Ala Leu Arg Ala Pro
        435                 440                 445
Lys Lys Trp Val Arg Ile Arg Asn Val Lys Tyr Ile Pro Val Lys Asn
    450                 455                 460
Val His Ser Asn
465

<210> SEQ ID NO 17
<211> LENGTH: 1404
<212> TYPE: DNA
<213> ORGANISM: Artificial Sequence
<220> FEATURE:
<223> OTHER INFORMATION: Synthetic Oligonucleotide

<400> SEQUENCE: 17
```

```
atgccaaaaa ataacaaaga agaagttaaa gaagtaaacc ttaattcagt acaagaggat      60
gcgttaaagt cctttacgac tggttatggt atcacacctg atacacaaac agatgcagga     120
gcattaagac gtgagttcct agacgaccaa atctcaatgc ttacttggac agagaatgat     180
ttaacattct ataagacat cgctaaaaaa ccagctacat ctacagtagc aaaatacgat      240
gtatacatgc aacatggtaa ggtaggtcat actagattta ctcgtgagat tggggtagca     300
ccagtaagtg accctaacat ccgtcaaaaa acagtaaata tgaaatttgc ttccgatact     360
aaaaacatca gtatcgcagc aggtctagta acaacattc aagacccaat gcaaattttg      420
actgacgatg ctatcgtaaa tattgctaaa acaattgagt gggcttcatt ctttggagat     480
tctgacttat cagatagccc agaaccacaa gcaggactag aatttgacgg cttggctaaa     540
cttattaacc aagataacgt tcatgatgct cgtggagcta gcttgactga agcttgtta      600
aaccaagcag cagtaatgat tagtaaaggt tatggtacac ctacagatgc ttacatgcca     660
gtaggggttc aagcagactt tgttaaccaa caactttcta acaaacaca acttgttcgc      720
gataacggaa acaacgtaag cgttggtttc aacatccaag gtttccattc agctcgtgga     780
tttatcaaac ttcacggttc tacagtaatg gaaaacgaac aaatcttaga tgaacgtatt     840
cttgctttac aacagctcc acaaccagct aaggtaactg caacacaaga agcaggtaaa      900
aaggacaat ttagagcaga agatttagca gcacatgaat ataaagttgt tgtaagttct      960
gacgatgcag agtctattgc aagtgaagtg gctacagcta cagttactgc aaaagatgac    1020
ggcgttaaac tagaaatcga attagctcca atgtatagct ctcgtccaca attcgtttca    1080
atctatagaa aaggtgcaga aacaggttta ttctacctaa tcgctcgtgt acctgctagc    1140
aaagcagaga caacgtaat cactttctac gacttaaacg actctattcc tgaaacagta     1200
gacgtattcg ttggtgaaat gtcggctaac gtagtacact tgtttgaatt actaccaatg    1260
atgagattac ctctagctca aattaacgca tctgttacat ttgcagtttt atggtatggc    1320
gcattagctc taagagcacc taagaaatgg gtacgtatta gaaacgttaa atatattcct    1380
gtaaaaaacg ttcatagcaa ctaa                                           1404
```

<210> SEQ ID NO 18
<211> LENGTH: 467
<212> TYPE: PRT
<213> ORGANISM: Artificial Sequence
<220> FEATURE:
<223> OTHER INFORMATION: Synthetic Polypeptide

<400> SEQUENCE: 18

```
Met Pro Lys Asn Asn Lys Glu Glu Val Lys Glu Val Asn Leu Asn Ser
1               5                   10                  15

Val Gln Glu Asp Ala Leu Lys Ser Phe Thr Thr Gly Tyr Gly Ile Thr
            20                  25                  30

Pro Asp Thr Gln Thr Asp Ala Gly Ala Leu Arg Arg Glu Phe Leu Asp
        35                  40                  45

Asp Gln Ile Ser Met Leu Thr Trp Thr Glu Asn Asp Leu Thr Phe Tyr
    50                  55                  60

Lys Asp Ile Ala Lys Lys Pro Ala Thr Ser Thr Val Ala Lys Tyr Asp
65                  70                  75                  80

Val Tyr Met Gln His Gly Lys Val Gly His Thr Arg Phe Thr Arg Glu
                85                  90                  95

Ile Gly Val Ala Pro Val Ser Asp Pro Asn Ile Arg Gln Lys Thr Val
            100                 105                 110
```

```
Asn Met Lys Phe Ala Ser Asp Thr Lys Asn Ile Ser Ile Ala Ala Gly
            115                 120                 125

Leu Val Asn Asn Ile Gln Asp Pro Met Gln Ile Leu Thr Asp Asp Ala
        130                 135                 140

Ile Val Asn Ile Ala Lys Thr Ile Glu Trp Ala Ser Phe Phe Gly Asp
145                 150                 155                 160

Ser Asp Leu Ser Asp Ser Pro Glu Pro Gln Ala Gly Leu Glu Phe Asp
                165                 170                 175

Gly Leu Ala Lys Leu Ile Asn Gln Asp Asn Val His Asp Ala Arg Gly
            180                 185                 190

Ala Ser Leu Thr Glu Ser Leu Leu Asn Gln Ala Ala Val Met Ile Ser
        195                 200                 205

Lys Gly Tyr Gly Thr Pro Thr Asp Ala Tyr Met Pro Val Gly Val Gln
210                 215                 220

Ala Asp Phe Val Asn Gln Gln Leu Ser Lys Gln Thr Gln Leu Val Arg
225                 230                 235                 240

Asp Asn Gly Asn Asn Val Ser Val Gly Phe Asn Ile Gln Gly Phe His
                245                 250                 255

Ser Ala Arg Gly Phe Ile Lys Leu His Gly Ser Thr Val Met Glu Asn
            260                 265                 270

Glu Gln Ile Leu Asp Glu Arg Ile Leu Ala Leu Pro Thr Ala Pro Gln
        275                 280                 285

Pro Ala Lys Val Thr Ala Thr Gln Glu Ala Gly Lys Lys Gly Gln Phe
290                 295                 300

Arg Ala Glu Asp Leu Ala Ala His Glu Tyr Lys Val Val Ser Ser
305                 310                 315                 320

Asp Asp Ala Glu Ser Ile Ala Ser Glu Val Ala Thr Ala Thr Val Thr
                325                 330                 335

Ala Lys Asp Asp Gly Val Lys Leu Glu Ile Glu Leu Ala Pro Met Tyr
            340                 345                 350

Ser Ser Arg Pro Gln Phe Val Ser Ile Tyr Arg Lys Gly Ala Glu Thr
        355                 360                 365

Gly Leu Phe Tyr Leu Ile Ala Arg Val Pro Ala Ser Lys Ala Glu Asn
370                 375                 380

Asn Val Ile Thr Phe Tyr Asp Leu Asn Asp Ser Ile Pro Glu Thr Val
385                 390                 395                 400

Asp Val Phe Val Gly Glu Met Ser Ala Asn Val Val His Leu Phe Glu
                405                 410                 415

Leu Leu Pro Met Met Arg Leu Pro Leu Ala Gln Ile Asn Ala Ser Val
            420                 425                 430

Thr Phe Ala Val Leu Trp Tyr Gly Ala Leu Ala Leu Arg Ala Pro Lys
        435                 440                 445

Lys Trp Val Arg Ile Arg Asn Val Lys Tyr Ile Pro Val Lys Asn Val
450                 455                 460

His Ser Asn
465

<210> SEQ ID NO 19
<211> LENGTH: 1404
<212> TYPE: DNA
<213> ORGANISM: Artificial Sequence
<220> FEATURE:
<223> OTHER INFORMATION: Synthetic Oligonucleotide

<400> SEQUENCE: 19
```

```
atgccaaaaa ataacaaaga agaagttaaa gaagtaaacc ttaattcagt acaagaggat        60
gcgttaaagt cctttacgac tggttatggt atcacacctg atacacaaac agatgcagga       120
gcattaagac gtgagttcct agacgaccaa atctcaatgc ttacttggac agagaatgat       180
ttaacattct ataaagacat cgctaaaaaa ccagctacat ctacagtagc aaaatacgat       240
gtatacatgc aacatggtaa ggtaggtcat actagattta ctcgtgagat tggggtagca       300
ccagtaagtg accctaacat ccgtcaaaaa acagtaaata tgaaatttgc ttccgatact       360
aaaaacatca gtatcgcagc aggtctagta acaacattca agacccaat gcaaattttg        420
actgacgatg ctatcgtaaa tattgctaaa acaattgagt gggcttcatt ctttggagat       480
tctgacttat cagatagccc agaaccacaa gcaggactag aatttgacgg cttggctaaa       540
cttattaacc aagataacgt tcatgatgct cgtggagcta gcttgactga aagcttgtta       600
aaccaagcag cagtaatgat tagtaaaggt tatggtacac ctacagatgc ttacatgcca       660
gtaggggttc aagcagactt tgttaaccaa caactttcta aacaaacaca acttgttcgc       720
gataacggaa acaacgtaag cgttggtttc aacatccaag gtttccattc agctcgtgga       780
tttatcaaac ttcacggttc tacagtaatg gaaacgaac aaatcttaga tgaacgtatt        840
cttgctttac aacagctcc acaaccagct aaggtaactg caacacaaga agcaggtaaa        900
aaggacaat ttagagcaga agatttagca gcacatgaat ataaagttgt tgtaagttct        960
gacgatgcag agtctattgc aagtgaagtg gctacagcta cagttactgc aaaagatgac      1020
ggcgttaaac tagaaatcga attagctcca atgtatagct ctcgtccaca attcgtttca      1080
atctatagaa aaggtgcaga aacaggttta ttctacctaa tcgctcgtgt acctgctagc      1140
aaagcagaga caacgtaat cactttctac gacttaaacg actctattcc tgaaacagta      1200
gacgtattcg ttggtgaaat gtcggctaac gtagtacact tgtttgaatt actaccaatg      1260
atgagattac ctctagctca aattaacgca tctgttacat ttgcagtttt atggtatggc      1320
gcattagctc taagagcacc taagaaatgg gtacgtatta gaaacgttaa atatattcct      1380
gtaaaaaacg ttcatagcaa ctaa                                             1404
```

<210> SEQ ID NO 20
<211> LENGTH: 467
<212> TYPE: PRT
<213> ORGANISM: Artificial Sequence
<220> FEATURE:
<223> OTHER INFORMATION: Synthetic Polypeptide

<400> SEQUENCE: 20

```
Met Pro Lys Asn Asn Lys Glu Glu Val Lys Glu Val Asn Leu Asn Ser
1               5                   10                  15

Val Gln Glu Asp Ala Leu Lys Ser Phe Thr Thr Gly Tyr Gly Ile Thr
                20                  25                  30

Pro Asp Thr Gln Thr Asp Ala Gly Ala Leu Arg Arg Glu Phe Leu Asp
            35                  40                  45

Asp Gln Ile Ser Met Leu Thr Trp Thr Glu Asn Asp Leu Thr Phe Tyr
        50                  55                  60

Lys Asp Ile Ala Lys Lys Pro Ala Thr Ser Thr Val Ala Lys Tyr Asp
65                  70                  75                  80

Val Tyr Met Gln His Gly Lys Val Gly His Thr Arg Phe Thr Arg Glu
                85                  90                  95

Ile Gly Val Ala Pro Val Ser Asp Pro Asn Ile Arg Gln Lys Thr Val
            100                 105                 110
```

```
Asn Met Lys Phe Ala Ser Asp Thr Lys Asn Ile Ser Ile Ala Ala Gly
        115                 120                 125

Leu Val Asn Asn Ile Gln Asp Pro Met Gln Ile Leu Thr Asp Asp Ala
    130                 135                 140

Ile Val Asn Ile Ala Lys Thr Ile Glu Trp Ala Ser Phe Phe Gly Asp
145                 150                 155                 160

Ser Asp Leu Ser Asp Ser Pro Glu Pro Gln Ala Gly Leu Glu Phe Asp
                165                 170                 175

Gly Leu Ala Lys Leu Ile Asn Gln Asp Asn Val His Asp Ala Arg Gly
            180                 185                 190

Ala Ser Leu Thr Glu Ser Leu Leu Asn Gln Ala Ala Val Met Ile Ser
        195                 200                 205

Lys Gly Tyr Gly Thr Pro Thr Asp Ala Tyr Met Pro Val Gly Val Gln
    210                 215                 220

Ala Asp Phe Val Asn Gln Gln Leu Ser Lys Gln Thr Gln Leu Val Arg
225                 230                 235                 240

Asp Asn Gly Asn Asn Val Ser Val Gly Phe Asn Ile Gln Gly Phe His
                245                 250                 255

Ser Ala Arg Gly Phe Ile Lys Leu His Gly Ser Thr Val Met Glu Asn
            260                 265                 270

Glu Gln Ile Leu Asp Glu Arg Ile Leu Ala Leu Pro Thr Ala Pro Gln
        275                 280                 285

Pro Ala Lys Val Thr Ala Thr Gln Glu Ala Gly Lys Lys Gly Gln Phe
    290                 295                 300

Arg Ala Glu Asp Leu Ala Ala His Glu Tyr Lys Val Val Ser Ser
305                 310                 315                 320

Asp Asp Ala Glu Ser Ile Ala Ser Glu Val Ala Thr Ala Thr Val Thr
                325                 330                 335

Ala Lys Asp Asp Gly Val Lys Leu Glu Ile Glu Leu Ala Pro Met Tyr
            340                 345                 350

Ser Ser Arg Pro Gln Phe Val Ser Ile Tyr Arg Lys Gly Ala Glu Thr
        355                 360                 365

Gly Leu Phe Tyr Leu Ile Ala Arg Val Pro Ala Ser Lys Ala Glu Asn
    370                 375                 380

Asn Val Ile Thr Phe Tyr Asp Leu Asn Asp Ser Ile Pro Glu Thr Val
385                 390                 395                 400

Asp Val Phe Val Gly Glu Met Ser Ala Asn Val Val His Leu Phe Glu
                405                 410                 415

Leu Leu Pro Met Met Arg Leu Pro Leu Ala Gln Ile Asn Ala Ser Val
            420                 425                 430

Thr Phe Ala Val Leu Trp Tyr Gly Ala Leu Ala Leu Arg Ala Pro Lys
        435                 440                 445

Lys Trp Val Arg Ile Arg Asn Val Lys Tyr Ile Pro Val Lys Asn Val
    450                 455                 460

His Ser Asn
465

<210> SEQ ID NO 21
<211> LENGTH: 1407
<212> TYPE: DNA
<213> ORGANISM: Artificial Sequence
<220> FEATURE:
<223> OTHER INFORMATION: Synthetic Oligonucleotide

<400> SEQUENCE: 21
```

```
atgccaaaaa ataacaaaga agaagaagtt aaagaagtaa accttaattc agtacaagag      60
gacgcgttaa agtcctttac aactggttat ggtatcacac ctgatacaca aacagatgca     120
ggagcattaa gacgtgagtt cctagacgac caaatctcaa tgcttacttg gacagagaat     180
gatttaacat tctataaaga catcgctaaa aaaccagcta catctacagt agcaaaatac     240
gatgtataca tgcaacatgg taaggtaggt catactagat ttactcgtga gattggggta     300
gcaccagtaa gtgaccctaa catccgtcaa aaaacagtaa atatgaaatt tgcttccgat     360
actaaaaaca tcagtatcgc agcaggtcta gtaaacaaca ttcaagaccc aatgcaaatt     420
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
ccagtagggg ttcaagcaga ctttgttaac caacaacttt ctaaacaaac acagcttgtt     720
cgtgataacg gaaacaacgt aagcgttggt ttcaacatcc aaggtttcca ttcagctcgt     780
ggatttatca aacttcacgg ttctacagta atggaaaacg aacaaatctt agatgaacgt     840
attcttgctt taccaacagc tccacaacca gctaaggtaa ctgcaacaca gaagcaggt      900
aaaaaaggac aatttagagc agaagactta gcagcacacg aatacaaagt tgttgtaagt     960
tctgacgatg cagagtctat tgcaagtgaa gtggctacag ctacagttac tgcaaaagat    1020
gacggcgtta aactagaaat cgagttagct ccaatgtaca gctcccgtcc acaattcgtt    1080
tcaatctata gaaaaggtgc agaaacaggt ttattctacc taatcgctcg tgtacctgct    1140
agcaaagcag agaacaacgt aatcactttc tatgacttaa acgactctat tcctgaaaca    1200
gtagacgtat tcgttggtga atgtctgcta acgtagtac acttgtttga attactacca    1260
atgatgagat tacctctagc tcaaattaac gcatctgtta catttgcagt tttatggtat    1320
ggagcattag ctctaagagc acctaagaaa tgggtacgta ttagaaacgt taaatatatt    1380
cctgtaaaaa acgttcatag caactaa                                        1407
```

<210> SEQ ID NO 22
<211> LENGTH: 468
<212> TYPE: PRT
<213> ORGANISM: Artificial Sequence
<220> FEATURE:
<223> OTHER INFORMATION: Synthetic Polypeptide

<400> SEQUENCE: 22

```
Met Pro Lys Asn Asn Lys Glu Glu Glu Val Lys Glu Val Asn Leu Asn
1               5                   10                  15

Ser Val Gln Glu Asp Ala Leu Lys Ser Phe Thr Thr Gly Tyr Gly Ile
            20                  25                  30

Thr Pro Asp Thr Gln Thr Asp Ala Gly Ala Leu Arg Arg Glu Phe Leu
        35                  40                  45

Asp Asp Gln Ile Ser Met Leu Thr Trp Thr Glu Asn Asp Leu Thr Phe
    50                  55                  60

Tyr Lys Asp Ile Ala Lys Lys Pro Ala Thr Ser Thr Val Ala Lys Tyr
65                  70                  75                  80

Asp Val Tyr Met Gln His Gly Lys Val Gly His Thr Arg Phe Thr Arg
                85                  90                  95

Glu Ile Gly Val Ala Pro Val Ser Asp Pro Asn Ile Arg Gln Lys Thr
            100                 105                 110
```

```
Val Asn Met Lys Phe Ala Ser Asp Thr Lys Asn Ile Ser Ile Ala Ala
            115                 120                 125

Gly Leu Val Asn Asn Ile Gln Asp Pro Met Gln Ile Leu Thr Asp Asp
130                 135                 140

Ala Ile Val Asn Ile Ala Lys Thr Ile Glu Trp Ala Ser Phe Phe Gly
145                 150                 155                 160

Asp Ser Asp Leu Ser Asp Ser Pro Glu Pro Gln Ala Gly Leu Glu Phe
                165                 170                 175

Asp Gly Leu Ala Lys Leu Ile Asn Gln Asp Asn Val His Asp Ala Arg
            180                 185                 190

Gly Ala Ser Leu Thr Glu Ser Leu Leu Asn Gln Ala Ala Val Met Ile
            195                 200                 205

Ser Lys Gly Tyr Gly Thr Pro Thr Asp Ala Tyr Met Pro Val Gly Val
210                 215                 220

Gln Ala Asp Phe Val Asn Gln Leu Ser Lys Gln Thr Gln Leu Val
225                 230                 235                 240

Arg Asp Asn Gly Asn Asn Val Ser Val Gly Phe Asn Ile Gln Gly Phe
                245                 250                 255

His Ser Ala Arg Gly Phe Ile Lys Leu His Gly Ser Thr Val Met Glu
            260                 265                 270

Asn Glu Gln Ile Leu Asp Glu Arg Ile Leu Ala Leu Pro Thr Ala Pro
275                 280                 285

Gln Pro Ala Lys Val Thr Ala Thr Gln Glu Ala Gly Lys Lys Gly Gln
290                 295                 300

Phe Arg Ala Glu Asp Leu Ala Ala His Glu Tyr Lys Val Val Ser
305                 310                 315                 320

Ser Asp Ala Glu Ser Ile Ala Ser Glu Val Ala Thr Ala Thr Val
                325                 330                 335

Thr Ala Lys Asp Asp Gly Val Lys Leu Glu Ile Glu Leu Ala Pro Met
            340                 345                 350

Tyr Ser Ser Arg Pro Gln Phe Val Ser Ile Tyr Arg Lys Gly Ala Glu
            355                 360                 365

Thr Gly Leu Phe Tyr Leu Ile Ala Arg Val Pro Ala Ser Lys Ala Glu
370                 375                 380

Asn Asn Val Ile Thr Phe Tyr Asp Leu Asn Asp Ser Ile Pro Glu Thr
385                 390                 395                 400

Val Asp Val Phe Val Gly Glu Met Ser Ala Asn Val His Leu Phe
                405                 410                 415

Glu Leu Leu Pro Met Met Arg Leu Pro Leu Ala Gln Ile Asn Ala Ser
            420                 425                 430

Val Thr Phe Ala Val Leu Trp Tyr Gly Ala Leu Ala Leu Arg Ala Pro
            435                 440                 445

Lys Lys Trp Val Arg Ile Arg Asn Val Lys Tyr Ile Pro Val Lys Asn
450                 455                 460

Val His Ser Asn
465

<210> SEQ ID NO 23
<211> LENGTH: 3729
<212> TYPE: DNA
<213> ORGANISM: Artificial Sequence
<220> FEATURE:
<223> OTHER INFORMATION: Synthetic Oligonucleotide

<400> SEQUENCE: 23
```

```
atgccaaaaa ataacaaaga agaagaagtt aaagaagtaa accttaattc agtacaagag      60
gacgcgttaa agtcctttac aactggttat ggtatcacac ctgatacaca aacagatgca     120
ggagcattaa gacgtgagtt cctagacgac caaatctcaa tgcttacttg gacagagaat     180
gatttaacat tctataaaga catcgctaaa aaaccagcta catctacagt agcaaaatac     240
gatgtataca tgcaacatgg taaggtaggt catactagat ttactcgtga gattggggta     300
gcaccagtaa gtgaccctaa catccgtcaa aaaacagtaa acatgaaatt tgcttccgat     360
actaaaaaca tcagtatcgc agcaggtcta gtaaacaaca ttcaagaccc aatgcaaatt     420
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
ccagtagggg ttcaagcaga cttttgttaac caacaacttt ctaaacaaac acaacttgtt     720
cgcgataacg gaaacaacgt aagcgttggt ttcaacatcc aaggtttcca ttcagctcgt     780
ggatttatca aacttcacgg ttctacagta atggaaaacg aacaaatctt agatgaacgt     840
attcttgctt taccaacagc tccacaacca gctaaggtaa ctgcaacaca agaagcaggt     900
aaaaaaggac aatttagagc agaagattta gcagcacatg aatataaagt tgttgtaagt     960
tctgacgatg cagagtctat tgcaagtgaa gtggctacag ctacagttac tgcaaaagat    1020
gacggcgtta aactagaaat cgaattagct ccaatgtata gctctcgtcc acaattcgtt    1080
tcaatctata gaaaaggtgc agaaacaggt ttattctacc taatcgctcg tgtacctgct    1140
agcaaagcag agaacaacgt aatcactttc tacgacttaa acgactctat tcctgaaaca    1200
gtagacgtat tcgttggtga aatgtcggct aacgtagtac acttgtttga attactacca    1260
atgatgagat tacctctagc tcaaattaac gcatctgtta catttgcagt tttatggtat    1320
ggcgcattag ctctaagagc acctaagaaa tgggtacgta ttagaaacgt taaatatatt    1380
cctgtaaaaa acgttcatag caactaagag gaggtaaata tatatggaag acgccaaaaa    1440
cataaagaaa ggcccggcgc cattctatcc tctagaggat ggaaccgctg gagagcaact    1500
gcataaggct atgaagagat acgccctggt tcctggaaca attgctttta cagatgcaca    1560
tatcgaggtg aacatcacgt acgcggaata cttcgaaatg tccgttcggt tggcagaagc    1620
tatgaaacga tatgggctga atacaaatca cagaatcgtc gtatgcagtg aaaactctct    1680
tcaattcttt atgccggtgt tgggcgcgtt atttatcgga gttgcagttg cgcccgcgaa    1740
cgacatttat aatgaacgtg aattgctcaa cagtatgaac atttcgcagc ctaccgtagt    1800
gtttgtttcc aaaaagggt tgcaaaaaat tttgaacgtg caaaaaaat taccaataat    1860 ccagaaaatt attatcatgg attctaaaac ggattaccag ggatttcagt cgatgtacac    1920
gttcgtcaca tctcatctac ctcccggttt taatgaatac gattttgtac cagagtcctt    1980
tgatcgtgac aaaacaattg cactgataat gaattcctct ggatctactg ggttacctaa    2040
gggtgtggcc cttccgcata gaactgcctg cgtcagattc tcgcatgcca gagatcctat    2100
ttttggcaat caaatcattc cggatactgc gattttaagt gttgttccat tccatcacgg    2160
ttttggaatg tttactacac tcggatattt gatatgtgga tttcgagtcg tcttaatgta    2220
tagatttgaa gaagagctgt ttttacgatc ccttcaggat tacaaaattc aaagtgcgtt    2280
gctagtacca accctatttt cattcttcgc caaaagcact ctgattgaca aatacgattt    2340
atctaattta cacgaaattg cttctggggg cgcacctctt tcgaaagaag tcggggaagc    2400
```

```
ggttgcaaaa cgcttccatc ttccagggat acgacaagga tatgggctca ctgagactac    2460
atcagctatt ctgattacac ccgaggggga tgataaaccg ggcgcggtcg gtaaagttgt    2520 tccattttt gaagcgaagg ttgtggatct ggataccggg aaaacgctgg gcgttaatca    2580
gagaggcgaa ttatgtgtca gaggacctat gattatgtcc ggttatgtaa acaatccgga    2640
agcgaccaac gccttgattg acaaggatgg atggctacat tctggagaca tagcttactg    2700
ggacgaagac gaacacttct tcatagttga ccgcttgaag tctttaatta aatacaaagg    2760
atatcaggtg gcccccgctg aattggaatc gatattgtta caacacccca acatcttcga    2820
cgcgggcgtg gcaggtcttc ccgacgatga cgccggtgaa cttccagccg ccgttgttgt    2880
tttggagcac ggaaagacga tgacggaaaa agagatcgtg gattacgtcg ccagtcaagt    2940
aacaaccgcg aaaagttgc gcggaggagt tgtgtttgtg gacgaagtac cgaaaggtct    3000
taccggaaaa ctcgacgcaa gaaaaatcag agagatcctc ataaaggcca gaagggcgg    3060 aaagtccaaa ttgtaataat tataggataa ttgaataaaa acagtataga gagcagataa    3120
atactgctct ctattttact aataaggagg atttaaattg ctaaaaata caaacttagc    3180 taattataaa aaagtgaata cacggtttgg aaatcttagt tttgacgaca aaggtatttc    3240
taatgactta acggaagaac agcaaaaaga attaggtaag cttcgaggat tcgaatatat    3300
taagacagaa cagaaaacaa aagaagaacc taagaaagaa gaacctaaga aagaaagtac    3360
agaaaatgaa ttagacagct tcttagctaa agagccttca atcaaagaat taaagaatt    3420 tgcgagtaaa aaaggcatta aaattgaaaa aactaagaaa aatgatataa ttgaagaact    3480
aaagagaggg taatgtataa tgtatggagg ttatgaagga caagattctt acgaataccc    3540
ttactcacat gggaaccta agcatgtaga gccagaaaaa gttgacgaat atgttctttc    3600
tgattatggt tggactgcgg aaacaattaa agcatacatg tatggtgttc gtgtagtaga    3660
ccctgaaaca ggagaggaaa tgggagacac cttctacaat catattatag aggttgccgt    3720
tgataaggc                                                          3729
```

<210> SEQ ID NO 24
<211> LENGTH: 3729
<212> TYPE: DNA
<213> ORGANISM: Artificial Sequence
<220> FEATURE:
<223> OTHER INFORMATION: Synthetic Oligonucleotide

<400> SEQUENCE: 24

```
atgccaaaaa ataacaaaga agaagaagtt aaagaagtaa accttaattc agtacaagag      60
gacgcgttaa agtcctttac aactggttat ggtatcacac ctgatacaca aacagatgca     120
ggagcattaa gacgtgagtt cctagacgac caaatctcaa tgcttacttg gacagagaat     180
gatttaacat tctataaaga catcgctaaa aaaccagcta catctacagt agcaaaatac     240
gatgtataca tgcaacatgg taaggtaggt catactagat ttactcgtga gattggggta     300
gcaccagtaa gtgaccctaa catccgtcaa aaaacagtaa acatgaaatt tgcttccgat     360
actaaaaaca tcagtatcgc agcaggtcta gtaaacaaca ttcaagaccc aatgcaaatt     420
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
```

```
ccagtagggg ttcaagcaga ctttgttaac caacaacttt ctaaacaaac acaacttgtt      720
cgcgataacg gaaacaacgt aagcgttggt ttcaacatcc aaggtttcca ttcagctcgt      780
ggatttatca aacttcacgg ttctacagta atggaaaacg aacaaatctt agatgaacgt      840
attcttgctt taccaacagc tccacaacca gctaaggtaa ctgcaacaca agaagcaggt      900 aaaaaggac aatttagagc agaagattta gcagcacatg aatataaagt tgttgtaagt      960
tctgacgatg cagagtctat tgcaagtgaa gtggctacag ctacagttac tgcaaaagat     1020
gacggcgtta aactagaaat cgaattagct ccaatgtata gctctcgtcc acaattcgtt     1080
tcaatctata gaaaggtgc agaaacaggt ttattctacc taatcgctcg tgtacctgct      1140
agcaaagcag agaacaacgt aatcactttc tacgacttaa acgactctat tcctgaaaca     1200
gtagacgtat tcgttggtga aatgtcggct aacgtagtac acttgtttga attactacca     1260
atgatgagat tacctctagc tcaaattaac gcatctgtta catttgcagt tttatggtat     1320
ggcgcattag ctctaagagc acctaagaaa tgggtacgta ttagaaacgt taaatatatt     1380
cctgtaaaaa acgttcatag caactaagag gaggtaaata tatatggaag acgccaaaaa     1440
cataaagaaa ggcccggcgc cattctatcc tctagaggat ggaaccgctg gagagcaact     1500
gcataaggct atgaagagat acgccctggt tcctggaaca attgcttta cagatgcaca     1560 tatcgaggtg aacatcacgt acgcggaata cttcgaaatg tccgttcggt tggcagaagc     1620
tatgaaacga tatgggctga atacaaatca cagaatcgtc gtatgcagtg aaaactctct     1680
tcaattcttt atgccggtgt tgggcgcgtt atttatcgga gttgcagttg cgcccgcgaa     1740
cgacatttat aatgaacgtg aattgctcaa cagtatgaac atttcgcagc ctaccgtagt     1800
gtttgtttcc aaaaaggggt tgcaaaaaat tttgaacgtg caaaaaaaat taccaataat     1860
ccagaaaatt attatcatgg attctaaaac ggattaccag ggatttcagt cgatgtacac     1920
gttcgtcaca tctcatctac ctcccggttt taatgaatac gattttgtac cagagtcctt     1980
tgatcgtgac aaaacaattg cactgataat gaattcctct ggatctactg ggttacctaa     2040
gggtgtggcc cttccgcata gaactgcctg cgtcagattc tcgcatgcca gagatcctat     2100
ttttggcaat caaatcattc cggatactgc gattttaagt gttgttccat tccatcacgg     2160
ttttggaatg tttactacac tcggatattt gatatgtgga tttcgagtcg tcttaatgta     2220
tagatttgaa gaagagctgt ttttacgatc ccttcaggat tacaaaattc aaagtgcgtt     2280
gctagtacca accctatttt cattcttcgc caaaagcact ctgattgaca aatacgattt     2340
atctaattta cacgaaattg cttctggggg cgcacctctt tcgaaagaag tcggggaagc     2400
ggttgcaaaa cgcttccatc ttccagggat acgacaagga tatgggctca ctgagactac     2460
atcagctatt ctgattacac ccgaggggga tgataaaccg ggcgcggtcg gtaaagttgt     2520
tccatttttt gaagcgaagg ttgtggatct ggataccggg aaaacgctgg gcgttaatca     2580
gagaggcgaa ttatgtgtca gaggacctat gattatgtcc ggttatgtaa acaatccgga     2640
agcgaccaac gccttgattg acaaggatgg atggctacat tctggagaca tagcttactg     2700
ggacgaagac gaacacttct tcatagttga ccgcttgaag tctttaatta aatacaaagg     2760
atatcaggtg gcccccgctg aattggaatc gatattgtta caaccccca acatcttcga     2820 cgcgggcgtg gcaggtcttc ccgacgatga cgccggtgaa cttccagccg ccgttgttgt     2880
tttggagcac ggaaagacga tgacggaaaa agagatcgtg gattacgtcg ccagtcaagt     2940
aacaaccgcg aaaaagttgc gcggaggagt tgtgtttgtg gacgaagtac cgaaaggtct     3000
taccggaaaa ctcgacgcaa gaaaaatcag agagatcctc ataaaggcca agaagggcgg     3060
```

-continued

| | | |
|---|---|---|
| aaagtccaaa ttgtaataat tataggataa ttgaataaaa acagtataga gagcagataa | 3120 | |
| atactgctct ctattttact aataaggagg atttaaattg ctaaaaaata caaacttagc | 3180 | |
| taattataaa aaagtgaata cacggtttgg aaatcttagt tttgacgaca aaggtatttc | 3240 | |
| taatgactta acgaagaac agcaaaaaga attaggtaag cttcgaggat tcgaatatat | 3300 | |
| taagacagaa cagaaaacaa aagaagaacc taagaaagaa gaacctaaga agaaagtac | 3360 | |
| agaaaatgaa ttagacagct tcttagctaa agagccttca atcaaagaat taaaagaatt | 3420 | |
| tgcgagtaaa aaaggcatta aaattgaaaa aactaagaaa aatgatataa ttgaagaact | 3480 | |
| aaagagaggg taatgtataa tgtatggagg ttatgaagga caagattctt acgaataccc | 3540 | |
| ttactcacat gggaacccta agcatgtaga gccagaaaaa gttgacgaat atgttctttc | 3600 | |
| tgattatggt tggactgcgg aaacaattaa agcatacatg tatggtgttc gtgtagtaga | 3660 | |
| ccctgaaaca ggagaggaaa tgggagacac cttctacaat catattatag aggttgccgt | 3720 | |
| tgataaggc | 3729 | |

<210> SEQ ID NO 25
<211> LENGTH: 3789
<212> TYPE: DNA
<213> ORGANISM: Artificial Sequence
<220> FEATURE:
<223> OTHER INFORMATION: Synthetic Oligonucleotide

<400> SEQUENCE: 25

| | | |
|---|---|---|
| atgccaaaaa ataacaaaga agaagaagtt aaagaagtaa accttaattc agtacaagag | 60 | |
| gacgcgttaa agtcctttac aactggttat ggtatcacac ctgatacaca aacagatgca | 120 | |
| ggagcattaa gacgtgagtt cctagacgac caaatctcaa tgcttacttg acagagaat | 180 | |
| gatttaacat tctataaaga catcgctaaa aaaccagcta catctacagt agcaaaatac | 240 | |
| gatgtataca tgcaacatgg taaggtaggt catactagat ttactcgtga gattggggta | 300 | |
| gcaccagtaa gtgaccctaa catccgtcaa aaaacagtaa acatgaaatt tgcttccgat | 360 | |
| actaaaaaca tcagtatcgc agcaggtcta gtaaacaaca ttcaagaccc aatgcaaatt | 420 | |
| ttgactgacg atgctatcgt aaatattgct aaaacaattg agtgggcttc attctttgga | 480 | |
| gattctgact tatcagatag cccagaacca caagcaggac tagaatttga cggcttggct | 540 | |
| aaacttatta accaagataa cgttcatgat gctcgtggag ctagcttgac tgaaagcttg | 600 | |
| ttaaaccaag cagcagtaat gattagtaaa ggttatggta cacctacaga tgcttacatg | 660 | |
| ccagtagggg ttcaagcaga ctttgttaac caacaacttt ctaaacaaac acaacttgtt | 720 | |
| cgcgataacg gaaacaacgt aagcgttggt ttcaacatcc aaggtttcca ttcagctcgt | 780 | |
| ggatttatca aacttcacgg ttctacagta atggaaaacg aacaaatctt agatgaacgt | 840 | |
| attcttgctt taccaacagc tccacaacca gctaaggtaa ctgcaacaca agaagcaggt | 900 | |
| aaaaaaggac aatttagagc agaagattta gcagcacatg aatataaagt tgttgtaagt | 960 | |
| tctgacgatg cagagtctat tgcaagtgaa gtggctacag ctacagttac tgcaaaagat | 1020 | |
| gacggcgtta aactagaaat cgaattagct ccaatgtata gctctcgtcc acaattcgtt | 1080 | |
| tcaatctata gaaaggtgc agaaacaggt ttattctacc taatcgctcg tgtacctgct | 1140 | |
| agcaaagcag agaacaacgt aatcactttc tacgacttaa acgactctat tcctgaaaca | 1200 | |
| gtagacgtat tcgttggtga aatgtcggct aacgtagtac acttgtttga attactacca | 1260 | |
| atgatgagat tacctctagc tcaaattaac gcatctgtta catttgcagt tttatggtat | 1320 | |

```
ggcgcattag ctctaagagc acctaagaaa tgggtacgta ttagaaacgt taaatatatt   1380
cctgtaaaaa acgttcatag caactaagag gaggtaaata tatatggaag acgccaaaaa   1440
cataaagaaa ggcccggcgc cattctatcc tctagaggat ggaaccgctg gagagcaact   1500
gcataaggct atgaagagat acgccctggt tcctggaaca attgctttta cagatgcaca   1560
tatcgaggtg aacatcacgt acgcggaata cttcgaaatg tccgttcggt tggcagaagc   1620
tatgaaacga tatgggctga atacaaatca cagaatcgtc gtatgcagtg aaaactctct   1680
tcaattcttt atgccggtgt tgggcgcgtt atttatcgga gttgcagttg cgcccgcgaa   1740
cgacatttat aatgaacgtg aattgctcaa cagtatgaac atttcgcagc ctaccgtagt   1800
gtttgtttcc aaaaaggggt tgcaaaaaat tttgaacgtg caaaaaaaat taccaataat   1860
ccagaaaatt attatcatgg attctaaaac ggattaccag ggatttcagt cgatgtacac   1920
gttcgtcaca tctcatctac ctcccggttt taatgaatac gattttgtac cagagtcctt   1980
tgatcgtgac aaaacaattg cactgataat gaattcctct ggatctactg ggttacctaa   2040
gggtgtggcc cttccgcata gaactgcctg cgtcagattc tcgcatgcca gagatcctat   2100
ttttggcaat caaatcattc cggatactgc gattttaagt gttgttccat tccatcacgg   2160
ttttggaatg tttactacac tcggatattt gatatgtgga tttcgagtcg tcttaatgta   2220
tagatttgaa gaagagctgt ttttacgatc ccttcaggat tacaaaattc aaagtgcgtt   2280
gctagtacca accctatttt cattcttcgc caaaagcact ctgattgaca atacgatttt   2340
atctaattta cacgaaattg cttctggggg cgcacctctt tcgaaagaag tcggggaagc   2400
ggttgcaaaa cgcttccatc ttccagggat acgacaagga tatgggctca ctgagactac   2460
atcagctatt ctgattacac ccgagggga tgataaaccg ggcgcggtcg gtaaagttgt   2520
tccattttt gaagcgaagg ttgtggatct ggataccggg aaaacgctgg gcgttaatca   2580
gagaggcgaa ttatgtgtca gaggacctat gattatgtcc ggttatgtaa caatccgga   2640
agcgaccaac gccttgattg acaaggatgg atggctacat tctggagaca tagcttactg   2700
ggacgaagac gaacacttct tcatagttga ccgcttgaag tctttaatta aatacaaagg   2760
atatcaggtg gcccccgctg aattggaatc gatattgtta caacaccca acatcttcga   2820
cgcgggcgtg gcaggtcttc ccgacgatga cgccggtgaa cttcccgccg ccgttgttgt   2880
tttggagcac ggaaagacga tgacggaaaa agagatcgtg gattacgtcg ccagtcaagt   2940
aacaaccgcg aaaaagttgc gcggaggagt tgtgtttgtg gacgaagtac cgaaaggtct   3000
taccggaaaa ctcgacgcaa gaaaaatcag agagatcctc ataaaggcca agaagggcgg   3060
aaagtccaaa ttgtaataat tataggataa ttgaataaaa acagtataga gagcagataa   3120
atactgctct ctattttact aataaggagg atttaaattg ctaaaaaata caaacttagc   3180
taattataaa aaagtgaata cacggtttgg aaatcttagt tttgacgaca aaggtatttc   3240
taatgactta acggaagaac agcaaaaaga attaggtaag cttcgaggat tcgaatatat   3300
taagacagaa cagaaaacaa aagaagaacc taagaaagaa gaacctaaga aagaagaacc   3360
taagaaagaa gaacctaaga agaagaacc taagaaagaa gaacctaaga agaaagtac   3420
agaaaatgaa ttagacagct tcttagctaa agagccttca atcaaagaat taaaagaatt   3480
tgcgagtaaa aaaggcatta aaattgaaaa aactaagaaa aatgatataa ttgaagaact   3540
aaagagaggg taatgtataa tgtatggagg ttatgaagga caagattctt acgaatacc   3600
ttactcacat gggaacccta agcatgtaga gccagaaaaa gttgacgaat atgttctttc   3660
tgattatggt tggactgcgg aaacaattaa agcatacatg tatggtgttc gtgtagtaga   3720
```

```
ccctgaaaca ggagaggaaa tgggagacac cttctacaat catattatag aggttgccgt   3780
tgataaggc                                                            3789

<210> SEQ ID NO 26
<211> LENGTH: 3789
<212> TYPE: DNA
<213> ORGANISM: Artificial Sequence
<220> FEATURE:
<223> OTHER INFORMATION: Synthetic Oligonucleotide

<400> SEQUENCE: 26
atgccaaaaa ataacaaaga agaagaagtt aaagaagtaa accttaattc agtacaagag     60
gacgcgttaa agtcctttac aactggttat ggtatcacac ctgatacaca aacagatgca    120
ggagcattaa gacgtgagtt cctagacgac caaatctcaa tgcttacttg dacagagaat    180
gatttaacat tctataaaga catcgctaaa aaaccagcta catctacagt agcaaaatac    240
gatgtataca tgcaacatgg taaggtaggt catactagat ttactcgtga gattggggta    300
gcaccagtaa gtgaccctaa catccgtcaa aaaacagtaa acatgaaatt tgcttccgat    360
actaaaaaca tcagtatcgc agcaggtcta gtaaacaaca ttcaagaccc aatgcaaatt    420
ttgactgacg atgctatcgt aaatattgct aaaacaattg agtgggcttc attctttgga    480
gattctgact tatcagatag cccagaacca caagcaggac tagaatttga cggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga ctttgttaac caacaacttt ctaaacaaac acaacttgtt    720
cgcgataacg gaaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900 aaaaaggac aatttagagc agaagattta gcagcacatg aatataaagt tgttgtaagt    960
tctgacgatg cagagtctat tgcaagtgaa gtggctacag ctacagttac tgcaaaagat   1020
gacggcgtta aactagaaat cgaattagct ccaatgtata gctctcgtcc acaattcgtt   1080
tcaatctata gaaaaggtgc agaaacaggt ttattctacc taatcgctcg tgtacctgct   1140
agcaaagcag agaacaacgt aatcactttc tacgacttaa acgactctat tcctgaaaca   1200
gtagacgtat tcgttggtga aatgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaagag gaggtaaata tatatggaag acgccaaaaa   1440
cataaagaaa ggcccggcgc cattctatcc tctagaggat ggaaccgctg gagagcaact   1500
gcataaggct atgaagagat acgccctggt tcctggaaca attgcttttta cagatgcaca   1560 tatcgaggtg aacatcacgt acgcggaata cttcgaaatg tccgttcggt tggcagaagc   1620
tatgaaacga tatgggctga atacaaatca cagaatcgtc gtatgcagtg aaaactctct   1680
tcaattcttt atgccggtgt tgggcgcgtt atttatcgga gttgcagttg cgcccgcgaa   1740
cgacatttat aatgaacgtg aattgctcaa cagtatgaac atttcgcagc ctaccgtagt   1800
gtttgtttcc aaaaaggggt tgcaaaaaat tttgaacgtg caaaaaaaat taccaataat   1860
ccagaaaatt attatcatgg attctaaaac ggattaccag ggatttcagt cgatgtacac   1920
```

| | |
|---|---|
| gttcgtcaca tctcatctac ctcccggttt taatgaatac gattttgtac cagagtcctt | 1980 |
| tgatcgtgac aaaacaattg cactgataat gaattcctct ggatctactg ggttacctaa | 2040 |
| gggtgtggcc cttccgcata gaactgcctg cgtcagattc tcgcatgcca gagatcctat | 2100 |
| ttttggcaat caaatcattc cggatactgc gattttaagt gttgttccat tccatcacgg | 2160 |
| ttttggaatg tttactacac tcggatattt gatatgtgga tttcgagtcg tcttaatgta | 2220 |
| tagatttgaa gaagagctgt ttttacgatc ccttcaggat tacaaaattc aaagtgcgtt | 2280 |
| gctagtacca accctatttt cattcttcgc caaaagcact ctgattgaca aatacgattt | 2340 |
| atctaattta cacgaaattg cttctggggg cgcacctctt tcgaagaag tcggggaagc | 2400 |
| ggttgcaaaa cgcttccatc ttccagggat acgacaagga tatgggctca ctgagactac | 2460 |
| atcagctatt ctgattacac ccgagggga tgataaaccg ggcgcggtcg gtaaagttgt | 2520 |
| tccattttt gaagcgaagg ttgtggatct ggataccggg aaaacgctgg gcgttaatca | 2580 |
| gagaggcgaa ttatgtgtca gaggacctat gattatgtcc ggttatgtaa caatccgga | 2640 |
| agcgaccaac gccttgattg acaaggatgg atggctacat tctggagaca tagcttactg | 2700 |
| ggacgaagac gaacacttct tcatagttga ccgcttgaag tctttaatta aatacaaagg | 2760 |
| atatcaggtg gcccccgctg aattggaatc gatattgtta caacacccca acatcttcga | 2820 |
| cgcgggcgtg gcaggtcttc ccgacgatga cgccggtgaa cttcccgccg ccgttgttgt | 2880 |
| tttgagcac ggaaagacga tgacggaaaa agagatcgtg gattacgtcg ccagtcaagt | 2940 |
| aacaaccgcg aaaaagttgc gcggaggagt tgtgtttgtg gacgaagtac cgaaaggtct | 3000 |
| taccggaaaa ctcgacgcaa gaaaaatcag agagatcctc ataaaggcca gaagggcgg | 3060 |
| aaagtccaaa ttgtaataat tataggataa ttgaataaaa acagtataga gagcagataa | 3120 |
| atactgctct ctattttact aataaggagg atttaaattg ctaaaaaata caaacttagc | 3180 |
| taattataaa aagtgaata cacggtttgg aaatcttagt tttgacgaca aggtatttc | 3240 |
| taatgactta acggaagaac agcaaaaaga attaggtaag cttcgaggat tcgaatatat | 3300 |
| taagacagaa cagaaaacaa agaagaacc taagaaagaa gaacctaaga agaagaacc | 3360 |
| taagaaagaa gaacctaaga agaagaacc taagaaagaa gaacctaaga agaaagtac | 3420 |
| agaaaatgaa ttagacagct tcttagctaa agagccttca atcaaagaat taaagaatt | 3480 |
| tgcgagtaaa aaaggcatta aaattgaaaa aactaagaaa aatgatataa ttgaagaact | 3540 |
| aaagagaggg taatgtataa tgtatggagg ttatgaagga caagattctt acgaatacc | 3600 |
| ttactcacat gggaacccta agcatgtaga gccagaaaaa gttgacgaat atgttctttc | 3660 |
| tgattatggt tggactgcgg aaacaattaa agcatacatg tatggtgttc gtgtagtaga | 3720 |
| ccctgaaaca ggagaggaaa tgggagacac cttctacaat catattatag aggttgccgt | 3780 |
| tgataaggc | 3789 |

<210> SEQ ID NO 27
<211> LENGTH: 3729
<212> TYPE: DNA
<213> ORGANISM: Artificial Sequence
<220> FEATURE:
<223> OTHER INFORMATION: Synthetic Oligonucleotide

<400> SEQUENCE: 27

| | |
|---|---|
| atgccaaaaa ataacaaaga agaagaagtt aaagaagtaa accttaattc agtacaagag | 60 |
| gacgcgttaa agtcctttac aactggttat ggtatcacac tgatacaca aacagatgca | 120 |
| ggagcattaa gacgtgagtt cctagacgac caaatctcaa tgcttacttg gacagagaat | 180 |

```
gatttaacat tctataaaga catcgctaaa aaaccagcta catctacagt agcaaaatac    240
gatgtataca tgcaacatgg taaggtaggt catactagat ttactcgtga gattggggta    300
gcaccagtaa gtgaccctaa catccgtcaa aaaacagtaa acatgaaatt tgcttccgat    360
actaaaaaca tcagtatcgc agcaggtcta gtaaacaaca ttcaagaccc aatgcaaatt    420
ttgactgacg atgctatcgt aaatattgct aaaacaattg agtgggcttc attctttgga    480
gattctgact tatcagatag cccagaacca caagcaggac tagaatttga cggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga ctttgttaac caacaacttt ctaaacaaac acaacttgtt    720
cgtgataacg aaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900
aaaaaaggac aatttagagc agaagattta gcagcacatg aatataaagt tgttgtaagt    960
tctgacgatg cagagtctat tgcaagtgaa gtggctacag ctacagttac tgcaaaagat   1020
gacggcgtta aactagaaat cgaattagct ccaatgtata gctctcgtcc acaattcgtt   1080
tcaatctata gaaaaggtgc agaaacaggt ttattctacc taatcgctcg tgtacctgct   1140
agcaaagcag agaacaacgt aatcactttc tacgacttaa acgactctat tcctgaaaca   1200
gtagacgtat tcgttggtga aatgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaagag gaggtaaata tatatggaag acgccaaaaa   1440
cataaagaaa ggcccggcgc cattctatcc tctagaggat ggaaccgctg gagagcaact   1500
gcataaggct atgaagagat acgccctggt tcctggaaca attgctttta cagatgcaca   1560
tatcgaggtg aacatcacgt acgcggaata cttcgaaatg tccgttcggt tggcagaagc   1620
tatgaaacga tatgggctga atacaaatca cagaatcgtc gtatgcagtg aaaactctct   1680
tcaattcttt atgccggtgt tgggcgcgtt atttatcgga gttgcagttg cgcccgcgaa   1740
cgacatttat aatgaacgtg aattgctcaa cagtatgaac atttcgcagc ctaccgtagt   1800
gtttgtttcc aaaaaggggt tgcaaaaaat tttgaacgtg caaaaaaaat taccaataat   1860
ccagaaaatt attatcatgg attctaaaac ggattaccag ggatttcagt cgatgtacac   1920
gttcgtcaca tctcatctac ctcccggttt taatgaatac gattttgtac cagagtcctt   1980
tgatcgtgac aaaacaattg cactgataat gaattcctct ggatctactg ggttacctaa   2040
gggtgtggcc cttccgcata gaactgcctg cgtcagattc tcgcatgcca gagatcctat   2100
ttttggcaat caaatcattc cggatactgc gattttaagt gttgttccat tccatcacgg   2160
ttttggaatg tttactacac tcggatattt gatatgtgga tttcgagtcg tcttaatgta   2220
tagatttgaa gaagagctgt ttttacgatc ccttcaggat tacaaaattc aaagtgcgtt   2280
gctagtacca accctatttt cattcttcgc caaaagcact ctgattgaca atacgattt    2340 atctaatttta cacgaaattg cttctggggg cgcacctctt tcgaaagaag tcggggaagc   2400
ggttgcaaaa cgcttccatc ttccagggat acgacaagga tatgggctca ctgagactac   2460
atcagctatt ctgattacac ccgaggggga tgataaaccg ggcgcggtcg gtaaagttgt   2520
```

```
tccattttttt gaagcgaagg ttgtggatct ggataccggg aaaacgctgg gcgttaatca    2580
gagaggcgaa ttatgtgtca gaggacctat gattatgtcc ggttatgtaa acaatccgga    2640
agcgaccaac gccttgattg acaaggatgg atggctacat tctggagaca tagcttactg    2700
ggacgaagac gaacacttct tcatagttga ccgcttgaag tctttaatta aatacaaagg    2760
atatcaggtg gcccccgctg aattggaatc gatattgtta caacaccca  acatcttcga    2820 cgcgggcgtg gcaggtcttc ccgacgatga cgccggtgaa cttccagccg ccgttgttgt    2880
tttggagcac ggaaagacga tgacggaaaa agagatcgtg gattacgtcg ccagtcaagt    2940
aacaaccgcg aaaaagttgc gcggaggagt tgtgtttgtg gacgaagtac cgaaaggtct    3000
taccggaaaa ctcgacgcaa gaaaaatcag agagatcctc ataaaggcca agaagggcgg    3060
aaagtccaaa ttgtaataat tataggataa ttgaataaaa acagtataga gagcagataa    3120
atactgctct ctattttact aataaggagg atttaaattg ctaaaaata  caaacttagc    3180 taattataaa aaagtgaata cacggtttgg aaatcttagt tttgacgaca aaggtatttc    3240
taatgactta acgaagaac  agcaaaaaga attaggtaag cttcgaggat tcgaatatat    3300
taagacagaa cagaaaacaa aagaagaacc taagaaagaa gaacctaaga agaaagtac    3360 agaaaatgaa ttagacagct tcttagctaa agagccttca atcaaagaat taaagaatt    3420 tgcgagtaaa aaaggcatta aaattgaaaa aactaagaaa aatgatataa ttgaagaact    3480
aaagagaggg taatgtataa tgtatggagg ttatgaagga caagattctt acgaataccc    3540
ttactcacat gggaacccta agcatgtaga gccagaaaaa gttgacgaat atgttctttc    3600
tgattatggt tggactgcgg aaacaattaa agcatacatg tatggtgttc gtgtagtaga    3660
ccctgaaaca ggagaggaaa tgggagacac cttctacaat catattatag aggttgccgt    3720
tgataaggc                                                            3729

<210> SEQ ID NO 28
<211> LENGTH: 3786
<212> TYPE: DNA
<213> ORGANISM: Artificial Sequence
<220> FEATURE:
<223> OTHER INFORMATION: Synthetic Oligonucleotide

<400> SEQUENCE: 28
atgccaaaaa ataacaaaga agaagttaaa gaagtaaacc ttaattcagt acaagaggat      60
gcgttaaagt cctttacgac tggttatggt atcacacctg atacacaaac agatgcagga     120
gcattaagac gtgagttcct agacgaccaa atctcaatgc ttacttggac agagaatgat     180
ttaacattct ataaagacat cgctaaaaaa ccagctacat ctacagtagc aaaatacgat     240
gtatacatgc aacatggtaa ggtaggtcat actagattta ctcgtgagat tggggtagca     300
ccagtaagtg accctaacat ccgtcaaaaa acagtaaata tgaaatttgc ttccgatact     360
aaaaacatca gtatcgcagc aggtctagta acaacattc  aagacccaat gcaaattttg     420
actgacgatg ctatcgtaaa tattgctaaa acaattgagt gggcttcatt cttttggagat    480 tctgacttat cagatagccc agaaccacaa gcaggactag aatttgacgg cttggctaaa     540
cttattaacc aagataacgt tcatgatgct cgtggagcta gcttgactga aagcttgtta     600
aaccaagcag cagtaatgat tagtaaaggt tatggtacac ctacagatgc ttacatgcca     660
gtaggggttc aagcagactt tgttaaccaa caactttcta aacaaacaca acttgttcgc     720
gataacggaa acaacgtaag cgttggtttc aacatccaag gtttccattc agctcgtgga     780
tttatcaaac ttcacggttc tacagtaatg gaaaacgaac aaatcttaga tgaacgtatt     840
```

```
cttgctttac caacagctcc acaaccagct aaggtaactg caacacaaga agcaggtaaa      900
aaaggacaat ttagagcaga agatttagca gcacatgaat ataaagttgt tgtaagttct      960
gacgatgcag agtctattgc aagtgaagtg gctacagcta cagttactgc aaaagatgac     1020
ggcgttaaac tagaaatcga attagctcca atgtatagct ctcgtccaca attcgtttca     1080
atctatagaa aaggtgcaga aacaggttta ttctacctaa tcgctcgtgt acctgctagc     1140
aaagcagaga acaacgtaat cactttctac gacttaaacg actctattcc tgaaacagta     1200
gacgtattcg ttggtgaaat gtcggctaac gtagtacact tgtttgaatt actaccaatg     1260
atgagattac ctctagctca aattaacgca tctgttacat ttgcagtttt atggtatggc     1320
gcattagctc taagagcacc taagaaatgg gtacgtatta gaaacgttaa atatattcct     1380
gtaaaaaacg ttcatagcaa ctaagaggag gtaaatatat atggaagacg ccaaaaacat     1440
aaagaaaggc ccggcgccat tctatcctct agaggatgga accgctggag agcaactgca     1500
taaggctatg aagagatacg ccctggttcc tggaacaatt gcttttacag atgcacatat     1560
cgaggtgaac atcacgtacg cggaatactt cgaaatgtcc gttcggttgg cagaagctat     1620
gaaacgatat gggctgaata caaatcacag aatcgtcgta tgcagtgaaa actctcttca     1680
attctttatg ccggtgttgg gcgcgttatt tatcggagtt gcagttgcgc ccgcgaacga     1740
catttataat gaacgtgaat tgctcaacag tatgaacatt tcgcagccta ccgtagtgtt     1800
tgtttccaaa aaggggttgc aaaaaatttt gaacgtgcaa aaaaaattac caataatcca     1860
gaaaattatt atcatggatt ctaaaacgga ttaccaggga tttcagtcga tgtacacgtt     1920
cgtcacatct catctacctc ccggttttaa tgaatacgat tttgtaccag agtcctttga     1980
tcgtgacaaa acaattgcac tgataatgaa ttcctctgga tctactgggt tacctaaggg     2040
tgtggccctt ccgcatagaa ctgcctgcgt cagattctcg catgccagag atcctatttt     2100
tggcaatcaa atcattccgg atactgcgat tttaagtgtt gttccattcc atcacggttt     2160
tggaatgttt actacactcg gatatttgat atgtggattt cgagtcgtct taatgtatag     2220
atttgaagaa gagctgtttt tacgatccct tcaggattac aaaattcaaa gtgcgttgct     2280
agtaccaacc ctattttcat tcttcgccaa aagcactctg attgacaaat acgatttatc     2340
taatttacac gaaattgctt ctgggggcgc acctctttcg aaagaagtcg ggaagcggt      2400
tgcaaaacgc ttccatcttc cagggatacg acaaggatat gggctcactg agactacatc     2460
agctattctg attacacccg agggggatga taaaccgggc gcggtcggta agttgttcc      2520
attttttgaa gcgaaggttg tggatctgga taccgggaaa acgctgggcg ttaatcagag     2580
aggcgaatta tgtgtcagag gacctatgat tatgtccggt tatgtaaaca atccggaagc     2640
gaccaacgcc ttgattgaca aggatggatg gctacattct ggagacatag cttactggga     2700
cgaagacgaa cacttcttca tagttgaccg cttgaagtct ttaattaaat acaaaggata     2760
tcaggtggcc cccgctgaat tggaatcgat attgttacaa cacccccaaca tcttcgacgc     2820
gggcgtggca ggtcttcccg acgatgacgc cggtgaactt cccgccgccg ttgttgtttt     2880
ggagcacgga aagacgatga cggaaaaaga tcgtggat tacgtcgcca gtcaagtaac      2940
aaccgcgaaa aagttgcgcg gaggagttgt gtttgtggac gaagtaccga aaggtcttac     3000
cggaaaactc gacgcaagaa aaatcagaga gatcctcata aaggccaaga agggcggaaa     3060
gtccaaattg taataattat aggataattg aataaaaaca gtatagagag cagataaata     3120
ctgctctcta ttttactaat aaggaggatt taaattgcta aaaaatacaa acttagctaa     3180
```

| | |
|---|---|
| ttataaaaaa gtgaatacac ggtttggaaa tcttagtttt gacgacaaag gtatttctaa | 3240 |
| tgacttaacg gaagaacagc aaaaagaatt aggtaagctt cgaggattcg aatatattaa | 3300 |
| gacagaacag aaaacaaaag aagaacctaa gaaagaagaa cctaagaaag aagaacctaa | 3360 |
| gaaagaagaa cctaagaaag aagaacctaa gaaagaagaa cctaagaaag aaagtacaga | 3420 |
| aaatgaatta gacagcttct tagctaaaga gccttcaatc aaagaattaa aagaatttgc | 3480 |
| gagtaaaaaa ggcattaaaa ttgaaaaaac taagaaaaat gatataattg aagaactaaa | 3540 |
| gagagggtaa tgtataatgt atggaggtta tgaaggacaa gattcttacg aatacccttta | 3600 |
| ctcacatggg aaccctaagc atgtagagcc agaaaaagtt gacgaatatg ttctttctga | 3660 |
| ttatggttgg actgcggaaa caattaaagc atacatgtat ggtgttcgtg tagtagaccc | 3720 |
| tgaaacagga gaggaaatgg gagacacctt ctacaatcat attatagagg ttgccgttga | 3780 |
| taaggc | 3786 |

<210> SEQ ID NO 29
<211> LENGTH: 3786
<212> TYPE: DNA
<213> ORGANISM: Artificial Sequence
<220> FEATURE:
<223> OTHER INFORMATION: Synthetic Oligonucleotide

<400> SEQUENCE: 29

| | |
|---|---|
| atgccaaaaa ataacaaaga agaagttaaa gaagtaaacc ttaattcagt acaagaggat | 60 |
| gcgttaaagt cctttacgac tggttatggt atcacacctg atacacaaac agatgcagga | 120 |
| gcattaagac gtgagttcct agacgaccaa atctcaatgc ttacttggac agagaatgat | 180 |
| ttaacattct ataaagacat cgctaaaaaa ccagctacat ctacagtagc aaaatacgat | 240 |
| gtatacatgc aacatggtaa ggtaggtcat actagattta ctcgtgagat tggggtagca | 300 |
| ccagtaagtg accctaacat ccgtcaaaaa acagtaaata tgaaatttgc ttccgatact | 360 |
| aaaaacatca gtatcgcagc aggtctagta acaacattc aagacccaat gcaaattttg | 420 |
| actgacgatg ctatcgtaaa tattgctaaa acaattgagt gggcttcatt ctttggagat | 480 |
| tctgacttat cagatagccc agaaccacaa gcaggactag aatttgacgg cttggctaaa | 540 |
| cttattaacc aagataacgt tcatgatgct cgtggagcta gcttgactga agcttgtta | 600 |
| aaccaagcag cagtaatgat tagtaaaggt tatggtacac ctacagatgc ttacatgcca | 660 |
| gtaggggttc aagcagactt tgttaaccaa caactttcta acaaacaca acttgttcgc | 720 |
| gataacggaa acaacgtaag cgttggtttc aacatccaag gtttccattc agctcgtgga | 780 |
| tttatcaaac ttcacggttc tacagtaatg gaaaacgaac aaatcttaga tgaacgtatt | 840 |
| cttgctttac caacagctcc acaaccagct aaggtaactg caacacaaga agcaggtaaa | 900 |
| aaaggacaat ttagagcaga agatttagca gcacatgaat ataagttgt tgtaagttct | 960 |
| gacgatgcag agtctattgc aagtgaagtg gctacagcta cagttactgc aaaagatgac | 1020 |
| ggcgttaaac tagaaatcga attagctcca atgtatagct ctcgtccaca attcgtttca | 1080 |
| atctatagaa aaggtgcaga acaggtttta ttctacctaa tcgctcgtgt acctgctagc | 1140 |
| aaagcagaga caacgtaat cactttctac gacttaaacg actctattcc tgaaacagta | 1200 |
| gacgtattcg ttggtgaaat gtcggctaac gtagtacact tgtttgaatt actaccaatg | 1260 |
| atgagattac ctctagctca aattaacgca tctgttacat ttgcagtttt atggtatggc | 1320 |
| gcattagctc taagagcacc taagaaatgg gtacgtatta gaaacgttaa atatattcct | 1380 |
| gtaaaaaacg ttcatagcaa ctaagaggag gtaaatatat atggaagacg ccaaaaacat | 1440 |

```
aaagaaaggc cggcgccat tctatcctct agaggatgga accgctggag agcaactgca    1500
taaggctatg aagagatacg ccctggttcc tggaacaatt gcttttacag atgcacatat    1560
cgaggtgaac atcacgtacg cggaatactt cgaaatgtcc gttcggttgg cagaagctat    1620
gaaacgatat gggctgaata caaatcacag aatcgtcgta tgcagtgaaa actctcttca    1680
attctttatg ccggtgttgg gcgcgttatt tatcggagtt gcagttgcgc ccgcgaacga    1740
catttataat gaacgtgaat tgctcaacag tatgaacatt tcgcagccta ccgtagtgtt    1800
tgtttccaaa aaggggttgc aaaaaatttt gaacgtgcaa aaaaaattac caataatcca    1860
gaaaattatt atcatggatt ctaaaacgga ttaccaggga tttcagtcga tgtacacgtt    1920
cgtcacatct catctacctc ccggttttaa tgaatacgat tttgtaccag agtcctttga    1980
tcgtgacaaa acaattgcac tgataatgaa ttcctctgga tctactgggt tacctaaggg    2040
tgtggccctt ccgcatagaa ctgcctgcgt cagattctcg catgccagag atcctatttt    2100
tggcaatcaa atcattccgg atactgcgat tttaagtgtt gttccattcc atcacggttt    2160
tggaatgttt actacactcg atatttgat atgtggattt cgagtcgtct taatgtatag    2220
atttgaagaa gagctgtttt tacgatccct tcaggattac aaaattcaaa gtgcgttgct    2280
agtaccaacc ctattttcat tcttcgccaa aagcactctg attgacaaat acgatttatc    2340
taatttacac gaaattgctt ctgggggcgc acctctttcg aaagaagtcg gggaagcggt    2400
tgcaaaacgc ttccatcttc cagggatacg acaaggatat gggctcactg agactacatc    2460
agctattctg attacacccg agggggatga taaaccgggc gcggtcggta agttgttcc    2520 atttttgaa gcgaaggttg tggatctgga taccgggaaa acgctgggcg ttaatcagag    2580
aggcgaatta tgtgtcagag gacctatgat tatgtccggt tatgtaaaca atccggaagc    2640
gaccaacgcc ttgattgaca aggatggatg gctacattct ggagacatag cttactggga    2700
cgaagacgaa cacttcttca tagttgaccg cttgaagtct ttaattaaat acaaaggata    2760
tcaggtggcc cccgctgaat tggaatcgat attgttacaa cacccaaca tcttcgacgc    2820 gggcgtggca ggtcttcccg acgatgacgc cggtgaactt cccgccgccg ttgttgtttt    2880
ggagcacgga aagacgatga cggaaaaaga gatcgtggat tacgtcgcca gtcaagtaac    2940
aaccgcgaaa aagttgcgcg gaggagttgt gtttgtggac gaagtaccga aaggtcttac    3000
cggaaaactc gacgcaagaa aaatcagaga gatcctcata aaggccaaga agggcggaaa    3060
gtccaaattg taataattat aggataattg aataaaaaca gtatagagag cagataaata    3120
ctgctctcta ttttactaat aaggaggatt taaattgcta aaaatacaa acttagctaa    3180 ttataaaaaa gtgaatacac ggtttggaaa tcttagtttt gacgacaaag gtatttctaa    3240
tgacttaacg gaagaacagc aaaaagaatt aggtaagctt cgaggattcg aatatattaa    3300
gacagaacag aaaacaaaag aagaacctaa gaaagaagaa cctaagaaag aagaacctaa    3360
gaaagaagaa cctaagaaag aagaacctaa gaaagaagaa cctaagaaag aagtacaga    3420 aaatgaatta gacagcttct tagctaaaga gccttcaatc aaagaattaa agaatttgc    3480 gagtaaaaaa ggcattaaaa ttgaaaaaac taagaaaaat gatataattg aagaactaaa    3540
gagagggtaa tgtataatgt atggaggtta tgaaggacaa gattcttacg aatacccta    3600 ctcacatggg aaccctaagc atgtagagcc agaaaaagtt gacgaatatg ttctttctga    3660
ttatggttgg actgcggaaa caattaaagc atacatgtat ggtgttcgtg tagtagaccc    3720
tgaaacagga gaggaaatgg gagacacctt ctacaatcat attatagagg ttgccgttga    3780
``` taaggc 3786

<210> SEQ ID NO 30
<211> LENGTH: 3729
<212> TYPE: DNA
<213> ORGANISM: Artificial Sequence
<220> FEATURE:
<223> OTHER INFORMATION: Synthetic Oligonucleotide

<400> SEQUENCE: 30

```
atgccaaaaa ataacaaaga agaagaagtt aaagaagtaa accttaattc agtacaagag      60
gacgcgttaa agtcctttac aactggttat ggtatcacac ctgatacaca aacagatgca     120
ggagcattaa gacgtgagtt cctagacgac caaatctcaa tgcttacttg gacagagaat     180
gatttaacat tctataaaga catcgctaaa aaaccagcta catctacagt agcaaaatac     240
gatgtataca tgcaacatgg taaggtaggt catactagat ttactcgtga gattggggta     300
gcaccagtaa gtgaccctaa catccgtcaa aaaacagtaa atatgaaatt tgcttccgat     360
actaaaaaca tcagtatcgc agcaggtcta gtaaacaaca ttcaagaccc aatgcaaatt     420
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaagcttg     600
ttaaaccaag cagcagtaat gattagtaaa ggttatggta cacctacaga tgcttacatg     660
ccagtagggg ttcaagcaga ctttgttaac caacaacttt ctaaacaaac acagcttgtt     720
cgtgataacg aaacaacgt aagcgttggt ttcaacatcc aaggtttcca ttcagctcgt     780
ggatttatca aacttcacgg ttctacagta atggaaaacg aacaaatctt agatgaacgt     840
attcttgctt taccaacagc tccacaacca gctaaggtaa ctgcaacaca agaagcaggt     900
aaaaaggac aatttagagc agaagactta gcagcacacg aatacaaagt tgttgtaagt     960
tctgacgatg cagagtctat tgcaagtgaa gtggctacag ctacagttac tgcaaaagat    1020
gacggcgtta aactagaaat cgagttagct ccaatgtaca gctcccgtcc acaattcgtt    1080
tcaatctata gaaaggtgc agaaacaggt ttattctacc taatcgctcg tgtacctgct    1140
agcaaagcag agaacaacgt aatcactttc tatgacttaa acgactctat tcctgaaaca    1200
gtagacgtat tcgttggtga aatgtctgct aacgtagtac acttgtttga attactacca    1260
atgatgagat tacctctagc tcaaattaac gcatctgtta catttgcagt tttatggtat    1320
ggagcattag ctctaagagc acctaagaaa tgggtacgta ttagaaacgt taaatatatt    1380
cctgtaaaaa acgttcatag caactaagag gaggtaaata tatatggaag acgccaaaaa    1440
cataagaaa ggcccggcgc cattctatcc tctagaggat ggaaccgctg gagagcaact    1500
gcataaggct atgaagagat acgccctggt tcctggaaca attgctttta cagatgcaca    1560
tatcgaggtg aacatcacgt acgcggaata cttcgaaatg tccgttcggt tggcagaagc    1620
tatgaaacga tatgggctga atacaaatca cagaatcgtc gtatgcagtg aaaactctct    1680
tcaattcttt atgccggtgt tgggcgcgtt atttatcgga gttgcagttg cgcccgcgaa    1740
cgacatttat aatgaacgtg aattgctcaa cagtatgaac atttcgcagc ctaccgtagt    1800
gtttgtttcc aaaaagggt tgcaaaaat tttgaacgtg caaaaaaat taccaataat    1860
ccagaaaatt attatcatgg attctaaaac ggattaccag ggatttcagt cgatgtacac    1920
gttcgtcaca tctcatctac ctcccggttt taatgaatac gattttgtac cagagtcctt    1980
tgatcgtgac aaaacaattg cactgataat gaattcctct ggatctactg ggttacctaa    2040
```

```
gggtgtggcc cttccgcata gaactgcctg cgtcagattc tcgcatgcca gagatcctat    2100
ttttggcaat caaatcattc cggatactgc gattttaagt gttgttccat tccatcacgg    2160
ttttggaatg tttactacac tcggatattt gatatgtgga tttcgagtcg tcttaatgta    2220
tagatttgaa gaagagctgt ttttacgatc ccttcaggat tacaaaattc aaagtgcgtt    2280
gctagtacca accctatttt cattcttcgc caaaagcact ctgattgaca aatacgattt    2340
atctaattta cacgaaattg cttctggggg cgcacctctt tcgaaagaag tcggggaagc    2400
ggttgcaaaa cgcttccatc ttccagggat acgacaagga tatgggctca ctgagactac    2460
atcagctatt ctgattacac ccgaggggga tgataaaccg ggcgcggtcg gtaaagttgt    2520
tccatttttt gaagcgaagg ttgtggatct ggataccggg aaaacgctgg gcgttaatca    2580
gagaggcgaa ttatgtgtca gaggacctat gattatgtcc ggttatgtaa caatccgga    2640 agcgaccaac gccttgattg acaaggatgg atggctacat tctggagaca tagcttactg    2700
ggacgaagac gaacacttct tcatagttga ccgcttgaag tctttaatta aatacaaagg    2760
atatcaggtg gcccccgctg aattggaatc gatattgtta caacacccca acatcttcga    2820
cgcgggcgtg gcaggtcttc ccgacgatga cgccggtgaa cttcccgccg ccgttgttgt    2880
tttggagcac ggaaagacga tgacggaaaa agagatcgtg gattacgtcg ccagtcaagt    2940
aacaaccgcg aaaagttgc gcggaggagt tgtgtttgtg gacgaagtac cgaaaggtct    3000
taccggaaaa ctcgacgcaa gaaaaatcag agagatcctc ataaaggcca gaagggcgg    3060 aaagtccaaa ttgtaataat tataggataa ttgaataaaa acagtataga gagcagataa    3120
atactgctct ctattttact aataaggagg atttaaattg ctaaaaaata caaacttagc    3180
taattataaa aaagtgaata cacgatttgg aaatcttagt tttgatgata aaggtatttc    3240
taatgaccta acggaagagc agcaaaaaga attaggtaag cttagaggat tcgaatatat    3300
taagacagaa cagaaaacga aagaagaacc taagaaagaa gaacctaaga agaaagtac    3360 agaaaatgaa ttagacagct tcttagctaa agaaccttca atcaaagaat taaagaatt    3420 tgcgagtaaa aaaggcatta aaattgaaaa aactaagaaa aatgatataa ttgaagaact    3480
aaagagaggg taatgtacaa tgtatggagg ttatgaagga caagattctt acgaataccc    3540
ttactcacac gggaacccta agcatgtaga gccagaaaaa gttgacgaat atgttctttc    3600
tgattatggc tggactgcgg aaacaattaa agcatacatg tatggtgttc gtgtagtaga    3660
ccctgaaaca ggagaggaaa tgggagacac cttctacaat catattatag aggttgccgt    3720
tgataaggc                                                           3729
```

<210> SEQ ID NO 31
<211> LENGTH: 2658
<212> TYPE: DNA
<213> ORGANISM: Artificial Sequence
<220> FEATURE:
<223> OTHER INFORMATION: Synthetic Oligonucleotide

<400> SEQUENCE: 31

```
atgccaaaaa ataacaaaga agaagaagtt aaagaagtaa accttaattc agtacaagag     60
gacgcgttaa agtcctttac aactggttat ggtatcacac ctgatacaca aacagatgca    120
ggagcattaa gacgtgagtt cctagacgac caaatctcaa tgcttacttg gacagagaat    180
gatttaacat tctataaaga catcgctaaa aaaccagcta catctacagt agcaaaatac    240
gatgtataca tgcaacatgg taaggtaggt catactagat ttactcgtga gattggggta    300
```

```
gcaccagtaa gtgaccctaa catccgtcaa aaaacagtaa acatgaaatt tgcttccgat    360
actaaaaaca tcagtatcgc agcaggtcta gtaaacaaca ttcaagaccc aatgcaaatt    420
ttgactgacg atgctatcgt aaatattgct aaaacaattg agtgggcttc attctttgga    480
gattctgact tatcagatag cccagaacca caagcaggac tagaatttga cggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga ctttgttaac caacaacttt ctaaacaaac acaacttgtt    720
cgcgataacg aaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900
aaaaaggac aatttagagc agaagattta gcagcacatg aatataaagt tgttgtaagt    960
tctgacgatg cagagtctat tgcaagtgaa gtggctacag ctacagttac tgcaaaagat   1020
gacggcgtta aactagaaat cgaattagct ccaatgtata gctctcgtcc acaattcgtt   1080
tcaatctata gaaaggtgc agaaacaggt ttattctacc taatcgctcg tgtacctgct   1140
agcaaagcag agaacaacgt aatcactttc tacgacttaa acgactctat tcctgaaaca   1200
gtagacgtat tcgttggtga atgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaataa taagaggagg taaatatata tggtcttcac   1440
actcgaagat ttcgttgggg actggcgaca gacagccggc tacaacctgg accaagtcct   1500
tgaacaggga ggtgtgtcca gtttgtttca gaatctcggg gtgtccgtaa ctccgatcca   1560
aaggattgtc ctgagcggtg aaaatgggct gaagatcgac atccatgtca tcatcccgta   1620
tgaaggtctg agcggcgacc aaatgggcca gatcgaaaaa attttttaagg tggtgtaccc   1680
tgtggatgat catcactta aggtgatcct gcactatggc acactggtaa tcgacggggt   1740
tacgccgaac atgatcgact atttcggacg gccgtatgaa ggcatcgccg tgttcgacgg   1800
caaaaagatc actgtaacag ggaccctgtg aacggcaac aaaattatcg acgagcgcct   1860
gatcaacccc gacggctccc tgctgttccg agtaaccatc aacggagtga ccggctggcg   1920
gctgtgcgaa cgcattctgg cgtaataatt ataggataat tgaataaaaa cagtatagag   1980
agcagataaa tactgctctc tattttacta ataaggagga tttaaattgc taaaaaatac   2040
aaacttagct aattataaaa aagtgaatac acggtttgga aatcttagtt ttgacgacaa   2100
aggtatttct aatgacttaa cggaagaaca gcaaaaagaa ttaggtaagc ttcgaggatt   2160
cgaatatatt aagacagaac agaaaacaaa agaagaacct aagaaagaag aacctaagaa   2220
agaagaacct aagaaagaag aacctaagaa agaagaacct aagaaagaag aacctaagaa   2280
agaaagtaca gaaaatgaat tagacagctt cttagctaaa gagccttcaa tcaaagaatt   2340
aaaagaattt gcgagtaaaa aaggcattaa aattgaaaaa actaagaaaa atgatataat   2400
tgaagaacta aagagagggt aatgtataat gtatggaggt tatgaaggac aagattctta   2460
cgaataccct tactcacatg gaaccctaa gcatgtagag ccagaaaaag ttgacgaata   2520
tgttctttct gattatggtt ggactgcgga acaattaaaa gcatacatgt atggtgttcg   2580
tgtagtagac cctgaaacag gagaggaaat gggagacacc ttctacaatc atattataga   2640
ggttgccgtt gataaggc                                                 2658
```

<210> SEQ ID NO 32
<211> LENGTH: 2598
<212> TYPE: DNA
<213> ORGANISM: Artificial Sequence
<220> FEATURE:
<223> OTHER INFORMATION: Synthetic Oligonucleotide

<400> SEQUENCE: 32

| | | | | | |
|---|---|---|---|---|---|
| atgccaaaaa | ataacaaaga | agaagaagtt | aaagaagtaa | accttaattc | agtacaagag | 60 |
| gacgcgttaa | agtcctttac | aactggttat | ggtatcacac | ctgatacaca | aacagatgca | 120 |
| ggagcattaa | gacgtgagtt | cctagacgac | caaatctcaa | tgcttacttg | dacagagaat | 180 |
| gatttaacat | tctataaaga | catcgctaaa | aaaccagcta | catctacagt | agcaaaatac | 240 |
| gatgtataca | tgcaacatgg | taaggtaggt | catactagat | ttactcgtga | gattggggta | 300 |
| gcaccagtaa | gtgaccctaa | catccgtcaa | aaaacagtaa | acatgaaatt | tgcttccgat | 360 |
| actaaaaaca | tcagtatcgc | agcaggtcta | gtaaacaaca | ttcaagaccc | aatgcaaatt | 420 |
| ttgactgacg | atgctatcgt | aaatattgct | aaaacaattg | agtgggcttc | attctttgga | 480 |
| gattctgact | tatcagatag | cccagaacca | caagcaggac | tagaatttga | cggcttggct | 540 |
| aaacttatta | accaagataa | cgttcatgat | gctcgtggag | ctagcttgac | tgaaagcttg | 600 |
| ttaaaccaag | cagcagtaat | gattagtaaa | ggttatggta | cacctacaga | tgcttacatg | 660 |
| ccagtagggg | ttcaagcaga | cttgtttaac | caacaacttt | ctaaacaaac | acaacttgtt | 720 |
| cgtgataacg | aaacaacgt | aagcgttggt | ttcaacatcc | aaggtttcca | ttcagctcgt | 780 |
| ggatttatca | aacttcacgg | ttctacagta | atggaaaacg | aacaaatctt | agatgaacgt | 840 |
| attcttgctt | taccaacagc | tccacaacca | gctaaggtaa | ctgcaacaca | agaagcaggt | 900 |
| aaaaaaggac | aatttagagc | agaagattta | gcagcacatg | aatataaagt | tgttgtaagt | 960 |
| tctgacgatg | cagagtctat | tgcaagtgaa | gtggctacag | ctacagttac | tgcaaaagat | 1020 |
| gacggcgtta | aactagaaat | cgaattagct | ccaatgtata | gctctcgtcc | acaattcgtt | 1080 |
| tcaatctata | gaaaggtgc | agaaacaggt | ttattctacc | taatcgctcg | tgtacctgct | 1140 |
| agcaaagcag | agaacaacgt | aatcactttc | tacgacttaa | cgactctat | tcctgaaaca | 1200 |
| gtagacgtat | tcgttggtga | aatgtcggct | aacgtagtac | acttgtttga | attactacca | 1260 |
| atgatgagat | tacctctagc | tcaaattaac | gcatctgtta | catttgcagt | tttatggtat | 1320 |
| ggcgcattag | ctctaagagc | acctaagaaa | tgggtacgta | ttagaaacgt | taaatatatt | 1380 |
| cctgtaaaaa | acgttcatag | caactaataa | taagaggagg | taaatatata | tggtcttcac | 1440 |
| actcgaagat | ttcgttgggg | actggcgaca | gacagccggc | tacaacctgg | accaagtcct | 1500 |
| tgaacaggga | ggtgtgtcca | gtttgtttca | gaatctcggg | gtgtccgtaa | ctccgatcca | 1560 |
| aaggattgtc | ctgagcggtg | aaaatgggct | gaagatcgac | atccatgtca | tcatcccgta | 1620 |
| tgaaggtctg | agcggcgacc | aaatgggcca | gatcgaaaaa | attttttaagg | tggtgtaccc | 1680 |
| tgtggatgat | catcactta | aggtgatcct | gcactatggc | acactggtaa | tcgacggggt | 1740 |
| tacgccgaac | atgatcgact | atttcggacg | gccgtatgaa | ggcatcgccg | tgttcgacgg | 1800 |
| caaaagatc | actgtaacag | ggaccctgtg | aacggcaac | aaaattatcg | acgagcgcct | 1860 |
| gatcaaccc | gacggctccc | tgctgttccg | agtaaccatc | aacggagtga | ccggctggcg | 1920 |
| gctgtgcgaa | cgcattctgg | cgtaataatt | ataggataat | tgaataaaaa | cagtatagag | 1980 |
| agcagataaa | tactgctctc | tatttttacta | ataaggagga | tttaaattgc | taaaaaatac | 2040 |

```
aaacttagct aattataaaa aagtgaatac acggtttgga aatcttagtt ttgacgacaa    2100
aggtatttct aatgacttaa cggaagaaca gcaaaaagaa ttaggtaagc ttcgaggatt    2160
cgaatatatt aagacagaac agaaaacaaa agaagaacct aagaaagaag aacctaagaa    2220
agaaagtaca gaaaatgaat tagacagctt cttagctaaa gagccttcaa tcaaagaatt    2280
aaaagaattt gcgagtaaaa aaggcattaa aattgaaaaa actaagaaaa atgatataat    2340
tgaagaacta aagagagggt aatgtataat gtatggaggt tatgaaggac aagattctta    2400 cgaatacccct tactcacatg ggaaccctaa gcatgtagag ccagaaaaag ttgacgaata    2460
tgttctttct gattatggtt ggactgcgga aacaattaaa gcatacatgt atggtgttcg    2520
tgtagtagac cctgaaacag gagaggaaat gggagacacc ttctacaatc atattataga    2580
ggttgccgtt gataaggc                                                 2598

<210> SEQ ID NO 33
<211> LENGTH: 2649
<212> TYPE: DNA
<213> ORGANISM: Artificial Sequence
<220> FEATURE:
<223> OTHER INFORMATION: Synthetic Oligonucleotide

<400> SEQUENCE: 33
atgccaaaaa ataacaaaga agaagttaaa gaagtaaacc ttaattcagt acaagaggat      60
gcgttaaagt cctttacgac tggttatggt atcacacctg atacaaaac agatgcagga     120 gcattaagac gtgagttcct agacgaccaa atctcaatgc ttacttggac agagaatgat     180
ttaacattct ataagacat cgctaaaaaa ccagctacat ctacagtagc aaaatacgat     240
gtatacatgc aacatggtaa ggtaggtcat actagattta ctcgtgagat tggggtagca     300
ccagtaagtg acccctaacat ccgtcaaaaa acagtaaata tgaaatttgc ttccgatact     360
aaaaacatca gtatcgcagc aggtctagta aacaacattc aagacccaat gcaaattttg     420
actgacgatg ctatcgtaaa tattgctaaa acaattgagt gggcttcatt ctttggagat     480
tctgacttat cagatagccc agaaccacaa gcaggactag aatttgacgg cttggctaaa     540
cttattaacc aagataacgt tcatgatgct cgtggagcta gcttgactga agcttgtta      600 aaccaagcag cagtaatgat tagtaaaggt tatggtacac ctacagatgc ttacatgcca     660
gtaggggttc aagcagactt tgttaaccaa caactttcta aacaaacaca acttgttcgc     720
gataacggaa acaacgtaag cgttggtttc aacatccaag gtttccattc agctcgtgga     780
tttatcaaac ttcacggttc tacagtaatg gaaaacgaac aaatcttaga tgaacgtatt     840
cttgctttac caacagctcc acaaccagct aaggtaactg caacacaaga agcaggtaaa     900
aaaggacaat ttagagcaga agatttagca gcacatgaat ataaagttgt tgtaagttct     960
gacgatgcag agtctattgc aagtgaagtg gctacagcta cagttactgc aaaagatgac    1020
ggcgttaaac tagaaatcga attagctcca atgtatagct ctcgtccaca attcgtttca    1080
atctatagaa aaggtgcaga acaggtttta ttctacctaa tcgtcgtgt acctgctagc    1140 aaagcagaga acaacgtaat cactttctac gacttaaacg actctattcc tgaaacagta    1200
gacgtattcg ttggtgaaat gtcggctaac gtagtacact tgtttgaatt actaccaatg    1260
atgagattac ctctagctca aattaacgca tctgttacat ttgcagtttt atggtatggc    1320
gcattagctc taagagcacc taagaaatgg gtacgtatta gaaacgttaa atatattcct    1380 gtaaaaacg ttcatagcaa ctaagaggag gtaaatatat atggtcttca cactcgaaga    1440
tttcgttggg gactggcgac agacagccgg ctacaacctg gaccaagtcc ttgaacaggg    1500
```

```
aggtgtgtcc agtttgtttc agaatctcgg ggtgtccgta actccgatcc aaaggattgt    1560
cctgagcggt gaaaatgggc tgaagatcga catccatgta atcatcccgt atgaaggtct    1620
gagcggcgac caaatgggcc agatcgaaaa aattttttaag gtggtgtacc ctgtggatga    1680
tcatcacttt aaggtgatcc tgcactatgg cacactggta atcgacgggg ttacgccgaa    1740
catgatcgac tatttcggac ggccgtatga aggcatcgcc gtgttcgacg gcaaaaagat    1800
cactgtaaca gggaccctgt ggaacggcaa caaaattatc gacgagcgcc tgatcaaccc    1860
cgacggctcc ctgctgttcc gagtaaccat caacggagtg accggctggc ggctgtgcga    1920
acgcattctg gcgtaataat tataggataa ttgaataaaa acagtataga gagcagataa    1980
atactgctct ctattttact aataaggagg atttaaattg ctaaaaaata caaacttagc    2040
taattataaa aaagtgaata cacggtttgg aaatcttagt tttgacgaca aaggtatttc    2100
taatgactta acggaagaac agcaaaaaga attaggtaag cttcgaggat tcgaatatat    2160
taagacagaa cagaaaacaa aagaagaacc taagaaagaa gaacctaaga aagaagaacc    2220
taagaaagaa gaacctaaga aagaagaacc taagaaagaa gaacctaaga agaaagtac    2280 agaaaatgaa ttagacagct tcttagctaa agagccttca atcaaagaat taaaagaatt    2340
tgcgagtaaa aaaggcatta aaattgaaaa aactaagaaa aatgatataa ttgaagaact    2400
aaagagaggg taatgtataa tgtatggagg ttatgaagga caagattctt acgaataccc    2460
ttactcacat gggaaccccta agcatgtaga gccagaaaaa gttgacgaat atgttctttc    2520
tgattatggt tggactgcgg aaacaattaa agcatacatg tatggtgttc gtgtagtaga    2580
ccctgaaaca ggagaggaaa tgggagacac cttctacaat catattatag aggttgccgt    2640
tgataaggc                                                             2649

<210> SEQ ID NO 34
<211> LENGTH: 2592
<212> TYPE: DNA
<213> ORGANISM: Artificial Sequence
<220> FEATURE:
<223> OTHER INFORMATION: Synthetic Oligonucleotide

<400> SEQUENCE: 34
atgccaaaaa ataacaaaga agaagaagtt aaagaagtaa accttaattc agtacaagag      60
gacgcgttaa agtcctttac aactggttat ggtatcacac tgatacaca aacagatgca     120 ggagcattaa gacgtgagtt cctagacgac caaatctcaa tgcttacttg gacagagaat     180
gatttaacat tctataaaga catcgctaaa aaaccagcta catctacagt agcaaaatac     240
gatgtataca tgcaacatgg taaggtaggt catactagat ttactcgtga gattggggta     300
gcaccagtaa gtgaccctaa catccgtcaa aaaacagtaa atatgaaatt tgcttccgat     360
actaaaaaca tcagtatcgc agcaggtcta gtaaacaaca ttcaagaccc aatgcaaatt     420
ttgactgacg atgctatcgt aaatattgct aaaacaattg agtgggcttc attctttgga     480
gattctgact tatcagatag cccagaacca caagcaggac tagaatttga cggcttggct     540
aaacttatta accaagataa cgttcatgat gctcgtggag ctagcttgac tgaaaagcttg    600 ttaaaccaag cagcagtaat gattagtaaa ggttatggta cacctacaga tgcttacatg     660
ccagtagggg ttcaagcaga ctttgttaac caacaacttt ctaaacaaac acagcttgtt     720
cgtgataacg gaaacaacgt aagcgttggt tcaacatcc aaggtttcca ttcagctcgt     780
ggatttatca aacttcacgg ttctacagta atggaaaacg aacaaatctt agatgaacgt     840
```

```
attcttgctt taccaacagc tccacaacca gctaaggtaa ctgcaacaca agaagcaggt    900
aaaaaaggac aatttagagc agaagactta gcagcacacg aatacaaagt tgttgtaagt    960
tctgacgatg cagagtctat tgcaagtgaa gtggctacag ctacagttac tgcaaaagat   1020
gacggcgtta aactagaaat cgagttagct ccaatgtaca gctcccgtcc acaattcgtt   1080
tcaatctata gaaaggtgc agaaacaggt ttattctacc taatcgctcg tgtacctgct    1140
agcaaagcag agaacaacgt aatcactttc tatgacttaa acgactctat tcctgaaaca   1200
gtagacgtat tcgttggtga aatgtctgct aacgtagtac acttgtttga attactacca   1260
atgatgagat tacctctagc tcaaattaac gcatctgtta catttgcagt tttatggtat   1320
ggagcattag ctctaagagc acctaagaaa tgggtacgta ttagaaacgt taaatatatt   1380
cctgtaaaaa acgttcatag caactaagag gaggtaaata tatatggtct tcacactcga   1440
agatttcgtt ggggactggc gacagacagc cggctacaac ctggaccaag tccttgaaca   1500
gggaggtgtg tccagtttgt ttcagaatct cggggtgtcc gtaactccga tccaaaggat   1560
tgtcctgagc ggtgaaaatg gctgaagat cgacatccat gtcatcatcc cgtatgaagg   1620
tctgagcggc gaccaaatgg gccagatcga aaaattttt aaggtggtgt accctgtgga   1680
tgatcatcac tttaaggtga tcctgcacta tggcacactg gtaatcgacg gggttacgcc   1740
gaacatgatc gactatttcg gacggccgta tgaaggcatc gccgtgttcg acggcaaaaa   1800
gatcactgta acagggaccc tgtggaacgg caacaaaatt atcgacgagc gcctgatcaa   1860
ccccgacggc tccctgctgt tccgagtaac catcaacgga gtgaccggct ggcggctgtg   1920
cgaacgcatt ctggcgtaat aattatagga taattgaata aaaacagtat agagagcaga   1980
taaatactgc tctctatttt actaataagg aggatttaaa ttgctaaaaa atacaaactt   2040
agctaattat aaaaaagtga atacacgatt tggaaatctt agttttgatg ataaaggtat   2100
ttctaatgac ctaacggaag agcagcaaaa agaattaggt aagcttagag gattcgaata   2160
tattaagaca gaacagaaaa cgaaagaaga acctaagaaa gaagaaccta agaaagaaag   2220
tacagaaaat gaattagaca gcttcttagc taaagaacct tcaatcaaag aattaaaaga   2280
atttgcgagt aaaaaaggca ttaaaattga aaaaactaag aaaaatgata taattgaaga   2340
actaaagaga gggtaatgta caatgtatgg aggttatgaa ggacaagatt cttacgaata   2400
cccttactca cacgggaacc ctaagcatgt agagccagaa aaagttgacg aatatgttct   2460
ttctgattat ggctggactg cggaaacaat taaagcatac atgtatggtg ttcgtgtagt   2520
agaccctgaa acaggagagg aaatgggaga caccttctac aatcatatta tagaggttgc   2580
cgttgataag gc                                                       2592
```

<210> SEQ ID NO 35
<211> LENGTH: 2613
<212> TYPE: DNA
<213> ORGANISM: Artificial Sequence
<220> FEATURE:
<223> OTHER INFORMATION: Synthetic Oligonucleotide

<400> SEQUENCE: 35

```
atgccaaaaa ataacaaaga agaagaagtt aaagaagtaa accttaattc agtacaagag     60
gatgcgttaa agtcctttac aactggttat ggtatcacac ctgatacaca aacagatgca    120
ggggcactaa gacgtgagtt cctagacgac caaatctcaa tgcttacttg gacagaaaat    180
gatttaacat tctacaaaga catcgctaaa aaaccagcta catctacagt agcaaaatac    240
gatgtgtaca tgcaacacgg taaagtaggt catactagat ttactcgtga gattggggta    300
```

-continued

```
gcaccagtaa gtgaccctaa catccgtcaa aaaacagtaa acatgaaatt tgcttctgat    360
actaaaaata ttagtatcgc agcaggtcta gtaaacaaca ttcaagaccc tatgcaaatt    420
ttgactgatg atgctatcgt aaatatcgct aaaacaattg agtgggcttc attctttgga    480
gattctgact tatcagatag cccagaacca caagcaggat tagaatttga tggcttggct    540
aaacttatta accaagataa cgttcatgat gctcgtggag ctagcttgac tgaaagcttg    600
ttaaaccaag cagcagtaat gattagtaaa ggttatggta cacctacaga tgcttacatg    660
ccagtagggg ttcaagcaga ctttgttaac caacaacttt ctaaacaaac acaacttgtt    720
cgcgataacg gaaacaacgt aagcgttggt ttcaacatcc aaggtttcca ttcagctcgt    780
ggatttatca aacttcacgg ttctacagta atggaaaacg aacaaatctt agatgaacgt    840
attcttgctt taccaacagc tccacaacca gctaaggtaa ctgcaacaca agaagcaggt    900
aaaaaaggac aatttagagc agaagattta gcagcacatg aatataaagt tgttgtaagt    960
tctgacgatg cagagtctat tgcaagtgaa gtggctacag ctacagttac tgcaaaagat   1020
gacggcgtta aactagaaat cgaattagct ccaatgtata gctctcgtcc acaattcgtt   1080
tcaatctata gaaaaggtgc agaaacaggt ttattctacc taatcgctcg tgtacctgct   1140
agcaaagcag agaacaacgt aatcactttc tacgacttaa cgactctat tcctgaaaca    1200
gtagacgtat tcgttggtga aatgtcggct aacgtagtac acttgtttga attactacca   1260
atgatgagat tacctctagc tcaaattaac gcatctgtta catttgcagt tttatggtat   1320
ggcgcattag ctctaagagc acctaagaaa tgggtacgta ttagaaacgt taaatatatt   1380
cctgtaaaaa acgttcatag caactaataa taagaggagg taaatatata tggtcttcac   1440
actcgaaagat ttcgttgggg actggcgaca gacagccggc tacaacctgg accaagtcct  1500
tgaacaggga ggtgtgtcca gtttgtttca gaatctcggg gtgtccgtaa ctccgatcca   1560
aaggattgtc ctgagcggtg aaaatgggct gaagatcgac atccatgtca tcatcccgta   1620
tgaaggtctg agcggcgacc aaatgggcca gatcgaaaaa attttttaagg tggtgtaccc   1680
tgtggatgat catcacttta aggtgatcct gcactatggc acactggtaa tcgacggggt   1740
tacgccgaac atgatcgact atttcggacg gccgtatgaa ggcatcgccg tgttcgacgg   1800
caaaaagatc actgtaacag ggaccctgtg aacggcaac aaaattatcg acgagcgcct    1860
gatcaacccc gacggctccc tgctgttccg agtaaccatc aacggagtga ccggctggcg   1920
gctgtgcgaa cgcattctgg cgtaataatt ataggataat tgaataaaaa cagtatagag   1980
agcagataaa tactgctctc tattttacta ataaggagga tttaaattgc taaaaaatac   2040
aaacttagct aattataaaa aagtgaatac acggtttgga atcttagtt ttgacgacaa    2100
aggtatttct aatgacttaa cggaagaaca gcaaaaagaa ttaggtaagc ttcgaggatt   2160
cgaatatatt aagacagaac agaaaacaaa agaagaacct aagaagaag aacctaagaa    2220
agaagaacct aagaagaaa gtacagaaaa tgaattagac agcttcttag ctaaagagcc   2280
ttcaatcaaa gaattaaaag aatttgcgag taaaaaggc attaaaattg aaaaaactaa    2340
gaaaaacgat ataattgaag aactaaagag agggtaatgt ataatgtatg gaggttatga   2400
aggacaagat tcttacgaat acccttactc acatgggaac cctaagcatg tagagccaga   2460
aaaagttgac gaatatgttc tttctgatta tggttggact gcggaaacaa ttaaagcata   2520
catgtatggt gttcgtgtag tagaccctga acaggagag gaaatgggag acaccttcta    2580
caatcatatt atagaggttg ccgttgataa ggc                                 2613
```

<210> SEQ ID NO 36
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 36
gaggaggtaa atatat                                                  16

<210> SEQ ID NO 37
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 37
ttacgccaag cttggctgca acgtgagttc ctagacgacc                        40

<210> SEQ ID NO 38
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 38
atgtttttgg cgtcttccat atatatttac ctcctcttag ttgctatgaa cgtttt      56

<210> SEQ ID NO 39
<211> LENGTH: 56
<212> TYPE: DNA
<213> ORGANISM: Artificial Sequence
<220> FEATURE:
<223> OTHER INFORMATION: Synthetic Oligonucleotide

<400> SEQUENCE: 39
aaaacgttca tagcaactaa gaggaggtaa atatatatgg aagacgccaa aaacat      56

<210> SEQ ID NO 40
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 40
attcaattat cctataatta ttacaatttg gactttccgc                        40

<210> SEQ ID NO 41
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 41
gcggaaagtc caaattgtaa taattatagg ataattgaat                        40

<210> SEQ ID NO 42
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 42
acgacggcca gtgaattccc agttactaac tgctctaatg          40

<210> SEQ ID NO 43
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 43
acgacggcca gtgaattccc agttactaac tgttctaatg          40

<210> SEQ ID NO 44
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 44
cctctagctc aaattaacgc atctgt          26

<210> SEQ ID NO 45
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 45
tggctctaca tgcttagggt tcc          23

<210> SEQ ID NO 46
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 46
tcttcgagtg tgaagaccat atatatttac ctcctcttag ttgc          44

<210> SEQ ID NO 47
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 47
ctaagaggag gtaaatatat atggtcttca cactcgaaga ttt          43

<210> SEQ ID NO 48
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 48
attcaattat cctataatta ttacgccaga atgcgttcgc          40

<210> SEQ ID NO 49

<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 49
gcgaacgcat tctggcgtaa taattatagg ataattgaat aaa         43

<210> SEQ ID NO 50
<211> LENGTH: 65
<212> TYPE: DNA
<213> ORGANISM: Artificial Sequence
<220> FEATURE:
<223> OTHER INFORMATION: Synthetic Oligonucleotide

<400> SEQUENCE: 50
aaaacgttca tagcaactaa taataagagg aggtaaatat atatggtctt cacactcgaa    60
gattt                                                                65

<210> SEQ ID NO 51
<211> LENGTH: 47
<212> TYPE: DNA
<213> ORGANISM: Artificial Sequence
<220> FEATURE:
<223> OTHER INFORMATION: Synthetic Oligonucleotide

<400> SEQUENCE: 51
atatttacct cctcttatta ttagttgcta tgaacgtttt ttacagg      47

<210> SEQ ID NO 52
<211> LENGTH: 40
<212> TYPE: DNA
<213> ORGANISM: Artificial Sequence
<220> FEATURE:
<223> OTHER INFORMATION: Synthetic Oligonucleotide

<400> SEQUENCE: 52
acgacggcca gtgaattccc tcgtggtgtt ctgactcccg              40

<210> SEQ ID NO 53
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 53
tgctatatta taggaacatg ggaa                              24

<210> SEQ ID NO 54
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 54
tgcttacatg ccagtagggg t                                 21

<210> SEQ ID NO 55
<211> LENGTH: 40
<212> TYPE: DNA
<213> ORGANISM: Artificial Sequence
<220> FEATURE:
<223> OTHER INFORMATION: Synthetic Oligonucleotide

```
<400> SEQUENCE: 55
acgacggcca gtgaattccc tcgtggtgtt ctgactcccg                            40

<210> SEQ ID NO 56
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 56
tggctctaca tgcttagggt tcc                                             23

<210> SEQ ID NO 57
<211> LENGTH: 26
<212> TYPE: DNA
<213> ORGANISM: Artificial Sequence
<220> FEATURE:
<223> OTHER INFORMATION: Synthetic Oligonucleotide

<400> SEQUENCE: 57
cctctagctc aaattaacgc atctgt                                          26

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 58
gtatgaaggt ctgagcggcg                                                 20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 59
gatctggccc atttggtcgc                                                 20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 60
cgcatagaac tgcctgcgtc                                                 20

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 61
caccccaaca tcttcgacgc                                                 20

<210> SEQ ID NO 62
```

```
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 62
gcgcaactgc aactccgata                                                  20

<210> SEQ ID NO 63
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 63

His His His His His His
1               5

<210> SEQ ID NO 64
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 64
attcaattat cctataatta ttaatggtga tggtgatgat gacctccacc tgctgccgcc      60
agaatgcgtt cgcaca                                                      76

<210> SEQ ID NO 65
<211> LENGTH: 46
<212> TYPE: DNA
<213> ORGANISM: Artificial Sequence
<220> FEATURE:
<223> OTHER INFORMATION: Synthetic Oligonucleotide

<400> SEQUENCE: 65
atcatcacca tcaccattaa taattatagg ataattgaat aaaaac                     46

<210> SEQ ID NO 66
<211> LENGTH: 67
<212> TYPE: DNA
<213> ORGANISM: Artificial Sequence
<220> FEATURE:
<223> OTHER INFORMATION: Synthetic Oligonucleotide

<400> SEQUENCE: 66
attcaattat cctataatta ttaatggtga tggtgatgat gtgctgccgc cagaatgcgt      60
tcgcaca                                                                67

<210> SEQ ID NO 67
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 67
taataagagg aggtaaatat atatgcatca tcaccatcac catggtggag gtgcagcagt      60
cttcacactc gaagatttcg                                                  80

<210> SEQ ID NO 68
```

```
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 68
agcaactaat aataagagga ggtaaatata tatgcatcat caccatcacc atgcagcagt    60
cttcacactc gaagatttcg                                                80

<210> SEQ ID NO 69
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 69
catcatcacc atcaccat                                                  18

<210> SEQ ID NO 70
<211> LENGTH: 11
<212> TYPE: PRT
<213> ORGANISM: Artificial Sequence
<220> FEATURE:
<223> OTHER INFORMATION: Synthetic Polypeptide

<400> SEQUENCE: 70

Ala Ala Gly Gly Gly His His His His His His
 1               5                  10

<210> SEQ ID NO 71
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 71
gcagcaggtg gaggtcatca tcaccatcac cat                                 33

<210> SEQ ID NO 72
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 72

Ala Ala His His His His His His
 1               5

<210> SEQ ID NO 73
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 73
gcagcacatc atcaccatca ccat                                           24

<210> SEQ ID NO 74
<211> LENGTH: 11
<212> TYPE: PRT
<213> ORGANISM: Artificial Sequence
```

<220> FEATURE:
<223> OTHER INFORMATION: Synthetic Polypeptide

<400> SEQUENCE: 74

His His His His His His Gly Gly Gly Ala Ala
1               5                   10

<210> SEQ ID NO 75
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 75
catcatcacc atcaccatgg tggaggtgca gca                                33

<210> SEQ ID NO 76
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 76

His His His His His His Ala Ala
1               5

<210> SEQ ID NO 77
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 77
catcatcacc atcaccatgc agca                                          24

<210> SEQ ID NO 78
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 78
cctagtgtac cagtatgata gtacatctct atgtgtccct cctcgccgca gttaattaaa   60
gtcagtgagc gaggaagcgc                                               80

<210> SEQ ID NO 79
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 79
gaacgaccga gcgcagcggc ggccgcgctg ataccgccgc tctcatagtt caagaaccca   60
aagtaccccc cccatagccc                                               80

<210> SEQ ID NO 80
<211> LENGTH: 60
<212> TYPE: DNA
<213> ORGANISM: Artificial Sequence
<220> FEATURE:

```
<223> OTHER INFORMATION: Synthetic Oligonucleotide

<400> SEQUENCE: 80
cctcataaag gccaagaagg gcggaaagtc caaattgtaa acggattcac cactccaaga    60

<210> SEQ ID NO 81
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 81
ataatcatag gtcctctgac acataattcg cctctctgat tcaacgacag gagcacgatc    60

<210> SEQ ID NO 82
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 82
aagaattgat tggctccaat tcttggagtg gtgaatccgt ttacaatttg gactttccgc    60

<210> SEQ ID NO 83
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 83
tcctggccac gggtgcgcat gatcgtgctc ctgtcgttga atcagagagg cgaattatgt    60

<210> SEQ ID NO 84
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 84
aatttactct ttactcttac agataacagg acactgaacg atggaagacg ccaaaaacat    60

<210> SEQ ID NO 85
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 85
attcaggcca cctcatgatg acctgtaaga aaagactcta ttacaatttg gactttccgc    60

<210> SEQ ID NO 86
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 86
ctcactaacg ggaacaacct caaccatag gagacacatc atggaagacg ccaaaaacat    60
```

```
<210> SEQ ID NO 87
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 87
tgtttgcgtg cttgattgat ttactcatgt tgtgctccta ttacaatttg gactttccgc      60

<210> SEQ ID NO 88
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 88
ttgtctttgg gtgttacctt gagtgtctct ctgtgtccct cctcgccgca gttaattaaa      60
gtcagtgagc gaggaagcgc                                                 80

<210> SEQ ID NO 89
<211> LENGTH: 90
<212> TYPE: DNA
<213> ORGANISM: Artificial Sequence
<220> FEATURE:
<223> OTHER INFORMATION: Synthetic Oligonucleotide

<400> SEQUENCE: 89
cccgaacgac cgagcgcagc ggcggccgcg ctgataccgc cgccgccggc gtctcacagt      60
gtacggacct aaagttcccc catagggggt                                      90

<210> SEQ ID NO 90
<211> LENGTH: 60
<212> TYPE: DNA
<213> ORGANISM: Artificial Sequence
<220> FEATURE:
<223> OTHER INFORMATION: Synthetic Oligonucleotide

<400> SEQUENCE: 90
ccaaggggtt aactagttac tcgagtgcgg ccgcaagctt ttacaatttg gactttccgc      60

<210> SEQ ID NO 91
<211> LENGTH: 80
<212> TYPE: DNA
<213> ORGANISM: Artificial Sequence
<220> FEATURE:
<223> OTHER INFORMATION: Synthetic Oligonucleotide

<400> SEQUENCE: 91
acattttctg gcgtcagtcc accagctaac ataaaatgta agctttcggg gctctcttgc      60
cttccaaccc agtcagaaat                                                 80
```

PHAGE-BASED BACTERIAL DETECTION ASSAY

RELATED APPLICATIONS

The present application claims priority to U.S. provisional application No. 61/837,152, filed Jun. 19, 2013, U.S. provisional application No. 61/844,399, filed Jul. 9, 2013, U.S. provisional application No. 61/879,640, filed Sep. 18, 2013, U.S. provisional application No. 61/884,931, filed Sep. 30, 2013, U.S. provisional application No. 61/884,935, filed Sep. 30, 2013, and U.S. provisional application No. 61/884,946, filed Sep. 30, 2013. The contents of the aforementioned applications are hereby incorporated by reference in their entireties.

INCORPORATION-BY-REFERENCE OF SEQUENCE LISTING

The contents of the text file named "SAM6-011_001US_v3_ST25.txt," which was created on Sep. 16, 2014 and is 132 KB in size, are hereby incorporated by reference in their entireties.

BACKGROUND OF THE INVENTION

Bacterial contamination and infection is a significant problem to public health and in many other areas. Bacterial food borne diseases pose a significant threat to human health, estimated to cause as many as about 76 million illnesses, 325,000 hospitalizations, and 5,000 deaths in the US annually.

For example, in 1996, juice that was contaminated with *Escherichia coli* was released into the public by a juice maker and resulted in one death and 66 illnesses. The company paid a $1.5 million fine, and the recall alone cost the company $6.5 million. In 2006, an *E. coli* O157:H7 outbreak from contaminated spinach originating from California resulted in 205 illnesses and 3 deaths. In 2011a listeriosis outbreak from cantaloupes from Colorado in July, August and September resulted in 30 deaths. That is the second deadliest recorded U.S. outbreak in terms of the number of deaths since the Centers for Disease Control and Prevention began tracking outbreaks in the 1970s. Another recall of cantaloupes in 2012 suggests that the food supply is still not safe and highlights the general and pervasive need for additional methods and reagents for testing the food supply to identify contamination.

Another example is bovine mastitis, an infection caused by bacterial cells those results in the inflammation of the bovine breast, reduction in milk yield and a decrease in milk quality. This condition is caused by the bacteria *Staphylococcus aureus* and *Staphylococcus agalactiae*. This reduction in milk yields and quality in the western world alone have been suggested to cause annual financial losses of $3.7 billion.

Another example is bovine *tuberculosis* (*Mycobacterium bovis*), a bacteria that causes financial loses worldwide. In 2005, for example, 12 of a herd of 55 cattle in a small Michigan farm tested positive for bovine *tuberculosis*. The farm was forced to destroy the entire herd of cattle, along with an entire herd of hogs. *Tuberculosis* testing in cattle requires the animal to be held for 2 days, and tests are false positive 5 percent of the time. Often entire herds have to be quarantined or destroyed. The annual worldwide financial losses have been estimated at $3 billion.

*Tuberculosis* is a leading cause of death worldwide. One third of the world's population is infected with *Mycobacterium tuberculosis*, the bacterium that causes *tuberculosis*. Every day 25,000 people are infected and 5,000 people die from the disease. Furthermore, due primarily to poor diagnosis, multidrug resistant strains of *M. tuberculosis* are emerging and the reemergence of *tuberculosis* as a worldwide epidemic has become a real threat. The worldwide annual market for *tuberculosis* diagnostics has been estimated at $1.8 billion.

MRSA is a drug-resistant version of the common *Staphylococcus aureus* bacteria and is carried by 2.5 million people in the US. A carrier can be a healthy individual, and still be highly contagious, due to the nature of the MRSA bacterium. The bacteria are highly contagious and spread by touch. Approximately 86% of all infections occur within hospitals, and these infections carry a 20% mortality rate. This bacterium costs an average of $21,000 over the standard costs to treat, and kills approximately 19,000 people in the US annually.

*Listeria monocytogenes* is an intracellular pathogen that can cause invasive disease in humans and animals. Approximately 99% of human listeriosis infections appear to be food borne. While *L. monocytogenes* has been isolated from a variety of raw and ready-to-eat foods, most human listeriosis infections appear to be caused by consumption of RTE foods that permit postcontamination growth of this pathogen. Listeriosis is estimated to be responsible for about 500 deaths per year in the United States, accounting for 28% of annual deaths attributable to known food-borne pathogens, second only to deaths due to *Salmonella* infections.

Methods and systems exist for detecting microbial contamination. Such methods and systems suffer from a number of drawbacks, including the need in most cases to remove a potentially contaminated sample from the environment where it is collected and transferring it to a laboratory environment, where the sample is placed in a culture environment for enrichment and growth over a long period of time, ranging from many hours to days. Additionally, because these labs are frequently offsite there is often a delay in the shipping of a sample to a laboratory. Once enriched, samples are typically analyzed using expensive equipment, traditional culturing methods, PCR and other methods. Thus, current processes often comprise a large time lag between sampling and a result, during which time the sampled conditions may have changed and the results of the assay cannot be utilized to diagnose an infection in a patient or to act on contamination in a lot of manufactured food, for example. Accordingly, new composition and methods for detecting microbial contamination are needed. The present invention addresses these needs.

SUMMARY OF THE INVENTION

The present invention describes a composition including at least one recombinant phage capable of infecting at least one target microbe. The target microbe may be obtained from an environmental sample. The recombinant phage comprises a heterologous nucleic acid sequence encoding a marker. The composition further includes at least one aqueous solution suitable for propagation of the at least one recombinant phage in the at least one target microbe.

The aqueous solution includes at least one nutrient; at least one selective agent suitable to inhibit growth of at least one non-target microbe in said environmental sample; at least one vitamin; at least one divalent metal; at least one buffering agent capable of maintaining the composition at pH 7.0-7.5; at least one agent suitable to neutralize a sanitizer present in said environmental sample; and at least one agent to prevent the decomposition of luciferin.

In some embodiments, the at least one recombinant phage is selected from LP48::ffluc, LP99::ffluc, LP101::ffluc, LP124::ffluc, LP125::ffluc, LP143::ffluc, A511::ffluc, P100::ffluc, LP40::nluc, LP124::nluc, LP125::nluc, A511::nluc, or P100::nluc.

In some embodiments, the at least one recombinant phage is present in the composition at a concentration of $1 \times 10^6$ to $1 \times 10^{11}$ pfu/ml. In some embodiments, the at least one recombinant phage is present in the composition at a concentration of $1 \times 10^7$ to $1 \times 10^8$ pfu/ml. In some embodiments, the at least one recombinant phage is present in the composition at a concentration of $1.5 \times 10^7$ pfu/ml. In some embodiments, the composition includes 3 recombinant phages and each recombinant phage is present in the composition at a concentration of $1.5 \times 10^7$ pfu/ml.

In some embodiments, the at least one nutrient in the aqueous solution comprises Brain Heart Infusion medium. In some embodiments, the at least one selective agent in the aqueous solution is selected from the group consisting of LiCl, acriflavine, nalidixic acid, and cycloheximide. In some embodiments, the at least one vitamin in the aqueous solution comprises yeast extract. In some embodiments, the at least one divalent metal in the aqueous solution comprise $CaCl_2$. In some embodiments, the at least one buffering agent in the aqueous solution comprises HEPES buffer. In some embodiments, the at least one neutralizing agent in the aqueous solution is selected from the group consisting of non-ionic detergents, oxygen scavengers and emulsifiers. In some embodiments, the at least one neutralizing agent or the at least one agent to prevent the decomposition of luciferin in the aqueous solution is selected from the group consisting of: sodium thiosulfate, polysorbate 80, HEPES and lecithin.

In some embodiments, the aqueous solutions comprises 1× Brain Heart Infusion medium; 0.5% LiCl; 0.002% nalidixic acid; 0.2% yeast extract; 2 mM $CaCl_2$, 40 mM HEPES, pH 7.4; 1 mM sodium metabisulfite; 0.1% sodium thiosulfate; 0.5% Polysorbate 80; and 0.1% lecithin.

In some embodiments, the aqueous solution comprises half-strength Brain Heart Infusion medium, 5% weight/volume glucose, 1% volume/volume glycerol, 1% weight/volume LiCl, and 0.002% weight/volume Nalidixic Acid.

In some embodiments, the marker encoded by the heterologous nucleic acid sequence is a luciferase. In some embodiments, the luciferase is at least 70% identical to SEQ ID NO: 2. In some embodiments, the luciferase is at least 70% identical to SEQ ID NO: 4. In some embodiments, the luciferase comprises and amino acid sequence selected from SEQ ID NO: 2 or SEQ ID NO: 4.

In some embodiments, the marker further comprises an affinity tag. In some embodiments, the affinity tag is a HIS tag.

In some embodiments, the target microbe is selected from the group consisting of *Salmonella, coliform* bacteria, *Escherichia, Shigella, Listeria, Clostridium, Vibrio, Enterobacteriacae, Staphylococcus, Bacillus, Campylobacter, Pseudomonas, Streptococcus, Acinetobacter, Klebsiella, Campylobacter,* and *Yersinia*. In some embodiments, the target microbe is *E. coli*. In some embodiments, the target microbe is *Listeria* selected from the group consisting of *Listeria innocua, Listeria monocytogenes, Listeria seeligeri, Listeria ivanovii, Listeria grayi, Listeria marthii, Listeria rocourti, Listeria welshimeri, Listeria floridensis, Listeria aquatic, Listeria cornellensis, Listeria riparia*, and *Listeria grandensis*.

In some embodiments, the present invention may comprise a kit including at least one recombinant phage capable of infecting at least one target microbe. The target microbe may be obtained from an environmental sample. The recombinant phage comprises a heterologous nucleic acid sequence encoding a marker. The composition further includes at least one aqueous solution suitable for propagation of the at least one recombinant phage in the at least one target microbe. The kit further includes an aqueous solution including at least one nutrient; at least one selective agent suitable to inhibit growth of at least one non-target microbe in said environmental sample; at least one vitamin; at least one divalent metal; at least one buffering agent capable of maintaining the composition at pH 7.0-7.5; at least one agent suitable to neutralize a sanitizer present in said environmental sample; and at least one agent to prevent the decomposition of luciferin. The kit also includes a solid substrate capable of supporting adhesion by the at least one target microbe.

In some embodiments, the present invention comprises a method of determining the presence or absence of a target microbe in an environmental sample. The method includes collecting an environmental sample; contacting the environmental sample with at least one recombinant phage capable of infecting at least one target microbe obtained from an environmental sample, said recombinant phage comprising a heterologous nucleic acid sequence encoding a marker; providing conditions to the phage-exposed environmental sample sufficient to allow the recombinant phage to infect the target microbe present in association with the environmental sample and production of the marker encoded by the heterologous nucleic acid sequence by the target microbe; and assaying the phage-exposed environmental sample to detect the presence or absence of the marker to determine the presence or absence of the target microbe. In the method, the time from contacting the environmental sample with the recombinant phage to detecting the presence or absence of the target microbe is between 1 minute and 6 hours.

In some embodiments, the at least one recombinant phage used in the method is selected from LP48::ffluc, LP99::ffluc, LP101::ffluc, LP124::ffluc, LP125::ffluc, LP143::ffluc, A511::ffluc, P100::ffluc, LP40::nluc, LP124::nluc, LP125::nluc, A511::nluc, or P100::nluc.

In some embodiments, providing conditions to the phage-exposed environmental sample sufficient to allow the recombinant phage to infect the target microbe present in association with the environmental sample includes exposing the phage-exposed environmental sample to at least one aqueous solution suitable for propagation of the at least one recombinant phage in the at least one target microbe. The aqueous solution includes at least one nutrient; at least one selective agent suitable to inhibit growth of at least one non-target microbe in said environmental sample; at least one vitamin; at least one divalent metal; at least one buffering agent capable of maintaining the composition at pH 7.0-7.5; at least one agent suitable to neutralize a sanitizer present in said environmental sample; and at least one agent to prevent the decomposition of luciferin.

In some embodiments, the time from contacting the environmental sample with the recombinant phage to detecting the presence or absence of the target microbe is 4 hours or less. In some embodiments, the time from contacting the environmental sample with the recombinant phage to detecting the presence or absence of the target microbe is 1 hour or less.

In some embodiments, assaying the phage-exposed environmental sample to detect the presence or absence of the marker to determine the presence or absence of the target microbe has a lower limit of detection of 100 target microbe cells 30 minutes after contacting the environmental sample with the recombinant phage. In some embodiments, assaying the phage-exposed environmental sample to detect the presence or absence of the marker to determine the presence or absence of the target microbe has a lower limit of detection of 10 target microbe cells 60 minutes after contacting the environmental sample with the recombinant phage. In some embodiments, assaying the phage-exposed environmental sample to detect the presence or absence of the marker to determine the presence or absence of the target microbe comprises a lower limit of detection of a single target microbe cell 180 minutes after contacting the environmental sample with the recombinant phage.

In some embodiments, the accuracy of the method is at least 90% on environmental samples and wherein the method has a lower limit of detection of about ten cells or fewer detected within about 60 minutes for control samples comprising a metabolically active target microbe. In some embodiments, the specificity of the method is at least 90%. In some embodiments, the sensitivity of the method is at least 80%.

DETAILED DESCRIPTION OF THE INVENTION

Unless otherwise defined herein, scientific and technical terms used in connection with the present disclosure shall have the meanings that are commonly understood by those of ordinary skill in the art. Further, unless otherwise required by context, singular terms shall include the plural and plural terms shall include the singular. Generally, nomenclatures used in connection with, and techniques of, biochemistry, enzymology, molecular and cellular biology, microbiology, genetics and protein and nucleic acid chemistry and hybridization described herein are those well-known and commonly used in the art. Certain references and other documents cited herein are expressly incorporated herein by reference. Additionally, all Genbank or other sequence database records cited herein are hereby incorporated herein by reference. In case of conflict, the present specification, including definitions, will control. The materials, methods, and examples are illustrative only and not intended to be limiting.

The methods and techniques of the present disclosure are generally performed according to conventional methods well known in the art and as described in various general and more specific references that are cited and discussed throughout the present specification unless otherwise indicated. See, e.g., Sambrook et al., *Molecular Cloning: A Laboratory Manual*, 3d ed., Cold Spring Harbor Laboratory Press, Cold Spring Harbor, N.Y. (2001); Ausubel et al., *Current Protocols in Molecular Biology*, Greene Publishing Associates (1992, and Supplements to 2002); Taylor and Drickamer, *Introduction to Glycobiology*, Oxford Univ. Press (2003); *Worthington Enzyme Manual*, Worthington Biochemical Corp., Freehold, N.J.; *Handbook of Biochemistry: Section A Proteins*, Vol I, CRC Press (1976); *Handbook of Biochemistry: Section A Proteins*, Vol II, CRC Press (1976); *Essentials of Glycobiology*, Cold Spring Harbor Laboratory Press (1999). Many molecular biology and genetic techniques applicable to phage are described in Clokie et al., *Bacteriophages: Methods and Protocols*, Vols. 1 and 2 (*Methods in Molecular Biology*, Vols. 501 and 502), Humana Press, New York, N.Y. (2009), which is hereby incorporated herein by reference.

This disclosure refers to sequence database entries (e.g., UniProt/SwissProt or GENBANK records) for certain amino acid and nucleic acid sequences that are published on the internet, as well as other information on the internet. The skilled artisan understands that information on the internet, including sequence database entries, is updated from time to time and that, for example, the reference number used to refer to a particular sequence can change. Where reference is made to a public database of sequence information or other information on the internet, it is understood that such changes can occur and particular embodiments of information on the internet can come and go. Because the skilled artisan can find equivalent information by searching on the internet, a reference to an internet web page address or a sequence database entry evidences the availability and public dissemination of the information in question.

Before the present recombinant phage, compositions, methods, and other embodiments are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

The term "comprising" as used herein is synonymous with "including" or "containing", and is inclusive or open-ended and does not exclude additional, unrecited members, elements or method steps.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe). An assay that occurs at least in part in vivo within a microbe may nonetheless occur in vitro if parts of the assay occur outside of the microbe in culture, for example.

As used herein, the term "isolated" refers to a substance or entity that has been (1) separated from at least some of the components with which it was associated when initially produced (whether in nature or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components.

The term "peptide" as used herein refers to a short polypeptide, e.g., one that typically contains less than about 50 amino acids and more typically less than about 30 amino acids. The term as used herein encompasses analogs and mimetics that mimic structural and thus biological function.

The term "polypeptide" encompasses both naturally-occurring and non-naturally occurring proteins, and fragments, mutants, derivatives and analogs thereof. A polypeptide may be monomeric or polymeric. Further, a polypeptide may comprise a number of different domains each of which has one or more distinct activities. For the avoidance of doubt, a "polypeptide" may be any length greater two amino acids.

The term "isolated protein" or "isolated polypeptide" is a protein or polypeptide that by virtue of its origin or source of derivation (1) is not associated with naturally associated components that accompany it in its native state, (2) exists in a purity not found in nature, where purity can be adjudged with respect to the presence of other cellular material (e.g., is free of other proteins from the same species) (3) is expressed by a cell from a different species, or (4) does not occur in nature (e.g., it is a fragment of a polypeptide found in nature or it includes amino acid analogs or derivatives not found in nature or linkages other than standard peptide bonds). Thus, a polypeptide that is chemically synthesized or synthesized in a cellular system different from the cell from which it naturally originates will be "isolated" from its naturally associated components. A polypeptide or protein may also be rendered substantially free of naturally associated components by isolation, using protein purification techniques well known in the art. As thus defined, "isolated" does not necessarily require that the protein, polypeptide, peptide or oligopeptide so described has been physically removed from a cell in which it was synthesized.

The term "polypeptide fragment" as used herein refers to a polypeptide that has a deletion, e.g., an amino-terminal and/or carboxy-terminal deletion compared to a full-length polypeptide, such as a naturally occurring protein. In an embodiment, the polypeptide fragment is a contiguous sequence in which the amino acid sequence of the fragment is identical to the corresponding positions in the naturally-occurring sequence. Fragments typically are at least 5, 6, 7, 8, 9 or 10 amino acids long, or at least 12, 14, 16 or 18 amino acids long, or at least 20 amino acids long, or at least 25, 30, 35, 40 or 45, amino acids, or at least 50 or 60 amino acids long, or at least 70 amino acids long, for example.

The term "fusion protein" refers to a polypeptide comprising a polypeptide or fragment coupled to heterologous amino acid sequences. Fusion proteins are useful because they can be constructed to contain two or more desired functional elements that can be from two or more different proteins. A fusion protein comprises at least 10 contiguous amino acids from a polypeptide of interest, or at least 20 or 30 amino acids, or at least 40, 50 or 60 amino acids, or at least 75, 100 or 125 amino acids. The heterologous polypeptide included within the fusion protein is usually at least 6 amino acids in length, or at least 8 amino acids in length, or at least 15, 20, or 25 amino acids in length. Fusions that include larger polypeptides, such as an IgG Fc region, and even entire proteins, such as the green fluorescent protein ("GFP") chromophore-containing proteins, have particular utility. Fusion proteins can be produced recombinantly by constructing a nucleic acid sequence which encodes the polypeptide or a fragment thereof in frame with a nucleic acid sequence encoding a different protein or peptide and then expressing the fusion protein. Alternatively, a fusion protein can be produced chemically by crosslinking the polypeptide or a fragment thereof to another protein.

As used herein, "recombinant" refers to a biomolecule, e.g., a gene or protein, that (1) is not associated with all or a portion of a polynucleotide in which the gene is found in nature, (2) is operatively linked to a polynucleotide which it is not linked to in nature, or (3) does not occur in nature. Preferably, "recombinant" refers to a biomolecule that does not occur in nature. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids. Thus, for example, a protein synthesized by a microorganism is recombinant, for example, if it is synthesized from an mRNA synthesized from a recombinant gene present in the cell. A phage is "recombinant" if it comprises a recombinant biomolecule. Preferably, a phage is "recombinant" if it comprises a recombinant biomolecule that does not occur in nature. Thus, for example and without limitation, a phage is recombinant if the genome of the phage comprises a recombinant nucleic acid sequence.

The term "polynucleotide", "nucleic acid molecule", "nucleic acid", or "nucleic acid sequence" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

A "synthetic" RNA, DNA or a mixed polymer is one created outside of a cell, for example one synthesized chemically.

The term "nucleic acid fragment" as used herein refers to a nucleic acid sequence that has a deletion, e.g., a 5'-terminal or 3'-terminal deletion compared to a full-length reference nucleotide sequence. In an embodiment, the nucleic acid fragment is a contiguous sequence in which the nucleotide sequence of the fragment is identical to the corresponding positions in the naturally-occurring sequence. In some embodiments fragments are at least 10, 15, 20, or 25 nucleotides long, or at least 20, 30, 40, 50, 60, 70, 80, 90, 100, 110, 120, 130, 140, or 150 nucleotides long. In some embodiments a fragment of a nucleic acid sequence is a fragment of an open reading frame sequence. In some embodiments such a fragment encodes a polypeptide fragment (as defined herein) of the protein encoded by the open reading frame nucleotide sequence.

As used herein, an "expression control sequence" refers to polynucleotide sequences that are necessary to affect the expression of coding sequences to which they are operatively linked. Expression control sequences are sequences that control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to encompass, at a minimum, any component whose presence is essential for expression, and can also encompass an additional component whose presence is advantageous, for example, leader sequences and fusion partner sequences.

As used herein, "operatively linked" or "operably linked" expression control sequences refers to a linkage in which the expression control sequence is contiguous with the gene of interest to control the gene of interest, as well as expression control sequences that act in trans or at a distance to control the gene of interest.

As used herein, "bacteriophage" refers to a virus that infects bacteria. Similarly, "archaeophage" refers to a virus that infects archaea. The term "phage" is used to refer to both types of viruses but in certain instances as indicated by the context may also be used as shorthand to refer to a bacteriophage or archaeophage specifically. Bacteriophage and archaeophage are obligate intracellular parasites that multiply inside bacteria/archaea by making use of some or all of the host biosynthetic machinery (i.e., viruses that infect bacteria/archaea). Though different bacteriophages and archaeophages may contain different materials, they all contain nucleic acid and protein, and can under certain circumstances be encapsulated in a lipid membrane. Depending upon the phage, the nucleic acid may be either DNA or RNA but typically not both and it can exist in various forms.

As used herein, "heterologous nucleic acid sequence" is any sequence placed at a location in the genome where it does not normally occur. A heterologous nucleic acid sequence may comprise a sequence that does not naturally occur in a particular bacteria/archaea and/or phage or it may comprise only sequences naturally found in the bacteria/archaea and/or phage, but placed at a non-normally occurring location in the genome. In some embodiments the heterologous nucleic acid sequence is not a natural phage sequence; in some embodiments it is a natural phage sequence, albeit from a different phage; while in still other embodiments it is a sequence that occurs naturally in the genome of the starting phage but is then moved to another site where it does not naturally occur, rendering it a heterologous sequence at that new site.

A "starting phage" or "starting phage genome" is a phage isolated from a natural or human made environment that has not been modified by genetic engineering, or the genome of such a phage.

A "recombinant phage" or "recombinant phage genome" is a phage that comprises a genome that has been genetically modified by insertion of a heterologous nucleic acid sequence into the phage, or the genome of the phage. In some embodiments the genome of a starting phage is modified by recombinant DNA technology to introduce a heterologous nucleic acid sequence into the genome at a defined site. In some embodiments the heterologous sequence is introduced with no corresponding loss of endogenous phage genomic nucleotides. In other words, if bases N1 and N2 are adjacent in the starting phage genome the heterologous sequence is inserted between N1 and N2. Thus, in the resulting recombinant genome the heterologous sequence is flanked by nucleotides N1 and N2. In some cases the heterologous sequence is inserted and endogenous nucleotides are removed or replaced with the exogenous sequence. For example, in some embodiments the exogenous sequence is inserted in place of some or all of an endogenous sequence which is removed. In some embodiments endogenous sequences are removed from a position in the phage genome distant from the site(s) of insertion of exogenous sequences.

A "coding sequence" or "open reading frame" is a sequence of nucleotides that encodes a polypeptide or protein. The termini of the coding sequence are a start codon and a stop codon.

As used herein, a "phage genome" includes naturally occurring phage genomes and derivatives thereof. Generally (though not necessarily), the derivatives possess the ability to propagate in the same hosts as the parent. In some embodiments the only difference between a naturally occurring phage genome and a derivative phage genome is at least one of a deletion and an addition of nucleotides from at least one end of the phage genome if the genome is linear or at least one point in the genome if the genome is circular.

As used herein, a "phage host cell" is a cell that can form phage from a particular type of phage genomic DNA. In some embodiments the phage genomic DNA is introduced into the cell by infection of the cell by a phage. That is, the phage binds to a receptor molecule on the outside of the host cell and injects its genomic DNA into the host cell. In some embodiments the phage genomic DNA is introduced into the cell using transformation or any other suitable technique. In some embodiments the phage genomic DNA is substantially pure when introduced into the cell. In some embodiments the phage genomic DNA is present in a vector when introduced into the cell. In one non-limiting exemplary embodiment the phage genomic DNA is present in a yeast artificial chromosome (YAC) that is introduced into the phage host cell by transformation or an equivalent technique. The phage genomic DNA is then copied and packaged into a phage particle following lysis of the phage host cell. The definition of "phage host cell" necessarily can vary from one phage to another. For example, *E. coli* may be a phage host cell for a particular type of phage while *Salmonella enterica* is not; and *Salmonella enterica* may be a phage host cell for another particular type of phage while *E. coli* is not.

As used herein, a "competent phage host cell" is a phage host cell that a phage particle can infect, and in which the phage's genome can direct production of phage particles from the cell. Thus, not all "phage host cells" are "competent phage host cells," but all "competent phage host cells" are "phage host cells."

As used herein, a "target microorganism" is the set of microorganisms that a detection assay is designed to detect. The "target microorganism" of the assay is the set of competent phage host cells of the recombinant phage used in the assay. In some embodiments the target microorganism of an assay is a single species of microorganism. In some embodiments the target microorganism of an assay is a single subspecies of microorganism. In some embodiments the target microorganism of an assay is a single strain of microorganism. In some embodiments the target microorganism comprises or consists of a single genus, species, subspecies, or strain of microorganism. In some embodiments the target microorganism comprises or consists of at least one genus, and/or at least one species, and/or at least one subspecies, and/or at least one strain of microorganism. In some embodiments the target microorganism of an assay comprises all known members of a single taxonomic group as well as some but not all members of another taxonomic group. Thus, for example, the target microorganism of an assay may be all members of a first genus and a subset of members of a second genus. In other embodiments the target microorganism of an assay is a more diverse group such as an entire genus or even a larger group. In some embodiments the target microorganism of an assay does not correspond to a generally accepted taxonomic classification. For example, the target microorganism of an assay may be a set of species of a genus of bacteria, and the set may not include all known strains of that genus. Alternatively or in addition, the target microorganism of an assay may be a set of subspecies of a species of bacteria, and the set may not include all known subspecies of that species. Alternatively or in addition, the target microorganism of an assay may be a set of strains of a species of bacteria, and the set may not include all known strains of that species. The composition of the "target microorganism" is determined by the host range of the recombinant phage(s) used in the assay. As disclosed herein, recombinant phage as disclosed herein provide specificity to the bacterial detection methods disclosed herein. In some embodiments a plurality of recombinant phage are used in an assay. If the specificity of at least two of the plurality of types of recombinant phage is different than the inclusion of the plurality of recombinant phage in the assay increases the scope of the target microorganisms of the assay. In some embodiments the specificity of at least one pair of recombinant phage used in an assay does not overlap. In some embodiments the specificity of all of the recombinant phage used in an assay are at least partially overlapping.

As used herein, a phage, including a recombinant phage, is "specific" for a target microorganism in the context of a detection method when the phage infects the target microorganism but does not infect other non-target microorganisms present in a sample tested by the assay method. A phage, including a recombinant phage, may be specific for a genus (e.g., E. coli) if the phage infects all known types of E. coli but it may also be considered specific for E. coli if it infects a subset of known types of E. coli but does not infect microorganisms that are not E. coli.

As used herein, a "collection device" is any device comprising a first portion designed to contact a solid surface suspected of comprising microbial contamination to remove and retain microbes present on the solid surface. The first portion collects and retains microbes in or on its surface. The first portion may be dry or wetted when the solid surface is contacted. Typically the collection device comprises a second portion for handling by a user. The second portion may be handled directly by the user or may be attached to a control means that moves the collection device. An example of such a device is a standard Q-tip swab. Another example is a Custom Sponge-Stick with Letheen Broth SSL10LET (manufactured by 3M). The 3M sponge stick with Letheen broth is a biocide-free cellulose sponge shipped in a sterile bag and hydrated with 10 mL of Letheen Broth. The plastic handle allows users to collect environmental samples without directly handling (and possibly contaminating) the sponge, as well as making it easier to reach into drains, pipes, and crevices to collect samples. The cellulose material collects and retains organisms in or on the sponge matrix. The Letheen Broth is present to help neutralize cleaning chemicals such as quaternary ammonia and preserve the viability of organisms for detection.

In some embodiments the first portion of the collection device comprises an organic material such as but not limited to cellulose, cotton, or other natural fibers that have useful properties such as at least one of a useful wettability, an ability to bind microbes under a first set of conditions and release the microbes under a second set of circumstances, resistance to abrasion and shelf life.

In some embodiments the first portion of the collection device comprises a synthetic material such as but not limited to polyester or polyurethane, that have useful properties such as at least one of a useful wettability, an ability to bind microbes under a first set of conditions and release the microbes under a second set of circumstances, resistance to abrasion and shelf life.

As used herein, "sensitivity" is the proportion of actual positive samples that are correctly identified as positive by an assay method. Actual positive samples are generally defined by using a validated assay used to detect the presence of a target microbe. In some embodiments the actual positives are defined by a method comprising culturing a sample to determine whether target microbes are present.

As used herein, "specificity" is the proportion of actual negative samples that are correctly identified as negative by an assay method. Actual negative samples are generally defined by using a validated assay used to detect the presence of a target microbe. In some embodiments the actual negatives are defined by a method comprising culturing a sample to determine whether target microbes are present.

As used herein, "accuracy" is the weighted composite of sensitivity and specificity in the overall sample group.

A. Phage

Phages include both bacteriophage and archaeophage, obligate intracellular parasites that multiply inside bacteria/archaea by making use of some or all of the host biosynthetic machinery (i.e., viruses that infect bacteria/archaea). Phages are obligate parasites with respect to both the step of identifying a host cell to infect and with respect to only being able to productively replicate their genome in an appropriate host cell. Though different phages may contain different materials, they all contain nucleic acid and protein, and may be covered by a lipid membrane. Depending upon the phage, the nucleic acid can be either DNA or RNA but not both and it can exist in various forms. The size of the nucleic acid varies depending upon the phage. The simplest phages only have genomes a few thousand nucleotides in size, while the more complex phages may have more than 100,000 nucleotides in their genome, in rare instances more than 1,000,000. The number of different kinds of protein and the amount of each kind of protein in the phage particle will vary depending upon the phage. The proteins function in infection and to protect the nucleic acid from nucleases in the environment.

Phages come in many different sizes and shapes. Most phages range in size from 24-200 nm in diameter. The head or capsid is composed of many copies of one or more different proteins. The nucleic acid is located in the head if it is present, which acts as a protective covering for it. Many but not all phages have tails attached to the phage head. The tail is a hollow tube through which the nucleic acid passes during infection. The size of the tail can vary and some phages do not even have a tail structure. In the more complex phages the tail is surrounded by a contractile sheath which contracts during infection of the bacterium. At the end of the tail, phages have a base plate and one or more tail fibers attached to it. The base plate and tail fibers are involved in the binding of the phage to the cell. Not all phages have base plates and tail fibers. In these instances other structures are involved in binding of the phage particle to the bacterium/archaea.

The first step in the infection process is the adsorption of the phage to the cell. This step is mediated by the tail fibers or by some analogous structure on those phages that lack tail fibers and it is reversible. The tail fibers attach to specific receptors on the cell and the host specificity of the phage (i.e. the bacteria/archaea that it is able to infect) is usually determined by the type of tail fibers that a phage has. The nature of the bacterial/archaeal receptor varies for different bacteria/archaea. Examples include proteins on the outer surface of the cell, constituents of the bacterial cell wall and membrane, e.g., LPS or teichoic acid, pili, and lipoproteins, to name a few. These biomolecules are on the cell for other purposes and phage have evolved to use them as receptors for infection.

The attachment of the phage to the cell via the tail fibers is a weak one and is reversible. Irreversible binding of phage to a cell is mediated by one or more of the components of the base plate. Phages lacking base plates have other ways of becoming tightly bound to the cell.

The irreversible binding of the phage to the cell results in the contraction of the sheath (for those phages which have a sheath) and the hollow tail fiber is pushed through the bacterial/archaeal envelope. Phages that don't have contractile sheaths use other mechanisms to get the phage particle through the bacterial/archaeal envelope. Some phages have enzymes that digest various components of the envelope.

When the phage has gotten through the envelope the nucleic acid from the head passes through the hollow tail and enters the cell. Usually, the only phage component that actually enters the cell is the nucleic acid. The remainder of the phage typically remains on the outside of the cell. There are some exceptions to this rule. This is different from animal cell viruses in which most of the virus particle usually gets into the cell.

Lytic or virulent phages are phages that can only multiply on bacteria/archaea and kill the cell by lysis at the end of the life cycle. The lifecycle of a lytic phage begins with an eclipse period. During the eclipse phase, no infectious phage particles can be found either inside or outside the cell. The phage nucleic acid takes over the host biosynthetic machinery and phage specified mRNAs and proteins are made. There is an orderly expression of phage directed macromolecular synthesis, just as one sees in animal virus infections. Early mRNAs code for early proteins that are needed for phage DNA synthesis and for shutting off host DNA, RNA and protein biosynthesis. In some cases the early proteins actually degrade the host chromosome. After phage DNA is made late mRNAs and late proteins are made. The late proteins are the structural proteins that comprise the phage as well as the proteins needed for lysis of the bacterial cell. Next, in the intracellular accumulation phase the nucleic acid and structural proteins that have been made are assembled and infectious phage particles accumulate within the cell. During the lysis and release phase the bacteria/archaea begin to lyse due to the accumulation of the phage lysis protein and intracellular phage are released into the medium. The number of particles released per infected cell can be as high as 1000 or more.

Lytic phage may be enumerated by a plaque assay. A plaque is a clear area that results in a lawn of bacterial/archaea grown on a solid media from the lysis of bacteria/archaea. The assay is performed at a low enough concentration of phage that each plaque arises from a single infectious phage. In the context of the assay, the infectious particle that gives rise to a plaque is called a PFU (plaque forming unit).

As described below, this disclosure provides recombinant phage comprising a genome comprising an open reading frame encoding a marker. The recombinant phage are based on a naturally occurring, or "starting phage."

In some embodiments of this disclosure a starting phage genome comprises at least 5 kilobases (kb), at least 10 kb, at least 15 kb, at least 20 kb, at least 25 kb, at least 30 kb, at least 35 kb, at least 40 kb, at least 45 kb, at least 50 kb, at least 55 kb, at least 60 kb, at least 65 kb, at least 70 kb, at least 75 kb, at least 80 kb, at least 85 kb, at least 90 kb, at least 95 kb, at least 100 kb, at least 105 kb, at least 110 kb, at least 115 kb, at least 120 kb, at least 125 kb, at least 130 kb, at least 135 kb, at least 140 kb, at least 145 kb, at least 150 kb, at least 175 kb, at least 200 kb, at least 225 kb, at least 250 kb, at least 275 kb, at least 300 kb, at least 325 kb, at least 350 kb, at least 325 kb, at least 350 kb, at least 375 kb, at least 400 kb, at least 425 kb, at least 450 kb, at least 475 kb, at least 500 kb, or more. In some embodiments of this disclosure a starting phage genome comprises from 5 kb to 50 kb, from 10 kb to 100 kb, from 50 kb to 200 kb, from 100 kb to 300 kb, from 200 kb to 400 kb, or from 300 kb to 500 kb.

In some embodiments of this disclosure a starting phage is a member of an order selected from Caudovirales, Microviridae, Corticoviridae, Tectiviridae, Leviviridae, Cystoviridae, Inoviridae, Lipothrixviridae, Rudiviridae, Plasmaviridae, and Fuselloviridae. In some embodiments the phage is a member of the order Caudovirales and is a member of a family selected from Myoviridae, Siphoviridae, and Podoviridae.

A primary criterion in selecting a starting phage is the host range of the phage. The host range of a phage may be defined using any method known in the art. Generally speaking, a method of defining the host range of a phage (i.e., a "host-range analysis") is performed by mixing the phage with each of a panel of host microbial cells under permissive conditions and determining whether the phage can infect the host and complete a lifecycle to lyse the host cells. In some embodiments the analysis alternatively or in addition also comprises determining whether the phage infects the host and become lysogenic.

In a phage host-range analysis the composition of the microbial panel used will depend on how the phage is to be used. A phage may be initially screened for its ability to infect different genera of bacteria, for example, such as *Escherichia, Pseudomonas, Staphylococcus, Salmonella*, and *Listeria*. A selected phage, such as a phage that infects and lyses a *Salmonella* strain can then optionally be screened further to determine which species or even strains of *Salmonella* it can infect and lyse.

The host range of a starting phage or a recombinant phage may be modified using any technique known in the art. In general, such techniques can be divided into two broad classes. The first is genetic modification, which may be rational, e.g., tail fiber swapping, or random, e.g., mutagenesis of targeted regions. The second is screening (either leveraging natural variations in phages or by introducing artificial variation into a population of phages such as with mutagenic agents. In some embodiments, a population of bacteriophages is incubated under permissive conditions in the presence of a non-permissive host. The population of bacteriophages comprises low-frequency variants with a different host range than the majority of phage in the population. Generating many populations of progeny bacteriophages and plating them on non-permissive hosts can lead to the isolation of progeny bacteriophages that display altered host range. In some embodiments the host range is expanded. In some embodiments the host range is shifted, meaning the loss of infective capability on some or all of the previously permissible hosts and the gain of new hosts. In some embodiments the modified host range is permanent and stable; in others it is transient. In some embodiments further rounds of selection on the same or different hosts converts a transient modified host range to a stable modified host range.

In some embodiments the starting phage or a recombinant phage is also selected based on at least one criterion in addition to host range. The at least one additional criteria may be selected from lifecycle characteristics, genome size and/or structure, natural resistance to bacterial defense systems, genome end structure, replication speed, burst size, infectivity, stability, and growth characteristics, among others. These features may also be modified in a starting phage or a recombinant phage, for example by use of the methods described in the preceding paragraph.

B. Recombinant Phage

In some embodiments a heterologous nucleic acid sequence is inserted into a starting phage genome to create a recombinant phage genome. In some embodiments the recombinant phage genome is further modified to create a different recombinant phage genome. In some embodiments the recombinant phage genome comprises at least one modification compared to the starting phage genome in addition to insertion of the heterologous nucleic acid sequence.

The heterologous nucleic acid sequence may be any nucleic acid sequence; however, it will most usually comprise at least one of an open reading frame and an expression control sequence. In some embodiments the heterologous nucleic acid sequence comprises an open reading frame and an expression control sequence. In some embodiments the expression control sequence is a promoter. In some embodiments it comprises at least two expression control sequences. In some embodiments the expression control sequence(s) is endogenous to the starting phage genome. In some embodiments it is not endogenous to the starting phage genome. In some embodiments the heterologous nucleic acid sequence comprises a nucleic acid sequence that is a modified version of an endogenous phage nucleic acid sequence. The open reading frame may encode a detectable marker. In some embodiments the length of the heterologous nucleic acid sequence is at least 100 bases, at least 200 based, at least 300 bases, at least 400 bases, at least 500 bases, at least 600 bases, at least 700 bases, at least 800 bases, at least 900 bases, at least 1.0 kilobase (kb), at least 1.1 kb, at least 1.2 kb, at least 1.3 kb, at least 1.4 kb, at least 1.5 kb, at least 1.6 kb, at least 1.7 kb, at least 1.8 kb, at least 1.9 kb, at least 2.0 kb, at least 2.1 kb, at least 2.2 kb, at least 2.3 kb, at least 2.4 kb, at least 2.5 kb, at least 2.6 kb, at least 2.7 kb, at least 2.8 kb, at least 2.9 kb, at least 3.0 kb, at least 3.1 kb, at least 3.2 kb, at least 3.3 kb, at least 3.4 kb, at least 3.5 kb, at least 3.6 kb, at least 3.7 kb, at least 3.8 kb, at least 3.9 kb, at least 4.0 kb, at least 4.5 kb, at least 5.0 kb, at least 5.5 kb, at least 5.5 kb, at least 6.0 kb, at least 6.5 kb, at least 7.0 kb, at least 7.5 kb, at least 8.0 kb, at least 8.5 kb, at least 9.0 kb, at least 9.5 kb, at least 10 kb, or more. In some embodiments the length of the heterologous nucleic acid sequence is 500 bases or less, 1.0 kb or less, 1.5 kb or less, 2.0 kb or less, 2.5 kb or less, 3.0 kb or less, 3.5 kb or less, 4.0 kb or less, 4.5 kb or less, 5.0 kb or less, 5.5 kb or less, 6.0 kb or less, 6.5 kb or less, 7.0 kb or less, 7.5 kb or less, 8.0 kb or less, 8.5 kb or less, 9.0 kb or less, 9.5 kb or less, or 10.0 kb or less.

In some embodiments the length of the heterologous nucleic acid sequence is from 100 to 500 bases, from 200 to 1,000 bases, from 500 to 1,000 bases, from 500 to 1,500 bases, from 1 kb to 2 kb, from 1.5 kb to 2.5 kb, from 2.0 kb to 3.0 kb, from 2.5 kb to 3.5 kb, from 3.0 kb to 4.0 kb, from 3.5 kb to 4.5 kb, from 4.0 kb to 5.0 kb, from 4.5 kb to 5.5 kb, from 5.0 kb to 6.0 kb, from 5.5 kb to 6.5 kb, from 6.0 kb to 7.0 kb, from 6.5 kb to 7.5 kb, from 7.0 kb to 8.0 kb, from 7.5 kb to 8.5 kb, from 8.0 kb to 9.0 kb, from 8.5 kb to 9.5 kb, or from 9.0 kb to 10.0 kb.

In some embodiments the ratio of the length of the heterologous nucleic acid sequence to the length of the starting phage genome is 0.05 or less, 0.10 or less, 0.15 or less, 0.20 or less, or 0.25 or less. In some embodiments the ratio of the length of the genome of the recombinant phage to the length of the genome of the corresponding starting phage is 1.05 or less, 1.10 or less, 1.15 or less, 1.20 or less, or 1.25 or less.

In some embodiments the heterologous nucleic acid sequence is inserted into the starting phage genome with no loss of endogenous starting phage genome sequence. In some embodiments the inserted heterologous nucleic acid sequence replaces endogenous starting phage genome sequence. In some such embodiments the heterologous nucleic acid sequence replaces an amount of endogenous genomic sequence that is less than the length of the heterologous nucleic acid sequence. Thus, in such embodiments the length of the recombinant phage genome is longer than the length of the starting phage genome. In some such embodiments the heterologous nucleic acid sequence replaces an amount of endogenous genomic sequence that is greater than the length of the heterologous nucleic acid sequence. Thus, in such embodiments the length of the recombinant phage genome is shorter than the length of the starting phage genome (unless additional heterologous sequences are added elsewhere in the genome). In some such embodiments the heterologous nucleic acid sequence replaces an amount of endogenous genomic sequence that is equal to the length of the heterologous nucleic acid sequence.

In some embodiments the heterologous nucleic acid sequence comprises an open reading frame.

In some embodiments the open reading frame encodes a detectable marker that confers at least one phenotype on a target microorganism host cell. The detectable marker may be a screenable marker and/or a selectable marker.

In some embodiments the heterologous nucleic acid sequence comprises at least one second open reading frame. In some embodiments the first and at least one second open reading frames are operatively linked to the same expression control sequence. In some embodiments the first and at least one second open reading frames are operatively linked to different expression control sequences.

In some embodiments the protein or polypeptide encoded by a heterologous open reading frame is modified to reduce cleavage by proteases present in phage host cells. For example, computational algorithms can be used to identify known protease cleavage sites and the sequence of the open reading frame may be modified using conservative substitutions to remove these sites. Alternatively, directed mutagenesis is used to evolve the open reading frame sequence to encode a product that has an increased resistance to at least one protease present in a phage host cell or in the culture of a phage host cell.

In some embodiments, recombinant phage can be constructed by direct transformation, for example, by transformation of engineered phage-YAC DNA into an appropriate host cell. These phage-YACs replicate, excise and package into infectious phage particles capable of repeated infection.

In this method, engineered YACs (yeast artificial chromosome) are recovered from yeast transformants comprising the YACs. In some embodiments this is accomplished by disrupting the yeast transformant by glass bead lysis thereby releasing the YACs from the transformed cells. The released YACs bearing phage are electroporated into an appropriate phage host cell and plated in a standard plaque assay. The inventors have produced plaques from a transformation of YACs bearing phage genomes. To date this has been successfully accomplished using E. coli phages (T3 and T7) and Salmonella phage (FelixO1). These results demonstrate production of functional phage from cloned phage genomes.

Any method known in the art can be used to make genetically modified phage from starting phage. For example, U.S. Pat. No. 5,824,468 discloses methods of making genetically modified phage. Alternative methods are disclosed in co-pending application Ser. No. 13/627,060, filed Sep. 26, 2012, and published as US 2013/0122549 A1 on May 16, 2013, which is hereby incorporated herein by reference. Alternative methods are disclosed in the Examples of this application.

C. Detectable Markers

Detectable markers include selectable and/or screenable markers. As used herein, a "selectable marker" is a marker that confers upon cells that possess the marker the ability to grow in the presence and/or absence of an agent that inhibits or stimulates, respectively, growth of similar cells that do not express the marker. Such cells can also be said to have a "selectable phenotype" by virtue of their expression of the selectable marker. For example, the ampicillin resistance gene (AmpR) confers the ability to grow in the presence of ampicillin on cells which possess and express the gene. (See Sutcliffe, J. G., *Proc Natl Acad Sci USA*. 1978 August; 75(8): 3737-3741.) Other nonlimiting examples include genes that confer resistance to chloramphenicol, kanamycin, and tetracycline. Other markers include URA3, TRP and LEU, which allow growth in the absence of said uracil, tryptophan and leucine, respectively.

As used herein, a "screenable marker" is a detectable label that that can be used as a basis to identify cells that express the marker. Such cells can also be said to have a "screenable phenotype" by virtue of their expression of the screenable marker. Any molecule that can be differentially detected and can be encoded by a recombinant phage can serve as a screenable marker. A screenable marker can be a nucleic acid molecule or a portion thereof, such as an RNA or a DNA molecule that is single or double stranded. Alternatively, a screenable marker can be a protein or a portion thereof. Suitable protein markers include enzymes that catalyze formation of a detectable reaction product. An example is a chemiluminescent protein such as luciferase or variations, such as luxAB, and β-galactosidase. Another example is the horseradish peroxidase enzyme. Proteins used to generate a luminescent signal fall into two broad categories: those that generate light directly (luciferases and related proteins) and those that are used to generate light indirectly as part of a chemical cascade (horseradish peroxidase). The most common bioluminescent proteins used in biological research are aequorin and luciferase. The former protein is derived from the jellyfish *Aequorea victoria* and can be used to determine calcium concentrations in solution. The luciferase family of proteins has been adapted for a broad range of experimental purposes. Luciferases from firefly and *Renilla* are the most commonly used in biological research. These proteins have also been genetically separated into two distinct functional domains that will generate light only when the proteins are closely co-localized. A variety of emission spectrum-shifted mutant derivatives of both of these proteins have been generated over the past decade. These have been used for multi-color imaging and co-localization within a living cell. The other groups of proteins used to generate chemiluminescent signal are peroxidases and phosphatases. Peroxidases generate peroxide that oxidizes luminol in a reaction that generates light. The most widely used of these is horseradish peroxidase (HRP), which has been used extensively for detection in western blots and ELISAs. A second group of proteins that have been employed in a similar fashion are alkaline phosphatases, which remove a phosphate from a substrate molecule, destabilizing it and initiating a cascade that results in the emission of light.

In some embodiments the heterologous nucleic acid sequence encoding a marker is selected from SEQ ID NO: 1; a sequence that is at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 99.5% homologous to SEQ ID NO: 1; and a sequence that hybridizes under stringent hybridization conditions to SEQ ID NO: 1. In some embodiments the marker is a protein comprising an amino acid sequence selected form SEQ ID NO: 2; a sequence that is at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 99.5% homologous to SEQ ID NO: 2; and an amino acid sequence encoded by a sequence that hybridizes under stringent hybridization conditions to SEQ ID NO: 1.

In some embodiments the heterologous nucleic acid sequence encoding a marker is selected from SEQ ID NO: 3; a sequence that is at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 99.5% homologous to SEQ ID NO: 3; and a sequence that hybridizes under stringent hybridization conditions to SEQ ID NO: 3. In some embodiments the marker is a protein comprising an amino acid sequence selected form SEQ ID NO: 4; a sequence that is at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 99.5% homologous to SEQ ID NO: 4; and an amino acid sequence encoded by a sequence that hybridizes under stringent hybridization conditions to SEQ ID NO: 3.

In some embodiments the marker is a luciferase or modified luciferase protein disclosed in paragraphs 0061 to 0093 of United States Patent Application Publication No. US 2010/0281552 A1. In some embodiments the heterologous nucleic acid sequence is a nucleic acid sequence that encodes a luciferase or modified luciferase protein disclosed in paragraphs 0061 to 0093 of United States Patent Application Publication No. US 2010/0281552 A1. Paragraphs 0061 to 0093 of United States Patent Application Publication No. US 2010/0281552 A1 are hereby incorporated herein by reference in their entirety for all purposes.

In some embodiments the marker is a luciferase or modified luciferase protein disclosed in paragraphs 0190 to 0206 of United States Patent Application Publication No. US 2012/0174242 A1. In some embodiments the heterologous nucleic acid sequence is a nucleic acid sequence that encodes a luciferase or modified luciferase protein disclosed in paragraphs 0190 to 0206 of United States Patent Application Publication No. US 2012/0174242 A1. Paragraphs 0190 to 0206 of United States Patent Application Publication No. US 2012/0174242 A1 are hereby incorporated herein by reference in their entirety for all purposes.

Other suitable screenable markers include fluorescent proteins. Fluorescent proteins include but are not limited to blue/UV fluorescent proteins (for example, TagBFP, Azurite, EBFP2, mKalama1, Sirius, Sapphire, and T-Sapphire), cyan fluorescent proteins (for example, ECFP, Cerulean, SCFP3A, mTurquoise, monomeric Midoriishi-Cyan, TagCFP, and mTFP1), green fluorescent proteins (for example, EGFP, Emerald, Superfolder GFP, Monomeric Azami Green, TagGFP2, mUKG, and mWasabi), yellow fluorescent proteins (for example, EYFP, Citrine, Venus, SYFP2, and TagYFP), orange fluorescent proteins (for example, Monomeric Kusabira-Orange, mKOK, mKO2, mOrange, and mOrange2), red fluorescent proteins (for example, mRaspberry, mCherry, mStrawberry, mTangerine, tdTomato, TagRFP, TagRFP-T, mApple, and mRuby), far-red fluorescent proteins (for example, mPlum, HcRed-Tandem, mKate2, mNeptune, and NirFP), near-IR fluorescent proteins (for example, TagRFP657, IFP1.4, and iRFP), long stokes-shift proteins (for example, mKeima Red, LSS-mKate1, and LSS-mKate2), photoactivatible fluorescent proteins (for example, PA-GFP, PAmCherry1, and PATagRFP), photoconvertible fluorescent proteins (for example, Kaede (green), Kaede (red), KikGR1 (green), KikGR1 (red), PS-CFP2, PS-CFP2, mEos2 (green), mEos2 (red), PSmOrange, and PSmOrange), and photoswitchable fluorescent proteins (for example, Dronpa). Several variants and alternatives to the listed examples are also well known to those of skill in the art and may be substituted in appropriate applications.

Other suitable markers include epitopes. For example, a protein comprising an epitope that can be detected with an antibody or other binding molecule is an example of a screenable marker. An antibody that recognizes the epitope can be directly linked to a signal generating moiety (such as by covalent attachment of a chemiluminescent or fluorescent protein) or it can be detected using at least one additional binding reagent such as a secondary antibody, directly linked to a signal generating moiety, for example. In some embodiments the epitope is not present in the proteins of the phage or the target microorganism so detection of the epitope in a sample indicates that the protein comprising the epitope was produced by the microorganism following infection by the recombinant phage comprising a gene encoding the protein comprising the epitope. In other embodiments the marker may be a purification tag in the context of a protein that is naturally present in the target microorganism or the phage. For example, the tag (e.g., a 6-His tag) can be used to purify the heterologous protein from other bacterial or phage proteins and the purified protein can then be detected, for example using an antibody.

D. Recombinant Phage Production

Skilled artisans are aware of many different methods that may be used and/or adapted for production of recombinant phage for use in the methods of this disclosure. An exemplary method is presented in Example 10. In general, for example, a phage lysate may be prepared using a recombinant phage according to this disclosure. To prepare the phage lysate a single colony of a competent phage host cell is inoculated in suitable liquid growth media and grown overnight at in a floor shaker. The next day, an aliquot of the culture is diluted into a larger volume of liquid growth media and grown until the $OD_{600}$ reaches an appropriate concentration. The culture is then inoculated with a recombinant phage to be propagated. The flask is then further cultured until lysate is cleared (E.g., $OD_{600}$ of <0.02). The lysate is then filtered through a 0.45 μm vacuum filter and then through a 0.22 μm vacuum filter, and stored at 4° C. until further purification.

Before use, phage particles are purified using methods generally as described in Sambrook and Russell, Molecular Cloning Volume 1, 3rd edition 2001. Briefly, phage particles are precipitated from the lysate using Protocol 6, "Precipitation of Bacteriophage Lambda Particles from Large-scale Lysates", at pp 2.43-2.44 (which is hereby incorporated herein by reference) with the following exceptions: the DNase and RNase steps were omitted as were the chloroform extraction steps. Phage particles are then purified using cesium chloride gradients using protocol 8, "Purification of Bacteriophage Lambda Particles by Isopycnic Centrifugation through CsCl Gradients", at pp 2.47-2.51 (which is hereby incorporated herein by reference), with the following exceptions: Step gradients are spun using the SW28 rotor for 2 hours at 22,000 rpm in a Beckman XL-90 ultracentrifuge; and Equilibrium gradients were spun using the 70.1ti rotor for 24 hours at 47,000 rpm in a Beckman XL-90 ultracentrifuge.

Upon harvest of the phage band from the equilibrium gradient, phages are dialyzed against 4 L of SM buffer in a Pierce G2 Slide-a-lyzer cassette (10,000 MWCO) for 24 h at 4° C. Phage stocks are then stored at 4 C until use.

As described herein it has been discovered that marker protein produced during production of the phage lysate may contaminate the phage stock produced. Contaminating marker will be added to the microbial detection assay together with the phage and may increase the background of the assay. In some embodiments this will in turn decrease the signal to noise ration of the assay compared to what it would be if the phage stock did not contain marker protein. This in turn may reduce the sensitivity and/or accuracy of the assay. A method described herein may optionally be used to catalytically inactivate marker protein present in the phage stock and thereby reduce the amount of active marker protein present in the phage stock. The method is based on the observation of the inventors that exposing a phage stock comprising a recombinant phage comprising a marker protein that is an enzyme to a substrate of the enzyme leads to catalytic inactivation of that enzyme (marker protein). In this way the amount of active marker protein present in the phage stock is reduced which may in some embodiments increase the signal to noise ratio attainable using the phage stock. This in turn may increase the sensitivity and/or accuracy of methods that use the phage stock.

As used herein, "catalytic inactivation" refers to exposure of a phage stock comprising a marker that is an enzyme to at least one condition that substantially reduces the catalytic activity of the marker protein. In this context substantially reduces means a reduction of at least about 50%, at least about 60%, at least about 70%, at least about 75%, at least about 80%, at least about 85%, at least about 90%, or at least about 95%. In some embodiments the exposure to at least one condition that substantially reduces the catalytic activity of the marker protein results in a reduction of the pfu/ml of the phage stock of less than about 25%, less than about 20%, less than about 15%, less than about 10%, or less than about 5%. In some embodiments the exposure to catalytic inactivation conditions is for a period of time of from about 1 hour to about 24 hours, from about 2 hours to about 12 hours, from about 3 hours to about 12 hours, from about 3 hours to about 6 hours, or from about 6 hours to about 24 hours.

In some embodiments the marker protein is a luciferase. In some embodiments the level of relative luminosity units (arising from contaminating marker luciferase protein) present in the phage stock following catalytic inactivation is less than $1\times10^{-4}$, less than $9\times10^{-5}$, less than $8\times10^{-5\prime}$, less than $7\times10^{-5}$, less than $6\times10^{-5}$, or less than $5\times10^{-5}$.

E. Target Microorganisms

The recombinant phage disclosed herein and the methods disclosed herein may be used to infect and detect any type of archaea and/or bacteria. In some embodiments the archaea is a Euryarcheota. In some embodiments the archaea is a Crenarcheota. In some embodiments the bacteria is a member of a phyla selected from Actinobacteria, Aquificae, Armatimonadetes, Bacteroidetes, Caldiserica, Chlamydiae, Chloroflexi, Chrysiogenetes, Cyanobacteria, Deferribacteres, Deinococcus-Thermus, Dictyoglomi, Elusimicrobia, Fibrobacteres, Firmicutes, Fusobacteria, Gemmatimonadetes, Nitrospirae, Planctomycetes, Proteobacteria, Spirochaetes, Synergistets, Tenericutes, Thermodesulfobacteria, Thermotogae. In some embodiments the bacteria is at least one Firmicutes selected from *Bacillus*, *Listeria*, and *Staphylococcus*. In some embodiments the bacteria is at least one Proteobacteria selected from *Acidobacillus, Aeromonas, Burkholderia, Neisseria, Shewanella, Citrobacter, Enterobacter, Erwinia, Escherichia, Klebsiella, Kluyvera, Morganella, Salmonella, Shigella, Yersinia, Coxiella, Rickettsia, Legionella, Avibacterium, Haemophilus, Pasteurella, Acinetobacter, Moraxella, Pseudomonas, Vibrio, Xanthomonas.*

In some embodiments the target bacteria is at least one Tenericutes selected from *Mycoplasma, Spiroplasma*, and *Ureaplasma*.

Common bacterial contaminates of food that may be detected using the phage and methods disclosed herein include, without limitation, *Salmonella, E. coli* (including without limitation pathogenic *E. coli, E. coli* O157:H7, Shiga-toxin producing *E. coli, E. coli* O26, O *E. coli* 111, *E. coli* O103, *E. coli* O121, *E. coli* O45 and *E. coli* O145), coliform bacteria (which include without limitation, *Citrobacter, Enterobacter, Hathia, Klebsiella, Serratia*), *Shigella, Listeria* (including without limitation *Listeria monocytogenes*), *Clostridium* (including without limitation *Clostridium botulinum* and *Clostridium perfringens*), *Vibrio* (including without limitation *Vibrio cholera* and *Vibrio vulnificus*), Enterobacteriacae, *Staphylococcus* (including without limitation *Staphylococcus aureus* and *Staphylococcus epidermis*), *Bacillus* (including without limitation *Bacillus cereus*), *Campylobacter* (including without limitation *Campylobacter jejuni*), *Pseudomonas, Streptococcus, Acinetobacter, Klebsiella, Campylobacter*, and *Yersinia*.

Common *Listeria* species include, without limitation, *Listeria innocua, Listeria monocytogenes, Listeria seeligeri, Listeria ivanovii, Listeria grayi, Listeria marthii, Listeria rocourti, Listeria welshimeri, Listeria floridensis, Listeria aquatic, Listeria cornellensis, Listeria riparia*, and *Listeria grandensis*. Some of which have been recently described (see Bakker et al., Int. J. of Systematic and Evolutionary Microbiology. 2014. 64: 1-8.)

F. Methods of Detecting the Detectable Marker

The detectable marker encoded by the heterologous nucleic acid sequence may be detected by any method known in the art. Skilled artisans will appreciate that in many embodiments the detectable marker may be detected using a method suited specifically to the class of marker used or the type of marker used. For example, if the detectable marker is a chemiluminescent or fluorescent protein, for example, the marker will often be detected by measuring the amount of light produced from the sample under appropriate conditions. For example, if the detectable marker is a luciferase the marker is detected by providing a substrate to the luciferase under conditions that allow the generation of light in a reaction catalyzed by the luciferase. For example, the chemical reaction catalyzed by firefly luciferase takes place in two steps:

luciferin+ATP→luciferyl adenylate+Ppi; and      1)

luciferyl adenylate+$O_2$→oxyluciferin+AMP+light.      2)

Light is emitted because the reaction forms oxyluciferin in an electronically excited state. The reaction releases a photon of light as oxyluciferin returns to the ground state. Step 1 is catalyzed by firefly luciferase. Accordingly, if the detectable marker is a firefly luciferase the marker may be detected by providing the luciferin substrate to the luciferase under conditions that allow the generation of light in a reaction catalyzed by the luciferase.

The chemical reaction for coelenterazine, of which Nano-Luc® is a derivative, proceeds as follows.

coelenterazine+$O_2$→coelenterazine-peroxide      1)

coelenterazine-peroxide→coelenteramide anion+ $CO_2$+light      2)

Light is emitted because the coelenterazine-peroxide decomposes spontaneously. More specifically the dioxetanone four-member ring splits the bonds as in the case of beetle luciferin. The exited state of the amide anion of coelenteramide emits light when the energy level transitions to the ground state, resulting in the emission of light in the 450-470 nm range, i.e. blue light in the visible spectrum.

In some embodiments the detectable marker may be detected using a method that is not suited specifically to the type of marker used. For example, the marker encoded by the heterologous nucleic acid sequence may be detected by measuring production of the marker protein using a standard method of measuring production of a protein of interest by a cell. For example, total protein or a fraction of total protein may be recovered from the sample, run on a polyacrylamide gel, and the gel stained with Coommassi stain to visualize the production of the marker protein. In a variation on this method the gel may be analyzed by Western blotting using an antibody, such as an antibody specific for the marker protein in order to detect production of the marker.

In some embodiments the detectable marker comprises a tag that is used for detection of production of the marker in the sample. In some embodiments the tag is an affinity tag used to purify and/or concentrate marker produced in the sample prior to detection. In some embodiments the marker is a 6×His tag. In some embodiments the tag is an epitope specifically recognized by an antibody that is used to purify and/or concentrate marker produced in the sample prior to detection, and/or that is used to detect the marker.

In some embodiments the marker is detected by a method that comprises direct observation of target microbe cells. As used herein, "direct observation" means that the method comprises identifying at least one cell as a spatially localized source of marker production. An example of such a method is use of a recombinant lysogenic phage to deliver the heterologous nucleic acid sequence encoding a fluorescent marker to a target microbe and then using a microscope to identify at least one cell that is fluorescent under appropriate illumination as a result of production of the marker protein.

In some embodiments the marker is detected by a method that does not comprise direct observation of target microbe cells. Such indirect observation methods do not comprise identifying at least one cell as a local source of marker production. Instead, the amount of marker produced in a sample is measured to determine indirectly the number of target microbes present in the sample that the recombinant phage has infected and which are producing the marker encoded by the heterologous nucleic acid sequence.

When the marker is a luciferase, in some embodiments assaying the sample to detect the presence and/or absence of the luciferase marker to determine the presence and/or absence of the target microbe comprises combining the marker produced by the target microbe with a luciferase substrate. In some embodiments the luciferase substrate is selected from a luciferin or a derivative thereof, and a coelenterazine or a derivative thereof. In some embodiments the coelenterazine or a derivative thereof is a molecule disclosed in paragraphs 0157 to 0189 of United States Patent Application Publication No. US 2012/0174242 A1.

The presence of the detectable marker may be assayed in the presence of the solid substrate or it may be assayed after separating an aliquot of produced marker from the phage-exposed collection device and/or phage-exposed solid substrate. For example, if a solid substrate surface (e.g., a drain in a food processing plant) is contacted with a collection device (e.g., 3M sponge stick); the collection device is contacted with a recombinant phage capable of infecting the target microbe and comprising a heterologous nucleic acid sequence encoding a marker, to provide a phage-exposed collection device; and conditions are provided to the phage-exposed collection device sufficient to allow the recombinant phage to infect a target microbe cell present in association with the collection device and production of the marker encoded by the heterologous nucleic acid sequence by the target microbe cell, the result is a solution comprising the collection device and further comprising produced marker. The solution may be assayed directly in the presence of the collection device or an aliquot may be removed and separated from the collection device and then assayed for the presence of the marker. Skilled artisans will appreciate that many permutations and variations on these procedures may be implemented in view of this disclosure. In general, a threshold value is applied to the assay to detect the presence of the detectable marker in order to determine whether the sample is positive or negative for the presence of the detectable marker (and therefore for the target microbe). In some embodiments the LLOD of the assay is determined by: (1) measuring the signal present in a set of control samples; and (2) adding three standard deviations to the mean measured signal. If the signal detected in a test assay is at or above the LLOD the test sample is scored as positive and if not then it is scored as negative. Skilled artisans are aware of many alternative approaches that may be substituted in appropriate circumstances.

In some embodiments the total amount of marker is assayed directly or indirectly in a continuous fashion. If the total amount of marker reaches a threshold at any time within a defined time period the assay is scored as positive.

G. Workflow

Skilled artisans will appreciate that the methods of this disclosure encompass and enable many different workflows for assaying microbial contamination. A non-limiting example is as follows.

1. Sample Collection and Preparation

Solid phase samples are collected using a Custom Sponge-Stick with Letheen Broth SSL10LET (3M). The 3M sponge stick with Letheen broth is a biocide-free cellulose sponge shipped in a sterile bag and hydrated with 10 mL of Letheen Broth. The plastic handle allows users to collect environmental samples without directly handling (and possibly contaminating) the sponge, as well as making it easier to reach into drains, pipes, and crevices to collect samples. The cellulose material collects and retains organisms in or on the sponge matrix. The Letheen Broth is present to help neutralize cleaning chemicals such as quaternary ammonia and preserve the viability of organisms for detection.

The plastic handle comes with a thumb guide to inform the point beyond which the user should refrain from touching to avoid possible contamination. Once the sample has been collected, the sponge is returned to the bag, and the plastic handle may be snapped off, allowing the bag to be sealed with only the sponge inside Remove a pre-moistened 3M Sponge Stick in Letheen Broth from the storage bag and swab a 4"×4" solid surface to collect following manufacturer's instructions. After collection return the sponge stick to the storage bag and close the bag.

After collecting a set of the samples, label a 50 mL conical tube for each environmental sample collected.

To prepare phage cocktail, add a pre-measured aliquot of at least one recombinant phage at a concentration of $1\times10^6$ to $1\times10^{11}$ pfu/ml. In another embodiment, the at least one recombinant phage may be at a concentration of $1\times10^7$ to $1\times10^8$ pfu/ml. In another embodiment, the at least one recombinant phage may be at a concentration of $1.5\times10^7$ pfu/ml. In another embodiment, three different recombinant phage may each be at a concentration of $1.5\times10^7$ pfu/m. The pre-measure recombinant phage are added to the Sponge Infection Buffer (SIB). The sponge infection buffer comprises at least one nutrient, at least one selective agent suitable to inhibit growth of a at least one non-target microbe in an environmental sample, at least one vitamin, at least one divalent metal, at least one buffering agent capable of maintain the composition at a pH of 7.0-7.5, at least one agent suitable to neutralize a sanitizer present in said environmental sample and at least one agent to prevent the decomposition of luciferin.

The sponge infection buffer may comprise half-strength Brain Heart Infusion (BHI) medium (18.5 g/L Difco BHI medium) supplemented with 5% weight/volume glucose, 1% volume/volume glycerol, 1% weight/volume Lithium Chloride, and 0.002% weight/volume Nalidixic Acid. This combination of supplements promotes *Listeria* recovery and growth inhibition of competitor microorganisms during the infection process.

In an alternative embodiment, the buffer may comprise the components of Table 1.

TABLE 1

| Components | Group | Function |
|---|---|---|
| 1x Brain Heart Infusion | Media (nutrients) | Support recovery and growth of stressed cells (provide hydrolyzed amino acids, sugars, minerals) |
| 0.5% LiCl 0.002% nalidixic acid | Selective agents | Prevent or limit growth of competing biologicals |
| 0.2% yeast extract | Vitamins (B complex) | Prevent oxidative stress |
| 2 mM CaCl2 | Divalent metals | Support enzymatic functions of cells, support phage activity |
| 40 mM HEPES, pH 7.4 | Buffering agents | Neutralize environmental pH extremes |
| 1 mM sodium metabisulfite | Neutralizer of sanitizers, oxygen scavenger | Prevent oxidative stress, neutralize glutaraldehyde, formaldehyde |
| 0.1% sodium thiosulfate | Neutralizer of sanitizers, oxygen scavenger | Neutralize halogens (iodine, chlorine, sodium hypochlorite, chlorine dioxide, peroxides, peroxyacids) |
| 0.5% Polysorbate 80 | Neutralizer of sanitizers, Non-ionic detergent | Neutralize biguanides (chlorhexidine), bis-phenols (hexachlorophene), phenolic compounds, cresols, formalin, to some extent quaternary ammonium compounds, organic acids, parabens, alcohols |
| 0.1% lecithin | Neutralizer of sanitizers, Emulsifier | Neutralize quaternary ammonium compounds, parabens |

The components of a sponge infection buffer are shown in the first column, in the second column, a category to which these components belong and in the third column a brief description of the role of these components in on sponge infection. It should be appreciated that some of the components of the buffer may be categorized into multiple groups. For example, HEPES buffer may serve as a buffering agent or as an agent to prevent the decomposition of luciferin. Furthermore, neutralizing agents may serve to neutralize chemicals or sanitizers that may be present in a target zone for collecting an environmental sample and these components may further serve to prevent the decomposition of luciferin.

2. Sample Infection:

To optionally allow for independent confirmation of presumed positive samples, the Letheen broth is optionally recovered from the sample. Holding the bag on an angle, squeeze the sponge to remove all of the liquid being careful to not allow reabsorption of the liquid into the sponge. Open the bag and using a serological pipette, transfer the liquid to the corresponding pre-labeled 50 mL conical.

Add 6 ml of the Sponge Infection Buffer with the added recombinant phage at a concentration of $1.5 \times 10^7$ pfu/ml final concentration. It should be appreciated that more than one recombinant phage may be used in an assay. For example, three recombinant phage may be used, each at a concentration of $1.5 \times 10^7$ pfu/ml.

Equilibrate the SIB into the sponge by massaging the sponge by gently squeezing, taking care not to allow the liquid to foam, about 15 times. Reabsorb all of the liquid back into the sponge after completing the massage.

Prepare 2 negative sponges by treating 2 sterile 3M Sponge sticks using the same sample handling process outlined above.

Place all sponges at 30° C.

3. Sample Specific Negatives

To optionally allow for correction of non-specific background present in the assay, a sample is optionally collected from each infection after 30 minutes.

Remove the sponges from 30° C. incubator and massage the sponge by gently squeezing, taking care not to allow the liquid to foam, about 15 times.

Squeeze all liquid out of sponge into bag taking care to hold the sponge in the bag but away from the liquid so as to avoid re-absorption by the sponge.

Transfer 300 uL to a sterile microcentrifuge tube and place the microcentrifuge tubes at 4 C.

To normalize the negatives and account for sponge-to-sponge variability in signal, add 150 uL from each of the 2 negative sponges to each of four microcentrifuge tubes.

Reclose the bag and massage by gently squeezing, taking care not to allow the liquid to foam, for about 15 seconds.

Reabsorb the liquid into the sponge.

Place sponges back at 30° C.

4. Timepoint Read

Reconstitute NanoGlo reagent by mixing NanoGlo Buffer and NanoGlo Substrate following manufacturer's instructions.

After four hours of incubation remove the samples from the incubator and massage the sponge for about 15 seconds. It should be appreciated, that in some embodiments of the method incubation time may vary such that the time from contacting the sample with the recombinant phage to detecting the presence or absence of the target microbe may take between 1 minute and 6 hours. In some embodiments, this time may be 4 hours or less. In some embodiments, this time may be hours or less.

Squeeze all liquid out of sponge into bag taking care to hold the sponge in the bag but away from the liquid so as to avoid re-absorption by the sponge.

Transfer 300 uL to a sterile microcentrifuge tube.

Spin microcentrifuge tubes at 16,100 rcf for 1 minute.

Transfer supernatant to a clean low-photon microcentrifuge tube.

Read the transferred samples in the Sirius L for 32 seconds, injecting 300 uL of NanoGlo Reagent (Promega Catalogue #N1130 or N1150) after 10 seconds.

To normalize the negatives and account for sponge-to-sponge variability in signal add 150 uL from each of the 2 negative sponges to each of four microcentrifuge tubes.

5. Sample Specific Negatives Read at 4 Hours

Remove microcentrifuge tubes from 4 C.

Spin at 16,100 rcf for 1 minute.

Transfer supernatants to a clean low-photon microcentrifuge tube.

Read samples same as 4 hour incubation samples.

Additional exemplary and non-limiting workflows are provided in the examples.

H. Target Cell Expansion

Methods of determining the presence and/or absence of a target microbe in a sample have typically required a step in which target cells are enriched in a sample by exposing the sample to cell growth conditions to expand the number of target cells present in positive samples. That expansion step is either performed prior to performing a detection method or it is itself integral to the detection method. In one instantiation the selective expansion is performed using microbe-specific enrichment media. This kind of media does necessitate the growth of the microbe to be enriched that is generally longer than a traditional culture broth. Enrichment broth contains both beneficial compounds for the growth of the target microbe, as well as inhibitory compounds for other microbes that are detrimental to the growth of the target microbe, or to the downstream assay steps. Continuing enrichment of the target microbe on different selective media is a method of assaying for the presence of the target microbe. Methods known in the art for example for food samples or food production environments or pharmaceutical environments can be found in the USDA Microbial Laboratory Guide (USDA-MLG), or the FDA Bacteriological Assay Methods volume (FDA-BAM). These methods take multiple days to arrive at a result that with high confidence can identify the target microbe. Other methods use molecular techniques such as enzyme-linked immunosorbent assays (ELISAs), lateral flow assay formats, or PCR-based detection methods. One ELISA lateral flow-based method is for example Biomerieux' VIDAS® assay. In that workflow, the sample is enriched for 24-48 hours in a specific enrichment medium, before it is treated specifically and then processed further using heat treatment and an automated ELISA lateral-flow workflow. The time to result post-enrichment is 90-120 minutes. A PCR-based approach focuses on amplifying identifying sequences from the target microbe. One assay is DuPont's BAX® system. In that workflow the sample is enriched for 24-28 hours in a specific enrichment medium, before it is treated specifically and then processed further, extracting the nucleic acid and manually processing the sample.

The methods disclosed herein may comprise a target cell expansion step. However, in several embodiments the methods of this disclosure do not comprise target cell expansion. Surprisingly, the inventors have found that in several embodiments a lower limit of detection of as low as 100 cells, 10 cells, or even a single cell may be achieved without expansion in certain embodiments. In certain embodiments this feature enables the methods of this disclosure to provide results more rapidly than prior art methods that comprise an expansion of target cells.

In some embodiments, assaying the phage-exposed environmental sample to detect the presence or absence of the marker to determine the presence or absence of the target microbe has a lower limit of detection of 100 target microbe cells 30 minutes after contacting the environmental sample with the recombinant phage. In some embodiments, assaying the phage-exposed environmental sample to detect the presence or absence of the marker to determine the presence or absence of the target microbe has a lower limit of detection of 10 target microbe cells 60 minutes after contacting the environmental sample with the recombinant phage. In some embodiments, assaying the phage-exposed environmental sample to detect the presence or absence of the marker to determine the presence or absence of the target microbe comprises a lower limit of detection of a single target microbe cell 180 minutes after contacting the environmental sample with the recombinant phage.

While the methods and recombinant phage disclosed herein in general render target cell expansion unnecessarily in many contexts, in some embodiments the methods of this disclosure comprise an expansion of target cells in a sample. Expansion will generally increase the sensitivity of an assay in comparison to a comparable assay done without an expansion step. It is presently believed that in some embodiments of the methods of this disclosure expansion of a sample from a source enables microbial cell detection at a lower limit of detection than would be achieved in a similar method that does not comprise expansion of target cells. In the course of expansion a single cell may divide at least one time so that the number of cells infected by phage during the course of the assay is greater than the number of cells that would be infected by phage during the course of a similar assay that does not comprise expansion of target cells. In some embodiments the expansion is for a period of time of from 10 minutes to 12 hours. In some embodiments the expansion is for a period of time of from 30 minutes to 8 hours. In some embodiments the expansion is for a period of time of from 1 hour to 8 hours. In some embodiments the expansion is for a period of time of from 2 hours to 6 hours. In some embodiments expansion is for a period of time sufficient to allow an average of at least 1 cell division of any living target microbes present in the sample. In some embodiments expansion is for a period of time sufficient to allow an average of at least 2 cell divisions of any living target microbes present in the sample. In some embodiments expansion is for a period of time sufficient to allow an average of at least 3 cell divisions of any living target microbes present in the sample. In some embodiments expansion is for a period of time sufficient to allow an average of at least 4 cell divisions of any living target microbes present in the sample. In some embodiments expansion is for a period of time sufficient to allow an average of at least 5 cell divisions of any living target microbes present in the sample. In some embodiments expansion is for a period of time sufficient to allow an average of at least 10 cell divisions of any living target microbes present in the sample. In some embodiments expansion is for a period of time sufficient to allow an average of from 1 to 10 cell divisions of any living target microbes present in the sample. In some embodiments expansion is for a period of time sufficient to allow an average of from 2 to 8 cell divisions of any living target microbes present in the sample. In some embodiments expansion is for a period of time sufficient to allow an average of from 3 to 6 cell divisions of any living target microbes present in the sample. In some embodiments expansion is for a period of time sufficient to allow for an average of about 1, about 2, about 3, about 4, about 5, about 6, about 7, about 8, about 9, or about 10 cell divisions of any living target microbes present in the sample.

In some embodiments a sample is split into at least two parts; a first part is used directly for a phage-based target microbe detection assay of this disclosure; and the second part is reserved for one or more uses selected from a confirmation phage-based target microbe detection assay and a different assay. In some embodiments the sample is expanded prior to separation of the parts while in other embodiments it is not. One or more of the parts may also be expanded after splitting.

I. Detection without Cell Proliferation

When phage infect target microbial cells they quickly co-opt the host cell's metabolic machinery for production of phage proteins and if the phage is lytic the host cell is soon lysed. Accordingly, infection of a microbial target cells in a sample by a phage has the effect of stopping target cell proliferation in the sample and ultimately results in lysis of all target cells in the sample. Thus, in some embodiments of the methods the concentration of phage used in the assay is high enough to substantially stop all host cell proliferation in the sample. In this context "substantially stopped" means that no host cells in the sample complete more than one full cell division cycle following contacting the sample with phage. People skilled in the art generally recognize the multiplicity of infection or MOI as a metric for the percentage of a population that is infected with an infectious unit. This is a statistical process and is generally understood to be modeled following a Poisson distribution, i.e. a MOI of 3 means that 95% of the population are infected with at least 1 infectious unit, whereas a MOI of 8 means that 100% of the population are infected.

One advantage of such embodiments is that handling and processing of the assay and disposal of the container in which the assay is conducted is safe and not likely to result in contamination by target microbes. This can be useful in contexts such as medical diagnosis and monitoring of food contamination, where it is imperative that microbial contaminants are not spread. It also increases the safety of the user of the assay.

J. Characterizing Bacterial Contamination

The high sensitivity and rapid speed of the assays disclosed herein enable methods of comparing bacterial contamination among a plurality of samples with a high accuracy. Accordingly, this disclosure also provides methods of comparing bacterial contamination among a plurality of solid substrates and/or of comparing bacterial contamination of one or a plurality of solid substrates over time.

In some embodiments at least two of the plurality of solid substrates are determined to contain different numbers of cells of the target microbe. This information may be used to characterize at least one feature of spread of contamination by the target microbe.

In some embodiments at least two of the plurality of samples are determined to contain about the same number of cells of the target microbe. This information may be used to characterize at least one feature of spread of contamination by the target microbe.

In some embodiments the plurality of solid substrates comprise samples collected from the same source at different timepoints. If a solid substrate analyzed at time T1 shows a first level of contamination by a target microbe and a subsequent analysis of the same solid substrate at time T2 shows a higher level of contamination by the target microbe in the sample, this indicates an increase in the level of contamination of the solid substrate by the target microbe during the interval of T1 to T2. Alternatively, if a solid substrate analyzed at time T1 shows a first level of contamination by a target microbe and a subsequent analysis of the same solid substrate at time T2 shows a lower level of contamination by the target microbe in the sample, this indicates a decrease in the level of contamination of the solid substrate by the target microbe during the interval of T1 to T2. Thus, this disclosure also provides methods of comparing a change in the level of contamination of a solid substrate by a target microbe over time.

In some embodiments the plurality of samples comprise samples collected from different solid substrate sources. If a sample collected from a source S1 shows a first level of contamination by a target microbe in the sample and a sample collected from a source S2 shows a higher level of contamination by the target microbe in the sample, this indicates that the level of contamination by the target microbe of source S2 is higher than the level of contamination by the target microbe of source S1. Thus, this disclosure also provides methods of comparing a level of contamination of different sources by a target microbe.

In some embodiments the plurality of samples comprises samples collected from at least one source at different timepoints and also comprises a plurality of samples collected from different sources. The plurality of samples collected from different sources may comprise samples collected at the same and/or different timepoints.

In some embodiments of the methods a different number of cells of the target microbe is determined to be present in the at least two samples and this difference is used to characterize at least one feature of spread of contamination by the target microbe. In some embodiments the at least one feature is a timecourse of the contamination. In some embodiments the at least one feature is a spatial distribution of the contamination.

In some embodiments of the methods a different number of cells of the target microbe is determined to be present in the at least two samples and this difference is used to monitor remediation of contamination by the target microbe. In some embodiments the at least one feature is a timecourse of the contamination. In some embodiments the at least one feature is a spatial distribution of the contamination.

In some embodiments about the same number of cells of the target microbe is determined to be present in the at least two samples and this feature is used to characterize at least one feature of spread of contamination by the target microbe. In some embodiments the at least one feature is a timecourse of the contamination. In some embodiments the at least one feature is a spatial distribution of the contamination.

In some embodiments of the methods about the same number of cells of the target microbe is determined to be present in the at least two samples and this feature is used to monitor remediation of contamination by the target microbe. In some embodiments the at least one feature is a timecourse of the contamination. In some embodiments the at least one feature is a spatial distribution of the contamination.

The recombinant phage of this disclosure may be used to detect the presence of bacteria. Detection of target bacteria is based on the ability of the recombinant phage to bind to a target bacteria, transfer of the phage genome into the target bacteria, and expression of the heterologous nucleic acid sequence encoding a marker by the bacteria. Accordingly, the specificity of a method of detecting target bacteria using recombinant phage comprising a heterologous nucleic acid sequence encoding a marker is based on the range of bacterial types that support expression of the marker following exposure to the phage. Sometimes the range of bacterial types that support expression of the marker following exposure to the phage is referred to herein as the "host range" of the phage. The set of bacterial types that make up the host range of the phage is sometimes referred to herein as "target bacteria" for the K. Amplification of Heterologous Marker Nucleic Acid Sequences Introduced into Target Microbes Infected with Recombinant Phage In the methods of this disclosure, maintaining the phage-exposed sample under infection conditions to allow the recombinant phage to infect target microbe cells in the sample and amplification of the heterologous marker nucleic acid sequence by at least one nucleic acid polymerase that is endogenous to the target microbe or encoded by the recombinant phage genome results in production of copies of the heterologous marker nucleic acid sequence in the sample if the target microbe is present in the sample. At that stage the sample comprising the amplified heterologous marker nucleic acid sequence also comprises a complex mixture of other components, including target cell debris and components and recombinant phage components. Typically the sample is processed at that stage to reduce the concentration of at least one of these other components and/or to increase the concentration of the amplified heterologous marker nucleic acid sequence.

Sample processing may include a step of target capture to specifically or non-specifically separate the amplified heterologous marker nucleic acid sequence from other sample components. Nonspecific target preparation methods may selectively precipitate nucleic acids from a substantially aqueous mixture, adhere nucleic acids to a support that is washed to remove other sample components, or use other means to physically separate nucleic acids, including STEC nucleic acid, from a mixture that contains other components. Other nonspecific target preparation methods may selectively separate RNA from DNA in a sample.

L. Amplification of Heterologous Marker Nucleic Acid Sequences Using a Recombinant Polymerase Many well-known methods of nucleic acid amplification require thermocycling to alternately denature double-stranded nucleic acids and hybridize primers; however, other well-known methods of nucleic acid amplification are isothermal. Exemplary amplification methods include polymerase chain reaction ("PCR"), the ligase chain reaction ("LCR"), strand displacement amplification ("SDA"), nucleic acid sequence based amplification ("NASBA"), self-sustained sequence replication, and transcription-mediated amplification ("TMA").

Suitable amplification conditions can be readily determined by a skilled artisan in view of the present disclosure. Amplification conditions, as disclosed herein, refer to conditions which permit nucleic acid amplification. Amplification conditions may, in some embodiments, be less stringent than "stringent hybridization conditions" as described herein. By "stringent hybridization conditions" is meant hybridization assay conditions wherein a specific detection probe is able to hybridize with target nucleic acids over other nucleic acids present in the test sample. It will be appreciated that these conditions may vary depending upon factors including the GC content and length of the probe, the hybridization temperature, the composition of the hybridization reagent or solution, and the degree of hybridization specificity sought.

Oligonucleotides used in the amplification reactions as disclosed herein may be specific for and hybridize to their intended targets under amplification conditions, but in certain embodiments may or may not hybridize under more stringent hybridization conditions. On the other hand, detection probes generally hybridize under stringent hybridization conditions.

In some embodiments, the heterologous marker nucleic acid sequence can also be amplified by a transcription-based amplification technique. As is discussed above, one transcription-based amplification system is transcription-mediated amplification (TMA), which employs an RNA polymerase to produce multiple RNA transcripts of a target region. Exemplary TMA amplification methods are described in, e.g., U.S. Pat. Nos. 4,868,105; 5,124,246;

5,130,238; 5,399,491; 5,437,990; 5,480,784; 5,554,516; and 7,374,885; and PCT Pub. Nos. WO 88/01302; WO 88/10315 and WO 95/03430.

The methods of this disclosure may include a TMA reaction that involves the use of a single primer TMA reaction, as is described in U.S. Pat. No. 7,374,885. In general, the single-primer TMA methods use a primer oligomer (e.g., a NT7 primer), a modified promoter-based oligomer (or "promoter-provider oligomer"; e.g., a T7 provider) that is modified to prevent the initiation of DNA synthesis from its 3' end (e.g., by including a 3'-blocking moiety) and, optionally, a blocker oligomer (e.g., a blocker) to terminate elongation of a cDNA from the target strand. Promoter-based oligomers provide an oligonucleotide sequence that is recognized by an RNA polymerase. This single primer TMA method synthesizes multiple copies of a target sequence and includes the steps of treating a target RNA that contains a target sequence with a priming oligomer and a binding molecule, where the primer hybridizes to the 3' end of the target strand. RT initiates primer extension from the 3' end of the primer to produce a cDNA which is in a duplex with the target strand (e.g., RNA×DNA). When a blocker oligomer, is used in the reaction, it binds to the target nucleic acid adjacent near the user designated 5' end of the target sequence. When the primer is extended by DNA polymerase activity of RT to produce cDNA, the 3' end of the cDNA is determined by the position of the blocker oligomer because polymerization stops when the primer extension product reaches the binding molecule bound to the target strand. Thus, the 3' end of the cDNA is complementary to the 5' end of the target sequence. The RNA×DNA duplex is separated when RNase (e.g., RNase H of RT) degrades the RNA strand, although those skilled in the art will appreciate that any form of strand separation may be used. Then, the promoter-provider oligomer hybridizes to the cDNA near the 3' end of the cDNA strand.

The promoter-provider oligomer includes a 5' promoter sequence for an RNA polymerase and a 3' target hybridizing region complementary to a sequence in the 3' region of the cDNA. The promoter-provider oligomer also has a modified 3' end that includes a blocking moiety that prevents initiation of DNA synthesis from the 3' end of the promoter-provider oligomer. In the promoter-provider×DNA duplex, the 3'-end of the cDNA is extended by DNA polymerase activity of RT using the promoter oligomer as a template to add a promoter sequence to the cDNA and create a functional double-stranded promoter.

An RNA polymerase specific for the promoter sequence then binds to the functional promoter and transcribes multiple RNA transcripts complementary to the cDNA and substantially identical to the target region sequence that was amplified from the initial target strand. The resulting amplified RNA can then cycle through the process again by binding the primer and serving as a template for further cDNA production, ultimately producing many amplicons from the initial target nucleic acid present in the sample. Some embodiments of the single-primer transcription-associated amplification method do not include the blocking oligomer and, therefore, the cDNA product made from the primer has an indeterminate 3' end, but the amplification steps proceed substantially as described above for all other steps.

The methods of this disclosure may also utilize a reverse transcription-mediated amplification (RTMA), various aspects of which are disclosed in, e.g., U.S. Pat. Appln. Pub. No. US 2006-0046265 A1. RTMA is an RNA transcription-mediated amplification system using two enzymes to drive the reaction: RNA polymerase and reverse transcriptase. RTMA is isothermal; the entire reaction is performed at the same temperature in a water bath or heat block. This is in contrast to other amplification reactions such as PCR that require a thermal cycler instrument to rapidly change the temperature to drive reaction.

RTMA can amplify either DNA or RNA, and can produce either DNA or RNA amplicons, in contrast to most other nucleic acid amplification methods that only produce DNA. RTMA has very rapid kinetics, resulting in a billion-fold amplification within 15-60 minutes. RTMA can be combined with a Hybridization Protection Assay (HPA), which uses a specific oligonucleotide probe labeled with an acridinium ester detector molecule that emits a chemiluminescent signal, for endpoint detection or with molecular torches for real-time detection. There are no wash steps, and no amplicon is ever transferred out of the tube, which simplifies the procedure and reduces the potential for contamination. Thus, the advantages of RTMA include amplification of multiple targets, results can be qualitative or quantitative, no transfers and no wash steps necessary, and detection can be in real time using molecular torches.

As an illustrative embodiment, the RTMA reaction is initiated by treating an RNA target sequence in a nucleic acid sample with both a tagged amplification oligomer and, optionally a blocking oligomer. The tagged amplification oligomer includes a target hybridizing region that hybridizes to a 3'-end of the target sequence and a tag region situated 5' to the target hybridizing region. The blocking oligomer hybridizes to a target nucleic acid containing the target sequence in the vicinity of the 5'-end of the target sequence. Thus, the target nucleic acid forms a stable complex with the tagged amplification oligomer at the 3'-end of the target sequence and the terminating oligonucleotide located adjacent to or near the determined 5'-end of the target sequence prior to initiating a primer extension reaction.

Unhybridized tagged amplification oligomers are then made unavailable for hybridization to a target sequence prior to initiating a primer extension reaction with the tagged priming oligonucleotide, preferably by inactivating and/or removing the unhybridized tagged priming oligonucleotide from the nucleic acid sample. Unhybridized tagged amplification oligomer that has been inactivated or removed from the system is then unavailable for unwanted hybridization to contaminating nucleic acids. In one example of removing unhybridized tagged amplification oligomer from a reaction mixture, the tagged amplification oligomer is hybridized to the target nucleic acid, and the tagged amplification oligomer target nucleic acid complex is removed from the unhybridized tagged amplification oligomer using a wash step. In this example, the tagged amplification oligomentarget nucleic acid complex may be further complexed to a target capture oligomer and a solid support. In one example of inactivating the unhybridized tagged amplification oligomer, the tagged amplification oligomers further comprise a target-closing region. In this example, the target hybridizing region of the tagged amplification oligomer hybridizes to target nucleic acid under a first set of conditions (e.g., stringency). Following the formation of the tagged amplification oligomentarget nucleic acid complex the unhybridized tagged amplification oligomer is inactivated under a second set of the conditions, thereby hybridizing the target closing region to the target hybridizing region of the unhybridized tagged amplification oligomer. The inactivated tagged amplification oligomer is then unavailable for hybridizing to contaminating nucleic acids. A wash step may also be included to remove the inactivated tagged amplification oligomers from the assay.

An extension reaction is then initiated from the 3'-end of the tagged amplification oligomer with a DNA polymerase, e.g., reverse transcriptase, to produce an initial amplification product that includes the tag sequence. The initial amplification product is then separated from the target sequence using an enzyme that selectively degrades the target sequence (e.g., RNAse H activity). Next, the initial amplification product is treated with a promoter-based oligomer having a target hybridizing region and an RNA polymerase promoter region situated 5' to the target hybridizing region, thereby forming a promoter-based oligomer:initial amplification product hybrid. The promoter-based oligomer may be modified to prevent the initiation of DNA synthesis, preferably by situating a blocking moiety at the 3'-end of the promoter-based oligomer (e.g., nucleotide sequence having a 3'-to-5' orientation). The 3'-end of the initial amplification product is then extended to add a sequence complementary to the promoter, resulting in the formation of a double-stranded promoter sequence. Multiple copies of a RNA product complementary to at least a portion of the initial amplification product are then transcribed using an RNA polymerase, which recognizes the double-stranded promoter and initiates transcription therefrom. As a result, the nucleotide sequence of the RNA product is substantially identical to the nucleotide sequence of the target nucleic acid and to the complement of the nucleotide sequence of the tag sequence.

The RNA products may then be treated with a tag-targeting oligomer, which hybridizes to the complement of the tag sequence to form a tag-targeting oligomer: RNA product hybrid, and the 3'-end of the tag-targeting oligomer is extended with the DNA polymerase to produce an amplification product complementary to the RNA product. The DNA strand of this amplification product is then separated from the RNA strand of this amplification product using an enzyme that selectively degrades the first RNA product (e.g., RNAse H activity). The DNA strand of the amplification product is treated with the promoter-based oligomer, which hybridizes to the 3'-end of the second DNA primer extension product to form a promoter-based oligomenamplification product hybrid. The promoter-based oligomer:amplification product hybrid then re-enters the amplification cycle, where transcription is initiated from the double-stranded promoter and the cycle continues, thereby providing amplification product of the target sequence.

Amplification product can then be used in a subsequent assay. One subsequent assay includes nucleic acid detection, preferably nucleic acid probe-based nucleic acid detection. The detection step may be performed using any of a variety of known ways to detect a signal specifically associated with the amplified target sequence, such as by hybridizing the amplification product with a labeled probe and detecting a signal resulting from the labeled probe. The detection step may also provide additional information on the amplified sequence, such as all or a portion of its nucleic acid base sequence.

Detection may be performed after the amplification reaction is completed, or may be performed simultaneous with amplifying the target region, e.g., in real time. In one embodiment, the detection step allows detection of the hybridized probe without removal of unhybridized probe from the mixture (see, e.g., U.S. Pat. Nos. 5,639,604 and 5,283,174).

The amplification methods as disclosed herein, in certain embodiments, also employ the use of one or more other types of oligonucleotides that are effective for improving the sensitivity, selectivity, efficiency, etc., of the amplification reaction.

M. Target Capture

In some embodiments a heterologous marker nucleic acid sequence is purified or enriched from a sample prior to nucleic acid amplification. Target capture, in general, refers to capturing a target polynucleotide onto a solid support, such as magnetically attractable particles, wherein the solid support retains the target polynucleotide during one or more washing steps of the target polynucleotide purification procedure. In this way, the target polynucleotide is substantially purified prior to a subsequent nucleic acid amplification step. Many target capture methods are known in the art and suitable for use in conjunction with the methods described herein. For example, any support may be used, e.g., matrices or particles free in solution, which may be made of any of a variety of materials, e.g., nylon, nitrocellulose, glass, polyacrylate, mixed polymers, polystyrene, silane polypropylene, or metal.

Illustrative examples use a support that is magnetically attractable particles, e.g., monodispersed paramagnetic beads to which an immobilized probe is joined directly (e.g., via covalent linkage, chelation, or ionic interaction) or indirectly (e.g., via a linker), where the joining is stable during nucleic acid hybridization conditions. In short, essentially any technique available to the skilled artisan may be used provided it is effective for purifying a target nucleic acid sequence of interest prior to amplification.

N. Detection of Heterologous Marker Nucleic Acid Sequence

Any labeling or detection system or both used to monitor nucleic acid hybridization can be used to detect heterologous marker nucleic acid sequences, including amplified heterologous marker nucleic acid sequences. Such systems are well known in the art.

Detection systems typically employ a detection oligonucleotide of one type or another in order to facilitate detection of the target nucleic acid of interest. Detection may either be direct (i.e., probe hybridized directly to the target) or indirect (i.e., a probe hybridized to an intermediate structure that links the probe to the target). A probe's target sequence generally refers to the specific sequence within a larger sequence, to which the probe hybridizes specifically. A detection probe may include target-specific sequences and other sequences or structures that contribute to the probe's three-dimensional structure, depending on whether the target sequence is present.

Essentially any of a number of well known labeling and detection systems that can be used for monitoring specific nucleic acid hybridization can be used in conjunction with the methods of this disclosure. Included among the collection of useful labels are fluorescent moieties (either alone or in combination with "quencher" moieties), chemiluminescent molecules, and redox-active moieties that are amenable to electronic detection methods. In some embodiments, preferred fluorescent labels include non-covalently binding labels (e.g., intercalating dyes) such as ethidium bromide, propidium bromide, chromomycin, acridine orange, and the like.

In some applications, probes exhibiting at least some degree of self-complementarity are desirable to facilitate detection of probe:target duplexes in a test sample without first requiring the removal of unhybridized probe prior to detection. By way of example, structures referred to as "molecular torches" and "molecular beacons" are designed to include distinct regions of self-complementarity and regions of target-complementarity. Molecular torches are fully described in U.S. Pat. Nos. 6,849,412, 6,835,542, 6,534,274, and 6,361,945, and molecular beacons are fully described in U.S. Pat. Nos. 5,118,801, 5,312,728, and 5,925,517.

Synthetic techniques and methods of attaching labels to nucleic acids and detecting labels are well known in the art.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

EXAMPLES

The following examples serve to more fully describe the manner of making and using certain embodiments of the inventions disclosed herein. These examples are presented for illustrative purposes and should not serve to limit the true scope of the inventions disclosed herein.

Example 1: Recombinant Listeria Phage

A novel phage engineering method was developed to create recombinant phage. This method is sometimes referred to herein as Phage Infective Engineering (PIE). This method allows insertion of a heterologous nucleic acid sequence into any desired location of a phage genome. The initial site chosen for insertion was that used in Loessner, et al. (Appl. Environ Microbiol., 62:1133-1140), downstream of the major capsid protein gene cps. The coding sequence (SEQ ID NO: 1) for the firefly luciferase (SEQ ID NO: 2) or the coding sequence (SEQ ID NO: 3) for the nanoluc luciferase (SEQ ID NO: 4) was inserted at this location.

The PIE method uses Phage Targeting Vectors PTVs which include the luciferase gene sequence flanked by ~1 KB of phage sequence directly upstream and downstream of the desired insertion site (referred to as an upstream homology region (UHR) and downstream homology region (DHR)). Each of these inserts was created using PCR primers that would amplify the desired amplicon, while adding 20 bp of homology to facilitate assembly. Plasmids were assembled using the GeneArt Seamless Assembly Kit (Life Technologies). The 3 inserts (UHR, luc, DHR) were assembled into the gram positive/gram negative shuttle vector pMK4, which was restriction-digested with SmaI and PstI (NEB).

The A511 phage genome sequence is available in Genbank (NC_009811). A511 phage may be obtained from ATCC (PTA-4608™).

The PIE method was used to insert the firefly luciferase gene (SEQ ID NO: 1) directly after the stop codon of the cps gene of A511, between bases 46,695 and 46,696 of the genomic sequence. No sequence was deleted from the phage genome. A 16 bp sequence containing a ribosome-binding site (GAGGAGGTAAATATAT) (SEQ ID NO: 36) was placed before the start (ATG) of the firefly luciferase gene.

To engineer phage A511, 1276 bases of the cps gene were amplified using oligos "pMAK upf" and "pMAK upr", forming the fragment "A511 UHR". The luciferase gene was amplified using primers "pMAK lucf" and "pMAK lucr", creating the fragment "A511 luc". The primer "pMAK lucf" also added a ribosome binding site (Shine-Dalgarno) upstream of the luciferase gene. The 1140 bp immediately after the cps stop codon was amplified using "pMAK dnf" and "pMAK dnr", named "A511 DHR".

These 3 amplicons were recombined into pMK4 which had been restriction digested with SmaI/PstI using the GeneArt Seamless Assembly Kit, according to the manufacturer's instructions. Once isolated in e. coli, the plasmid was sequenced to verify correct amplification and assembly. Upon verification, the plasmid was transformed into the L. monocytogenes strain EGD-e and selected on BHI-chloramphenicol (10 μg/ml) agar plates.

Once the PTV was successfully transformed into EGD-e, the initial recombination was performed: An overnight culture of the A511::FF PTV-containing EGD-e was diluted 1:100 and allowed to grow to an OD600 of 0.1. This culture was then diluted back to an OD600 of 0.02 and mixed with $1 \times 10^5$ pfu/ml of wild-type A511 phage in a 2 ml volume. This infection was cultured at 30° C., shaken at 50 rpm overnight.

To assess whether recombination had occurred, the infection was assayed on the following day. First, the lysate was mixed with chloroform to kill any remaining cells, and to destroy the background luciferase made by the PTV. The phage is chloroform-resistant, which is a common trait in bacteriophages. 4% v/v CHCl3 was added to the lysate, vortexed, spun down, and the supernatant was recovered. A test infection was done, adding a 1:10 dilution of an overnight culture of EGD-e was mixed with the recombinant lysate (90 μl cell dilution, 10 μl phage lysate). A control infection was set up without cells. The infections were incubated statically at 30° C. for 3 hr, then assayed for luminescence on the Glomax 20/20. 20 μl of the infection was mixed with 100 μl of Promega Luciferase Assay Reagent (20 μl of lysate and 20 μl of NanoGlo for the NanoLuc phages), then read using a 10 second integration (1 s for NanoGlo). The recombinant lysate produced light, indicating that there were recombinant phage in the lysate.

In order to enrich and isolate the recombinant phage, it needed to be separated away from the wild-type phages present in the recombinant lysate. Successive rounds of dilution and division were employed. Lysates were made with 10-fold dilutions of input phages, and screened for the presence of recombinant phage by assaying the lysates for luciferase activity.

The recombination efficiency was estimated to be $1:1 \times 10^5$ to $1:1 \times 10^6$. In order to isolate a pure recombinant lysate, the methods described in (Appl. Environ Microbiol. 62:1133-1140) were modified as follows. The initial recombinant lysate was titered. 20 1-ml lysates were set up each with $1 \times 10^6$, $1 \times 10^5$, and $1 \times 10^4$ pfu/ml of the recombinant lysate: 1 ml EGD-e @ OD 0.02, $1 \times 10^x$ phages; O/N, 30° C., 50 rpm. On the following day, the CHCl3 treatment was done, as described above, for each lysate. The lysates were used to set up infections as above. Each lysate was assayed on the Glomax 20/20 (20 μl infection, 100 μl Reagent for FF, 20 μl infection, 20 μl NanoGlo for nluc). The goal was to locate the lysate that was made with the fewest number of phages that exhibits luminescence upon infection. Once this lysate was identified, it was titered and used to set up lysates with $1 \times 10^3$, $1 \times 10^2$ and $1 \times 10^1$ pfu/ml. Once a luminescent lysate was isolated that had been made with 1×10² phages, this lysate was plated for single plaques. Plaques were picked into SM buffer. These "soakates" were diluted 1:10 in dH2O and assayed by PCR using "DBONO360" and "DBONO361" to look for the presence of recombinant junctions between the luciferase gene and phage sequence.

The P100 phage genomic sequence is available in Genbank (DQ004855). P100 may be obtained from ATCC (PTA-4383™).

The luciferase insertion site for P100 was also downstream of the same cps gene. The location of the firefly luciferase insertion in P100 is between base 13,196 and 13,197 of the P100 genomic sequence.

P100 was engineered in the same manner as A511 with the following exceptions: the "P100 DHR" fragment was amplified using the primers "pMAK dnf" and "pMAK dnr P100". The single recombinant plaque was identified by picking the plaque into 100 µl SM buffer. 10 µl of this soakate was mixed with 50 µl of luciferin and luminescence was seen on the luminometer. This method of identifying positives was utilized in subsequent recombinant phage isolation.

The following phages were engineered using the firefly luciferase gene and the methods described for A511::ffluc: LP48, LP124, LP125, LP99, LP101, and LP143.

The following phages were engineered using the NanoLuc gene: A511, P100, LP40, LP124 and LP125.

The PTV for A511::nluc was constructed by amplifying the following PCR fragments: Using an A511 lysate as the template, the UHR fragment was generated using oligos pMAK upf and DBONO356; the DHR fragment was amplified using oligos DBONO359 and pMAK dnr. Using the Promega plasmid pNL1.1 as a template, the NanoLuc fragment was amplified using oligos DBONO357 and DBONO358. The assembly and subsequent PIE methods were similar to those described.

The PTV and engineering for P100::nluc was performed in the same way as for A511::nluc, with the exception that the DHR fragment was amplified using the oligo pMAK dnr P100 rather than pMAK dnr.

The PTVs for LP124, LP125, and LP40 were constructed in the same way as A511::nluc, with the following changes. The DHR fragment amplified was shorter to allow for more efficient assembly of the plasmid, using oligos DBONO359 and DBONO382. Also, the insertion site was modified by adding two additional stop codons (TAATAA) directly downstream of the cps gene of these phages. These 6 bases were added by creating additional primers DBONO379 and DBONO380. The UHR fragments for these phages were amplified using oligos pMAK upf and DBONO380. The NanoLuc fragments were amplified using oligos DBONO379 and DBONO358.

The following oligonucleotides were used in the PIE methods:

pMAK upf:
(SEQ ID NO: 37)
TTACGCCAAGCTTGGCTGCAACGTGAGTTCCTAGACGACC pMAK upr:
(SEQ ID NO: 38)
ATGTTTTTGGCGTCTTCCATATATATTTACCTCCTCTTAGTTGCTATGAA
CGTTTT pMAK lucf:
(SEQ ID NO: 39)
AAAACGTTCATAGCAACTAAGAGGAGGTAAATATATATGGAAGACGCCAA
AAACAT pMAK lucr:
(SEQ ID NO: 40)
ATTCAATTATCCTATAATTATTACAATTTGGACTTTCCGC pMAK dnf:
(SEQ ID NO: 41)
GCGGAAAGTCCAAATTGTAATAATTATAGGATAATTGAAT pMAK dnr:
(SEQ ID NO: 42)
ACGACGGCCAGTGAATTCCCAGTTACTAACTGCTCTAATG pMAK dnr P100:
(SEQ ID NO: 43)
ACGACGGCCAGTGAATTCCCAGTTACTAACTGTTCTAATG

DBONO360:
(SEQ ID NO: 44)
CCTCTAGCTCAAATTAACGCATCTGT

DBONO361:
(SEQ ID NO: 45)
TGGCTCTACATGCTTAGGGTTCC

DBONO356:
(SEQ ID NO: 46)
TCTTCGAGTGTGAAGACCATATATATTTACCTCCTCTTAGTTGC

DBONO357:
(SEQ ID NO: 47)
CTAAGAGGAGGTAAATATATATGGTCTTCACACTCGAAGATTT

DBONO358:
(SEQ ID NO: 48)
ATTCAATTATCCTATAATTATTACGCCAGAATGCGTTCGC

DBONO359:
(SEQ ID NO: 49)
GCGAACGCATTCTGGCGTAATAATTATAGGATAATTGAATAAA

DBONO379:
(SEQ ID NO: 50)
AAAACGTTCATAGCAACTAATAATAAGAGGAGGTAAATATATATGGTCTT
CACACTCGAAGATTT

DBONO380:
(SEQ ID NO: 51)
ATATTTACCTCCTCTTATTATTAGTTGCTATGAACGTTTTTACAGG

DBONO382:
(SEQ ID NO: 52)
ACGACGGCCAGTGAATTCCCTCGTGGTGTTCTGACTCCCG.

In subsequent experiments some modifications were made to the method. During PTV construction it was discovered that the DHR fragment was often missing from the assembled plasmid. This was overcome by shortening the length of the fragment used, utilizing oligo DBONO382.

In a modified approach, following determining the titer of the recombinant lysate, the enrichment process was sometimes conducted as follows and was used to make the nanoluc phages.

96-well microtiter plates were used to grow the PIE lysates at a 200 µl volume. For the FF lysates, the initial step was making 96 lysates at 1×10⁶ pfu/lysate (5×10⁶ pfu/ml), 96 at 1×10⁵, and 96 at 1×10⁴. For the NanoLuc phages, it was found that the recombination efficiency of the recombinant lysate was significantly higher, and that dilutions down to 1×10⁰ pfu/lysate could be used. These lysates were made by incubating at 30° C., shaking at 50 rpm overnight.

The lysates were assayed using the appropriate luciferase assay system (ff or nanoglo). Instead of using the lysates to infect fresh cells, it was found that the background signal of the lysate itself was an indication of the presence of recombinant phage.

Upon identification of a lysate made from the fewest number of phages, that lysate was used to set up new 96-well lysates using fewer phages. Once an approximate recombinant frequency of 1:10-1:100 was reached, the phages were plated on agar plates to isolate single plaques as described above.

These methods were used to create recombinant phage comprising either a heterologous open reading frame encoding the ff luciferase or an open reading frame encoding the nanoluc luciferase. In order to confirm the integrity of the inserted payload and the surrounding sequence in the recombinant phages, a fragment was amplified by PCR and sequenced. This fragment spanned the inserted sequence, beginning in the cps gene, crossing through the firefly or nanoluc gene, and crossing into the downstream sequence. The full cps gene was also PCR amplified using oligos DBONO398 and pMAK upr

```
DBONO398:
                                    (SEQ ID NO: 53)
TGCTATATTATAGGAACATGGGAA.
```

The gene was sequenced using oligos DBONO273, DBONO398, and pMAK upr.

The PCR fragment was amplified using primers:

```
DBONO273:
                                    (SEQ ID NO: 54)
TGCTTACATGCCAGTAGGGGT;
and DBONO382:
                                    (SEQ ID NO: 55)
ACGACGGCCAGTGAATTCCCTCGTGGTGTTCTGACTCCCG
```

The nanoluc phages were sequenced using oligos:

```
DBONO273;

DBONO382;

DBONO361:
                                    (SEQ ID NO: 56)
TGGCTCTACATGCTTAGGGTTCC;

DBONO360:
                                    (SEQ ID NO: 57)
CCTCTAGCTCAAATTAACGCATCTGT;

DBONO362:
                                    (SEQ ID NO: 58)
GTATGAAGGTCTGAGCGGCG
and DBONO363:
                                    (SEQ ID NO: 59)
GATCTGGCCCATTTGGTCGC.
```

The firefly phages were sequenced using oligos:

```
DBONO273;

DBONO382;

DBONO360;

DBONO361;

DBONO274:
                                    (SEQ ID NO: 60)
CGCATAGAACTGCCTGCGTC;

DBONO151:
                                    (SEQ ID NO: 61)
CACCCCAACATCTTCGACGC;
and DBONO152:
                                    (SEQ ID NO: 62)
GCGCAACTGCAACTCCGATA
```

Sequencing was performed by Genewiz, Inc. Using the Geneious software package, alignments were made and a consensus sequence was generated for each phage.

The following recombinant phages have been created and the insertion site regions sequenced as described above:

Phages Containing an Inserted Firefly Luciferase:
LP48::ffluc (SEQ ID NO: 23);
LP99::ffluc (SEQ ID NO: 24);
LP101::ffluc (SEQ ID NO: 25);
LP124::ffluc (SEQ ID NO: 26);
LP125::ffluc (SEQ ID NO: 27);
LP143::ffluc (SEQ ID NO: 28);
A511::ffluc (SEQ ID NO: 29); and
P100::ffluc (SEQ ID NO: 30).

Phages Containing an Inserted Nanoluc Luciferase:
LP124::nluc (SEQ ID NO: 31);
LP125::nluc (SEQ ID NO: 32);
A511::nluc (SEQ ID NO: 33);
P100::nluc (SEQ ID NO: 34); and
LP40::nluc (SEQ ID NO: 35).

The insertion site regions of the phages comprising an inserted firefly luciferase coding sequence contain the following parts as indicated in Table 2.

TABLE 2

|  | LP48 | LP99 | LP101 | LP124 | LP125 | LP143 | A511 | P100 |
|---|---|---|---|---|---|---|---|---|
| cps gene | 1-1407 | 1-1407 | 1-1407 | 1-1407 | 1-1407 | 1-1404 | 1-1404 | 1-1407 |
| RBS (inserted) | 1408-1423 | 1408-1423 | 1408-1423 | 1408-1423 | 1408-1423 | 1405-1420 | 1405-1420 | 1408-1423 |
| Firefly Luciferase | 1424-3076 | 1424-3076 | 1424-3076 | 1424-3076 | 1424-3076 | 1421-3073 | 1421-3073 | 1424-3076 |
| Downstream genes | 3077-3729 | 3077-3789 | 3077-3789 | 3077-3789 | 3077-3729 | 3074-3786 | 3074-3786 | 3077-3729 |

The insertion site regions of the phages comprising an inserted nanoluc luciferase coding sequence contain the following parts as indicated in Table 3.

TABLE 3

|  | LP124::nluc | LP125::nluc | A511::nluc | P100::nluc | LP40::nluc |
|---|---|---|---|---|---|
| cps gene | 1-1407 | 1-1407 | 1-1404 | 1-1407 | 1-1407 |
| additional stop codons (inserted) | 1408-1413 | 1408-1413 | n/a | n/a | 1408-1413 |
| RBS (inserted) | 1414-1429 | 1414-1429 | 1405-1420 | 1408-1423 | 1414-1429 |
| NanoLuc | 1430-1945 | 1430-1945 | 1421-1936 | 1424-1939 | 1430-1945 |
| Downstream genes | 1946-2658 | 1946-2598 | 1937-2649 | 1940-2592 | 1946-2613 |

The cps open reading frames and encoded proteins for each phage are listed in Table 4.

TABLE 4

| Phage | Cps Gene Sequence | Cps Protein Sequence |
|---|---|---|
| LP40 | 5 | 6 |
| LP48 | 7 | 8 |
| LP99 | 9 | 10 |
| LP101 | 11 | 12 |
| LP124 | 13 | 14 |
| LP125 | 15 | 16 |
| LP143 | 17 | 18 |
| A511 | 19 | 20 |
| P100 | 21 | 22 |

All of the above phages were engineered using the methods described above. Partial genome sequences showed that the primers used for A511 could be used to create PTVs for LP48, LP124, and LP125. No genome sequence was available at the time for LP99, LP101 or LP143. Using the A511 PTV primers, it was possible to amplify the appropriate fragments for PTV construction in the same manner as A511. This reflects homology between the cps gene regions across those phages. The luciferase gene insertion site was at the same location (after the cps gene stop codon TAA) as in A511::ffluc.

Engineering of HIS-Tagged Phages

To allow for the concentration of signal produced by the infection of listeria by recombinant phages, alternate versions of recombinant phage were produced that included a HIS tag. The 6xHIS tag (SEQ ID NO: 63) is a commonly used affinity tag for concentrating and purifying recombinant proteins.

HIS tags are commonly placed at the N-terminus or C-terminus of a protein, as it is often unknown a priori which location is optimal. Depending on the structure of the protein being tagged, as well as interactions with substrates, the tag sequence can interfere with, inhibit, or enhance enzyme function. For this reason phages were engineered with the HIS tag at either the N- or C-terminus Further, often times a spacer sequence comprising a small number of amino acid residues is place between the HIS tag and the gene being tagged. The size, charge, and other characteristics of this spacer can effect interactions with the enzyme, substrate, or HIS-binding beads/resins/antibodies. For this reason 2 different spacer were used between the HIS tag and the Nanoluc protein.

The HIS-tagged nanoluc versions of A511, LP124, and LP40 were constructed using the same methods as the untagged phages. The HIS tag and spacer were introduced during PTV construction by adding sequence to the oligos used to amplify the various DNA fragments. The oligos used in constructing the PTVs for A511, LP124 and LP40 are common to all 3 phages.

4 versions of each phage were constructed:
a. C-terminal long spacer
b. C-terminal short spacer
c. N-terminal long spacer
d. N-terminal short spacer Oligos used to construct C-terminal long spacer PTV:
a. UHR fragment: pMAK upf and DBONO380
b. NLUC fragment: DBONO379 and DBONO400
c. DHR fragment: DBONO401 and DBONO382

Oligos used to construct C-terminal short spacer PTV:
a. UHR fragment: pMAK upf and DBONO380
b. NLUC fragment: DBONO379 and DBONO402
c. DHR fragment: DBONO401 and DBONO382

Oligos used to construct N-terminal long spacer PTV:
a. UHR fragment: pMAK upf and DBONO380
b. NLUC fragment: DBONO403 and DBONO358
c. DHR fragment: DBONO359 and DBONO382

Oligos used to construct N-terminal short spacer PTV:
a. UHR fragment: pMAK upf and DBONO380
b. NLUC fragment: DBONO404 and DBONO358
c. DHR fragment: DBONO359 and DBONO382

Once PTVs were constructed and verified, the rest of the PIE process was carried out as described above.

Oligo sequences:
DBONO400:
(SEQ ID NO: 64)
ATTCAATTATCCTATAATTATTAATGGTGATGGTGATGATGACCTCCACC
TGCTGCCGCCAGAATGCGTTCGCACA

DBONO401:
(SEQ ID NO: 65)
ATCATCACCATCACCATTAATAATTATAGGATAATTGAATAAAAAC

DBONO402:
(SEQ ID NO: 66)
ATTCAATTATCCTATAATTATTAATGGTGATGGTGATGATGTGCTGCCGC
CAGAATGCGTTCGCACA

```
DBONO403:
                                       (SEQ ID NO: 67)
TAATAAGAGGAGGTAAATATATATGCATCATCACCATCACCATGGTGGAG
GTGCAGCAGTCTTCACACTCGAAGATTTCG

DBONO404:
                                       (SEQ ID NO: 68)
AGCAACTAATAATAAGAGGAGGTAAATATATATGCATCATCACCATCACC
ATGCAGCAGTCTTCACACTCGAAGATTTCG

HIS tag amino acid
sequence:
                                       (SEQ ID NO: 63)
HHHHHH HIS tag DNA sequence:
                                       (SEQ ID NO: 69)
CATCATCACCATCACCAT C-terminal HIS with long spacer amino acid
sequence:
                                       (SEQ ID NO: 70)
AAGGGHHHHHH C-terminal HIS with long spacer DNA sequence:
                                       (SEQ ID NO: 71)
GCAGCAGGTGGAGGTCATCATCACCATCACCAT C-terminal HIS with short spacer amino acid
sequence:
                                       (SEQ ID NO: 72)
AAHHHHHH C-terminal HIS with short spacer DNA sequence:
                                       (SEQ ID NO: 73)
GCAGCACATCATCACCATCACCAT N-terminal HIS with long spacer amino acid
sequence:
                                       (SEQ ID NO: 74)
HHHHHHGGGAA N-terminal HIS with long spacer DNA sequence:
                                       (SEQ ID NO: 75)
CATCATCACCATCACCATGGTGGAGGTGCAGCA N-terminal HIS with short spacer amino acid
sequence:
                                       (SEQ ID NO: 76)
HHHHHHAA N-terminal HIS with short spacer DNA sequence:
                                       (SEQ ID NO: 77)
CATCATCACCATCACCATGCAGCA
```

The insertion locations for each of the twelve tagged enzymes are provided in Table 5. The numbering is the same as in the preceding tables in this example.

TABLE 5

| Phage | Tag Location | Spacer | Inserted between bases |
|---|---|---|---|
| A511 | C-terminal | Long | 1933-1934 |
| LP124 | C-terminal | Long | 1941-1942 |
| LP40 | C-terminal | Long | 1941-1942 |
| A511 | C-terminal | Short | 1933-1934 |
| LP124 | C-terminal | Short | 1941-1942 |
| LP40 | C-terminal | Short | 1941-1942 |
| A511 | N-terminal | Long | 1423-1424 |
| LP124 | N-terminal | Long | 1432-1433 |
| LP40 | N-terminal | Long | 1432-1433 |
| A511 | N-terminal | Short | 1423-1424 |
| LP124 | N-terminal | Short | 1432-1433 |
| LP40 | N-terminal | Short | 1432-1433 |

The recombinant phage described in this example were deposited on May 16, 2013, with the American Type Culture Collection (ATCC®). The deposits were made under the terms of the Budapest Treaty on the International Recognition of the Deposit of Microorganisms for the Purposes of Patent Procedure. The ATCC® Patent Deposit Designations for the deposits are provided in Table 6.

TABLE 6

| Phage | ATCC Patent Deposit Designation |
|---|---|
| LP48::ffluc | PTA-120333 |
| LP125::ffluc | PTA-120334 |
| LP40::nluc | PTA-120335 |
| A511::nluc | PTA-120336 |
| P100::ffluc | PTA-120337 |
| LP124::nluc | PTA-120338 |
| LP101::ffluc | PTA-120339 |
| LP99::ffluc | PTA-120340 |
| LP143::ffluc | PTA-120341 |
| A511::ffluc | PTA-120342 |
| P100::nluc | PTA-120343 |
| LP124:ffluc | PTA-120344 |
| LP125::nluc | PTA-120345 |

Additional sequences are listed below in Table 7.

TABLE 7

```
SEQ ID NO: 1 - FF luc open reading frame
ATGGAAGACGCCAAAAACATAAAGAAAGGCCCGGCGCCATTCTATCCTCTAGAGGATGGAACCGCTG
GAGAGCAACTGCATAAGGCTATGAAGAGATACGCCCTGGTTCCTGGAACAATTGCTTTTACAGATGCA
CATATCGAGGTGAACATCACGTACGCGGAATACTTCGAAATGTCCGTTCGGTTGGCAGAAGCTATGAA
ACGATATGGGCTGAATACAAATCACAGAATCGTCGTATGCAGTGAAAACTCTCTTCAATTCTTTATGCC
GGTGTTGGGCGCGTTATTTATCGGAGTTGCAGTTGCGCCCGCGAACGACATTTATAATGAACGTGAAT
TGCTCAACAGTATGAACATTTCGCAGCCTACCGTAGTGTTTGTTTCCAAAAAGGGGTTGCAAAAAATTT
TGAACGTGCAAAAAAAATTACCAATAATCCAGAAAATTATTATCATGGATTCTAAAACGGATTACCAG
GGATTTCAGTCGATGTACACGTTCGTCACATCTCATCTACCTCCCGGTTTTAATGAATACGATTTTGTA
CCAGAGTCCTTTGATCGTGACAAAACAATTGCACTGATAATGAATTCCTCTGGATCTACTGGGTTACCT
AAGGGTGTGGCCCTTCCGCATAGAACTGCCTGCGTCAGATTCTCGCATGCCAGAGATCCTATTTTTGGC
AATCAAATCATTCCGGATACTGCGATTTTAAGTGTTGTTCCATTCCATCACGGTTTTGGAATGTTTACT
ACACTCGGATATTTGATATGTGGATTTCGAGTCGTCTTAATGTATAGATTTGAAGAAGAGCTGTTTTTA
CGATCCCTTCAGGATTACAAAATTCAAAGTGCGTTGCTAGTACCAACCCTATTTTCATTCTTCGCCAAA
AGCACTCTGATTGACAAATACGATTTATCTAATTTACACGAAATTGCTTCTGGGGGCGCACCTCTTTCG
AAAGAAGTCGGGGAAGCGGTTGCAAAACGCTTCCATCTTCCAGGGATACGACAAGGATATGGGCTCA
CTGAGACTACATCAGCTATTCTGATTACACCCGAGGGGGATGATAAACCGGGCGCGGTCGGTAAAGTT
GTTCCATTTTTTGAAGCGAAGGTTGTGGATCTGGATACCGGGAAAACGCTGGGCGTTAATCAGAGAGG
CGAATTATGTGTCAGAGGACCTATGATTATGTCCGGTTATGTAAACAATCCGGAAGCGACCAACGCCT
TGATTGACAAGGATGGATGGCTACATTCTGGAGACATAGCTTACTGGGACGAAGACGAACACTTCTTC
ATAGTTGACCGCTTGAAGTCTTTAATTAAATACAAAGGATATCAGGTGGCCCCCGCTGAATTGGAATC
GATATTGTTACAACACCCCAACATCTTCGACGCGGGCGTGGCAGGTCTTCCCGACGATGACGCCGGTG
```

TABLE 7-continued

```
AACTTCCCGCCGCCGTTGTTGTTTTGGAGCACGGAAAGACGATGACGGAAAAAGAGATCGTGGATTAC
GTCGCCAGTCAAGTAACAACCGCGAAAAAGTTGCGCGGAGGAGTTGTGTTTGTGGACGAAGTACCGA
AAGGTCTTACCGGAAAACTCGACGCAAGAAAAATCAGAGAGATCCTCATAAAGGCCAAGAAGGGCGG
AAAGTCCAAATTGTAA

SEQ ID NO: 2 - FF luc amino acid sequence
MEDAKNIKKGPAPFYPLEDGTAGEQLHKAMKRYALVPGTIAFTDAHIEVNITYAEYFEMSVRLAEAMKRY
GLNTNHRIVVCSENSLQFFMPVLGALFIGVAVAPANDIYNERELLNSMNISQPTVVFVSKKGLQKILNVQKK
LPIIQKIIIMDSKTDYQGFQSMYTFVTSHLPPGFNEYDFVPESFDRDKTIALIMNSSGSTGLPKGVALPHRTAC
VRFSHARDPIFGNQIIPDTAILSVVPFHHGFGMFTTLGYLICGFRVVLMYRFEEELFLRSLQDYKIQSALLVPT
LFSFFAKSTLIDKYDLSNLHEIASGGAPLSKEVGEAVAKRFHLPGIRQGYGLTETTSAILITPEGDDKPGAVG
KVVPFFEAKVVDLDTGKTLGVNQRGELCVRGPMIMSGYVNNPEATNALIDKDGWLHSGDIAYWDEDEHF
FIVDRLKSLIKYKGYQVAPAELESILLQHPNIFDAGVAGLPDDDAGELPAAVVVLEHGKTMTEKEIVDYVA
SQVTTAKKLRGGVVFVDEVPKGLTGKLDARKIREILIKAKKGGKSKL SEQ ID NO: 3 - Nanoluc open reading frame
ATGGTCTTCACACTCGAAGATTTCGTTGGGGACTGGCGACAGACAGCCGGCTACAACCTGGACCAAGT
CCTTGAACAGGGAGGTGTGTCCAGTTTGTTTCAGAATCTCGGGGTGTCCGTAACTCCGATCCAAAGGA
TTGTCCTGAGCGGTGAAAATGGGCTGAAGATCGACATCCATGTCATCATCCCGTATGAAGGTCTGAGC
GGCGACCAAATGGGCCAGATCGAAAAAATTTTTAAGGTGGTGTACCCTGTGGATGATCATCACTTTAA
GGTGATCCTGCACTATGGCACACTGGTAATCGACGGGGTTACGCCGAACATGATCGACTATTTCGGAC
GGCCGTATGAAGGCATCGCCGTGTTCGACGGCAAAAAGATCACTGTAACAGGGACCCTGTGGAACGG
CAACAAAATTATCGACGAGCGCCTGATCAACCCCGACGGCTCCCTGCTGTTCCGAGTAACCATCAACG
GAGTGACCGGCTGGCGGCTGTGCGAACGCATTCTGGCGTAA SEQ ID NO: 4 - Nanoluc amino acid sequence
MVFTLEDFVGDWRQTAGYNLDQVLEQGGVSSLFQNLGVSVTPIQRIVLSGENGLKIDIHVIIPYEGLSGDQM
GQIEKIFKVVYPVDDHHFKVILHYGTLVIDGVTPNMIDYFGRPYEGIAVFDGKKITVTGTLWNGNKIIDERLI
NPDGSLLFRVTINGVTGWRLCERILA SEQ ID NO: 5 - LP040 Cps open reading frame
ATGCCAAAAAATAACAAAGAAGAAGAAGTTAAAGAAGTAAACCTTAATTCAGTACAAGAGGATGCGT
TAAAGTCCTTTACAACTGGTTATGGTATCACACCTGATACACAAACAGATGCAGGGGCACTAAGACGT
GAGTTCCTAGACGACCAAATCTCAATGCTTACTTGGACAGAAAATGATTTAACATTCTACAAAGACAT
CGCTAAAAAACCAGCTACATCTACAGTAGCAAAATACGATGTGTACATGCAACACGGTAAAGTAGGT
CATACTAGATTTACTCGTGAGATTGGGGTAGCACCAGTAAGTGACCCTAACATCCGTCAAAAAACAGT
AAACATGAAATTTGCTTCTGATACTAAAAATATTAGTATCGCAGCAGGTCTAGTAAACAACATTCAAG
ACCCTATGCAAATTTTGACTGATGATGCTATCGTAAATATCGAATGGGCTTCATTCT
TTGGAGATTCTGACTTATCAGATAGCCCAGAACCACAAGCAGGATTAGAATTTGATGGCTTGGCTAAA
CTTATTAACCAAGATAACGTTCATGATGCTCGTGGAGCTAGCTTGACTGAAAGCTTGTTAAACCAAGC
AGCAGTAATGATTAGTAAAGGTTATGGTACACCTACAGATGCTTACATGCCAGTAGGGGTTCAAGCAG
ACTTTGTTAACCAACAACTTTCTAAACAAACACAACTTGTTCGCGATAACGGAAACAACGTAAGCGTT
GGTTTCAACATCCAAGGTTTCCATTCAGCTCGTGGATTTATCAAACTTCACGGTTCTACAGTAATGGAA
AACGAACAAATCTTAGATGAACGTATTCTTGCTTTACCAACAGCTCCACAACCAGCTAAGGTAACTGC
AACACAAGAAGCAGGTAAAAAAGGACAATTTAGAGCAGAAGATTTAGCAGCACATGAATATAAAGTT
GTTGTAAGTTCTGACGATGCAGAGTCTATTGCAAGTGAAGTGGCTACAGCTACAGTTACTGCAAAAGA
TGACGGCGTTAAACTAGAAATCGAATTAGCTCCAATGTATAGCTCTCGTCCACAATTCGTTTCAATCTA
TAGAAAAGGTGCAGAAACAGGTTTATTCTACCTAATCGCTCGTGTACCTGCTAGCAAAGCAGAGAACA
ACGTAATCACTTTCTACGACTTAAACGACTCTATTCCTGAAACAGTAGACGTATTCGTTGGTGAAATGT
CGGCTAACGTAGTACACTTGTTTGAATTACTACCAATGATGAGATTACCTCTAGCTCAAATTAACGCAT
CTGTTACATTTGCAGTTTTATGGTATGGCGCATTAGCTCTAAGAGCACCTAAGAAATGGGTACGTATTA
GAAACGTTAAATATATTCCTGTAAAAAACGTTCATAGCAACTAA SEQ ID NO: 6 - LP40 Cps protein
MPKNNKEEEVKEVNLNSVQEDALKSFTTGYGITPDTQTDAGALRREFLDDQISMLTWTENDLTFYKDIAK
KPATSTVAKYDVYMQHGKVGHTRFTREIGVAPVSDPNIRQKTVNMKFASDTKNISIAAGLVNNIQDPMQIL
TDDAIVNIAKTIEWASFFGDSDLSDSPEPQAGLEFDGLAKLINQDNVHDARGASLTESLLNQAAVMISKGY
GTPTDAYMPVGVQADFVNQQLSKQTQLVRDNGNNVSVGFNIQGFHSARGFIKLHGSTVMENEQILDERIL
ALPTAPQPAKVTATQEAGKKGQFRAEDLAAHEYKVVVSSDDAESIASEVATATVTAKDDGVKLEIELAPM
YSSRPQFVSIYRKGAETGLFYLIARVPASKAENNVITFYDLNDSIPETVDVFVGEMSANVVHLFELLPMMRL
PLAQINASVTFAVLWYGALALRAPKKWVRIRNVKYIPVKNVHSN SEQ ID NO: 7 - LP48 Cps open reading frame
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGATTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACA
```

TABLE 7-continued

```
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAA

SEQ ID NO: 8 - LP48 protein
MPKNNKEEEVKEVNLNSVQEDALKSFTTGYGITPDTQTDAGALRREFLDDQISMLTWTENDLTFYKDIAK
KPATSTVAKYDVYMQHGKVGHTRFTREIGVAPVSDPNIRQKTVNMKFASDTKNISIAAGLVNNIQDPMQIL
TDDAIVNIAKTIEWASFFGDSDLSDSPEPQAGLEFDGLAKLINQDNVHDARGASLTESLLNQAAVMISKGY
GTPTDAYMPVGVQADFVNQQLSKQTQLVRDNGNNVSVGFNIQGFHSARGFIKLHGSTVMENEQILDERIL
ALPTAPQPAKVTATQEAGKKGQFRAEDLAAHEYKVVVSSDDAESIASEVATATVTAKDDGVKLEIELAPM
YSSRPQFVSIYRKGAETGLFYLIARVPASKAENNVITFYDLNDSIPETVDVFVGEMSANVVHLFELLPMMRL
PLAQINASVTFAVLWYGALALRAPKKWVRIRNVKYIPVKNVHSN SEQ ID NO: 9 - LP099 Cps open reading frame
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAA SEQ ID NO: 10 - LP099 Cps protein
MPKNNKEEEVKEVNLNSVQEDALKSFTTGYGITPDTQTDAGALRREFLDDQISMLTWTENDLTFYKDIAK
KPATSTVAKYDVYMQHGKVGHTRFTREIGVAPVSDPNIRQKTVNMKFASDTKNISIAAGLVNNIQDPMQIL
TDDAIVNIAKTIEWASFFGDSDLSDSPEPQAGLEFDGLAKLINQDNVHDARGASLTESLLNQAAVMISKGY
GTPTDAYMPVGVQADFVNQQLSKQTQLVRDNGNNVSVGFNIQGFHSARGFIKLHGSTVMENEQILDERIL
ALPTAPQPAKVTATQEAGKKGQFRAEDLAAHEYKVVVSSDDAESIASEVATATVTAKDDGVKLEIELAPM
YSSRPQFVSIYRKGAETGLFYLIARVPASKAENNVITFYDLNDSIPETVDVFVGEMSANVVHLFELLPMMRL
PLAQINASVTFAVLWYGALALRAPKKWVRIRNVKYIPVKNVHSN SEQ ID NO: 11 - LP101 Cps open reading frame
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAA SEQ ID NO: 12 - LP101 Cps protein
MPKNNKEEEVKEVNLNSVQEDALKSFTTGYGITPDTQTDAGALRREFLDDQISMLTWTENDLTFYKDIAK
KPATSTVAKYDVYMQHGKVGHTRFTREIGVAPVSDPNIRQKTVNMKFASDTKNISIAAGLVNNIQDPMQIL
TDDAIVNIAKTIEWASFFGDSDLSDSPEPQAGLEFDGLAKLINQDNVHDARGASLTESLLNQAAVMISKGY
GTPTDAYMPVGVQADFVNQQLSKQTQLVRDNGNNVSVGFNIQGFHSARGFIKLHGSTVMENEQILDERIL
ALPTAPQPAKVTATQEAGKKGQFRAEDLAAHEYKVVVSSDDAESIASEVATATVTAKDDGVKLEIELAPM
YSSRPQFVSIYRKGAETGLFYLIARVPASKAENNVITFYDLNDSIPETVDVFVGEMSANVVHLFELLPMMRL
PLAQINASVTFAVLWYGALALRAPKKWVRIRNVKYIPVKNVHSN
```

TABLE 7-continued

SEQ ID NO: 13 - LP124 Cps open reading frame
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAA SEQ ID NO: 14 - LP124 Cps protein
MPKNNKEEEVKEVNLNSVQEDALKSFTTGYGITPDTQTDAGALRREFLDDQISMLTWTENDLTFYKDIAK
KPATSTVAKYDVYMQHGKVGHTRFTREIGVAPVSDPNIRQKTVNMKFASDTKNISIAAGLVNNIQDPMQIL
TDDAIVNIAKTIEWASFFGDSDLSDSPEPQAGLEFDGLAKLINQDNVHDARGASLTESLLNQAAVMISKGY
GTPTDAYMPVGVQADFVNQQLSKQTQLVRDNGNNVSVGFNIQGFHSARGFIKLHGSTVMENEQILDERIL
ALPTAPQPAKVTATQEAGKKGQFRAEDLAAHEYKVVVSSDDAESIASEVATATVTAKDDGVKLEIELAPM
YSSRPQFVSIYRKGAETGLFYLIARVPASKAENNVITFYDLNDSIPETVDVFVGEMSANVVHLFELLPMMRL
PLAQINASVTFAVLWYGALALRAPKKWVRIRNVKYIPVKNVHSN SEQ ID NO: 15 - LP125 Cps open reading frame
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGTGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAA SEQ ID NO: 16 - LP125 Cps protein
MPKNNKEEEVKEVNLNSVQEDALKSFTTGYGITPDTQTDAGALRREFLDDQISMLTWTENDLTFYKDIAK
KPATSTVAKYDVYMQHGKVGHTRFTREIGVAPVSDPNIRQKTVNMKFASDTKNISIAAGLVNNIQDPMQIL
TDDAIVNIAKTIEWASFFGDSDLSDSPEPQAGLEFDGLAKLINQDNVHDARGASLTESLLNQAAVMISKGY
GTPTDAYMPVGVQADFVNQQLSKQTQLVRDNGNNVSVGFNIQGFHSARGFIKLHGSTVMENEQILDERIL
ALPTAPQPAKVTATQEAGKKGQFRAEDLAAHEYKVVVSSDDAESIASEVATATVTAKDDGVKLEIELAPM
YSSRPQFVSIYRKGAETGLFYLIARVPASKAENNVITFYDLNDSIPETVDVFVGEMSANVVHLFELLPMMRL
PLAQINASVTFAVLWYGALALRAPKKWVRIRNVKYIPVKNVHSN SEQ ID NO: 17 - LP143 Cps open reading frame
ATGCCAAAAAATAACAAAGAAGAAGTTAAAGAAGTAAACCTTAATTCAGTACAAGAGGATGCGTTAA
AGTCCTTTACGACTGGTTATGGTATCACACCTGATACACAAACAGATGCAGGAGCATTAAGACGTGAG
TTCCTAGACGACCAAATCTCAATGCTTACTTGGACAGAGAATGATTTAACATTCTATAAAGACATCGCT
AAAAAACCAGCTACATCTACAGTAGCAAAATACGATGTATACATGCAACATGGTAAGGTAGGTCATA
CTAGATTTACTCGTGAGATTGGGGTAGCACCAGTAAGTGACCCTAACATCCGTCAAAAAACAGTAAAT
ATGAAATTTGCTTCCGATACTAAAAACATCAGTATCGCAGCAGGTCTAGTAAACAACATTCAAGACCC
AATGCAAATTTTGACTGACGATGCTATCGTAAATATTGCTAAAACAATTGAGTGGGCTTCATTCTTTGG
AGATTCTGACTTATCAGATAGCCCAGAACCACAAGCAGGACTAGAATTTGACGGCTTGGCTAAACTTA
TTAACCAAGATAACGTTCATGATGCTCGTGGAGCTAGCTTGACTGAAAGCTTGTTAAACCAAGCAGCA
GTAATGATTAGTAAAGGTTATGGTACACCTACAGATGCTTACATGCCAGTAGGGGTTCAAGCAGACTT
TGTTAACCAACAACTTTCTAAACAAACACAACTTGTTCGCGATAACGGAAACAACGTAAGCGTTGGTT
TCAACATCCAAGGTTTCCATTCAGCTCGTGGATTTATCAAACTTCACGGTTCTACAGTAATGGAAACG
AACAAATCTTAGATGAACGTATTCTTGCTTTACCAACAGCTCCACAACCAGCTAAGGTAACTGCAACA
CAAGAAGCAGGTAAAAAAGGACAATTTAGAGCAGAAGATTTAGCAGCACATGAATATAAAGTTGTTG TABLE 7-continued

```
TAAGTTCTGACGATGCAGAGTCTATTGCAAGTGAAGTGGCTACAGCTACAGTTACTGCAAAAGATGAC
GGCGTTAAACTAGAAATCGAATTAGCTCCAATGTATAGCTCTCGTCCACAATTCGTTTCAATCTATAGA
AAAGGTGCAGAAACAGGTTTATTCTACCTAATCGCTCGTGTACCTGCTAGCAAAGCAGAGAACAACGT
AATCACTTTCTACGACTTAAACGACTCTATTCCTGAAACAGTAGACGTATTCGTTGGTGAAATGTCGGC
TAACGTAGTACACTTGTTTGAATTACTACCAATGATGAGATTACCTCTAGCTCAAATTAACGCATCTGT
TACATTTGCAGTTTTATGGTATGGCGCATTAGCTCTAAGAGCACCTAAGAAATGGGTACGTATTAGAA
ACGTTAAATATATTCCTGTAAAAAACGTTCATAGCAACTAA

SEQ ID NO: 18 - LP143 Cps protein
MPKNNKEEVKEVNLNSVQEDALKSFTTGYGITPDTQTDAGALRREFLDDQISMLTWTENDLTFYKDIAKK
PATSTVAKYDVYMQHGKVGHTRFTREIGVAPVSDPNIRQKTVNMKFASDTKNISIAAGLVNNIQDPMQILT
DDAIVNIAKTIEWASFFGDSDLSDSPEPQAGLEFDGLAKLINQDNVHDARGASLTESLLNQAAVMISKGYG
TPTDAYMPVGVQADFVNQQLSKQTQLVRDNGNNVSVGFNIQGFHSARGFIKLHGSTVMENEQILDERILAL
PTAPQPAKVTATQEAGKKGQFRAEDLAAHEYKVVVSSDDAESIASEVATATVTAKDDGVKLEIELAPMYS
SRPQFVSIYRKGAETGLFYLIARVPASKAENNVITFYDLNDSIPETVDVFVGEMSANVVHLFELLPMMRLPL
AQINASVTFAVLWYGALALRAPKKWVRIRNVKYIPVKNVHSN SEQ ID NO: 19 - A511 Cps open reading frame
ATGCCAAAAAATAACAAAGAAGAAGTTAAAGAAGTAAACCTTAATTCAGTACAAGAGGATGCGTTAA
AGTCCTTTACGACTGGTTATGGTATCACACCTGATACACAAACAGATGCAGGAGCATTAAGACGTGAG
TTCCTAGACGACCAAATCTCAATGCTTACTTGGACAGAGAATGATTTAACATTCTATAAAGACATCGCT
AAAAAAACCAGCTACATCTACAGTAGCAAAATACGATGTATACATGCAACATGGTAAGGTAGGTCATA
CTAGATTTACTCGTGAGATTGGGGTAGCACCAGTAAGTGACCCTAACATCCGTCAAAAAACAGTAAAT
ATGAAATTTGCTTCCGATACTAAAAACATCAGTATCGCAGCAGGTCTAGTAAACAACATTCAAGACCC
AATGCAAATTTTGACTGACGATGCTATCGTAAATATTGCTAAAACAATTGAGTGGGCTTCATTCTTTGG
AGATTCTGACTTATCAGATAGCCCAGAACCACAAGCAGGACTAGAATTTGACGGCTTGGCTAAACTTA
TTAACCAAGATAACGTTCATGATGCTCGTGGAGCTAGCTTGACTGAAAGCTTGTTAAACCAAGCAGCA
GTAATGATTAGTAAAGGTTATGGTACACCTACAGATGCTTACATGCCAGTAGGGGTTCAAGCAGACTT
TGTTAACCAACAACTTTCTAAACAAACACAACTTGTTCGCAGTAACGGAAACAACGTAAGCGTTGGTT
TCAACATCCAAGGTTTCCATTCAGCTCGTGGATTTATCAAACTTCACGGTTCTACAGTAATGGAAAACG
AACAAATCTTAGATGAACGTATTCTTGCTTTACCAACAGCTCCACAACCAGCTAAGGTAACTGCAACA
CAAGAAGCAGGTAAAAAAGGACAATTTAGAGCAGAAGATTTAGCAGCACATGAATATAAAGTTGTTG
TAAGTTCTGACGATGCAGAGTCTATTGCAAGTGAAGTGGCTACAGCTACAGTTACTGCAAAAGATGAC
GGCGTTAAACTAGAAATCGAATTAGCTCCAATGTATAGCTCTCGTCCACAATTCGTTTCAATCTATAGA
AAAGGTGCAGAAACAGGTTTATTCTACCTAATCGCTCGTGTACCTGCTAGCAAAGCAGAGAACAACGT
AATCACTTTCTACGACTTAAACGACTCTATTCCTGAAACAGTAGACGTATTCGTTGGTGAAATGTCGGC
TAACGTAGTACACTTGTTTGAATTACTACCAATGATGAGATTACCTCTAGCTCAAATTAACGCATCTGT
TACATTTGCAGTTTTATGGTATGGCGCATTAGCTCTAAGAGCACCTAAGAAATGGGTACGTATTAGAA
ACGTTAAATATATTCCTGTAAAAAACGTTCATAGCAACTAA SEQ ID NO: 20 - A511 Cps protein
MPKNNKEEVKEVNLNSVQEDALKSFTTGYGITPDTQTDAGALRREFLDDQISMLTWTENDLTFYKDIAKK
PATSTVAKYDVYMQHGKVGHTRFTREIGVAPVSDPNIRQKTVNMKFASDTKNISIAAGLVNNIQDPMQILT
DDAIVNIAKTIEWASFFGDSDLSDSPEPQAGLEFDGLAKLINQDNVHDARGASLTESLLNQAAVMISKGYG
TPTDAYMPVGVQADFVNQQLSKQTQLVRDNGNNVSVGFNIQGFHSARGFIKLHGSTVMENEQILDERILAL
PTAPQPAKVTATQEAGKKGQFRAEDLAAHEYKVVVSSDDAESIASEVATATVTAKDDGVKLEIELAPMYS
SRPQFVSIYRKGAETGLFYLIARVPASKAENNVITFYDLNDSIPETVDVFVGEMSANVVHLFELLPMMRLPL
AQINASVTFAVLWYGALALRAPKKWVRIRNVKYIPVKNVHSN SEQ ID NO: 21 - P100 Cps open reading frame
ATGCCAAAAAATAACAAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AATATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAGCTTGTTCGTGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGCTTAGCAGCACACGAATACAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAGTTAGCTCCAATGTACAGCTCCCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTATGACTTAAACGACTCTATTCCTGAAACAGTAGACGTATTCGTTGGTGAAATGTC
TGCTAACGTAGTACACTTGTTTGAATTACTACCAATGATGAGATTACCTCTAGCTCAAATTAACGCATC
TGTTACATTTGCAGTTTTATGGTATGGAGCATTAGCTCTAAGAGCACCTAAGAAATGGGTACGTATTAG
AAACGTTAAATATATTCCTGTAAAAAACGTTCATAGCAACTAA SEQ ID NO: 22 - P100 Cps protein
MPKNNKEEEVKEVNLNSVQEDALKSFTTGYGITPDTQTDAGALRREFLDDQISMLTWTENDLTFYKDIAK
KPATSTVAKYDVYMQHGKVGHTRFTREIGVAPVSDPNIRQKTVNMKFASDTKNISIAAGLVNNIQDPMQIL
TDDAIVNIAKTIEWASFFGDSDLSDSPEPQAGLEFDGLAKLINQDNVHDARGASLTESLLNQAAVMISKGY
GTPTDAYMPVGVQADFVNQQLSKQTQLVRDNGNNVSVGFNIQGFHSARGFIKLHGSTVMENEQILDERIL
ALPTAPQPAKVTATQEAGKKGQFRAEDLAAHEYKVVVSSDDAESIASEVATATVTAKDDGVKLEIELAPM
YSSRPQFVSIYRKGAETGLFYLIARVPASKAENNVITFYDLNDSIPETVDVFVGEMSANVVHLFELLPMMRL
PLAQINASVTFAVLWYGALALRAPKKWVRIRNVKYIPVKNVHSN
```

TABLE 7-continued

```
SEQ ID NO: 23 - LP48::ffluc
ATGCCAAAAAATAACAAGAAGAAGAAGTAAAGAAGTAAACCTTAATTCAGTACAAGAGGACGCGT
TAAAGTCCTTTACAACTGGTTATGGTATCACACCTGATACACAAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAAGAGGAGGTAAATATATATGGAAGAC
GCCAAAAACATAAAGAAAGGCCCGGCGCCATTCTATCCTCTAGAGGATGGAACCGCTGGAGAGCAAC
TGCATAAGGCTATGAAGAGATACGCCCTGGTTCCTGGAACAATTGCTTTTACAGATGCACATATCGAG
GTGAACATCACGTACGCGGAATACTTCGAAATGTCCGTTCGGTTGGCAGAAGCTATGAAACGATATGG
GCTGAATACAAATCACAGAATCGTCGTATGCAGTGAAAACTCTCTTCAATTCTTTATGCCGGTGTTGGG
CGCGTTATTTATCGGAGTTGCAGTTGCGCCCGCGAACGACATTTATAATGAACGTGAATTGCTCAACA
GTATGAACATTTCGCAGCCTACCGTAGTGTTTGTTTCCAAAAAGGGGTTGCAAAAAATTTTGAACGTG
CAAAAAAATTACCAATAATCCAGAAAATTATTATCATGGATTCTAAAACGGATTACCAGGGATTTCA
GTCGATGTACACGTTCGTCACATCTCATCTACCTCCCGGTTTTAATGAATACGATTTTGTACCAGAGTC
CTTTGATCGTGACAAAACAATTGCACTGATAATGAATTCCTCTGGATCTACTGGGTTACCTAAGGGTGT
GGCCCTTCCGCATAGAACTGCCTGCGTCAGATTCTCGCATGCCAGAGATCCTATTTTTGGCAATCAAAT
CATTCCGGATACTGCGATTTTAAGTGTTGTTCCATTCCATCACGGTTTTGGAATGTTTACTACACTCGG
ATATTTGATATGTGGATTTCGAGTCGTCTTAATGTATAGATTTGAAGAAGAGCTGTTTTTACGATCCCT
TCAGGATTACAAAATTCAAAGTGCGTTGCTAGTACCAACCCTATTTTCATTCTTCGCCAAAAGCACTCT
GATTGACAAATACGATTTATCTAATTTACACGAAATTGCTTCTGGGGGCGCACCTCTTTCGAAAGAAGT
CGGGGAAGCGGTTGCAAAACGCTTCCATCTTCCAGGGATACGACAAGGATATGGGCTCACTGAGACTA
CATCAGCTATTCTGATTACACCCGAGGGGGATGATAAAACGGGCGCGGTCGGTAAAGTTGTTCCATTT
TTTGAAGCGAAGGTTGTGGATCTGGATACCGGGAAAACGCTGGGCGTTAATCAGAGAGGCGAATTAT
GTGTCAGAGGACCTATGATTATGTCCGGTTATGTAAACAATCCGGAAGCGACCAACGCCTTGATTGAC
AAGGATGGATGGCTACATTCTGGAGACATAGCTTACTGGGACGAAGACGAACATTTCTTCATAGTTGA
CCGCTTGAAGTCTTTAATTAAATACAAAGGATATCAGGTGGCCCCCGCTGAATTGGAATCGATATTGTT
ACAACACCCCAACATCTTCGACGCGGGCGTGGCAGGTCTTCCCGACGATGACGCCGGTGAACTTCCAG
CCGCCGTTGTTGTTTGGAGCACGGAAAGACGATGACGGAAAAAGAGATCGTGGATTACGTCGCCAGT
CAAGTAACAACCGCGAAAAAGTTGCGCGGAGGAGTTGTGTTTGTGGACGAAGTACCGAAAGGTCTTA
CCGGAAAACTCGACGCAAGAAAAATCAGAGAGATCCTCATAAAGGCCAAGAAGGGCGGAAAGTCCA
AATTGTAATAATTATAGGATAATTGAATAAAAACAGTATAGAGAGCAGATAAATACTGCTCTCTATTT
TACTAATAAGGAGGATTTAAATTGCTAAAAAATACAAACTTAGCTAATTATAAAAAAGTGAATACACG
GTTTGGAAATCTTAGTTTTGACGACAAAGGTATTTCTAATGACTTAACGGAAGAACAGCAAAAAGAAT
TAGGTAAGCTTCGAGGATTCGAATATATTAAGACAGAACAGAAAACAAAAGAAGAACCTAAGAAAGA
AGAACCTAAGAAAGAAAGTACAGAAAATGAATTAGACAGCTTCTTAGCTAAAGAGCCTTCAATCAAA
GAATTAAAAGAATTTGCGAGTAAAAAAGGCATTAAAAATTGAAAAAACTAAGAAAAATGATATAATTG
AAGAACTAAAGAGAGGGTAATGTATAATGTATGGAGGTTATGAAGGACAAGATTCTTACGAATACCC
TTACTCACATGGGAACCCTAAGCATGTAGAGCCAGAAAAAGTTGACGAATATGTTCTTTCTGATTATG
GTTGGACTGCGGAAACAATTAAAGCATACATGTATGGTGTTCGTGTAGTAGACCCTGAAACAGGAGAG
GAAATGGGAGACACCTTCTACAATCATATTATAGAGGTTGCCGTTGATAAGGC SEQ ID NO: 24 - LP99::ffluc
ATGCCAAAAAATAACAAGAAGAAGAAGTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAAGAGGAGGTAAATATATATGGAAGAC
```

TABLE 7-continued

```
GCCAAAAACATAAAGAAAGGCCCGGCGCCATTCTATCCTCTAGAGGATGGAACCGCTGGAGAGCAAC
TGCATAAGGCTATGAAGAGATACGCCCTGGTTCCTGGAACAATTGCTTTTACAGATGCACATATCGAG
GTGAACATCACGTACGCGGAATACTTCGAAATGTCCGTTCGGTTGGCAGAAGCTATGAAACGATATGG
GCTGAATACAAATCACAGAATCGTCGTATGCAGTGAAAACTCTCTTCAATTCTTTATGCCGGTGTTGGG
CGCGTTATTTATCGGAGTTGCAGTTGCGCCCGCGAACGACATTTATAATGAACGTGAATTGCTCAACA
GTATGAACATTTCGCAGCCTACCGTAGTGTTTGTTTCCAAAAAGGGGTTGCAAAAAATTTTGAACGTG
CAAAAAAAATTACCAATAATCCAGAAAATTATTATCATGGATTCTAAAACGGATTACCAGGGATTTCA
GTCGATGTACACGTTCGTCACATCTCATCTACCTCCCGGTTTTAATGAATACGATTTTGTACCAGAGTC
CTTTGATCGTGACAAAACAATTGCACTGATAATGAATTCCTCTGGATCTACTGGGTTACCTAAGGGTGT
GGCCCTTCCGCATAGAACTGCCTGCGTCAGATTCTCGCATGCCAGAGATCCTATTTTTGGCAATCAAAT
CATTCCGGATACTGCGATTTTAAGTGTTGTTCCATTCCATCACGGTTTTGGAATGTTTACTACACTCGG
ATATTTGATATGTGGATTTCGAGTCGTCTTAATGTATAGATTTGAAGAAGAGCTGTTTTTACGATCCCT
TCAGGATTACAAAATTCAAAGTGCGTTGCTAGTACCAACCCTATTTTCATTCTTCGCCAAAAGCACTCT
GATTGACAAATACGATTTATCTAATTTACACGAAATTGCTTCTGGGGGCGCACCTCTTTCGAAAGAAGT
CGGGGAAGCGGTTGCAAAACGCTTCCATCTTCCAGGGATACGACAAGGATATGGGCTCACTGAGACTA
CATCAGCTATTCTGATTACACCCGAGGGGATGATAAACCGGGCGCGGTCGGTAAAGTTGTTCCATTT
TTTGAAGCGAAGGTTGTGGATCTGGATACCGGGAAAACGCTGGGCGTTAATCAGAGAGGCGAATTAT
GTGTCAGAGGACCTATGATTATGTCCGGTTATGTAAACAATCCGGAAGCGACCAACGCCTTGATTGAC
AAGGATGGATGGCTACATTCTGGAGACATAGCTTACTGGGACGAAGACGAACACTTCTTCATAGTTGA
CCGCTTGAAGTCTTTAATTAAATACAAAGGATATCAGGTGGCCCCCGCTGAATTGGAATCGATATTGTT
ACAACACCCCAACATCTTCGACGCGGGCGTGGCAGGTCTTCCCGACGATGACGCCGGTGAACTTCCCG
CCGCCGTTGTTGTTTTGGAGCACGGAAAGACGATGACGGAAAAAGAGATCGTGGATTACGTCGCCAGT
CAAGTAACAACCGCGAAAAAGTTGCGCGGAGGAGTTGTGTTTGTGGACGAAGTACCGAAAGGTCTTA
CCGGAAAACTCGACGCAAGAAAATCAGAGAGATCCTCATAAAGGCCAAGAAGGGCGGAAAGTCCA
AATTGTAATAATTATAGGATAATTGAATAAAAACAGTATAGAGAGCAGATAAATACTGCTCTCTATTT
TACTAATAAGGAGGATTTAAATTGCTAAAAAATACAAACTTAGCTAATTATAAAAAGTGAATACACG
GTTTGGAAATCTTAGTTTTGACGACAAAGGTATTTCTAATGACTTAACGGAAGAACAGCAAAAAGAAT
TAGGTAAGCTTCGAGGATTCGAATATATTAAGACAGAACAGAAAACAAAGAAGAACCTAAGAAAGA
AGAACCTAAGAAAGAAGAACCTAAGAAAGAAGAACCTAAGAAAGAAGAACCTAAGAAAGAAGAACC
TAAGAAAGAAAGTACAGAAAATGAATTAGACAGCTTCTTAGCTAAAGAGCCTTCAATCAAAGAATTA
AAAGAATTTGCGAGTAAAAAAGGCATTAAAATTGAAAAAACTAAGAAAAATGATATAATTGAAGAAC
TAAAGAGAGGGTAATGTATAATGTATGGAGGTTATGAAGGACAAGATTCTTACGAATACCCTTACTCA
CATGGGAACCCTAAGCATGTAGAGCCAGAAAAAGTTGACGAATATGTTCTTTCTGATTATGGTTGGAC
TGCGGAAACAATTAAAGCATACATGTATGGTGTTCGTGTAGTAGACCCTGAAACAGGAGAGGAAATG
GGAGACACCTTCTACAATCATATTATAGAGGTTGCCGTTGATAAGGC

SEQ ID NO: 25 - LP101::ffluc
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGCCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTGACTGACGATGCTATCGTAAATATTGCTAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAAGGAAAAGAATATATATGGAAGAC
GCCAAAAACATAAAGAAAGGCCCGGCGCCATTCTATCCTCTAGAGGATGGAACCGCTGGAGAGCAAC
TGCATAAGGCTATGAAGAGATACGCCCTGGTTCCTGGAACAATTGCTTTTACAGATGCACATATCGAG
GTGAACATCACGTACGCGGAATACTTCGAAATGTCCGTTCGGTTGGCAGAAGCTATGAAACGATATGG
GCTGAATACAAATCACAGAATCGTCGTATGCAGTGAAAACTCTCTTCAATTCTTTATGCCGGTGTTGGG
CGCGTTATTTATCGGAGTTGCAGTTGCGCCCGCGAACGACATTTATAATGAACGTGAATTGCTCAACA
GTATGAACATTTCGCAGCCTACCGTAGTGTTTGTTTCCAAAAAGGGGTTGCAAAAAATTTTGAACGTG
CAAAAAAAATTACCAATAATCCAGAAAATTATTATCATGGATTCTAAAACGGATTACCAGGGATTTCA
GTCGATGTACACGTTCGTCACATCTCATCTACCTCCCGGTTTTAATGAATACGATTTTGTACCAGAGTC
CTTTGATCGTGACAAAACAATTGCACTGATAATGAATTCCTCTGGATCTACTGGGTTACCTAAGGGTGT
GGCCCTTCCGCATAGAACTGCCTGCGTCAGATTCTCGCATGCCAGAGATCCTATTTTTGGCAATCAAAT
CATTCCGGATACTGCGATTTTAAGTGTTGTTCCATTCCATCACGGTTTTGGAATGTTTACTACACTCGG
ATATTTGATATGTGGATTTCGAGTCGTCTTAATGTATAGATTTGAAGAAGAGCTGTTTTTACGATCCCT
TCAGGATTACAAAATTCAAAGTGCGTTGCTAGTACCAACCCTATTTTCATTCTTCGCCAAAAGCACTCT
GATTGACAAATACGATTTATCTAATTTACACGAAATTGCTTCTGGGGGCGCACCTCTTTCGAAAGAAGT
CGGGGAAGCGGTTGCAAAACGCTTCCATCTTCCAGGGATACGACAAGGATATGGGCTCACTGAGACTA
CATCAGCTATTCTGATTACACCCGAGGGGATGATAAACCGGGCGCGGTCGGTAAAGTTGTTCCATTT
TTTGAAGCGAAGGTTGTGGATCTGGATACCGGGAAAACGCTGGGCGTTAATCAGAGAGGCGAATTAT
GTGTCAGAGGACCTATGATTATGTCCGGTTATGTAAACAATCCGGAAGCGACCAACGCCTTGATTGAC
AAGGATGGATGGCTACATTCTGGAGACATAGCTTACTGGGACGAAGACGAACACTTCTTCATAGTTGA
CCGCTTGAAGTCTTTAATTAAATACAAAGGATATCAGGTGGCCCCCGCTGAATTGGAATCGATATTGTT
ACAACACCCCAACATCTTCGACGCGGGCGTGGCAGGTCTTCCCGACGATGACGCCGGTGAACTTCCCG
CCGCCGTTGTTGTTTTGGAGCACGGAAAGACGATGACGGAAAAAGAGATCGTGGATTACGTCGCCAGT
```

TABLE 7-continued

```
CAAGTAACAACCGCGAAAAAGTTGCGCGGAGGAGTTGTGTTTGTGGACGAAGTACCGAAAGGTCTTA
CCGGAAAACTCGACGCAAGAAAATCAGAGAGATCCTCATAAAGGCCAAGAGGGCGGAAAGTCCA
AATTGTAATAATTATAGGATAATTGAATAAAAACAGTATAGAGAGCAGATAAATACTGCTCTCTATTT
TACTAATAAGGAGGATTTAAATTGCTAAAAAATACAAACTTAGCTAATTATAAAAAAGTGAATACACG
GTTTGGAAATCTTAGTTTTGACGACAAAGGTATTTCTAATGACTTAACGGAAGAACAGCAAAAAGAAT
TAGGTAAGCTTCGAGGATTCGAATATATTAAGACAGAACAGAAAACAAAAGAAGAACCTAAGAAAGA
AGAACCTAAGAAAGAAGAACCTAAGAAAGAAGAACCTAAGAAAGAAGAACCTAAGAAAGAAGAACC
TAAGAAAGAAAGTACAGAAAATGAATTAGACAGCTTCTTAGCTAAAGAGCCTTCAATCAAAGAATTA
AAAGAATTTGCGAGTAAAAAAGGCATTAAAATTGAAAAAACTAAGAAAAATGATATAATTGAAGAAC
TAAAGAGAGGGTAATGTATAATGTATGGAGGTTATGAAGGACAAGATTCTTACGAATACCCTTACTCA
CATGGGAACCCTAAGCATGTAGAGCCAGAAAAAGTTGACGAATATGTTCTTTCTGATTATGGTTGGAC
TGCGGAAACAATTAAAGCATACATGTATGGTGTTCGTGTAGTAGACCCTGAAACAGGAGAGGAAATG
GGAGACACCTTCTACAATCATATTATAGAGGTTGCCGTTGATAAGGC

SEQ ID NO: 26 - LP124::ffluc
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAACCAGCTACATCTACAGTAGCAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGCACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAAGAGGAGGTAAATATATATGGAAGAC
GCCAAAAACATAAAGAAAGGCCCGGCGCCATTCTATCCTCTAGAGGATGGAACCGCTGGAGACAAC
TGCATAAGGCTATGAAGAGATACGCCCTGGTTCCTGGAACAATTGCTTTTACAGATGCACATATCGAG
GTGAACATCACGTACGCGGAATACTTCGAAATGTCCGTTCGGTTGGCAGAAGCTATGAAACGATATGG
GCTGAATACAAATCACAGAATCGTCGTATGCAGTGAAAACTCTCTTCAATTCTTTATGCCGGTGTTGGG
CGCGTTATTTATCGGAGTTGCAGTTGCGCCCGCGAACGACATTTATAATGAACGTGAATTGCTCAACA
GTATGAACATTTCGCAGCCTACCGTAGTGTTTGTTTCCAAAAAGGGGTTGCAAAAAATTTTGAACGTG
CAAAAAAATTACCAATAATCCAGAAAATTATTATCATGGATTCTAAAACGGATTACCAGGGATTTCA
GTCGATGTACACGTTCGTCACATCTCATCTACCTCCCGGTTTTAATGAATACGATTTTGTACCAGAGTC
CTTTGATCGTGACAAAACAATTGCACTGATAATGAATTCCTCTGGATCTACTGGGTTACCTAAGGGTGT
GGCCCTTCCGCATAGAACTGCCTGCGTCAGATTCTCGCATGCCAGAGATCCTATTTTTGGCAATCAAAT
CATTCCGGATACTGCGATTTTAAGTGTTGTTCCATTCCATCACGGTTTTGGAATGTTTACTACACTCGG
ATATTTGATATGTGGATTTCGAGTCGTCTTAATGTATAGATTTGAAGAAGAGCTGTTTTTACGATCCCT
TCAGGATTACAAAATTCAAAGTGCGTTGCTAGTACCAACCCTATTTTCATTCTTCGCCAAAAGCACTCT
GATTGACAAATACGATTTATCTAATTTACACGAAATTGCTTCTGGGGGCGCACCTCTTTCGAAAGAAGT
CGGGGAAGCGGTTGCAAAACGCTTCCATCTTCCAGGGATACGACAAGGATATGGGCTCACTGAGACTA
CATCAGCTATTCTGATTACACCCGAGGGGGATGATAAACCGGGCGCGGTCGGTAAAGTTGTTCCATTT
TTTGAAGCGAAGGTTGTGGATCTGGATACCGGGAAAACGCTGGGCGTTAATCAGAGAGGCGAATTAT
GTGTCAGAGGACCTATGATTATGTCCGGTTATGTAAACAATCCGGAAGCGACCAACGCCTTGATTGAC
AAGGATGGATGGCTACATTCTGGAGACATAGCTTACTGGGACGAAGACGAACACTTCTTCATAGTTGA
CCGCTTGAAGTCTTTAATTAAATACAAAGGATATCAGGTGGCCCCCGCTGAATTGGAATCGATATTGTT
ACAACACCCCAACATCTTGACGCGGGCGTGGCAGGTCTTCCCGACGATGACGCCGGTGAACTTCCCG
CCGCCGTTGTTGTTTTGGAGCACGGAAAGACGATGACGGAAAAAGGATCGTGGATTACGTCGCCAGT
CAAGTAACAACCGCGAAAAAGTTGCGCGGAGGAGTTGTGTTTGTGGACGAAGTACCGAAAGGTCTTA
CCGGAAAACTCGACGCAAGAAAATCAGAGAGATCCTCATAAAGGCCAAGAGGGCGGAAAGTCCA
AATTGTAATAATTATAGGATAATTGAATAAAAACAGTATAGAGAGCAGATAAATACTGCTCTCTATTT
TACTAATAAGGAGGATTTAAATTGCTAAAAAATACAAACTTAGCTAATTATAAAAAAGTGAATACACG
GTTTGGAAATCTTAGTTTTGACGACAAAGGTATTTCTAATGACTTAACGGAAGAACAGCAAAAAGAAT
TAGGTAAGCTTCGAGGATTCGAATATATTAAGACAGAACAGAAAACAAAAGAAGAACCTAAGAAAGA
AGAACCTAAGAAAGAAGAACCTAAGAAAGAAGAACCTAAGAAAGAAGAACCTAAGAAAGAAGAACC
TAAGAAAGAAAGTACAGAAAATGAATTAGACAGCTTCTTAGCTAAAGAGCCTTCAATCAAAGAATTA
AAAGAATTTGCGAGTAAAAAAGGCATTAAAATTGAAAAAACTAAGAAAAATGATATAATTGAAGAAC
TAAAGAGAGGGTAATGTATAATGTATGGAGGTTATGAAGGACAAGATTCTTACGAATACCCTTACTCA
CATGGGAACCCTAAGCATGTAGAGCCAGAAAAAGTTGACGAATATGTTCTTTCTGATTATGGTTGGAC
TGCGGAAACAATTAAAGCATACATGTATGGTGTTCGTGTAGTAGACCCTGAAACAGGAGAGGAAATG
GGAGACACCTTCTACAATCATATTATAGAGGTTGCCGTTGATAAGGC SEQ ID NO: 27 - LP125::ffluc
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAACCAGCTACATCTACAGTAGCAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
```

TABLE 7-continued

```
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGTGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAAGAGGAGGTAAATATATATGGAAGAC
GCCAAAAACATAAAGAAAGGCCCGGCGCCATTCTATCCTCTAGAGGATGGAACCGCTGGAGAGCAAC
TGCATAAGGCTATGAAGAGATACGCCCTGGTTCCTGGAACAATTGCTTTTACAGATGCACATATCGAG
GTGAACATCACGTACGCGGAATACTTCGAAATGTCCGTTCGGTTGGCAGAAGCTATGAAACGATATGG
GCTGAATACAAATCACAGAATCGTCGTATGCAGTGAAAACTCTCTTCAATTCTTTATGCCGGTGTTGGG
CGCGTTATTTATCGGAGTTGCAGTTGCGCCCGCGAACGACATTTATAATGAACGTGAATTGCTCAACA
GTATGAACATTTCGCAGCCTACCGTAGTGTTTGTTTCCAAAAAGGGGTTGCAAAAAATTTTGAACGTG
CAAAAAAATTACCAATAATCCAGAAAATTATTATCATGGATTCTAAAACGGATTACCAGGGATTTCA
GTCGATGTACACGTTCGTCACATCTCATCTACCTCCCGGTTTTAATGAATACGATTTTGTACCAGAGTC
CTTTGATCGTGACAAAACAATTGCACTGATAATGAATTCCTCTGGATCTACTGGGTTACCTAAGGGTGT
GGCCCTTCCGCATAGAACTGCCTGCGTCAGATTCTCGCATGCCAGAGATCCTATTTTTGGCAATCAAAT
CATTCCGGATACTGCGATTTTAAGTGTTGTTCCATTCCATCACGGTTTTGGAATGTTTACTACACTCGG
ATATTTGATATGTGGATTTCGAGTCGTCTTAATGTATAGATTTGAAGAAGAGCTGTTTTTACGATCCCT
TCAGGATTACAAAATTCAAAGTGCGTTGCTAGTACCAACCCTATTTTCATTCTTCGCCAAAAGCACTCT
GATTGACAAATACGATTTATCTAATTTACACGAAATTGCTTCTGGGGGCGCACCTCTTTCGAAAGAAGT
CGGGGAAGCGGTTGCAAAACGCTTCCATCTTCCAGGGATACGACAAGGATATGGGCTCACTGAGACTA
CATCAGCTATTCTGATTACACCCGAGGGGGATGATAAACCGGGCGCGGTCGGTAAAGTTGTTCCATTT
TTTGAAGCGAAGGTTGTGGATCTGGATACCGGGAAAACGCTGGGCGTTAATCAGAGAGGCGAATTAT
GTGTCAGAGGACCTATGATTATGTCCGGTTATGTAAACAATCCGGAAGCGACCAACGCCTTGATTGAC
AAGGATGGATGGCTACATTCTGGAGACATAGCTTACTGGGACGAAGACGAACACTTCTTCATAGTTGA
CCGCTTGAAGTCTTTAATTAAATACAAAGGATATCAGGTGGCCCCGCTGAATTGGAATCGATATTGTT
ACAACACCCCAACATCTTCGACGCGGGCGTGGCAGGTCTTCCCGACGATGACGCCGGTGAACTTCCAG
CCGCCGTTGTTGTTTGGAGCACGGAAAGACGATGACGGAAAAAGAGATCGTGGATTACGTCGCCAGT
CAAGTAACAACCGCGAAAAAGTTGCGCGGAGGAGTTGTGTTTGTGGACGAAGTACCGAAAGGTCTTA
CCGGAAAACTCGACGCAAGAAAAATCAGAGAGATCCTCATAAAGGCCAAGAAGGGCGGAAAGTCCA
AATTGTAATAATTATAGGATAATTGAATAAAAACAGTATAGAGAGCAGATAAATACTGCTCTCTATTT
TACTAATAAGGAGGATTTAAATTGCTAAAAAATACAAACTTAGCTAATTATAAAAAAGTGAATACACG
GTTTGGAAATCTTAGTTTTGACGACAAAGGTATTTCTAATGACTTAACGGAAGAACAGCAAAAGAAT
TAGGTAAGCTTCGAGGATTCGAATATATTAAGACAGAACAGAAACAAAAGAAGAACCTAAGAAAGA
AGAACCTAAGAAAGAAAGTACAGAAAATGAATTAGACAGCTTCTTAGCTAAAGAGCCTTCAATCAAA
GAATTAAAAGAATTTGCGAGTAAAAAAGGCATTAAAATTGAAAAAACTAAGAAAAATGATATAATTG
AAGAACTAAAGAGAGGGTAATGTATAATGTATGGAGGTTATGAAGGACAAGATTCTTACGAATACCC
TTACTCACATGGGAACCCTAAGCATGTAGAGCCAGAAAAAGTTGACGAATATGTTCTTTCTGATTATG
GTTGGACTGCGGAAACAATTAAAGCATACATGTATGGTGTTCGTGTAGTAGACCCTGAAACAGGAGAG
GAAATGGGAGACACCTTCTACAATCATATTATAGAGGTTGCCGTTGATAAGGC
```

SEQ ID NO: 28 - LP143::ffluc
```
ATGCCAAAAAATAACAAAGAAGAAGTTAAAGAAGTAAACCTTAATTCAGTACAAGAGGATGCGTTAA
AGTCCTTTACGACTGGTTATGGTATCACACCTGATCACAAACAGATGCAGGAGCATTAAGACGTGAG
TTCCTAGACGACCAAATCTCAATGCTTACTTGGACAGAGAATGATTTAACATTCTATAAAGACATCGCT
AAAAAACCAGCTACATCTACAGTAGCAAAATACGATGTATACATGCAACATGGTAAGGTAGGTCATA
CTAGATTTACTCGTGAGATTGGGGTAGCACCAGTAAGTGACCCTAACATCCGTCAAAAAACAGTAAAT
ATGAAATTTGCTTCCGATACTAAAAACATCAGTATCGCAGCAGGTCTAGTAAACAACATTCAAGACCC
AATGCAAATTTTGACTGACGATGCTATCGTAAATATTGCTAAACAATTGAGTGGGCTTCATCTTTGG
AGATTCTGACTTATCAGATAGCCCAGAACCACAAGCAGGACTAGAATTTGACGGCTTGGCTAAACTTA
TTAACCAAGATAACGTTCATGATGCTCGTGGAGCTAGCTTGACTGAAAGCTTGTTAAACCAAGCAGCA
GTAATGATTAGTAAAGGTTATGGTACACCTACAGATGCTTACATGCCAGTAGGGGTTCAAGCAGACTT
TGTTAACCAACAACTTTCTAAACAAACACAACTTGTTCGCGATAACGGAAACAACGTAAGCGTTGGTT
TCAACATCCAAGGTTTCCATTCAGCTCGTGGATTTATCAAACTTCACGGTTCTACAGTAATGGAACG
AACAAATCTTAGATGAACGTATTCTTGCTTTACCAACAGCTCCACAACCAGCTAAGGTAACTGCAACA
CAAGAAGCAGGTAAAAAAGGACAATTTAGAGCAGAAGATTTAGCAGCACATGAATATAAAGTTGTTG
TAAGTTCTGACGATGCAGAGTCTATTGCAAGTGAAGTGGCTACAGCTACAGTTACTGCAAAAGATGAC
GGCGTTAAACTAGAAATCGAATTAGCTCCAATGTATAGCTCTCGTCCACAATTCGTTTCAATCTATAGA
AAAGGTGCAGAAACAGGTTTATTCTACCTAATCGCTCGTGTACCTGCTAGCAAAGCAGAGAACAACGT
AATCACTTTCTACGACTTAAACGACTCTATTCCTGAAACAGTAGACGTATTCGTTGGTGAAATGTCGGC
TAACGTAGTACACTTGTTTGAATTACTACCAATGATGAGATTACCTCTAGCTCAAATTAACGCATCTGT
TACATTTGCAGTTTATGGTATGGCGCATTAGCTCTAAGAGCACCTAAGAAATGGGTACGTATTAGAA
ACGTTAAATATATTCCTGTAAAAAACGTTCATAGCAACTAAGAGGAGGTAAATATATATGGAAGACGC
CAAAAACATAAAGAAAGGCCCGGCGCCATTCTATCCTCTAGAGGATGGAACCGCTGGAGAGCAACTG
CATAAGGCTATGAAGAGATACGCCCTGGTTCCTGGAACAATTGCTTTTACAGATGCACATATCGAGGT
GAACATCACGTACGCGGAATACTTCGAAATGTCCGTTCGGTTGGCAGAAGCTATGAAACGATATGGGC
TGAATACAAATCACAGAATCGTCGTATGCAGTGAAAACTCTCTTCAATTCTTTATGCCGGTGTTGGGCG
CGTTATTTATCGGAGTTGCAGTTGCGCCCGCGAACGACATTTATAATGAACGTGAATTGCTCAACAGT
ATGAACATTTCGCAGCCTACCGTAGTGTTTGTTTCCAAAAAGGGGTTGCAAAAAATTTTGAACGTGCA
AAAAAATTACCAATAATCCAGAAAATTATTATCATGGATTCTAAAACGGATTACCAGGGATTTCAGT
CGATGTACACGTTCGTCACATCTCATCTACCTCCCGGTTTTAATGAATACGATTTTGTACCAGAGTCCT
TGATCGTGACAAAACAATTGCACTGATAATGAATTCCTCTGGATCTACTGGGTTACCTAAGGGTGTG
```

TABLE 7-continued

```
GCCCTTCCGCATAGAACTGCCTGCGTCAGATTCTCGCATGCCAGAGATCCTATTTTTGGCAATCAAATC
ATTCCGGATACTGCGATTTTAAGTGTTGTTCCATTCCATCACGGTTTTGGAATGTTTACTACACTCGGAT
ATTTGATATGTGGATTTCGAGTCGTCTTAATGTATAGATTTGAAGAAGAGCTGTTTTTACGATCCCTTC
AGGATTACAAAATTCAAAGTGCGTTGCTAGTACCAACCCTATTTTCATTCTTCGCCAAAAGCACTCTGA
TTGACAAATACGATTTATCTAATTTACACGAAATTGCTTCTGGGGGCGCACCTCTTTCGAAAGAAGTCG
GGGAAGCGGTTGCAAAACGCTTCCATCTTCCAGGGATACGACAAGGATATGGGCTCACTGAGACTACA
TCAGCTATTCTGATTACACCCGAGGGGATGATAAACCGGGCGCGGTCGGTAAAGTTGTTCCATTTTTT
GAAGCGAAGGTTGTGGATCTGGATACCGGGAAAACGCTGGGCGTTAATCAGAGAGGCGAATTATGTG
TCAGAGGACCTATGATTATGTCCGGTTATGTAAACAATCCGGAAGCGACCAACGCCTTGATTGACAAG
GATGGATGGCTACATTCTGGAGACATAGCTTACTGGGACGAAGACGAACACTTCTTCATAGTTGACCG
CTTGAAGTCTTTAATTAAATACAAAGGATATCAGGTGGCCCCCGCTGAATTGGAATCGATATTGTTAC
AACACCCCAACATCTTCGACGCGGGCGTGGCAGGTCTTCCCGACGATGACGCCGGTGAACTTCCCGCC
GCCGTTGTTGTTTTGGAGCACGGAAAGACGATGACGGAAAAAGAGATCGTGGATTACGTCGCCAGTCA
AGTAACAACCGCGAAAAAGTTGCGCGGAGGAGTTGTGTTTGTGGACGAAGTACCGAAAGGTCTTACC
GGAAAACTCGACGCAAGAAAATCAGAGAGATCCTCATAAAGGCCAAGAAGGGCGGAAAGTCCAAA
TTGTAATAATTATAGGATAATTGAATAAAAACAGTATAGAGAGCAGATAAATACTGCTCTCTATTTTA
CTAATAAGGAGGATTTAAATTGCTAAAAAATACAAACTTAGCTAATTATAAAAAAGTGAATACACGGT
TTGGAAATCTTAGTTTTGACGACAAAGGTATTTCTAATGACTTAACGGAAGAACAGCAAAAAGAATTA
GGTAAGCTTCGAGGATTCGAATATATTAAGACAGAACAGAAAACAAAGAAGAACCTAAGAAAGAA
GAACCTAAGAAAGAAGAACCTAAGAAAGAAGAACCTAAGAAAGAAGAACCTAAGAAAGAAGAACCT
AAGAAAGAAAGTACAGAAAATGAATTAGCACAGCTTCTTAGCTAAAGAGCCTTCAATCAAAGAATTAA
AAGAATTTGCGAGTAAAAAAGGCATTAAAATTGAAAAAACTAAGAAAAATGATATAATTGAAGAACT
AAAGAGAGGGTAATGTATAATGTATGGAGGTTATGAAGGACAAGATTCTTACGAATACCCTTACTCAC
ATGGGAACCCTAAGCATGTAGAGCCAGAAAAAGTTGACGAATATGTTCTTTCTGATTATGGTTGGACT
GCGGAAACAATTAAAGCATACATGTATGGTGTTCGTGTAGTAGACCCTGAAACAGGAGAGGAAATGG
GAGACACCTTCTACAATCATATTATAGAGGTTGCCGTTGATAAGGC
```

SEQ ID NO: 29 - A511::ffluc
```
ATGCCAAAAAATAACAAAGAAGAAGTTAAAGAAGTAAACCTTAATTCAGTACAAGAGGATGCGTTAA
AGTCCTTTACGACTGGTTATGGTATCACACCTGATACACAAACAGATGCAGGAGCATTAAGACGTGAG
TTCCTAGACGACCAAATCTCAATGCTTACTTGGACAGAGAATGATTTAACATTCTATAAAGACATCGCT
AAAAAACCAGCTACATCTACAGTAGCAAAATACGATGTATACATGCAACATGGTAAGGTAGGTCATA
CTAGATTTACTCGTGAGATTGGGGTAGCACCAGTAAGTGACCCTAACATCCGTCAAAAAACAGTAAAT
ATGAAATTTGCTTCCGATACTAAAAACATCAGTATCGCAGCAGGTCTAGTAAACAACATTCAAGACCC
AATGCAAATTTTGACTGACGATGCTATCGTAAATATTGCTAAAACAATTGAGTGGGCTTCATTCTTTGG
AGATTCTGACTTATCAGATAGCCCAGAACCACAAGCAGGACTAGAATTTGACGGCTTGGCTAAACTTA
TTAACCAAGATAACGTTCATGATGCTCGTGGAGCTAGCTTGACTGAAAGCTTGTTAAACCAAGCAGCA
GTAATGATTAGTAAAGGTTATGGTACACCTACAGATGCTTACATGCCAGTAGGGGTTCAAGCAGACTT
TGTTAACCAACAACTTTCTAAACAAACACAACTTGTTCGCGATAACGGAAACAACGTAAGCGTTGGTT
TCAACATCCAAGGTTTCCATTCAGCTCGTGGATTTATCAAACTTCACGGTTCTACAGTAATGGAAAACG
AACAAATCTTAGATGAACGTATTCTTGCTTTACCAACAGCTCCACAACCAGCTAAGGTAACTGCAACA
CAAGAAGCAGGTAAAAAAGGACAATTTAGAGCAGAAAGATTTAGCAGGCACATGAATATAAAGTTGTTG
TAAGTTCTGACGATGCAGAGTCTATTGCAAGTGAAGTGGCTACAGCTACAGTTACTGCAAAAGATGAC
GGCGTTAAACTAGAAATCGAATTAGCTCCAATGTATAGCTCTCGTCCACAATTCGTTTCAATCTATAGA
AAAGGTGCAGAAACAGGTTTATTCTACCTAATCGCTCGTGTACCTGCTAGCAAAGCAGAGAACAACGT
AATCACTTTCTACGACTTAAACGACTCTATTCCTGAAACAGTAGACGTATTCGTTGGTGAAATGTCGGC
TAACGTAGTACACTTGTTTGAATTACTACCAATGATGAGATTACCTCTAGCTCAAATTAACGCATCTGT
TACATTTGCAGTTTTATGGTATGGCGCATTAGCTCTAAGAGCACCTAAGAATGGGTACGTATTAGAA
ACGTTAAATATATTCCTGTAAAAAACGTTCATAGCAACTAAGAGGAGGTAAATATATATGGAAGACGC
CAAAAACATAAAGAAAGGCCCGGCGCCATTCTATCCTCTAGAGGATGGAACCGCTGGAGAGCAACTG
CATAAGGCTATGAAGAGATACGCCCTGGTTCCTGGAACAATTGCTTTTACAGATGCACATATCGAGGT
GAACATCACGTACGCGGAATACTTCGAAATGTCCGTTCGGTTGGCAGAAGCTATGAAACGATATGGGC
TGAATACAAATCACAGAATCGTCGTATGCAGTGAAAACTCTCTTCAATTCTTTATGCCGGTGTTGGGCG
CGTTATTTATCGGAGTTGCAGTTGCGCCCGCGAACGACATTTATAATGAACGTGAATTGCTCAACAGT
ATGAACATTTCGCAGCCTACCGTAGTGTTTGTTTCCAAAAAGGGGTTGCAAAAAATTTTGAACGTGCA
AAAAAAATTACCAATAATCCAGAAAATTATTATCATGGATTCTAAAACGGATTACCAGGGATTTCAGT
CGATGTACACGTTCGTCACATCTCATCTACCTCCCGGTTTTAATGAATACGATTTTGTACCAGAGTCCT
TTGATCGTGACAAAACAATTGCACTGATAATGAATTCCTCTGGATCTACTGGGTTACCTAAGGGTGTG
GCCCTTCCGCATAGAACTGCCTGCGTCAGATTCTCGCATGCCAGAGATCCTATTTTTGGCAATCAAATC
ATTCCGGATACTGCGATTTTAAGTGTTGTTCCATTCCATCACGGTTTTGGAATGTTTACTACACTCGGAT
ATTTGATATGTGGATTTCGAGTCGTCTTAATGTATAGATTTGAAGAAGAGCTGTTTTTACGATCCCTTC
AGGATTACAAAATTCAAAGTGCGTTGCTAGTACCAACCCTATTTTCATTCTTCGCCAAAAGCACTCTGA
TTGACAAATACGATTTATCTAATTTACACGAAATTGCTTCTGGGGGCGCACCTCTTTCGAAAGAAGTCG
GGGAAGCGGTTGCAAAACGCTTCCATCTTCCAGGGATACGACAAGGATATGGGCTCACTGAGACTACA
TCAGCTATTCTGATTACACCCGAGGGGATGATAAACCGGGCGCGGTCGGTAAAGTTGTTCCATTTTTT
GAAGCGAAGGTTGTGGATCTGGATACCGGGAAAACGCTGGGCGTTAATCAGAGAGGCGAATTATGTG
TCAGAGGACCTATGATTATGTCCGGTTATGTAAACAATCCGGAAGCGACCAACGCCTTGATTGACAAG
GATGGATGGCTACATTCTGGAGACATAGCTTACTGGGACGAAGACGAACACTTCTTCATAGTTGACCG
CTTGAAGTCTTTAATTAAATACAAAGGATATCAGGTGGCCCCCGCTGAATTGGAATCGATATTGTTAC
AACACCCCAACATCTTCGACGCGGGCGTGGCAGGTCTTCCCGACGATGACGCCGGTGAACTTCCCGCC
GCCGTTGTTGTTTTGGAGCACGGAAAGACGATGACGGAAAAAGAGATCGTGGATTACGTCGCCAGTCA
AGTAACAACCGCGAAAAAGTTGCGCGGAGGAGTTGTGTTTGTGGACGAAGTACCGAAAGGTCTTACC
GGAAAACTCGACGCAAGAAAATCAGAGAGATCCTCATAAAGGCCAAGAAGGGCGGAAAGTCCAAA
TTGTAATAATTATAGGATAATTGAATAAAAACAGTATAGAGAGCAGATAAATACTGCTCTCTATTTTA
CTAATAAGGAGGATTTAAATTGCTAAAAAATACAAACTTAGCTAATTATAAAAAAGTGAATACACGGT
TTGGAAATCTTAGTTTTGACGACAAAGGTATTTCTAATGACTTAACGGAAGAACAGCAAAAAGAATTA
GGTAAGCTTCGAGGATTCGAATATATTAAGACAGAACAGAAAACAAAGAAGAACCTAAGAAAGAA
GAACCTAAGAAAGAAGAACCTAAGAAAGAAGAACCTAAGAAAGAAGAACCTAAGAAAGAAGAACCT
AAGAAAGAAAGTACAGAAAATGAATTAGCACAGCTTCTTAGCTAAAGAGCCTTCAATCAAAGAATTAA
AAGAATTTGCGAGTAAAAAAGGCATTAAAATTGAAAAAACTAAGAAAAATGATATAATTGAAGAACT
```

TABLE 7-continued

AAAGAGAGGGTAATGTATAATGTATGGAGGTTATGAAGGACAAGATTCTTACGAATACCCTTACTCAC
ATGGGAACCCTAAGCATGTAGAGCCAGAAAAAGTTGACGAATATGTTCTTTCTGATTATGGTTGGACT
GCGGAAACAATTAAAGCATACATGTATGGTGTTCGTGTAGTAGACCCTGAAACAGGAGAGGAAATGG
GAGACACCTTCTACAATCATATTATAGAGGTTGCCGTTGATAAGGC

SEQ ID NO: 30 - P100::ffluc
ATGCCAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AATATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAGCTTGTTCGTGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGACTTAGCAGCACACGAATACAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAGTTAGCTCCAATGTACAGCTCCCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTATGACTTAAACGACTCTATTCCTGAAACAGTAGACGTATTCGTTGGTGAAATGTC
TGCTAACGTAGTACACTTGTTTGAATTACTACCAATGATGAGATTACCTCTAGCCTCAAATTAACGCATC
TGTTACATTTGCAGTTTTATGGTATGGAGCATTAGCTCTAAGAGCACCTAAGAAATGGGTACGTATTAG
AAACGTTAAATATATTCCTGTAAAAAACGTTCATAGCAACTAAGAGGAGGTAAATATATATGGAAGAC
GCCAAAAACATAAAGAAAGGCCCGGCGCCATTCTATCCTCTAGAGGATGGAACCGCTGGAGAGCAAC
TGCATAAGGCTATGAAGAGATACGCCCTGGTTCCTGGAACAATTGCTTTTACAGATGCACATATCGAG
GTGAACATCACGTACGCGGAATACTTCGAAATGTCCGTTCGGTTGGCAGAAGCTATGAAACGATATGG
GCTGAATACAAATCACAGAATCGTCGTATGCAGTGAAAACTCTCTTCAATTCTTTATGCCGGTGTTGGG
CGCGTTATTTATCGGAGTTGCAGTTGCGCCCGCGAACGACATTTATAATGAACGTGAATTGCTCAACA
GTATGAACATTTCGCAGCCTACCGTAGTGTTTGTTTCCAAAAAGGGGTTGCAAAAAATTTTGAACGTG
CAAAAAAAATTACCAATAATCCAGAAAATTATTATCATGGATTCTAAAACGGATTACCAGGGATTTCA
GTCGATGTACACGTTCGTCACATCTCATCTACCTCCCGGTTTTAATGAATACGATTTTGTACCAGAGTC
CTTTGATCGTGACAAAACAATTGCACTGATAATGAATTCCTCTGGATCTACTGGGTTACCTAAGGGTGT
GGCCCTTCCGCATAGAACTGCCTGCGTCAGATTCTCGCATGCCAGAGATCCTATTTTGGCAATCAAAT
CATTCCGGATACTGCGATTTTAAGTGTTGTTCCATTCCATCACGGTTTTGGAATGTTTACTACACTCGG
ATATTTGATATGTGGATTTCGAGTCGTCTTAATGTATAGATTTGAAGAAGAGCTGTTTTTACGATCCCT
TCAGGATTACAAAATTCAAAGTGCGTTGCTAGTACCAACCCTATTTTCATTCTTCGCCAAAAGCACTCT
GATTGACAAATACGATTTATCTAATTTACACGAAATTGCTTCTGGGGGCGCACCTCTTTCGAAAGAAGT
CGGGGAAGCGGTTGCAAAACGCTTCCATCTTCCAGGGATACGACAAGGATATGGGCTCACTGAGACTA
CATCAGCTATTCTGATTACACCCGAGGGGGATGATAAACCGGGCGCGGTCGGTAAAGTTGTTCCATTT
TTTGAAGCGAAGGTTGTGGATCTGGATACCGGGAAAACGCTGGGCGTTAATCAGAGAGGCGAATTAT
GTGTCAGAGGACCTATGATTATGTCCGGTTATGTAAACAATCCGGAAGCGACCAACGCCTTGATTGAC
AAGGATGGATGGCTACATTCTGGAGACATAGCTTACTGGGACGAAGACGAACAATTCTTCATAGTTGA
CCGCTTGAAGTCTTTAATTAAATACAAAGGATATCAGGTGGCCCCCGCTGAATTGGAATCGATATTGTT
ACAACACCCCAACATCTTCGACGCGGGCGTGGCAGGTCTTCCCGACGATGACGCCGGTGAACTTCCCG
CCGCCGTTGTTGTTTTGGAGCACGGAAAGACGATGACGGAAAAAGAGATCGTGGATTACGTCGCCAGT
CAAGTAACAACCGCGAAAAAGTTGCGCGGAGGAGTTGTGTTTGTGGACGAAGTACCGAAAGGTCTTA
CCGGAAAACTCGACGCAAGAAAATCAGAGAGATCCTCATAAAGGCCAAGAAGGGCGGAAAGTCCA
AATTGTAATAATTATAGGATAATTGAATAAAAACAGTATAGAGAGCAGATAAATACTGCTCTCTATTT
TACTAATAAGGAGGATTTAAATTGCTAAAAAATACAAACTTAGCTAATTATAAAAAAGTGAATACACG
ATTTGGAAATCTTAGTTTTGATGATAAAGGTATTTCTAATGACCTAACGGAAGAGCAGCAAAAAGAAT
TAGGTAAGCTTAGAGGATTCGAATATATTAAGACAGAACAGAAAACGAAAGAAGAACCTAAGAAAGA
AGAACCTAAGAAAGAAAGTACAGAAATGAATTAGACAGCTTCTTAGCTAAAGAACCTTCAATCAAA
GAATTAAAAGAATTTGCGAGTAAAAAAGGCATTAAAATTGAAAAAACTAAGAAAAATGATATAATTG
AAGAACTAAAAGAGAGGGTAATGTACAATGTATGGAGGTTATGAAGGACAAGATTCTTACGAATACCC
TTACTCACACGGGAACCCTAAGCATGTAGAGCCAGAAAAAGTTGACGAATATGTTCTTTCTGATTATG
GCTGGACTGCGGAAACAATTAAAGCATACATGTATGGTGTTCGTGTAGTAGACCCTGAAACAGGAGA
GGAAATGGGAGACACCTTCTACAATCATATTATAGAGGTTGCCGTTGATAAGGC SEQ ID NO: 31 - LP124::nluc
ATGCCAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGCGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTATTCTACCTAATCGCTCGTGTACCTGCTAGCAAAGCAGAGAACAA TABLE 7-continued

```
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAATAATAAGAGGAGGTAAATATATATG
GTCTTCACACTCGAAGATTTCGTTGGGGACTGGCGACAGACAGCCGGCTACAACCTGGACCAAGTCCT
TGAACAGGGAGGTGTGTCCAGTTTGTTTCAGAATCTCGGGGTGTCCGTAACTCCGATCCAAAGGATTG
TCCTGAGCGGTGAAAATGGGCTGAAGATCGACATCCATGTCATCATCCCGTATGAAGGTCTGAGCGGC
GACCAAATGGGCCAGATCGAAAAAATTTTTAAGGTGGTGTACCCTGTGGATGATCATCACTTTAAGGT
GATCCTGCACTATGGCACACTGGTAATCGACGGGGTTACGCCGAACATGATCGACTATTTCGGACGGC
CGTATGAAGGCATCGCCGTGTTCGACGGCAAAAAGATCACTGTAACAGGGACCCTGTGGAACGGCAA
CAAAATTATCGACGAGCGCCTGATCAACCCCGACGGCTCCCTGCTGTTCCGAGTAACCATCAACGGAG
TGACCGGCTGGCGGCTGTGCGAACGCATTCTGGCGTAATAATTATAGGATAATTGAATAAAAACAGTA
TAGAGAGCAGATAAATACTGCTCTCTATTTTACTAATAAGGAGGATTTAAATTGCTAAAAAATACAAA
CTTAGCTAATTATAAAAAGTGAATACACGGTTTGGAAATCTTAGTTTTGACGACAAAGGTATTTCTA
ATGACTTAACGGAAGAACAGCAAAAAGAATTAGGTAAGCTTCGAGGATTCGAATATATTAAGACAGA
ACAGAAAACAAAAGAAGAACCTAAGAAAGAAGAACCTAAGAAAGAAGAACCTAAGAAAGAAGAACC
TAAGAAGAAGAACCTAAGAAAGAAGAACCTAAGAAAGAAAGTACAGAAAATGAATTAGACAGCTT
CTTAGCTAAAGAGCCTTCAATCAAAGAATTAAAAGAATTTGCGAGTAAAAAAGGCATTAAAATTGAA
AAAACTAAGAAAATGATATAATTGAAGAACTAAAGAGAGGGTAATGTATAATGTATGGAGGTTATG
AAGGACAAGATTCTTACGAATACCCTTACTCACATGGGAACCCTAAGCATGTAGAGCCAGAAAAAGTT
GACGAATATGTTCTTTCTGATTATGGTTGGACTGCGGAAACAATTAAAGCATACATGTATGGTGTTCGT
GTAGTAGACCCTGAAACAGGAGAGGAAATGGGAGCACCTTCTACAATCATATTATAGAGGTTGCCGT
TGATAAGGC

SEQ ID NO: 32 - LP125::nluc
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AACATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAACTTGTTCGTGATAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGATTTAGCAGCACATGAATATAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAATTAGCTCCAATGTATAGCTCTCGTCCACAATTCGTTTCAATCTAT
AGAAAAGGTGCAGAAACAGGTTTTATTCTACCTAATCGCTCGTGGTACCTGCTAGCAAAGCAGAGAACAA
CGTAATCACTTTCTACGACTTAAACGACTCTATTCCTGAAACAGTAGACGTATTCGTTGGTGAAATGTC
GGCTAACGTAGTACACTTGTTTGAATTACTACCAATGATGAGATTACCTCTAGCTCAAATTAACGCATC
TGTTACATTTGCAGTTTTATGGTATGGCGCATTAGCTCTAAGAGCACCTAAGAAATGGGTACGTATTAG
AAACGTTAAATATATTCCTGTAAAAAACGTTCATAGCAACTAATAATAAGAGGAGGTAAATATATATG
GTCTTCACACTCGAAGATTTCGTTGGGGACTGGCGACAGACAGCCGGCTACAACCTGGACCAAGTCCT
TGAACAGGGAGGTGTGTCCAGTTTGTTTCAGAATCTCGGGGTGTCCGTAACTCCGATCCAAAGGATTG
TCCTGAGCGGTGAAAATGGGCTGAAGATCGACATCCATGTCATCATCCCGTATGAAGGTCTGAGCGGC
GACCAAATGGGCCAGATCGAAAAAATTTTTAAGGTGGTGTACCCTGTGGATGATCATCACTTTAAGGT
GATCCTGCACTATGGCACACTGGTAATCGACGGGGTTACGCCGAACATGATCGACTATTTCGGACGGC
CGTATGAAGGCATCGCCGTGTTCGACGGCAAAAAGATCACTGTAACAGGGACCCTGTGGAACGGCAA
CAAAATTATCGACGAGCGCCTGATCAACCCCGACGGCTCCCTGCTGTTCCGAGTAACCATCAACGGAG
TGACCGGCTGGCGGCTGTGCGAACGCATTCTGGCGTAATAATTATAGGATAATTGAATAAAAACAGTA
TAGAGAGCAGATAAATACTGCTCTCTATTTTACTAATAAGGAGGATTTAAATTGCTAAAAAATACAAA
CTTAGCTAATTATAAAAAGTGAATACACGGTTTGGAAATCTTAGTTTTGACGACAAAGGTATTTCTA
ATGACTTAACGGAAGAACAGCAAAAAGAATTAGGTAAGCTTCGAGGATTCGAATATATTAAGACAGA
ACAGAAAACAAAAGAAGAACCTAAGAAAGAAGAACCTAAGAAAGAAAGTACAGAAAATGAATTAGA
CAGCTTCTTAGCTAAAGAGCCTTCAATCAAAGAATTAAAAGAATTTGCGAGTAAAAAAGGCATTAAAA
TTGAAAAAACTAAGAAAATGATATAATTGAAGAACTAAAGAGAGGGTAATGTATAATGTATGGAGG
TTATGAAGGACAAGATTCTTACGAATACCCTTACTCACATGGGAACCCTAAGCATGTAGAGCCAGAAA
AAGTTGACGAATATGTTCTTTCTGATTATGGTTGGACTGCGGAAACAATTAAAGCATACATGTATGGT
GTTCGTGTAGTAGACCCTGAAACAGGAGAGGAAATGGGAGCACCTTCTACAATCATATTATAGAGGT
TGCCGTTGATAAGGC SEQ ID NO: 33 - A511::nluc
ATGCCAAAAAATAACAAAGAAGAAGTTAAAGAAGTAAACCTTAATTCAGTACAAGAGGATGCGTTAA
AGTCCTTTACGACTGGTTATGGTATCACACCTGATACACAAACAGATGCAGGAGCATTAAGACGTGAG
TTCCTAGACGACCAAATCTCAATGCTTACTTGGACAGAGAATGATTTAACATTCTATAAAGACATCGCT
AAAAAACCAGCTACATCTACAGTAGCAAAATACGATGTATACATGCAACATGGTAAGGTAGGTCATA
CTAGATTTACTCGTGAGATTGGGGTAGCACCAGTAAGTGACCCTAACATCCGTCAAAAAACAGTAAAT
ATGAAATTTGCTTCCGATACTAAAAACATCAGTATCGCAGCAGGTCTAGTAAACAACATTCAAGACCC
AATGCAAATTTTGACTGACGATGCTATCGTAAATATTGCTAAAACAATTGAGTGGGCTTCATTCTTTGG
AGATTCTGACTTATCAGATAGCCCAGAACCACAAGCAGGACTAGAATTTGACGGCTTGGCTAAACTTA
TTAACCAAGATAACGTTCATGATGCTCGTGGAGCTAGCTTGACTGAAAAGCTTGTTAAACCAAGCAGCA
GTAATGATTAGTAAAGGTTATGGTACACCTACAGATGCTTACATGCCAGTAGGGGTTCAAGCAGACTT
TGTTAACCAACAACTTTCTAAACAAACACAACTTGTTCGCGATAACGGAAACAACGTAAGCGTTGGTT
TCAACATCCAAGGTTTCCATTCAGCTCGTGGATTTATCAAACTTCACGGTTCTACAGTAATGGAAAACG
AACAAATCTTAGATGAACGTATTCTTGCTTTACCAACAGCTCCACAACCAGCTAAGGTAACTGCAACA
CAAGAAGCAGGTAAAAAAGGACAATTTAGAGCAGAAGATTTAGCAGCACATGAATATAAAGTTGTTG
```

TABLE 7-continued

TAAGTTCTGACGATGCAGAGTCTATTGCAAGTGAAGTGGCTACAGCTACAGTTACTGCAAAAGATGAC
GGCGTTAAACTAGAAATCGAATTAGCTCCAATGTATAGCTCTCGTCCACAATTCGTTTCAATCTATAGA
AAAGGTGCAGAAACAGGTTTATTCTACCTAATCGCTCGTGTACCTGCTAGCAAAGCAGAGAACAACGT
AATCACTTTCTACGACTTAAACGACTCTATTCCTGAAACAGTAGACGTATTCGTTGGTGAAATGTCGGC
TAACGTAGTACACTTGTTTGAATTACTACCAATGATGAGATTACCTCTAGCTCAAATTAACGCATCTGT
TACATTTGCAGTTTATGGTATGGCGCATTAGCTCTAAGAGCACCTAAGAAATGGGTACGTATTAGAA
ACGTTAAATATATTCCTGTAAAAAACGTTCATAGCAACTAAGAGGAGGTAAATATATATGGTCTTCAC
ACTCGAAGATTTCGTTGGGGACTGGCGACAGACAGCCGGCTACAACCTGGACCAAGTCCTTGAACAGG
GAGGTGTGTCCAGTTTGTTTCAGAATCTCGGGGTGTCCGTAACTCCGATCCAAAGGATTGTCCTGAGCG
GTGAAAATGGGCTGAAGATCGACATCCATGTAATCATCCCGTATGAAGGTCTGAGCGGCGACCAAATG
GGCCAGATCGAAAAATTTTTAAGGTGGTGTACCCTGTGGATGATCATCACTTTAAGGTGATCCTGCA
CTATGGCACACTGGTAATCGACGGGGTTACGCCGAACATGATCGACTATTTCGGACGGCCGTATGAAG
GCATCGCCGTGTTCGACGGCAAAAAGATCACTGTAACAGGGACCCTGTGGAACGGCAACAAAATTAT
CGACGAGCGCCTGATCAACCCCGACGGCTCCCTGCTGTTCCGAGTAACCATCAACGGAGTGACCGGCT
GGCGGCTGTGCGAACGCATTCTGGCGTAATAATTATAGGATAATTGAATAAAAACAGTATAGAGAGC
AGATAAATACTGCTCTCTATTTTACTAATAAGGAGGATTTAAATTGCTAAAAAATACAAACTTAGCTA
ATTATAAAAAAGTGAATACACGGTTTGGAAATCTTAGTTTTTGACGACAAAGGTATTTCTAATGACTTA
ACGGAAGAACAGCAAAAAGAATTAGGTAAGCTTCGAGGATTCGAATATATTAAGACAGAACAGAAAA
CAAAAGAAGAACCTAAGAAAGAAGAACCTAAGAAAGAAGAACCTAAGAAAGAAGAACCTAAGAAAG
AAGAACCTAAGAAAGAAGAACCTAAGAAAGAAAGTACAGAAAATGAATTAGACAGCTTCTTAGCTAA
AGAGCCTTCAATCAAAGAATTAAAAGAATTTGCGAGTAAAAAAGGCATTAAAATTGAAAAAACTAAG
AAAAATGATATAATTGAAGAACTAAAGAGAGGGTAATGTATAATGTATGGAGGTTATGAAGGACAAG
ATTCTTACGAATACCCTTACTCACATGGGAACCCTAAGCATGTAGAGCCAGAAAAAGTTGACGAATAT
GTTCTTTCTGATTATGGTTGGACTGCGGAAACAATTAAAGCATACATGTATGGTGTTCGTGTAGTAGAC
CCTGAAACAGGAGAGGAAATGGGAGACACCTTCTACAATCATATTATAGAGGTTGCCGTTGATAAGGC

SEQ ID NO: 34 - P100::nluc
ATGCCAAAAAATAACAAAGAAGAAGAAGTTAAAGAAGTAAACCTTAATTCAGTACAAGAGGACGCGT
TAAAGTCCTTTACAACTGGTTATGGTATCACACCTGATACACAAACAGATGCAGGAGCATTAAGACGT
GAGTTCCTAGACGACCAAATCTCAATGCTTACTTGGACAGAGAATGATTTAACATTCTATAAAGACAT
CGCTAAAAAACCAGCTACATCTACAGTAGCAAAATACGATGTATACATGCAACATGGTAAGGTAGGTC
ATACTAGATTTACTCGTGAGATTGGGGTAGCACCAGTAAGTGACCCTAACATCCGTCAAAAAACAGTA
AATATGAAATTTGCTTCCGATACTAAAAACATCAGTATCGCAGCAGGTCTAGTAAACAACATTCAAGA
CCCAATGCAAATTTTGACTGACGATGCTATCGTAAATATTGCTAAAACAATTGAGTGGGCTTCATTCTT
TGGAGATTCTGACTTATCAGATAGCCCAGAACCACAAGCAGGACTAGAATTTGACGGCTTGGCTAAAC
TTATTAACCAAGATAACGTTCATGATGCTCGTGGAGCTAGCTTGACTGAAAGCTTGTTAAACCAAGCA
GCAGTAATGATTAGTAAAGGTTATGGTACACCTACAGATGCTTACATGCCAGTAGGGGTTCAAGCAGA
CTTTGTTAACCAACAACTTTCTAAACAAACACAGCTTGTTCGCAGCAGGTCTAGTAACGGAAACAACGTAAGCGTTG
GTTTCAACATCCAAGGTTTCCATTCAGCTCGTGGATTTATCAAACTTCACGGTTCTACAGTAATGGAAA
ACGAACAAATCTTAGATGAACGTATTCTTGCTTTACCAACAGCTCCACAACCAGCTAAGGTAACTGCA
ACACAAGAAGCAGGTAAAAAAGGACAATTTAGAGCAGAAGACTTAGCAGCACACGAATACAAAGTTG
TTGTAAGTTCTGACGATGCAGAGTCTATTGCAAGTGAAGTGGCTACAGCTACAGTTACTGCAAAAGAT
GACGGCGTTAAACTAGAAATCGAGTTAGCTCCAATGTACAGCTCCCGTCCACAATTCGTTTCAATCTAT
AGAAAAGGTGCAGAAACAGGTTTATTCTACCTAATCGCTCGTGTACCTGCTAGCAAAGCAGAGAACAA
CGTAATCACTTTCTATGACTTAAACGACTCTATTCCTGAAACAGTAGACGTATTCGTTGGTGAAATGTC
TGCTAACGTAGTACACTTGTTTGAATTACTACCAATGATGAGATTACCTCTAGCTCAAATTAACGCATC
TGTTACATTTGCAGTTTATGGTATGGAGCATTAGCTCTAAGAGCACCTAAGAAATGGGTACGTATTAG
AAACGTTAAATATATTCCTGTAAAAAACGTTCATAGCAACTAAGAGGAGGTAAATATATATGGTCTTC
ACACTCGAAGATTTCGTTGGGGACTGGCGACAGACAGCCGGCTACAACCTGGACCAAGTCCTTGAACA
GGGAGGTGTGTCCAGTTTGTTTCAGAATCTCGGGGTGTCCGTAACTCCGATCCAAAGGATTGTCCTGA
GCGGTGAAAATGGGCTGAAGATCGACATCCATGTCATCATCCCGTATGAAGGTCTGAGCGGCGACCAA
ATGGGCCAGATCGAAAAATTTTTAAGGTGGTGTACCCTGTGGATGATCATCACTTTAAGGTGATCCT
GCACTATGGCACACTGGTAATCGACGGGGTTACGCCGAACATGATCGACTATTTCGGACGGCCGTATG
AAGGCATCGCCGTGTTCGACGGCAAAAAGATCACTGTAACAGGGACCCTGTGGAACGGCAACAAAAT
TATCGACGAGCGCCTGATCAACCCCGACGGCTCCCTGCTGTTCCGAGTAACCATCAACGGAGTGACCG
GCTGGCGGCTGTGCGAACGCATTCTGGCGTAATAATTATAGGATAATTGAATAAAAACAGTATAGAGA
GCAGATAAATACTGCTCTCTATTTTACTAATAAGGAGGATTTAAATTGCTAAAAAATACAAACTTAGC
TAATTATAAAAAAGTGAATACACGATTTGGAAATCTTAGTTTTGATGATAAAGGTATTTCTAATGACCTT
AACGGAAGAGCAGCAAAAAGAATTAGGTAAGCTTAGAGGATTCGAATATATTAAGACAGAACAGAAA
ACGAAAGAAGAACCTAAGAAAGAAGAACCTAAGAAAGAAAGTACAGAAAATGAATTAGACAGCTTC
TTAGCTAAAGAACCTTCAATCAAAGAATTAAAAGAATTTGCGAGTAAAAAAGGCATTAAAATTGAAA
AACTAAGAAAAATGATATAATTGAAGAACTAAAGAGAGGGTAATGTACAATGTATGGAGGTTATGA
AGGACAAGATTCTTACGAATACCCTTACTCACACGGGAACCCTAAGCATGTAGAGCCAGAAAAAGTTG
ACGAATATGTTCTTTCTGATTATGGCTGGACTGCGGAAACAATTAAAGCATACATGTATGGTGTTCGTG
TAGTAGACCCTGAAACAGGAGAGGAAATGGGAGACACCTTCTACAATCATATTATAGAGGTTGCCGTT
GATAAGGC SEQ ID NO: 35 - LP40::nluc
ATGCCAAAAAATAACAAAGAAGAAGAAGTTAAAGAAGTAAACCTTAATTCAGTACAAGAGGATGCGT
TAAAGTCCTTTACAACTGGTTATGGTATCACACCTGATACACAAACAGATGCAGGGGCACTAAGACGT
GAGTTCCTAGACGACCAAATCTCAATGCTTACTTGGACAGAAAGATGATTTAACATTCTACAAAGACAT
CGCTAAAAAACCAGCTACATCTACAGTAGCAAAATACGATGTGTACATGCAACACGGTAAAGTAGGT
CATACTAGATTTACTCGTGAGATTGGGGTAGCACCAGTAAGTGACCCTAACATCCGTCAAAAAACAGT
AAACATGAAATTTGCTTCTGATACTAAAAATATTAGTATCGCAGCAGGTCTAGTAAACAACATTCAAG
ACCCTATGCAAATTTTGACTGATGATGCTATCGTAAATATCGCTAAAACAATTGAGTGGGCTTCATTCT
TTGGAGATTCTGACTTATCAGATAGCCCAGAACCACAAGCAGGATTAGAATTTGATGGCTTGGCTAAA
CTTATTAACCAAGATAACGTTCATGATGCTCGTGGAGCTAGCTTGACTGAAAGCTTGTTAAACCAAGC
AGCAGTAATGATTAGTAAAGGTTATGGTACACCTACAGATGCTTACATGCCAGTAGGGGTTCAAGCAG
ACTTTGTTAACCAACAACTTTCTAAACAAACACTTGTTCGCGATAACGAAACAACGTAAGCGTT
GGTTTCAACATCCAAGGTTTCCATTCAGCTCGTGGATTTATCAAACTTCACGGTTCTACAGTAATGGAA TABLE 7-continued

```
AACGAACAAATCTTAGATGAACGTATTCTTGCTTTACCAACAGCTCCACAACCAGCTAAGGTAACTGC
AACACAAGAAGCAGGTAAAAAAGGACAATTTAGAGCAGAAGATTTAGCAGCACATGAATATAAAGTT
GTTGTAAGTTCTGACGATGCAGAGTCTATTGCAAGTGAAGTGGCTACAGCTACAGTTACTGCAAAAGA
TGACGGCGTTAAACTAGAAATCGAATTAGCTCCAATGTATAGCTCTCGTCCACAATTCGTTTCAATCTA
TAGAAAAGGTGCAGAAACAGGTTTATTCTACCTAATCGCTCGTGTACCTGCTAGCAAAGCAGAGAACA
ACGTAATCACTTTCTACGACTTAAACGACTCTATTCCTGAAACAGTAGACGTATTCGTTGGTGAAATGT
CGGCTAACGTAGTACACTTGTTTGAATTACTACCAATGATGAGATTACCTCTAGCTCAAATTAACGCAT
CTGTTACATTTGCAGTTTTATGGTATGGCGCATTAGCTCTAAGAGCACCTAAGAAATGGGTACGTATTA
GAAACGTTAAATATATTCCTGTAAAAAACGTTCATAGCAACTAATAATAAGAGGAGGTAAATATATAT
GGTCTTCACACTCGAAGATTTCGTTGGGGACTGGCGACAGACAGCCGGCTACAACCTGGACCAAGTCC
TTGAACAGGGAGGTGTGTCCAGTTTGTTTCAGAATCTCGGGGTGTCCGTAACTCCGATCCAAAGGATT
GTCCTGAGCGGTGAAAATGGGCTGAAGATCGACATCCATGTCATCATCCCGTATGAAGGTCTGAGCGG
CGACCAAATGGGCCAGATCGAAAAAATTTTTAAGGTGGTGTACCCTGTGGATGATCATCACTTTAAGG
TGATCCTGCACTATGGCACACTGGTAATCGACGGGGTTACGCCGAACATGATCGACTATTTCGGACGG
CCGTATGAAGGCATCGCCGTGTTCGACGGCAAAAAGATCACTGTAACAGGGACCCTGTGGAACGGCA
ACAAAATTATCGACGAGCGCCTGATCAACCCCGACGGCTCCCTGCTGTTCCGAGTAACCATCAACGGA
GTGACCGGCTGGCGGCTGTGCGAACGCATTCTGGCGTAATAATTATAGGATAATTGAATAAAAACAGT
ATAGAGAGCAGATAAATACTGCTCTCTATTTTACTAATAAGGAGGATTTAAATTGCTAAAAAATACAA
ACTTAGCTAATTATAAAAAGTGAATACACGGTTTGGAAATCTTAGTTTTGACGACAAAGGTATTTCT
AATGACTTAACGGAAGAACAGCAAAAAGAATTAGGTAAGCTTCGAGGATTCGAATATATTAAGACAG
AACAGAAAACAAAAGAAGAACCTAAGAAAGAAGAACCTAAGAAAGAACCTAAGAAAGAAAGTA
CAGAAAATGAATTAGACAGCTTCTTAGCTAAAGAGCCTTCAATCAAAGAATTAAAAGAATTTGCGAGT
AAAAAAGGCATTAAAATTGAAAAAACTAAGAAAAACGATATAATTGAAGAACTAAAGAGAGGGTAA
TGTATAATGTATGGAGGTTATGAAGGACAAGATTCTTACGAATACCCTTACTCACATGGGAACCCTAA
GCATGTAGAGCCAGAAAAAGTTGACGAATATGTTCTTTCTGATTATGGTTGGACTGCGGAAACAATTA
AAGCATACATGTATGGTGTTCGTGTAGTAGACCCTGAAACAGGAGAGGAAATGGGAGACACCTTCTAC
AATCATATTATAGAGGTTGCCGTTGATAAGGC
```

Example 2: Preparation of Recombinant Phage

Phage lysates (stocks) were prepared as follows. A single colony of *Listeria monocytogenes* (for example EGD-e, at ATCC) was inoculated in 5 ml of 0.5×BHI liquid and grown overnight at 30° C. in a floor shaker at 200 rpm. The next day, 5 ml of the culture was diluted into 500 ml of 0.5×BHI in a 1000 ml flask and grown for 4 hours at 30° C. in a floor shaker at 200 rpm, or until the $OD_{600}$ reached 0.15. The culture was then inoculated with $1\times10^8$ pfu/ml of a recombinant phage described in Example 9 to be propagated. The flask was returned to 30° C., and shaken at 50 rpm for 4 hours or until lysate was cleared ($OD_{600}$ of <0.02). The lysate was then filtered through a 0.45 µm vacuum filter and then through a 0.22 µm vacuum filter, and stored at 4° C. until purification as described below.

Before use, phage particles were purified using methods generally as described in Sambrook and Russell, Molecular Cloning Volume 1, 3rd edition 2001. Briefly, phage particles were precipitated from the lysate using Protocol 6, "Precipitation of Bacteriophage Lambda Particles from Large-scale Lysates", at pp 2.43-2.44 (which is hereby incorporated herein by reference) with the following exceptions: the DNase and RNase steps were omitted as were the chloroform extraction steps. Phage particles were then purified using cesium chloride gradients using protocol 8, "Purification of Bacteriophage Lambda Particles by Isopycnic Centrifugation through CsCl Gradients", at pp 2.47-2.51 (which is hereby incorporated herein by reference), with the following exceptions: Step gradients were spun using the SW28 rotor for 2 hours at 22,000 rpm in a Beckman XL-90 ultracentrifuge; and Equilibrium gradients were spun using the 70.1ti rotor for 24 hours at 47,000 rpm in a Beckman XL-90 ultracentrifuge.

Upon harvest of the phage band from the equilibrium gradient, phages were dialyzed against 4 L of SM buffer in a Pierce G2 Slide-a-lyzer cassette (10,000 MWCO) for 24 h at 4° C. Phage stocks were then stored at 4 C until use.

Example 3: Sensitivity and Speed of the Assay Using the Recombinant Phage

Stocks of phage LP40::nluc, LP124::nluc, and A511::nluc were prepared according to Examples herein. Those phage were used to detect *Listeria* in this assay. The example examines the lower limit of detection achieved by the assay and the speed of the assay.

Cultures of *Listeria* were grown to saturation in 0.5×BHI media overnight at 30° C. The culture was diluted 1:5 in fresh 0.5×BHI media and allowed to recover at 30° C. for 2 hours. The recovered culture was subsequently serially diluted in the same media from $1\times10^{-1}$ to $1\times10^{-8}$. Cell concentrations at each of these dilutions were determined by plating on non-selective media. 100 ul of each cell dilution was subsequently incubated with 100 ul of recombinant phage cocktail for 30 minutes, 60 minutes, 120 minutes, or 180 minutes. The recombinant phage cocktail was LP40::nluc, LP124::nluc, and A511::nluc at final concentrations of $1\times10^7$ each, for a total phage final concentration of $3\times10^7$. At the end of the incubation the results were measured by adding 1V of NanoGlo (NanoGlo buffer and substrate at a 1:50 ratio), incubating on the bench for 2 minutes, and reading in a Sirius L luminometer (Titertek Berthold) for 10 seconds, using 1 second integrations. The average of ten readings was used to determine the RLU value for the sample. The lower limit of detection (LLOD) was determined by the established method of measuring the average of three independent negative reactions and adding 3 standard deviations.

The results show that at 30 minutes the LLOD is 100 cells, at 60 minutes the LLOD is 10 cells, and at 120 and 180 minutes the assay is able to detect a single cell.

In a second experiment, cultures of *Listeria* were grown to saturation in 0.5×BHI media overnight at 30° C. The culture was diluted 1:5 in fresh 0.5×BHI media and allowed to recover at 30° C. for 2 hours. The recovered culture was subsequently diluted in the same media at dilutions of $1\times10^{-1}$, $1\times10^{-2}$, $1\times10^{-3}$, $1\times10^{-4}$, $1\times10^{-5}$, $1\times10^{-6}$, $1\times10^{-7}$, $5\times10^{-7}$, and $1\times10^{-8}$. Cell concentrations at each of these dilutions were determined by plating on non-selective media. 5 independent dilutions were performed and assayed.

Briefly, 100 ul of each cell dilution was subsequently incubated with 100 ul of recombinant phage for the indicated time and the products assayed as described above. Lower limit of detection (LLOD) was determined by the established method of measuring the average of three independent negative reactions and adding 3 standard deviations.

The expected approximate number of cells in each sample, at each dilution, are indicated along the X-axis. As for any cell dilution, a normal distribution of cell numbers is expected across aliquots. This is seen in the data. The negative control samples show a very consistent level of background luminescence. Three of the five tested aliquots at the lowest dilution were indistinguishable from the background, indicating that those samples did not contain any cells. The fourth aliquot gave a signal of about 250-275 RLU above the background and the fifth a signal of about 500-550 RLU above background, indicating that those samples contained one and two infectable target cells, respectively. A similar relationship is present in the second lowest dilution (expected 4-6 cells per aliquot). There the assay distinguishes samples that contain 1, 7, 5, 5, and 4 cells, respectively.

Note that in this example the signal generated from a single target cell happens to be about the same as the background, and therefore the signal generated when a single cell is detected is about twice that of the background. While that relationship will not necessarily be present in all assays according to this disclosure, a skilled artisan will appreciate that it is not necessary. What is important is that the method allows discrimination of cell number at a single cell resolution over a range of at least 1 to 10 cells. Above that range the exact number of cells becomes more approximate because of variability in the signal generated per cell.

Example 4: Cell Recovery from Sponge

Environmental microbial samples are often found attached to solid substrates, such as the surface of a piece of equipment in a food processing plant or to a food product itself. Collection of samples from such contexts for microbial contamination testing is often challenging. For example, it may be necessary to test a sample of a food product itself to determine whether the food product is contaminated and this necessarily means that food components will be present during the test unless time consuming and expensive steps are taken to remove them. Likewise, collection of samples from environmental surfaces (of food, equipment, drains, etc.) most often results in collection of environmental contaminants such as cleaning agents and biofilm components, in addition to any microbes that may be present. This example addresses the impact of such contaminates in the context of a phage-based microbial detection assay.

These issues were addressed in the context of solid phase samples collected using a Custom Sponge-Stick with Letheen Broth SSL10LET (3M). The 3M sponge stick with Letheen broth is a biocide-free cellulose sponge shipped in a sterile bag and hydrated with 10 mL of Letheen Broth. The plastic handle allows users to collect environmental samples without directly handling (and possibly contaminating) the sponge, as well as making it easier to reach into drains, pipes, and crevices to collect samples. The cellulose material collects and retains organisms in or on the sponge matrix. The Letheen Broth is present to help neutralize cleaning chemicals such as quaternary ammonia and preserve the viability of organisms for detection.

The plastic handle comes with a thumb guide to inform the point beyond which the user should refrain from touching to avoid possible contamination. Once the sample has been collected, the sponge is returned to the bag, and the plastic handle may be snapped off, allowing the bag to be sealed with only the sponge inside.

*L. monocytogenes* strain 1839 was refreshed (1 mL in 4 mL BHI) for 2 h, shaking at 30° C. The OD of the refreshed 1839 was determined and converted to an approximate cell concentration (cfu/mL=$2.0\times10^9$*OD-$9.0\times10^7$). The cells were then serially dilute (1:10) in Letheen broth, making 7 mL of dilution closest to $1\times10^6$ cfu/mL (typically $1\times10^{-2}$ dilution).

Buffer was removed from a 3M sponge stick. One mL of the dilution closest to $1\times10^6$ cfu/mL was added to buffer removed from sponge. One mL of the dilution closest to $1\times10^6$ cfu/mL was also added to the sponge. Both samples were incubated for 60 min. at room temp.

The sponge was then squeezed to extract buffer/cells. 100 uL of buffer was removed from each condition and added to each of the 1.5 mL Eppendorf tubes, respectively.

Each tube was then infected with 100 uL of A511:ff at $1.0\times10^7$ pfu/mL. 20 uL of each infection was then plated and incubated at 30 C for 3 h.

The amount of nanoluc protein recovered from the sponge was then quantified as follows. NanoGlo buffer and Substrate was mixed according to instructions supplied by Promega (1:50, substrate:buffer). 1 volume of sample and 1 volume of NanoGlo was then mixed in an eppendorf tube, and incubated on the bench for 2 minutes.

The amount of luminescence was read using a Sirius L luminometer (Titertech Berthold) for 10 seconds, 1 second integrations.

An average of 10 readings was used to determine the RLU value for the sample.

To determine cell recovery, 100 uL of $1\times10^{-4}$, $1\times10^{-5}$, and $1\times10^{-6}$ Letheen broth dilutions were plated on 0.5×BHI plates. 100 uL from the cell dilution was added to the sponge in sponge buffer. 1:10 and 1:100 dilutions were prepared of cells from sponge, cells in sponge buffer, and cells from 3M Letheen Broth. 100 uL of undiluted, 1:10, and 1:100 dilutions were then plated on BHI plates and incubated @ 30 degrees o/n. The number of cells recovered from the sponge was compared to the number of cells that saw only the Letheen Broth buffer. CFU for sponge recovered cells/CFU Letheen Broth Recovery*100%=Cell Recovery %.

The results of both assays presented in this example are provided in Table 8.

TABLE 8

| | Sponge Recovery Compared to No Sponge Control (%) | Sponge Recovery % CV (by RLU) | Letheen Broth Recovery % CV (by RLU) |
|---|---|---|---|
| Nov. 12, 2012 | 26.59% | 22.60% | 1.34% |
| Nov. 13, 2012 | 28.87% | 4.07% | 4.23% |
| Nov. 14, 2012 | 28.96% | 21.46% | 4.74% |

These experiments showed that approximately 28% of cells are recovered from a sponge compared to the control. The percentage of cells recovered from a given sponge is also more variable than cells in buffer alone. Given that these are healthy, planktonic cells (and that 1 million of them are added to the sponge), additional challenges may be encountered in recovering cells from sponges used to collect environmental samples where fewer cells are present.

This finding has significant implications for phage-based bacterial detection assays utilized in the context of samples associated with solid substrates. Assay formats that rely on removing sample cells from the collection sponge so that the cells may be infected by phage off sponge rely on recover of a sufficient proportion of cells from the sponge so that assay sensitivity is not compromised. For example, in an assay configured for detection in 1 mL of material (out of 5-7 mL recovered by squeezing the sponge), these data imply that less than 20% of the starting material is sampled. Given that <30% of cells are typically recovered from the sponge matrix, this has a significant impact on assay sensitivity, since the assay would only have approximately 7% of the total starting cells collected by the sponge accessible for detection.

This result suggests that, for these types of samples, alternative assay formats will be more efficient and yield a higher accuracy, sensitivity, and/or specificity.

Example 5: Recovery of Phage and Luciferase from a Sponge

An alternative to collecting samples potentially contaminated by a microbe using a solid substrate, removing cells (if present) from the solid substrate into a liquid, and then combining the liquid with a phage, is to instead combine the phage (in a liquid) directly with the sponge so that the phage has an opportunity to infect target cells that may be present in association with the sponge. This would allow the phage to infect any target cells associated with the sponge whether or not those cells are recoverable from the sponge. A sensitive method of detection would then be facilitated by sampling the liquid and assaying for marker produced by target microbes (if present) that were infected by the phage. This, assay format would avoid the issues identified in Example 4.

The efficiency of this type of assay format will, in turn, depend in part on the proportion of the phage and/or marker released from the solid substrate and accessible for downstream detection. For example, if too high of a proportion of the phage and/or marker is trapped in the solid substrate and rendered inaccessible to the assay that would reduce assay performance. A preliminary experiment to evaluate this issue was based on recovery of phage and luciferase enzyme following incubation with a sponge.

Protocol, Run 1: 4 mL each of A511:nluc unfiltered lysate, starting titer $1.2\times10^{10}$ pfu/mL, and diluted titers at $4.0\times10^{9}$, $4.0\times10^{8}$, and $4.0\times10^{7}$ pfu/mL were prepared.

For each lysate dilution:

1. A 3M Sponge stick #SSL10LET was squeezed so that as much Letheen as possible was removed from it. 3 mL of the Letheen was transferred to a 15 mL conical. 1 mL of lysate dilution was added to this 15 mL conical.

2. A second sponge was squeezed so that as much Letheen as possible was removed from it and transferred to a 15 mL conical. 3 mL of this was added back to the sponge stick bag, without allowing it to touch the sponge. 1 mL of lysate dilution was added to this liquid and it was mixed and the mixture was soaked up with the sponge.

3. Conical tubes and sponges were incubated with the added phage at 30° C. for 3 hours.

Detection of RLU background:

From each incubated conical, 100 uL was transferred into each of 3 microcentrifuge tubes.

From each incubated sponge, as much liquid as possible was squeezed out and transferred to a 15 ml, conical. 100 uL was transferred from the conical into each of 3 microcentrifuge tubes.

All microcentrifuge tubes were read in the Sirius L luminometer for a total of 40 seconds, injecting 100 µL of Promega NanoGlo Reagent #N1130 at 20 seconds.

Titer:

From each conical (incubated or squeezed from sponge post-incubation), 100 uL was transferred into each of 3 wells of a 96-well titer plate. The solution was serially diluted by 10-folds 8 times. Each set of dilutions was plated 3 times on a prepared BHI plate with a lawn of 1839 cells.

Protocol, Run 2: Protocol 1 was repeated using LP124:nluc unfiltered lysate, starting titer 1.2E10 pfu/mL.

The results demonstrate an approximately 30% recovery of both phage titer and RLU signal from phage added to the 3M Sponge stick. This indicates that approximately 70% of any phage or luciferase associated with the sponge during a microbe detection assay will be bound to or otherwise trapped in it. This suggests the need for use of a higher phage concentration of phage to get adequate signal out of an infection that takes place in the presence of the sponge.

Importantly, this recovery level implies that assays that rely on infection of cells in association with a solid substrate and recovery of phage and luciferase enzyme following infection is a feasible assay format. The results also imply that this assay format may have a higher accuracy, sensitivity, and/or specificity compared to a suspension-phase assay format.

Example 6: Assay Sensitivity

This experiment investigated the sensitivity of assay formats that utilize infection of target cells in a non-suspension context.

Protocol:

20 ml, of a cocktail of A511:nluc and LP124:nluc phage was prepared at $4.0\times10^{7}$ pfu/mL of total phage.

4 mL of 1839 cells were prepared in a dilution series $1\times10^{-01}$ to $1\times10^{-08}$. The final cell count of the undiluted culture was $5.1\times10^{9}$ cfu/mL.

For each cell dilution:

A sponge was squeezed and as much Letheen as possible was removed from it. 2 mL of this squeezate was transferred to a 15 mL conical. 1 mL of cells was added at the correct dilution and 1 mL of phage.

A second sponge was squeezed and as much Letheen as possible was removed from it and transferred to a 15 mL conical. The volume extracted was noted and a corresponding volume that was not removed from the sponge (10 mL−volume extracted=volume not extracted). 2 mL of this was added back to the bag, not allowing it to touch the sponge. 1 mL of cells at the correct dilution and 1 mL of phage was added to this letheen and mixed. The complete volume was then brought into contact with and soaked up by the sponge.

The conical tubes and the sponges were then incubated with the phage added at 30° C. for 3 hours.

From each incubated conical, 100 uL was transferred into each of 3 eppendorf tubes.

From each incubated sponge, as much liquid as possible was squeezed out and transferred to a 15 mL conical. 100 uL from the conical was then transferred into each of 3 eppendorf tubes.

All microcentrifuge tubes were then read in the Sirius L luminometer for a total of 40 seconds, injecting 100 μL of Promega NanoGlo Reagent #N1130 at 20 seconds.

The results are presented in Table 9.

TABLE 9

| Strain 1839 cfu | Average RLU signal of A511::nluc/ LP124::nluc infection in Letheen Broth | Average RLU signal of A511::nluc/ LP124::nluc infection in 3M Spongestick | Average RLU signal in 3M Spongestick soaked in Letheen Broth compared to Average RLU signal in Letheen Broth |
|---|---|---|---|
| 1.28E+07 | Instrument upper limit exceeded | Instrument upper limit exceeded | N/A |
| 1.28E+06 | Instrument upper limit exceeded | 13709047.1 | N/A |
| 1.28E+05 | 9135828.5 | 1587765.8 | 17% |
| 1.28E+04 | 1138586.6 | 204633.2 | 18% |
| 1.28E+03 | 124133.9 | 14955.9 | 12% |
| 1.28E+02 | 11348.7 | 2552.9 | 22% |
| 1.28E+01 | 1732.7 | 432.3 | 25% |
| 1.28E+00 | 723.4 | 285.8 | 40% |
| Negative Control | 486.6 | 261.7 | 54% |

These data indicate that infection on the sponge yields a detectable signal at a sensitivity of below 13 cells.

Example 7: Assay Duration

This example addresses the effect on assay performance of the duration of time between 1) combining the phage with the sponge and providing conditions to the phage-exposed sponge sufficient to allow the recombinant phage to infect a target microbe cell present in the sample and production of the marker encoded by the heterologous nucleic acid sequence by the target microbe cell; and 2) removing media from the incubated sponge support and phage for the purpose of detecting marker.

Protocol:
Run 1:
Day 1:

Forty sponges of environmental samples were collected from drains and equipment at a fish packing/processing facility and five were randomly selected.

From the same lot of 3M sponge sticks used to collect samples, a new, sterile sponge was chosen and used as a negative control.

From each sponge, all liquid was squeezed out and transferred to a sterile 50 mL conical tube. 10 ml, 0.5× Brain Heart Infusion media with 5% Glucose and 1% Glycerol was added to the sponge. The bag was massaged gently for 15 seconds to disperse liquid. 40 mL UVM selective media was then added to the 50 mL conical. Sponges were placed at 30° C. for 1 hour. Conical tubes, caps loosened, were placed at 30° C. for 24 hours.

After 1 hour, sponges were removed from the 30° C. incubator. For each sponge, all liquid was squeezed out into a corner of the bag, 1 mL of a $1.1 \times 10^9$ pfu/mL (of total phage) cocktail of A511::nluc, P100::nluc and LP124::nluc phages was added and mixed. All liquid was then absorbed back into the sponge. The sponge was massaged gently for 15 seconds to disperse liquid. The sponges were then placed back at 30° C. for 3 hours.

After 3 hours, the sponges were removed from the 30° C. incubator. For each sponge, all liquid was squeezed into a corner of the bag, and 900 uL was transferred (300 uL each) into 3 microcentrifuge tubes. Each sample was read using a SiriusL luminometer for a total of 40 seconds, injecting 100 μL of Promega NanoGlo Reagent #N1130 at 20 seconds. This procedure was repeated at 5, 7, 9, and ~24 hours.

Note: At the 5 hour time point, due to poor signal seen in all samples including those expected to give high signal, a clarifying spin was added prior to reading the samples in the Sirius L. 300 uL from each sample was added to a second microcentrifuge tube and spun at 16.1 rcf for 1 minute. The supernatants were then transferred to new microcentrifuge tube and read in the same manner as the other tubes.

Day 2:

100 uL from each bag was plated on a MOX agar plate after taking the 24 hour time point for RLU determination. 100 mL of UVM was added to the bag. The bag was incubated at 30° C. for 24 hours.

Read UVM-enriched squeezates after 24 hours: Removed 50 mL conical tubes from 30° C. incubator. Transferred 1 mL from each conical to a microcentrifuge tube. Spun the microcentrifuge tubes at 4,000 g for 1 minute, removed the supernatant and resuspended the pellet in 100 uL of 1.0E7 phage. Placed microcentrifuge tubes at 30° C. for 3 hours.

After 3 hours, removed the microcentrifuge tubes from the 30° C. incubator and spin at max speed for 1 minute. Transferred 50 uL of the supernatant to a well on a 96-well luminometer plate. Read in the Glomax 96-well luminometer injecting 50 uL NanoGlo per well and reading each well for 1 second with a 2 second delay.

Plated 100 uL from each 50 mL conical on a MOX agar plate for culture confirmation.

Day 3:

Read UVM-enriched sponges after 24 hours: Removed sponges from 30° C. incubator. Transferred 1 mL from each to a microcentrifuge tube. Spun the microcentrifuge tubes at 4,000 g for 1 minute, removed the supernatant and resuspend the pellet in 100 uL of 1.0E7 phage. Placed microcentrifuge tubes at 30° C. for 3 hours.

After 3 hours, removed the microcentrifuge tubes from the 30° C. incubator and spun at max speed for 1 minute. Transferred 50 uL of the supernatant to a well on a 96-well luminometer plate. Read in the Glomax 96-well luminometer injecting 50 uL NanoGlo per well and reading each well for 1 second with a 2 second delay.

Plated 100 uL from each bag on a MOX agar plate for culture confirmation.

Run 2: Repeated procedure detailed above, adding the pre-read clarifying spin at all time points.

Results are presented in Table 10.

TABLE 10

| Timepoint | 3 hours | 5 hours | 7 hours | 9 hours | 24 hours |
|---|---|---|---|---|---|
| Run 1 Accuracy without spin | 20% | 20% | 20% | 20% | 40% |
| Run 1 Accuracy with spin | N/A | 40% | 40% | 40% | 40% |
| Run 2 Accuracy with spin | 60% | 60% | 80% | 80% | 80% |

The Run 1 results demonstrate that adding the pre-read clarifying spin of samples improves the accuracy at 5 hours to what it is at 24 hours without the clarifying spin. Run 2 demonstrates that this spin improves accuracy at 3 hours to what it is at 5 hours, indicating samples read at 3 hours post-infection yield reasonable accuracy.

Example 8: Metabolic Stimulation

Phage-based detection assays of environmental samples have traditionally been performed utilizing an enrichment step to amplify the number of target cells present in a sample. One effect of such conditions is that they may provide metabolic stimulation compared to cells in samples not treated in this manner. This example demonstrates that a separate metabolic stimulation step is not required in certain embodiments of the assays disclosed herein.

40 environmental samples were collected from drains and equipment at a fish processing facility and ten were randomly selected. The samples were split into 2 groups of 5. The second set of 5 were samples taken from the same set of 5 sites as the first set. That is to say, the two sets represent duplicates.

From the same 3M lot of sponge sticks, two new, sterile sponges were used as negative controls.

Protocol 1: (Samples 1-5)

All of the liquid was squeezed out of each sponge and transferred to a sterile 50 mL conical tube. 3.5 mL 0.5× Brain Heart Infusion media with 5% Glucose and 1% Glycerol was added to each sponge. The sponge was massaged gently for 15 seconds to disperse liquid. Added 40 mL UVM selective media to the 50 mL conical. Placed sponges at 30° C. for 1 hour. Placed conical tubes, caps loosened, at 30° C. for 24 hours.

After 1 hour, removed sponges from 30° C. incubator. For each sponge, squeezed all liquid into a corner of the bag, added 1.5 mL 0.5× Brain Heart Infusion with 1% Glucose 5% Glycerol, 6% Lithium Chloride and 0.12% Nalidixic Acid and 1 mL of a $6.0 \times 10^8$ pfu/mL (of total phage) cocktail of A511::nluc, P100::nluc and LP124::nluc phages and mixed. Absorbed all liquid back into the sponge. Massaged gently for 15 seconds to disperse liquid. Placed sponges back at 30° C. for 3 hours.

After 3 hours, removed sponges from 30° C. incubator. For each sponge, squeezed all liquid into a corner of the bag, transferred 300 uL into a microcentrifuge tube. Spun at 16.1 rcf for 1 minute and transferred supernatant to a new tube. Read in the Sirius L luminometer for a total of 40 seconds, injecting 100 μL of Promega NanoGlo Reagent #N1130 at 20 seconds.

After the read, removed 500 uL of the liquid in each bag and plated on a MOX agar plate. Added 100 mL of UVM selective media to the sponge and place at 30° C. for 24 hours.

Protocol 2: (Samples 6-10)

From each sponge, squeezed out all liquid and transferred it to a sterile 50 mL conical tube. Added 3.5 mL 0.5× Brain Heart Infusion with 5% Glucose and 1% Glycerol media into a corner of the bag, added 1.5 mL 0.5× Brain Heart Infusion with 1% Glucose 5% Glycerol, 6% Lithium Chloride and 0.12% Nalidixic Acid and 1 mL of a $6.0 \times 10^8$ pfu/mL (of total phage) cocktail of A511::nluc, P100::nluc and LP124::nluc phages and mixed. Absorbed all liquid back into the sponge. Massaged gently for 15 seconds to disperse liquid. Placed sponges at 30° C. for 4 hours.

Added 40 mL UVM selective media to the 50 mL conical. Put conical tubes, caps loosened, at 30° C. for 24 hours.

After 4 hours, removed sponges from 30° C. incubator. For each sponge, squeezed all liquid into a corner of the bag, transferred 300 uL into a microcentrifuge tube. Spun at 16.1 rcf for 1 minute and transferred supernatant to a new tube. Read in the Sirius L luminometer for a total of 40 seconds, injecting 100 μL of Promega NanoGlo Reagent #N1130 at 20 seconds.

After the read, removed 500 uL of the liquid in each bag and plated it on a MOX agar plate. Added 100 ml of UVM selective media to the sponge and placed at 30° C. for 24 hours.

Day 2:

Read UVM-enriched squeezates and sponges after 24 hours: Removed 50 mL conical tubes and sponge bags from 30° C. incubator. Transferred 1 mL from each conical/sponge to a microcentrifuge tube. Spun the microcentrifuge tubes at 6,000 g for 2 minute, removed the supernatant and resuspend the pellet in 100 uL of $1.0 \times 10^7$ phage. Placed microcentrifuge tubes at 30° C. for 3 hours.

After 3 hours, removed the microcentrifuge tubes from the 30° C. incubator and spun at 16.1 rcf for 1 minute. Transferred 50 uL of the supernatant to a well on a 96-well luminometer plate. Read in the Glomax 96-well luminometer injecting 50 uL NanoGlo per well and reading each well for 1 second with a 2 second delay.

Plate 100 uL from each 50 mL conical on a MOX agar plate for culture confirmation.

The results are presented in Table 11.

TABLE 11

| Phage Infection Protocol | Accuracy |
| --- | --- |
| Protocol 1: 1 hour wake-up, 3 hour infection | 60% |
| Protocol 2: No wake-up, 4 hour infection | 60% |

The rational for Protocol 1 was that cells present in samples may not be metabolically active and this may cause the cells to be refractory to phage infection and/or production of a marker encoded by the phage. If so, it was thought that adding one hour of metabolic stimulation before combining the cells with the phage could put the cells into a state that rendered them more susceptible to infection by the phage and/or to production of the marker encoded by the phage. This result indicates that adding the hour that would have been used for wake-up to the infection time yields the same level of accuracy as having the wake-up step. This is significant in several ways. For example, it implies that adding additional wake-up period (beyond 1 hour) is unlikely to increase accuracy of the assay. It also demonstrates that a wakeup step (in the absence of phage) is not necessary for assay performance. These points are important because the commercialization and usefulness of an assay is generally increased when the number of steps requiring user participation is decreased. It also demonstrates that the total assay time between sample collection and result may be very short.

Example 9: Effect of Phage Concentration

It is well known, and demonstrated herein, that microbial samples obtained from a solid support environment are more difficult to detect in microbial assays including phage-based assays. The data provided herein also demonstrates that infection of target microbe cells not in suspension impacts several assay parameters. This implies that optimal phage concentrations for use in microbe detection assays determined in other contexts may not be directly applicable to this context. Accordingly, an investigation of the relationship between phage concentration and assay performance was undertaken.

A direct comparison of the impact of phage concentration across 10 environmental samples taken from three different test points within a single facility on a single day was performed.

Forty (40) environmental samples were collected from two floor drains and one piece of equipment (a scale in shipping & receiving area) within a facility. Test points were swabbed with a sponge stick, and the sponge stick was returned to the bag. The plastic stick was broken off from the sponge and the bag was sealed and transported back to the lab. 12 additional sponges were opened and had the sponge stick removed without swabbing any surface. These sponges act as negative controls for a set.

A phage cocktail of A511::nluc, LP40::nluc, and LP124::nluc was prepared by combining and diluting a stock concentration of each phage to $9\times10^9$ pfu/mL, $4.5\times10^9$ pfu/mL, $2.25\times10^8$ pfu/mL, and $9\times10^8$ pfu/mL. In each cocktail each phage was present at an equal pfu/mL and the numbers are of total phage pfu/mL. That is, the corresponding values for each individual phage in the cocktail are ⅓ of the listed value.

All liquid was removed from the sponges with a single, firm squeeze; the liquid was then transferred to a 50 mL conical tube containing 20 mL of UVM enrichment broth using a serological pipette. These tubes were placed at 30° C. overnight.

14 mL of phage cocktail was added to 70 mL of sponge infection buffer. 6 mL of sponge infection buffer/phage mixture was then added to each sponge; 10 samples plus 3 negatives were tested in parallel for each phage concentration.

After adding the phage, the sponge was gently massaged 3-4 times to distribute the liquid throughout the sponge. Each sponge received one firm squeeze to extract the liquid from the sponge. 500 uL of the liquid was transferred from the sponge to a 1.5 mL microcentrifuge tube using a pipette. The sponge bags were then resealed and placed in a 30° C. incubator for 4 h.

The tubes were spun at 14,000×g for 60 seconds. 300 uL of the liquid was transferred to a new microcentrifuge tube. Each tube had 300 uL of NanoGlo buffer/substrate mixture added to it 4 minutes prior to detection, and each sample was detected in a Berthold SiriusL Luminometer using a 20 second kinetic read with 1 second integration time. This constitutes a T0 read, which is a sample-specific control for each sponge.

After 4 hours, the bags were removed from the incubator. Each sponge received one firm squeeze to extract the liquid from the sponge. 500 uL of the liquid was transferred from the sponge to a 1.5 mL microcentrifuge tube using a pipette.

Two hours later, after 6 hours or total incubation the bags were again removed from the incubator. Each sponge received one firm squeeze to extract the liquid from the sponge. 500 uL of the liquid was transferred from the sponge to a 1.5 mL microcentrifuge tube using a pipette.

The tubes were spun at 14,000×g for 60 seconds. 300 uL of the liquid was transferred to a new microcentrifuge tube. Each tube had 300 uL of NanoGlo buffer/substrate mixture added to it 4 minutes prior to detection, and each sample was detected in a Berthold SiriusL Luminometer using a 20 second kinetic read with 1 second integration time. This read is considered a T4 read, which when compared to the T0 can give an indication of whether or not the specific sponge is behaving aberrantly. However, this aspect was not used to call positives or negatives in this example.

Mean RLU values were calculated for each sample. The mean value of the negative samples was calculated, as well as the standard deviation. Threshold is determined according to the following formula:

Threshold={1.2*[(Neg Avg)+(3*(StDev of Neg Avg))]}

Any mean RLU output above the threshold was called a positive. Anything at or below the threshold was called a negative.

The following day, the liquid enrichments are removed from the incubator and 100 uL of each enrichment is plated on MOX agar plates. The plates are placed at 35° C. for 24-28 hours, after which, they are inspected for L. mono colonies. The enrichments are also sent to a third-party lab for confirmation. Metrics are represented as % of samples that match the third-party lab confirmation results. Data for the 4 hour timepoint are presented in Table 12. Data for the 6 hour timepoint are presented in Table 13.

TABLE 12

(4 Hours)

|  | 1x | 2.5x | 5x | 10x |
| --- | --- | --- | --- | --- |
| Sensitivity | 40% | 60% | 60% | 100% |
| Accuracy | 70% | 70% | 80% | 100% |
| Specificity | 100% | 80% | 100% | 100% |

(1x = 9E8 pfu/mL)

TABLE 13

(6 Hours)

|  | 1x | 2.5x | 5x | 10x |
| --- | --- | --- | --- | --- |
| Sensitivity | 40% | 100% | 60% | 100% |
| Accuracy | 70% | 100% | 80% | 100% |
| Specificity | 100% | 100% | 100% | 100% |

(1x = 9E8 pfu/mL)

These data demonstrate a significant improvement in assay performance using four and six hour incubations when the phage concentration is increased from 9e8 pfu/mL to 9e9 pfu/mL. This finding is unexpected and surprising, because the tested phage cocktail has demonstrated high performance when used in a completely liquid assay format at phage concentrations of $1\times10^7$ and lower (data not shown). Without wishing to be bound by theory it is speculated that environmental samples (especially the dirtier ones) have components in them that require a higher concentration of phage to reach a similar effective concentration as seen in the liquid assay. Even so, it was also unpredictable that these very high phage concentrations would yield a benefit because the multiplicity of infection is on the order of 1,000,000:1 or greater, and this suggested that adding more phage would not be necessary and could even be detrimental to the assay if the cells were overwhelmed by phage before being able to produce a detectable level of NanoLuc protein.

Example 10: Catalytic Inactivation Reduces Background in Phage Preparations

Phage preparations for the recombinant nluc phage disclosed herein, made using the PEG precipitation and Cesium Chloride gradient methods, tend to have RLU/PFU values of $1\times10^{-4}$ to $4\times10^{-4}$. This indicates that the nluc protein encoded by the recombinant phage genome is synthesized during preparation of the lysate and then is associated with the phage recovered from the lysate.

These values yield backgrounds that are still higher than would be preferred. In seeking to further reduce the background of the phage preparations, multiple efforts were made. These included: 1) Multiple PEG precipitations steps (no improvements observed); 2) Multiple step gradients (no improvements observed), 3) Multiple continuous gradients (no improvements observed); and 4) Removal of additional background with HIS beads/resins (0-15% reduction in background, variable depending on different preps).

In order to increase the signal to noise ratio obtainable when using the phage assay system, an attempt was made to catalytically inactivate the excess enzyme left over from the phage preparation process by incubating the phage with the NanoGlo substrate of the nanoluc enzyme.

Protocol

Diluted concentrated phage suspension (from cesium chloride gradient, post-dialysis) to $1\times10^{11}$ in SM buffer in a suitable volume (2-5 ml).

In a 50 ml conical tube, mixed 1 volume of NanoGlo (Promega) by adding NanoGlo substrate to NanoGlo buffer at a 1:50 ratio.

Combined 1 volume of phage suspension to 1 volume of NanoGlo.

Incubated statically at 30° C. for 24 hours.

Using a needle and syringe, transferred the phage/nanoglo to a dialysis cassette (Pierce Slide-a-lyzer G2 dialysis cassette, 10,000 MWCO).

Dialyzed against 5 L of SM buffer 0/N at 4° C.

Used a needle and syringe, remove the dialyzed phage suspension from the cassette and transfer to a 50 ml conical tube.

Titered and use as needed.

This catalytic inactivation protocol has repeatedly resulted in large RLU/PFU reductions, typically down to $\sim5\times10^{-5}$ RLU/PFU. Two recent catalytic inactivation batches are presented below in Table 14:

TABLE 14

|  | Pre burnout RLU/PFU | Post burnout RLU/PFU | % reduction |
| --- | --- | --- | --- |
| Burnout 1 | 1.89e−4 | 5.63e−5 | 70.2 |
| Burnout 2 | 1.80e−4 | 6.50e−5 | 63.8 |

In a separate experiment, catalytic inactivation times of 0 hours, 3 hours, 6 hours, and 24 hours were compared. The results showed that a 3 h catalytic inactivation removed 90% background luminescence, a 6 h catalytic inactivation removed 92%, and a 24 h catalytic inactivation removed 97% of the luminescence. A 0 h catalytic inactivation removed 79% of the luminescence, if followed by the same dialysis as the other catalytic inactivation protocols. This latter result is because the NanoGlo substrate is present during at least part of the dialysis procedure. Interestingly, it was also observed across experiments that the catalytic inactivation protocol has repeatedly resulted in RLU/PFU reductions down to ~5e-5 RLU/PFU independently of the starting background prior to catalytic inactivation. In this way catalytic inactivation may also be used to decrease batch to batch variability and in turn increase the accuracy of the assay across batches.

The high effectiveness of catalytic inactivation was surprising for several reasons. For example, the nluc enzyme is known to be very stable and is chloroform resistant. Additionally, because the contaminating nluc could not be completely separated from the phage despite numerous methods of separation (CsCl, Tangential flow filtration, ultrafiltration, etc.) it was not clear whether the enzyme would be sufficiently accessible to the Nanoglo substrate. It was also unclear whether 0-24 hours would allow for enough catalytic cycles for the enzyme to be sufficiently damaged that its catalytic activity would be compromised. It was also unclear whether the phage would be compromised by the longer catalytic incubation times. As shown below, a comparison of assays performed using phage prepared with a catalytic inactivation step to those without it demonstrates that the benefits of catalytic inactivation outweigh any costs.

Example 11: Use of Phage Preparations Prepared Using Catalytic Inactivation

This example addresses the effect on the assay of using a phage preparation that has had the background reduced by catalytic inactivation.

Preparations of LP40::nluc, A511::nluc, and LP124::nluc prepared with and without catalytic inactivation were compared. In all cases the phage were combined into cocktails at equal concentrations of each phage. The concentrations tested were $1\times10^9$ pfu/mL, $1\times10^8$ pfu/mL, and $1\times10^7$ pfu/mL of total phage. Phage cocktails were diluted in 0.5×BHI. 1 mL of an overnight, stationary phase L. monocytogenes 1839 culture was diluted into 4 mL of 0.5×BHI and incubated, shaking, at 30° C. for 2 h. The culture was then serially diluted in 0.5×BHI out to the $1\times10^{-8}$ dilution. The dilutions were plated on 0.5×BHI Agar plates for cell counts.

40 uL of each dilution was transferred to 1.5 mL microcentrifuge tubes in sextuplicates. 40 uL of 0.5×BHI was transferred to 1.5 mL microcentrifuge tubes in sextuplicates in parallel as a control. The sextuplicates were broken out into individual dilution series. Each series was infected with 40 uL of a given phage concentration, either catalytically inactivated or untreated. Infections were incubated for 3 h at 30° C. After incubation, infections were transferred in triplicate to 96-well plates for detection. Plates were read with a 2 second delay time and 1-second integration time.

Results were compared across phage concentration and by whether the phage was catalytically inactivated or not. The threshold for this assay is determined by taking the average RLU of the negative samples (phage only in 0.5×BHI), and adding 3 standard deviations to that average. Sensitivity is determined by finding the intersection between the threshold and the best-fit line for the dilution series, which is called the Lower Limit of Detection (LLOD).

The data showed that at the $1\times10^7$ concentration of phage, there is no difference in background or threshold between the catalytically inactivated and untreated phage. At the higher concentrations of phage, there is clear separation between the threshold of the catalytically inactivated phage and the threshold of the untreated phage. At the $1\times10^9$ concentration of phage, this affects the sensitivity of the assay, as it becomes more difficult to detect single cells. The LLOD of the $1\times10^9$ catalytically inactivated phage was a single cell in this assay. The LLOD of the $1\times10^9$ untreated phage was 19 cells in this assay.

This data suggests that as the concentration of phage increases, the background increases correspondingly. In some cases this increase may be of a degree that the greater variability in absolute RLU output between the negative samples will tend to raise the threshold beyond the point at which a single cell can be detected. This effect may be reduced by the use of catalytically inactivated phage preparations.

These data also demonstrate that while the lower background provided by the catalytically inactivated phage preparation may not be essential in applications that utilize relatively lower concentrations of phage, at higher concentrations of phage (all else equal) the background reduction has a benefit to the sensitivity of the assay. Clearly, such a situation may occur when assaying samples of bacteria in association with a solid substrate. In those situations the higher phage concentration provides more accuracy but that benefit is limited somewhat by the concomitant higher background. Use of catalytically inactivated phage preps will allow a fuller realization of the benefits of using the higher phage concentration with such samples.

Example 12: Analysis of Bacterial Contamination on Solid Surfaces

The samples analyzed in this example were collected from a variety of solid surfaces at various locations within food processing plants, including drains, floors, walls, equipment (scales, carts, tables, machinery, etc.)

Environmental samples were collected from various test locations at multiple sites. The collection protocol was as follows. Solid phase samples were collected using a Custom Sponge-Stick with Letheen Broth SSL10LET (3M). The 3M sponge stick with Letheen broth is a biocide-free cellulose sponge shipped in a sterile bag and hydrated with 10 mL of Letheen Broth. The plastic handle allows users to collect environmental samples without directly handling (and possibly contaminating) the sponge, as well as making it easier to reach into drains, pipes, and crevices to collect samples. The cellulose material collects and retains organisms in or on the sponge matrix. The Letheen Broth is present to help neutralize cleaning chemicals such as quaternary ammonia and preserve the viability of organisms for detection.

The plastic handle comes with a thumb guide to inform the point beyond which the user should refrain from touching to avoid possible contamination. Once the sample was collected, the sponge was returned to the bag, and the plastic handle was snapped off, allowing the bag to be sealed with only the sponge inside The pre-moistened 3M Sponge Sticks in Letheen Broth were removed from their storage bag and a 4"×4" solid surface was swabbed to collect samples following manufacturer's instructions. After collection the sponge stick was returned to the storage bag and the bag was closed until further processing.

For each set of samples from a given site, 3 additional sponges were opened and had the sponge stick removed without swabbing any surface. These sponges act as negative controls for a set. Two data sets were excluded because they showed moderate to high signal suppression and did not return a signal equivalent to the negative samples, making it impossible to determine differences in signal between positive and negative samples and leading to the hypothesis that there may have been an issue with this particular prep of phage, which was used for both sets of samples. This hypothesis is currently being tested.

A phage cocktail of LP40::nluc, A511::nluc, and LP124::nluc was prepared by combining and diluting stocks of each phage to give a final concentration of total phage of $9\times10^9$ pfu/mL. The phage preps had been treated with the catalytic inactivation protocol described in Example 10. The background luminosity present in the phage preps used in this example that had not been treated with catalytic inactivation ranged from Prior to catalytic inactivation, the phage preps used on beta samples ranged from 12,000 RLU to 81,000 RLU (at $9\times10^9$ pfu/mL). The background luminosity present in the phage preps used in this example that had been treated with catalytic inactivation ranged from ranged from 1500 to 10,000 RLU (at $9\times10^9$ pfu/mL).

All liquid was removed from the sponges with a single, firm squeeze; the liquid was then transferred to a 50 mL conical tube containing 20 mL of UVM enrichment broth using a serological pipette. These tubes were placed at 30° C. overnight.

14 mL of phage cocktail was added to 70 mL (or 42 mL) of sponge infection buffer. 6 mL (or 3 mL) of sponge infection buffer/phage mixture was then added to each sponge; 10 samples plus 3 negatives. The sponge infection buffer is half-strength Brain Heart Infusion (BHI) medium (18.5 g/L Difco BHI medium) supplemented with 5% weight/volume glucose, 1% volume/volume glycerol, 1% weight/volume Lithium Chloride, and 0.002% weight/volume Nalidixic Acid. This combination of supplements promotes *Listeria* recovery and growth inhibition of competitor microorganisms during the infection process.

After adding the phage, the sponge was gently massaged 3-4 times to distribute the liquid throughout the sponge. Each sponge received one firm squeeze to extract the liquid from the sponge. 500 uL of the liquid was transferred from the bag to a 1.5 mL microcentrifuge tube using a pipette. The sponge bags were then resealed and placed in a 30° C. incubator for 4 h.

The tubes were spun at 14,000×g for 60 seconds. 300 uL of the liquid was transferred to a new microcentrifuge tube. Each tube had 300 uL of NanoGlo buffer/substrate mixture added to it 4 minutes prior to detection, and each sample was detected in a Berthold SiriusL Luminometer using a 20 second kinetic read with 1 second integration time. This constitutes a T0 read, which serves as a sample-specific control for each sponge.

After 4 hours, the bags were removed from the incubator. Each sponge received one firm squeeze to extract the liquid from the sponge. 500 uL of the liquid was transferred from the sponge to a 1.5 mL microcentrifuge tube using a pipette.

The tubes were spun at 14,000×g for 60 seconds. 300 uL of the liquid was transferred to a new microcentrifuge tube. Each tube had 300 uL of NanoGlo buffer/substrate mixture added to it 4 minutes prior to detection, and each sample was detected in a Berthold SiriusL Luminometer using a 20 second kinetic read with 1 second integration time. This read is considered a T4 read.

Mean RLU values were calculated for each sample. The mean value of the negative samples was calculated, as well as the standard deviation. Threshold is determined according to the following formula:

$$\text{Threshold} = [(\text{Neg Avg}) + (3*(\text{StDev of Neg Avg}))]$$

Any mean RLU output above the threshold was called a positive. Any value at or below the threshold was called a negative. Anything below the threshold was called a negative.

The following day, the liquid enrichments were removed from the incubator and 100 uL of each enrichment is plated on MOX agar plates. The plates were placed at 35° C. for 24-28 hours, after which, they were inspected for L. mono colonies. The enrichments were also sent to a third-party lab for confirmation.

The results are presented in Table 15. The number of positives and the number of negatives in the table are based on the third-party lab confirmation results. The accuracy, sensitivity, and specificity are presented as the percent of samples that match the third-party lab confirmation results.

TABLE 15

| Catalytic Inactivation | Accuracy | Sensitivity | Specificity | Number of Positives | Number of Negatives |
|---|---|---|---|---|---|
| No | 69% | 34% | 92% | 437 | 601 |
| Yes | 93% | 88% | 96% | 36 | 64 |

Example 13: His-Tagged Luciferase

Phage-based microbial detection assays that utilize infection on a solid substrate may encounter many environmental factors that may impact performance of the assay on environmental samples in certain situations. This example investigates the feasibility of using a tagged marker, such as a tagged marker encoded by a heterologous nucleic acid sequence in the genome of a recombinant phage. In this assay a HIS-tag was added in different configurations to the nanoluc enzyme.

This experiment utilized the HIS-tagged nanoluc protein that is associated with phage lysate preparations of the disclosed recombinant phage that encode a heterologous HIS-tagged luciferase protein. Using these preparations for this assay provides a ready source of HIS-tagged luciferase. It also allows for evaluation of the effectiveness of HIS-tags to concentrate HIS-tagged luciferase in the presence of the very phage that are utilized in the microbe detection assays disclosed herein.

Materials and Methods:

Phage lysates of the LP40::nluc-L, LP40::nluc-S, LP124::nluc-L, LP124::nluc-S, A511::nluc-L, and A511::nluc-S phage were prepared as described in Example 2.

Magnetic beads were purchased from Life Technologies (His-Tag Dynal beads Cat.10103D). The binding buffer used was 0.5×BHI containing 5% glycerol, 1% glucose, 300 mM NaCl, and 0.01% Tween20. The elution buffer used was 0.5×BHI containing 5% glycerol, 1% glucose, and 300 mM imidazole. Ten ml of each tested phage lysate was prepared at a $1.0 \times 10^{-05}$ dilution in binding buffer. 350 ul aliquots were collected from each tube for measurement of the initial RLU value.

Magnetic beads were prepared by collecting enough aliquots for each sample plus overage, then placed in a 1.5 ml tube and the tube was inserted into a magnetic stand. After a two minute separation time all liquid was removed without disturbing the beads, the beads were washed with binding buffer, and finally the beads were re-suspended with binding buffer in the original volume.

10 ul of beads were dispensed into each tube of phage lysate, and the tubes were placed on a rotating platform and incubated for 20 min. Following incubation, the tubes were placed in a magnetic stand, the beads were allowed to separate from the liquid for 2 min, and 350 ul was collected from each tube for measurement of the unbound RLU value. All liquid was then removed from each tube, the beads were re-suspended in 1 ml of binding buffer and transferred to 1.5 ml tubes. Following a magnetic separation step all liquid was removed again and the beads were treated with 350 ul of elution buffer for 10 min with gentle rotation. Following a final magnetic separation step all liquid was removed for measurement of released RLU values.

Luminescence measurements were performed in a plate reader using triplicates of 100 ul aliquots and 100 ul of NanoGlo Luciferase Assay solution (Promega, Cat. #N1110). The measurements were used to calculate the percentage of starting NanoLuc protein bound and released from the beads.

Results and Discussion:

The results are presented in Table 16. The % NanoLuc bound is the difference between initial value for that sample and the unbound value for that sample. In data not shown the efficiency of elution was determined to be about 95%. A comparison of the initial RLU value to the RLU value released from the beads is a measure of the actual signal increase resulting from concentrating the signal using beads.

TABLE 16

| | N-terminal-HisTag | | | C-terminal-HisTag | | |
|---|---|---|---|---|---|---|
| Phage | initial RLU value | % NanoLuc bound | RLU value released from beads | initial RLU value | % NanoLuc bound | RLU value released from beads |
| LP40::nluc-L | 3521 | 72.0 | 155502 | 128665 | 31.2 | 1608845 |
| LP40::nluc-S | 1975565 | 75.5 | 70347485 | 237457 | 23.0 | 2684421 |
| LP124::nluc-L | 8998 | 73.1 | 311342 | 543178 | 27.1 | 5604857 |
| LP124::nluc-S | 3687788 | 73.1 | 142415616 | 314806 | 28.0 | 3449935 |
| A511::nluc-L | 5775 | 72.1 | 235155 | 350031 | 25.7 | 4169733 |
| A511::nluc-S | 48200829 | 68.3 | 1675885824 | 166872 | 21.0 | 1967920 |

Evaluation of binding efficiencies for two series of phage lysates revealed that phages with an N-terminal His Tag exhibited much higher binding efficiency to cobalt modified magnetic beads over C-terminal series. These data demonstrate that accessibility of the His Tag was superior for the N-terminal attachment. RLU values of initial signal were highest for phage obtained from N-terminal strains containing the shorter spacer. These strains also gave the highest released signal value. These results demonstrate that attachment of a tag to a marker protein is a feasible approach for concentrating the signal in the context of the assays disclosed herein. This optional step may increase assay performance in some contexts.

Example 14: Assay Performance in the Presence of Selective Agents

Assays for *Listeria* contamination that specifically detect live cells have conventionally involved a step in which target microbes present in samples are grown for a period of time. This wake up period then renders the cells amenable to further processing in the assay. Most commonly assays have also included an extended culture period so that the number of cells in the culture increases dramatically and then the increased number of cells is detected. In such assays detection of target microbes does not occur until after metabolic activity of the cells is promoted by so-called wake up or repair conditions. Phage-based bacterial detection methods that assay environmental samples and discriminate for live cells have also relied on an extended culture period when the target cells proliferate.

In their paper (Busch and Donnelly, 1992) "Development of a Repair-Enrichment Broth for Resuscitation of Heat-Injured *Listeria monocytogenes* and *Listeria innocua*," Appl. Environ. Microbiol., Vol. 58, No. 1, pp. 14-20, the authors developed a *Listeria* Repair Broth (LRB). The LRP is an enrichment broth based on Tripticase Soy Broth (TSB) supplemented with glucose, yeast extract, Magnesium sulfate, and pyruvate, and buffered with the addition of MOPS. Each of these supplements were found to independently facilitate repair of heat-injured *Listeria* in 5 h or less.

To evaluate the effect of repair prior to the addition of growth inhibitors (selective agents) the authors compared recovery of heat-injured *Listeria* cells when grown in different selective enrichment media vs. LRB. To do this, an initial inoculum of injured cells was added to FDA enrichment broth (FDA), *Listeria* Enrichment Broth (LEB) and UVM enrichment broth (UVM), or to LRB. After 5 h recovery, selective agents (acriflavine, nalidixic acid, and cycloheximide) at the same concentrations used in FDA and LEB were added to LRB. All cultures were incubated for a total of 24 h, and then cell counts were obtained by plating on non-selective media. The final *Listeria* populations after 24 h of incubation in selective enrichment media (FDA, LEB, UVM) were $1.7 \times 10^8$ to $9.1 \times 10^8$ CFU/ml; populations in LRB consistently averaged $2.5 \times 10^{11}$ to $8.2 \times 10^{11}$ CFU/ml. The authors concluded that failure to use a nonselective repair-enrichment step when recovering *Listeria* will allow injured cells to escape detection on culture-based methods.

In Pritchard and Donnelly, 1999 "Combined secondary enrichment of primary enrichment broths increases *Listeria* detection," Journal of Food Protection, Vol. 62, No. 5, pp. 532-535, the Donnelly group tried to replicate the results of their 1992 paper using real-world samples instead of heat-injured *Listeria* cells. They obtained both environmental samples and food samples, with 23.8% testing positive for *Listeria* by at least one of the methods tested. What they found is that using LRB or UVM alone does not increase the likelihood of identifying *Listeria*-positive samples, but doing a combined secondary enrichment of both enrichment broths does. For that they either split the sample in two, enrich each half on UVM or LRB for 24 h, and then combine portions of both primary enrichments onto a secondary enrichment for 24 h and then detect by culture from there, or do the full procedure with both primary enrichments and then doing independent secondary enrichments.

The assays disclosed herein are able to detect contamination by live *Listeria* cells over very short periods of time. In some embodiments the assays also incorporate selection agents that selectively suppress the growth of non-target microbes that may be present in a sample. Of course, such agents very likely also impact the growth of *Listeria* in the samples—although to a lesser degree. This use of selective suppression is thought to reduce variability of assay performance. In view of the presence of selection agents and the short period of the assay (which requires efficient infection of target cells by phage), the literature on *Listeria* repair suggested that a wake up period would be necessary to achieve maximum performance of the assay. As described above, however, at least one wake up format did not impact the performance of the assay on environmental samples collected from food processing facilities.

To determine the effect of the addition of selective agents (Acriflavine 0.012 g/L and Nalidixic acid 0.02 g/L) on detection of *Listeria* in assays of this disclosure, ten-fold dilutions ($1 \times 10^{-1}$ to $1 \times 10^{-8}$) of an overnight culture of *L. monocytogenes* strain 1839 were made on 0.5×BHI and six spots of 250 uL of each dilution were dried on a stainless steel surface for 18 h. As a negative control, six spots of sterile 0.5×BHI were also dried onto the surface. After the 18 h, the spots were swabbed with 3M sponge-sticks containing Letheen broth as described herein, and the sponges were incubated in their bags at 30° C. for two hours. After the two hours, excess Letheen broth (4-5 mL) was removed from the sponge, and 6 mL of either 0.5×BHIgg (half strength BHI with Glycerol and Glucose) or SIB (BHIgg+selective agents) containing equal parts of LP40::nluc, A511::nluc, and LP124::nluc at $2.25 \times 10^8$ pfu/mL total phage, were added to three sponges/dilution and to the three negatives. After a 4 h incubation at 30° C., the sponges were squeezed and 400 uL from each sponge was removed, centrifuged, and 300 uL transferred to a new tube for detection with 300 uL of the detection reagent. To determine the limit of detection three negatives (with either BHIgg or SIB, depending on the set) were used.

If selective agents interfere with assay performance, the sensitivity of the assay will decrease on the set containing the selective agents, and/or the amount of light (RLU) coming from sponges found positive by the assay will be lower when compared to BHIgg. If instead there is no effect, sensitivity and RLUs will be similar on both sets.

The data are presented in Table 17. The reported values for each sample are presented as RLU/300 uL of each sponge liquid. Non-italicized text in the table indicate that the RLU obtained is higher than the LLOD (identified as a positive result) while italicized text indicate that measured TLU is lower than the LLOD (identified as a negative result). The reported average represents the average RLU of three sponges/dilution/condition. The light output observed between positive samples of each set (SIB vs. BHIgg) is not statistically different (p>0.5), suggesting that addition of selective agents does not affect the level of signal obtained from each condition.

TABLE 17

| Dilution of cell used to dry down | SIB1 | SIB2 | SIB3 | SIB Average | BHigg1 | BHigg2 | BHigg3 | BHigg Average |
|---|---|---|---|---|---|---|---|---|
| 1.00E−01 | 240458.94 | 93709.88 | 70048.38 | 134739.06 | 124661.50 | 101142.50 | 451041.94 | 225615.31 |
| 1.00E−02 | 9640.31 | 9135.81 | 12862.88 | 10546.33 | 8251.88 | 9371.50 | 13202.63 | 10275.33 |
| 1.00E−03 | 8258.94 | *7145.81* | *6633.06* | *7345.94* | *6633.44* | *6303.44* | 7120.06 | *6685.65* |
| 1.00E−04 | 6510.50 | 7158.94 | 7208.19 | 6959.21 | 5862.06 | 5727.38 | 5738.50 | 5775.98 |
| 1.00E−05 | *7333.50* | *7488.38* | *7368.19* | *7396.69* | *5988.44* | *6376.69* | *6163.19* | *6176.10* |
| 1.00E−06 | *6337.38* | *7180.56* | *7843.56* | *7120.50* | *6011.31* | *5762.06* | *6311.25* | *6028.21* |

TABLE 17-continued

| Dilution of cell used to dry down | SIB1 | SIB2 | SIB3 | SIB Average | BHigg1 | BHigg2 | BHigg3 | BHigg Average |
|---|---|---|---|---|---|---|---|---|
| 1.00E−07 | 6883.06 | 6742.25 | 6459.75 | 6695.02 | 6432.56 | 6264.00 | 6237.38 | 6311.31 |
| 1.00E−08 | 6801.13 | 7430.69 | 6956.31 | 7062.71 | 5789.88 | 6676.00 | 5890.63 | 6118.83 |
| Negatives | 6393.375 | 6449.9375 | 6779.4375 | | 5621.125 | 5948.9375 | 5968.375 | |
| Lower Limit of detection | | 7517.7 | | | | 6716.2 | | |

This result is unexpected in view of the well-known need to resuscitate Listeria collected from environmental samples prior to assaying for the presence of live cells. This result means that selective agents may be used in the context of this assay without degrading assay performance.

Example 15: Listeria Panel

A bacterial strain panel comprising a diverse combination of Listeria species and subspecies was selected for characterization of Listeria phages. The panel comprises strains that have been isolated from various geographic and environmental niches including food processing plants and food retail locations. Special consideration was given to obtain bacterial strains from food processing environments with sufficient geographic separation to maximize natural variation within the bacterial strain panel.

The panel as assembled initially contained 272 Listeria isolates and represents the four major species of Listeria (L. monocytogenes, L. innocua, L. welshmeri and L. seelingri) (Table 18). Within each species the panel comprises representative isolates of various subspecies to ensure sufficient depth of coverage to allow for meaningful extrapolation of the data to the subspecies in general. The selection of strains for the bacterial panel were based on the prevalence of particular strains within the food environment and associated with human disease. Environmental screening of retail food stores used allelotyping to identify the most commonly identified Listeria subspecies and identified that certain allelotypes were often highly represented among the population of species identified. (Williams, S. K. et al., J Food Prot 74, 63-77 (2011); Sauders, B. D. et al., Appl Environ Microbiol 78, 4420-4433 (2012).) Ten (10) L. monocytogenes strains from each of the most common ribotypes represented from isolates from food and human disease were selected for the collection. These populations are largely overlapping and have a strong correlation in prevalence and, therefore, represent the strains most useful to identify in food processing plants. When looking at breadth of coverage of L. monocytogenes strains based on ribotypes isolated in human disease and food processing plants, the panel as constructed represents ~86% and 91% coverage, respectively. The purpose for selecting 10 strains of each L. monocytogenes ribotype was to allow for the identification of natural variation within a group to ensure a reasonably complete coverage of the L. monocytogenes species.

To expand beyond L. monocytogenes and cover other species within the genus additional species and subspecies variation was considered to select further strains for the panel. Again, focus was placed on the species and subspecies that are commonly identified in food processing plants. Ten (10) isolates representing each of the most common allelotypes of L. welshmeri, L. innocua and L. selelingri were selected. The panel as constructed covers 96% of the L. innocua, 98% of the L. selelingri, and 100% of the L. welshmeri ribotypes identified by Saunders et al. and provides an accurate representation of the Listeria genus. The Listeria host panel as assembled thus serves as a tool for the analysis of the host range of any bacteriophage against the Listeria genus. Accordingly, this panel can be used to define target bacteria of any given phage.

The genus, species, and subspecies of the members of the panel is provided in Table 18.

TABLE 18

| Identifier | Strain Name | Genus/Species | Subspecies |
|---|---|---|---|
| NP1900 | FSL R8-5085 | Listeria innocua | sig B allelotype 11 |
| NP1901 | FSL R8-5091 | Listeria innocua | sig B allelotype 11 |
| NP1902 | FSL R8-5098 | Listeria innocua | sig B allelotype 11 |
| NP1903 | FSL R8-5255 | Listeria innocua | sig B allelotype 11 |
| NP1904 | FSL R8-5293 | Listeria innocua | sig B allelotype 11 |
| NP1905 | FSL R8-5295 | Listeria innocua | sig B allelotype 11 |
| NP1906 | FSL R8-5306 | Listeria innocua | sig B allelotype 11 |
| NP1907 | FSL R8-5440 | Listeria innocua | sig B allelotype 11 |
| NP1908 | FSL R8-5442 | Listeria innocua | sig B allelotype 11 |
| NP1909 | FSL R8-5448 | Listeria innocua | sig B allelotype 11 |
| NP1912 | FSL R8-7061 | Listeria innocua | sig B allelotype 22 |
| NP1959 | FSL S4-158 | Listeria innocua | sig B allelotype 22 |
| NP1960 | FSL S10-784 | Listeria innocua | sig B allelotype 22 |
| NP1961 | FSL F6-1168 | Listeria innocua | sig B allelotype 22 |
| NP1962 | FSL R8-5961 | Listeria innocua | sig B allelotype 22 |
| NP1963 | FSL R8-6922 | Listeria innocua | sig B allelotype 22 |
| NP1964 | FSL R8-7352 | Listeria innocua | sig B allelotype 22 |
| NP1965 | FSL R8-5598 | Listeria innocua | sig B allelotype 22 |
| NP1966 | FSL R8-6733 | Listeria innocua | sig B allelotype 22 |
| NP1967 | FSL R8-5942 | Listeria innocua | sig B allelotype 22 |
| NP1915 | FSL R8-7548 | Listeria innocua | sig B allelotype 37 |
| NP1997 | FSL R8-5764 | Listeria innocua | sig B allelotype 37 |
| NP1998 | FSL R8-5802 | Listeria innocua | sig B allelotype 37 |
| NP1999 | FSL R8-6012 | Listeria innocua | sig B allelotype 37 |
| NP2000 | FSL R8-6355 | Listeria innocua | sig B allelotype 37 |
| NP2001 | FSL R8-6369 | Listeria innocua | sig B allelotype 37 |
| NP2002 | FSL R8-6476 | Listeria innocua | sig B allelotype 37 |
| NP2003 | FSL R8-7175 | Listeria innocua | sig B allelotype 37 |
| NP2004 | FSL R8-6888 | Listeria innocua | sig B allelotype 37 |
| NP2005 | FSL R8-6672 | Listeria innocua | sig B allelotype 37 |
| NP1916 | FSL R8-6667 | Listeria innocua | sig B allelotype 56 |
| NP2006 | FSL S10-1311 | Listeria innocua | sig B allelotype 56 |
| NP2007 | FSL F6-1159 | Listeria innocua | sig B allelotype 56 |
| NP2008 | FSL F6-1126 | Listeria innocua | sig B allelotype 56 |
| NP2009 | FSL S6-120 | Listeria innocua | sig B allelotype 56 |
| NP2010 | FSL R8-5594 | Listeria innocua | sig B allelotype 56 |
| NP2011 | FSL R8-7181 | Listeria innocua | sig B allelotype 56 |
| NP2012 | FSL R2-632 | Listeria innocua | sig B allelotype 56 |
| NP2013 | FSL L3-851 | Listeria innocua | sig B allelotype 56 |
| NP2014 | FSL S10-1377 | Listeria innocua | sig B allelotype 56 |
| NP 1869 | WSLC 3009 | Listeria ivanovii | sig B allelotype 73 |
| NP 1840 | FSL J1-208 | Listeria monocytogenes | ribotype DUP-10142 |
| NP 1839 | FSL F6-367 | Listeria monocytogenes | ribotype DUP-1030A |
| NP2024 | FSL F6-267 | Listeria monocytogenes | ribotype DUP-1030A |
| NP2025 | FSL F6-406 | Listeria monocytogenes | ribotype DUP-1030A |
| NP2026 | FSL H5-592 | Listeria monocytogenes | ribotype DUP-1030A |
| NP2027 | FSL H1-219 | Listeria monocytogenes | ribotype DUP-1030A |
| NP2028 | FSL H1-121 | Listeria monocytogenes | ribotype DUP-1030A |
| NP2029 | FSL W3-072 | Listeria monocytogenes | ribotype DUP-1030A |
| NP2030 | FSL N4-239 | Listeria monocytogenes | ribotype DUP-1030A |
| NP2031 | FSL N3-293 | Listeria monocytogenes | ribotype DUP-1030A |
| NP2032 | FSL F3-319 | Listeria monocytogenes | ribotype DUP-1030A |
| NP1879 | FSL N4-221 | Listeria monocytogenes | ribotype DUP-1030B |
| NP2033 | FSL F2-738 | Listeria monocytogenes | ribotype DUP-1030B |
| NP2034 | FSL N3-881 | Listeria monocytogenes | ribotype DUP-1030B |
| NP2035 | FSL N4-048 | Listeria monocytogenes | ribotype DUP-1030B |
| NP2036 | FSL N4-696 | Listeria monocytogenes | ribotype DUP-1030B |

TABLE 18-continued

| Identifier | Strain Name | Genus/Species | Subspecies |
|---|---|---|---|
| NP2037 | FSL N4-242 | *Listeria monocytogenes* | ribotype DUP-1030B |
| NP2038 | FSL H4-364 | *Listeria monocytogenes* | ribotype DUP-1030B |
| NP2039 | FSL H4-147 | *Listeria monocytogenes* | ribotype DUP-1030B |
| NP2040 | FSL H4-946 | *Listeria monocytogenes* | ribotype DUP-1030B |
| NP2041 | FSL S4-461 | *Listeria monocytogenes* | ribotype DUP-1030B |
| NP2042 | FSL F6-206 | *Listeria monocytogenes* | ribotype DUP-1038B |
| NP2043 | FSL F6-224 | *Listeria monocytogenes* | ribotype DUP-1038B |
| NP2044 | FSL L3-739 | *Listeria monocytogenes* | ribotype DUP-1038B |
| NP2045 | FSL N3-008 | *Listeria monocytogenes* | ribotype DUP-1038B |
| NP2046 | FSL N3-022 | *Listeria monocytogenes* | ribotype DUP-1038B |
| NP2047 | FSL J1-108 | *Listeria monocytogenes* | ribotype DUP-1038B |
| NP2048 | FSL J1-119 | *Listeria monocytogenes* | ribotype DUP-1038B |
| NP2049 | FSL C1-122 | *Listeria monocytogenes* | ribotype DUP-1038B |
| NP2050 | FSL J1-126 | *Listeria monocytogenes* | ribotype DUP-1038B |
| NP1880 | FSL L3-159 | *Listeria monocytogenes* | ribotype DUP-1039A |
| NP2051 | FSL F3-285 | *Listeria monocytogenes* | ribotype DUP-1039A |
| NP2052 | FSL R6-288 | *Listeria monocytogenes* | ribotype DUP-1039A |
| NP2053 | FSL N1-021 | *Listeria monocytogenes* | ribotype DUP-1039A |
| NP2054 | FSL H1-208 | *Listeria monocytogenes* | ribotype DUP-1039A |
| NP2055 | FSL N3-034 | *Listeria monocytogenes* | ribotype DUP-1039A |
| NP2056 | FSL L5-072 | *Listeria monocytogenes* | ribotype DUP-1039A |
| NP2057 | FSL S6-131 | *Listeria monocytogenes* | ribotype DUP-1039A |
| NP2058 | FSL N3-278 | *Listeria monocytogenes* | ribotype DUP-1039A |
| NP2059 | FSL R2-282 | *Listeria monocytogenes* | ribotype DUP-1039A |
| NP1881 | FSL T1-323 | *Listeria monocytogenes* | ribotype DUP-1039B |
| NP2060 | FSL H5-770 | *Listeria monocytogenes* | ribotype DUP-1039B |
| NP2061 | FSL F6-207 | *Listeria monocytogenes* | ribotype DUP-1039B |
| NP2062 | FSL F6-236 | *Listeria monocytogenes* | ribotype DUP-1039B |
| NP2063 | FSL H5-795 | *Listeria monocytogenes* | ribotype DUP-1039B |
| NP2064 | FSL N3-246 | *Listeria monocytogenes* | ribotype DUP-1039B |
| NP2065 | FSL R2-062 | *Listeria monocytogenes* | ribotype DUP-1039B |
| NP2066 | FSL R2-437 | *Listeria monocytogenes* | ribotype DUP-1039B |
| NP2067 | FSL M1-004 | *Listeria monocytogenes* | ribotype DUP-1039B |
| NP2068 | FSL L4-352 | *Listeria monocytogenes* | ribotype DUP-1039B |
| NP2069 | FSL F6-605 | *Listeria monocytogenes* | ribotype DUP-1039C |
| NP2070 | FSL V1-001 | *Listeria monocytogenes* | ribotype DUP-1039C |
| NP2071 | FSL F6-464 | *Listeria monocytogenes* | ribotype DUP-1039C |
| NP2072 | FSL R8-2748 | *Listeria monocytogenes* | ribotype DUP-1039C |
| NP2073 | FSL R6-908 | *Listeria monocytogenes* | ribotype DUP-1039C |
| NP2074 | FSL L3-802 | *Listeria monocytogenes* | ribotype DUP-1039C |
| NP2075 | FSL F3-056 | *Listeria monocytogenes* | ribotype DUP-1039C |
| NP2076 | FSL J2-020 | *Listeria monocytogenes* | ribotype DUP-1039C |
| NP2077 | FSL S4-914 | *Listeria monocytogenes* | ribotype DUP-1039C |
| NP1882 | FSL H5-725 | *Listeria monocytogenes* | ribotype DUP-1042A |
| NP2078 | FSL F6-467 | *Listeria monocytogenes* | ribotype DUP-1042A |
| NP2079 | FSL F6-655 | *Listeria monocytogenes* | ribotype DUP-1042A |
| NP2080 | FSL F6-352 | *Listeria monocytogenes* | ribotype DUP-1042A |
| NP2081 | FSL H5-781 | *Listeria monocytogenes* | ribotype DUP-1042A |
| NP2082 | FSL K2-147 | *Listeria monocytogenes* | ribotype DUP-1042A |
| NP2083 | FSL V1-026 | *Listeria monocytogenes* | ribotype DUP-1042A |
| NP2084 | FSL H5-572 | *Listeria monocytogenes* | ribotype DUP-1042A |
| NP2085 | FSL K2-065 | *Listeria monocytogenes* | ribotype DUP-1042A |
| NP2086 | FSL H4-120 | *Listeria monocytogenes* | ribotype DUP-1042A |
| NP2087 | FSL F6-184 | *Listeria monocytogenes* | ribotype DUP-1042B |
| NP2088 | FSL F6-191 | *Listeria monocytogenes* | ribotype DUP-1042B |
| NP2089 | FSL H1-099 | *Listeria monocytogenes* | ribotype DUP-1042B |
| NP2090 | FSL J1-116 | *Listeria monocytogenes* | ribotype DUP-1042B |
| NP2091 | FSL R2-192 | *Listeria monocytogenes* | ribotype DUP-1042B |
| NP2092 | FSL J1-225 | *Listeria monocytogenes* | ribotype DUP-1042B |
| NP2093 | FSL R2-500 | *Listeria monocytogenes* | ribotype DUP-1042B |
| NP2094 | FSL R2-501 | *Listeria monocytogenes* | ribotype DUP-1042B |
| NP2095 | FSL E1-159 | *Listeria monocytogenes* | ribotype DUP-1042B |
| NP2096 | FSL F6-355 | *Listeria monocytogenes* | ribotype DUP-1042C |
| NP2097 | FSL F6-382 | *Listeria monocytogenes* | ribotype DUP-1042C |
| NP2098 | FSL F3-200 | *Listeria monocytogenes* | ribotype DUP-1042C |
| NP2099 | FSL K2-143 | *Listeria monocytogenes* | ribotype DUP-1042C |
| NP2100 | FSL N1-176 | *Listeria monocytogenes* | ribotype DUP-1042C |
| NP2101 | FSL N1-417 | *Listeria monocytogenes* | ribotype DUP-1042C |
| NP2102 | FSL L3-051 | *Listeria monocytogenes* | ribotype DUP-1042C |
| NP2103 | FSL T1-107 | *Listeria monocytogenes* | ribotype DUP-1042C |
| NP2104 | FSL T1-408 | *Listeria monocytogenes* | ribotype DUP-1042C |
| NP1883 | FSL T1-922 | *Listeria monocytogenes* | ribotype DUP-1043A |
| NP2105 | FSL F6-396 | *Listeria monocytogenes* | ribotype DUP-1043A |
| NP2106 | FSL H5-806 | *Listeria monocytogenes* | ribotype DUP-1043A |
| NP2107 | FSL F6-551 | *Listeria monocytogenes* | ribotype DUP-1043A |
| NP2108 | FSL F6-446 | *Listeria monocytogenes* | ribotype DUP-1043A |
| NP2109 | FSL F6-315 | *Listeria monocytogenes* | ribotype DUP-1043A |
| NP2110 | FSL V1-022 | *Listeria monocytogenes* | ribotype DUP-1043A |
| NP2111 | FSL R2-132 | *Listeria monocytogenes* | ribotype DUP-1043A |
| NP2112 | FSL R2-273 | *Listeria monocytogenes* | ribotype DUP-1043A |
| NP2113 | FSL N3-277 | *Listeria monocytogenes* | ribotype DUP-1043A |
| NP1884 | FSL H1-251 | *Listeria monocytogenes* | ribotype DUP-1044A |
| NP2114 | FSL F6-358 | *Listeria monocytogenes* | ribotype DUP-1044A |
| NP2115 | FSL F6-194 | *Listeria monocytogenes* | ribotype DUP-1044A |
| NP2116 | FSL R2-763 | *Listeria monocytogenes* | ribotype DUP-1044A |
| NP2117 | FSL R2-765 | *Listeria monocytogenes* | ribotype DUP-1044A |
| NP2118 | FSL R2-764 | *Listeria monocytogenes* | ribotype DUP-1044A |
| NP2119 | FSL N1-225 | *Listeria monocytogenes* | ribotype DUP-1044A |
| NP2120 | FSL N1-227 | *Listeria monocytogenes* | ribotype DUP-1044A |
| NP2121 | FSL N1-048 | *Listeria monocytogenes* | ribotype DUP-1044A |
| NP2122 | FSL K2-131 | *Listeria monocytogenes* | ribotype DUP-1044A |
| NP1885 | FSL L3-501 | *Listeria monocytogenes* | ribotype DUP-1044B |
| NP2123 | FSL F6-222 | *Listeria monocytogenes* | ribotype DUP-1044B |
| NP2124 | FSL F6-249 | *Listeria monocytogenes* | ribotype DUP-1044B |
| NP2125 | FSL N3-065 | *Listeria monocytogenes* | ribotype DUP-1044B |
| NP2126 | FSL H4-699 | *Listeria monocytogenes* | ribotype DUP-1044B |
| NP2127 | FSL L4-241 | *Listeria monocytogenes* | ribotype DUP-1044B |
| NP2128 | FSL S4-643 | *Listeria monocytogenes* | ribotype DUP-1044B |
| NP2129 | FSL R2-073 | *Listeria monocytogenes* | ribotype DUP-1044B |
| NP2130 | FSL F3-224 | *Listeria monocytogenes* | ribotype DUP-1044B |
| NP2131 | FSL N4-334 | *Listeria monocytogenes* | ribotype DUP-1044B |
| NP1886 | FSL R2-069 | *Listeria monocytogenes* | ribotype DUP-1044E |
| NP2132 | FSL R2-070 | *Listeria monocytogenes* | ribotype DUP-1044E |
| NP1887 | FSL H1-030 | *Listeria monocytogenes* | ribotype DUP-1045B |
| NP2133 | FSL F6-421 | *Listeria monocytogenes* | ribotype DUP-1045B |
| NP2134 | FSL F6-449 | *Listeria monocytogenes* | ribotype DUP-1045B |
| NP2135 | FSL J2-054 | *Listeria monocytogenes* | ribotype DUP-1045B |
| NP2136 | FSL S4-024 | *Listeria monocytogenes* | ribotype DUP-1045B |
| NP2137 | FSL H1-111 | *Listeria monocytogenes* | ribotype DUP-1045B |
| NP2138 | FSL K2-022 | *Listeria monocytogenes* | ribotype DUP-1045B |
| NP2139 | FSL S4-066 | *Listeria monocytogenes* | ribotype DUP-1045B |
| NP2140 | FSL R2-067 | *Listeria monocytogenes* | ribotype DUP-1045B |
| NP2141 | FSL R2-293 | *Listeria monocytogenes* | ribotype DUP-1045B |
| NP2142 | FSL F6-323 | *Listeria monocytogenes* | ribotype DUP-1052A |
| NP2143 | FSL F6-216 | *Listeria monocytogenes* | ribotype DUP-1052A |
| NP2144 | FSL F6-321 | *Listeria monocytogenes* | ribotype DUP-1052A |
| NP2145 | FSL V1-117 | *Listeria monocytogenes* | ribotype DUP-1052A |
| NP2146 | FSL H5-846 | *Listeria monocytogenes* | ribotype DUP-1052A |
| NP2147 | FSL L3-055 | *Listeria monocytogenes* | ribotype DUP-1052A |
| NP2148 | FSL T1-313 | *Listeria monocytogenes* | ribotype DUP-1052A |
| NP2149 | FSL R8-0875 | *Listeria monocytogenes* | ribotype DUP-1052A |
| NP2150 | FSL R2-317 | *Listeria monocytogenes* | ribotype DUP-1052A |
| NP1888 | FSL L4-019 | *Listeria monocytogenes* | ribotype DUP-1053A |
| NP2151 | FSL F6-335 | *Listeria monocytogenes* | ribotype DUP-1053A |
| NP2152 | FSL R6-653 | *Listeria monocytogenes* | ribotype DUP-1053A |
| NP2153 | FSL L3-135 | *Listeria monocytogenes* | ribotype DUP-1053A |
| NP2154 | FSL L3-143 | *Listeria monocytogenes* | ribotype DUP-1053A |
| NP2155 | FSL L3-167 | *Listeria monocytogenes* | ribotype DUP-1053A |
| NP2156 | FSL N3-031 | *Listeria monocytogenes* | ribotype DUP-1053A |
| NP2157 | FSL J1-101 | *Listeria monocytogenes* | ribotype DUP-1053A |
| NP2158 | FSL F6-154 | *Listeria monocytogenes* | ribotype DUP-1053A |
| NP2159 | FSL R2-499 | *Listeria monocytogenes* | ribotype DUP-1053A |
| NP1889 | FSL T1-027 | *Listeria monocytogenes* | ribotype DUP-1062A |
| NP2160 | FSL F6-325 | *Listeria monocytogenes* | ribotype DUP-1062A |
| NP2161 | FSL F6-220 | *Listeria monocytogenes* | ribotype DUP-1062A |
| NP2162 | FSL F6-319 | *Listeria monocytogenes* | ribotype DUP-1062A |
| NP2163 | FSL F6-365 | *Listeria monocytogenes* | ribotype DUP-1062A |
| NP2164 | FSL F6-360 | *Listeria monocytogenes* | ribotype DUP-1062A |
| NP2165 | FSL F6-313 | *Listeria monocytogenes* | ribotype DUP-1062A |
| NP2166 | FSL R2-031 | *Listeria monocytogenes* | ribotype DUP-1062A |
| NP2167 | FSL R2-050 | *Listeria monocytogenes* | ribotype DUP-1062A |
| NP2168 | FSL R2-078 | *Listeria monocytogenes* | ribotype DUP-1062A |
| NP1890 | FSL T1-041 | *Listeria monocytogenes* | ribotype DUP-1062D |
| NP2169 | FSL F6-264 | *Listeria monocytogenes* | ribotype DUP-1062D |
| NP2170 | FSL F3-146 | *Listeria monocytogenes* | ribotype DUP-1062D |
| NP2171 | FSL F3-194 | *Listeria monocytogenes* | ribotype DUP-1062D |
| NP2172 | FSL H4-122 | *Listeria monocytogenes* | ribotype DUP-1062D |
| NP2173 | FSL H4-286 | *Listeria monocytogenes* | ribotype DUP-1062D |
| NP2174 | FSL R6-646 | *Listeria monocytogenes* | ribotype DUP-1062D |
| NP2175 | FSL T1-041 | *Listeria monocytogenes* | ribotype DUP-1062D |
| NP2176 | FSL F7-002 | *Listeria monocytogenes* | ribotype DUP-1062D |
| NP2177 | FSL X1-005 | *Listeria monocytogenes* | ribotype DUP-1062D |
| NP 1878 | EGD-e | *Listeria monocytogenes* | |
| NP1911 | FSL R8-7641 | *Listeria seeligeri* | sig B allelotype 20 |
| NP1950 | FSL S10-030 | *Listeria seeligeri* | sig B allelotype 20 |
| NP1951 | FSL S10-320 | *Listeria seeligeri* | sig B allelotype 20 |

TABLE 18-continued

| Identifier | Strain Name | Genus/Species | Subspecies |
|---|---|---|---|
| NP1952 | FSL S10-1602 | *Listeria seeligeri* | sig B allelotype 20 |
| NP1953 | FSL L5-075 | *Listeria seeligeri* | sig B allelotype 20 |
| NP1954 | FSL L5-046 | *Listeria seeligeri* | sig B allelotype 20 |
| NP1955 | FSL L5-104 | *Listeria seeligeri* | sig B allelotype 20 |
| NP1956 | FSL R8-7575 | *Listeria seeligeri* | sig B allelotype 20 |
| NP1957 | FSL S4-178 | *Listeria seeligeri* | sig B allelotype 20 |
| NP1958 | FSL S4-135 | *Listeria seeligeri* | sig B allelotype 20 |
| NP1913 | FSL R8-6826 | *Listeria seeligeri* | sig B allelotype 24 |
| NP1968 | FSL S10-034 | *Listeria seeligeri* | sig B allelotype 24 |
| NP1969 | FSL S10-1611 | *Listeria seeligeri* | sig B allelotype 24 |
| NP1970 | FSL L5-054 | *Listeria seeligeri* | sig B allelotype 24 |
| NP1971 | FSL L5-085 | *Listeria seeligeri* | sig B allelotype 24 |
| NP1972 | FSL R8-6868 | *Listeria seeligeri* | sig B allelotype 24 |
| NP1973 | FSL R8-6545 | *Listeria seeligeri* | sig B allelotype 24 |
| NP1974 | FSL R8-6949 | *Listeria seeligeri* | sig B allelotype 24 |
| NP1975 | FSL S4-167 | *Listeria seeligeri* | sig B allelotype 24 |
| NP1976 | FSL S4-180 | *Listeria seeligeri* | sig B allelotype 24 |
| NP1891 | FSL R8-5241 | *Listeria seeligeri* | sig B allelotype 3 |
| NP1892 | FSL R8-5247 | *Listeria seeligeri* | sig B allelotype 3 |
| NP1893 | FSL R8-5253 | *Listeria seeligeri* | sig B allelotype 3 |
| NP1894 | FSL R8-5513 | *Listeria seeligeri* | sig B allelotype 3 |
| NP1895 | FSL R8-6629 | *Listeria seeligeri* | sig B allelotype 3 |
| NP1896 | FSL R8-6635 | *Listeria seeligeri* | sig B allelotype 3 |
| NP1897 | FSL R8-6659 | *Listeria seeligeri* | sig B allelotype 3 |
| NP1898 | FSL R8-6665 | *Listeria seeligeri* | sig B allelotype 3 |
| NP1899 | FSL R8-6852 | *Listeria seeligeri* | sig B allelotype 3 |
| NP1990 | FSL H6-027 | *Listeria seeligeri* | sig B allelotype 35 |
| NP1991 | FSL H6-079 | *Listeria seeligeri* | sig B allelotype 35 |
| NP1992 | FSL H6-185 | *Listeria seeligeri* | sig B allelotype 35 |
| NP1993 | FSL R8-6874 | *Listeria seeligeri* | sig B allelotype 35 |
| NP1994 | FSLR8-6880 | *Listeria seeligeri* | sig B allelotype 35 |
| NP1995 | FSL R8-7629 | *Listeria seeligeri* | sig B allelotype 35 |
| NP1996 | FSL S4-544 | *Listeria seeligeri* | sig B allelotype 35 |
| NP1910 | FSL R8-7026 | *Listeria welshimeri* | sig B allelotype 15 |
| NP1945 | FSL L5-079 | *Listeria welshimeri* | sig B allelotype 15 |
| NP1946 | FSL S10-1450 | *Listeria welshimeri* | sig B allelotype 15 |
| NP1947 | FSL S10-1451 | *Listeria welshimeri* | sig B allelotype 15 |
| NP1948 | FSL S4-081 | *Listeria welshimeri* | sig B allelotype 15 |
| NP1949 | FSL S4-101 | *Listeria welshimeri* | sig B allelotype 15 |
| NP1977 | FSL N1-064 | *Listeria welshimeri* | sig B allelotype 27 |
| NP1978 | FSL R8-8163 | *Listeria welshimeri* | sig B allelotype 27 |
| NP1979 | FSL R8-7524 | *Listeria welshimeri* | sig B allelotype 27 |
| NP1980 | FSL R8-7486 | *Listeria welshimeri* | sig B allelotype 27 |
| NP1981 | FSL R8-6035 | *Listeria welshimeri* | sig B allelotype 27 |
| NP1982 | FSL R8-5807 | *Listeria welshimeri* | sig B allelotype 27 |
| NP1983 | FSL S4-182 | *Listeria welshimeri* | sig B allelotype 27 |
| NP1984 | FSL R2-630 | *Listeria welshimeri* | sig B allelotype 27 |
| NP1985 | FSL F6-1131 | *Listeria welshimeri* | sig B allelotype 27 |
| NP1914 | FSL R8-7454 | *Listeria welshimeri* | sig B allelotype 32 |
| NP1986 | FSL R8-7041 | *Listeria welshimeri* | sig B allelotype 32 |
| NP1987 | FSL R8-5837 | *Listeria welshimeri* | sig B allelotype 32 |
| NP1988 | FSL R8-6136 | *Listeria welshimeri* | sig B allelotype 32 |
| NP1989 | FSL S4-289 | *Listeria welshimeri* | sig B allelotype 32 |
| NP1917 | FSL R8-1903 | *Listeria welshimeri* | sig B allelotype 89 |
| NP2015 | FSL S10-114 | *Listeria welshimeri* | sig B allelotype 89 |
| NP2016 | FSL S10-115 | *Listeria welshimeri* | sig B allelotype 89 |
| NP2017 | FSL S10-117 | *Listeria welshimeri* | sig B allelotype 89 |
| NP2018 | FSL S10-119 | *Listeria welshimeri* | sig B allelotype 89 |
| NP2019 | FSL S10-121 | *Listeria welshimeri* | sig B allelotype 89 |
| NP2020 | FSL R8-0056 | *Listeria welshimeri* | sig B allelotype 89 |
| NP2021 | FSL R8-1198 | *Listeria welshimeri* | sig B allelotype 89 |
| NP2022 | FSL R8-7403 | *Listeria welshimeri* | sig B allelotype 89 |
| NP2023 | FSL R2-631 | *Listeria welshimeri* | sig B allelotype 89 |

Example 16: Plate-Based Phage Host Range Assay

In order to quantify the host range a given bacteriophage the plaque forming efficiency of the bacteriophage on a given isolate was standardized to a reference strain for the bacteriophage, normally the strain used for bacteriophage production. To determine the plaque forming efficiency a dilution series for the phage is generated and titered on each host. Before the work reported herein, this was the standard method of phage host range analysis. See, e.g., Sambrook et al., *Molecular Cloning: A Laboratory Manual*, 3d ed., Cold Spring Harbor Laboratory Press, Cold Spring Harbor, N.Y. (2001).

The *Listeria* bacterial strain panel was used to determine the host range for a particular bacteriophage. To do this a culture of each *Listeria* strain to be tested was started in 5 ml of LBL1 and grown overnight at 30 C in an orbital shaker and allowed to grow for 16 hours. For each bacterial host strain 30 μl of the 16-hour culture was mixed with 270 μl of fresh LBL1 medium. To each cell dilution, 4 ml of LBL1 soft agar was added and overlayed onto LBL1 agar in 100 mm petri dish. The soft agar overlay was allowed to cool and solidify at room temperature. Additionally, a reference strain (FSL F6-367 for A511 and P100) was treated in a similar manner to the host range isolates. A 10-fold dilution series of the bacteriophage in LBL1 medium was prepared from $10^{-1}$ to $10^{-8}$. 5 μl of each dilution of the bacteriophage was spotted onto the soft agar overlay and the liquid was allowed to adsorb and then the plate was incubated at 30 C for 16 hours. After incubation the plaques present at each dilution series were counted and compared to the reference strain to provide an efficiency of plaquing for each host range isolate. The host range was represented as a percentage of the titer observed on the experimental host compared to the reference strain. Bacterial strains that showed a plaquing efficiency greater than 10% (Table 19, italicized and bolded text) of the reference strain were considered to be within the host range. Bacterial strains that showed a plaquing efficiency less than 10% but greater than 0.01% (Table 19, italicized text) of the reference strain were considered to be weakly susceptible to the phage. Bacterial strains that showed a plaquing efficiency less than 0.01% (Table 19, plain text) of the reference strain were considered to be outside of the host range for a phage. A phenomenon that was seen for many of the bacterial strains tested was what has been described in the literature and art as "extra cellular killing" (ECK) (Table 19, empty cells), see e.g. Shaw et al. (J Immunol Methods. 1983; 56(1):75-83). A strain was defined as demonstrating ECK for a particular phage when at high phage concentration completely cleared the lawn, however, subsequent dilutions did not produce clearing.

The plate-based host range determination allowed for a rough approximation of the host range of A511 and P100 against the *Listeria* isolate library. Of the 272 strains tested in the bacterial strain library 67 and 120 strains supported plaque formation by A511 and P100, respectively (Table 19). The greatest limitations of this method were the length of time needed to process the entire library for a give bacteriophage and the inability to determine the entire host range due to the ECK phenomenon. For the bacteriophage A511 and P100, of the 272 bacterial strains in the host range panel tested, 117 and 42, respectively, showed ECK and hence provided no information about the host range for these strains. Additionally, in view of the ECK phenomenon and because of the general differences between bacteria growing on a plate and bacteria growing in a liquid culture, it was hypothesized that the plate-based method for determining host range may not represent the host range for a liquid-based application.

Example 17: A Liquid Culture Phage Host Range Assay

The prevalence of the extra-cellular killing (ECK) phenomenon demonstrated by both A511 and P100 in the plate-based host range method demonstrates that the plate based is not as useful as it could be for determining the host range for either phage. To overcome those deficiencies a novel liquid-based host range assay was developed. The liquid-based host range assay is an end point assay where the ability of a phage to infect a particular bacterial isolate is determined by comparing the optical density of a culture with or without bacteriophage.

The *Listeria* host panel strain collection was struck out on Brain Heart Infusion (BHI) agar plates and single colonies were inoculated in 1 ml BHI liquid in a 2-ml 96-deep well dish, covered with a sterile breathable sterile membrane and grown at 30 C for 16 hours. Each of the 16-hour cultures from the 96-well plates were diluted 1:10,000 in 198 µl of LBL1 in a 300 µl flat-bottom optical 96-well plate and then either $1 \times 10^5$ pfu of the bacteriophage or an equivalent volume of LBL1 was added to each well of the 96-well plate. This concentration of bacteriophage and bacterial cell dilutions was to approximate a multiplicity of infection (MOI) of 1 in each well. After addition of the phage or control, the plates were incubated at 26 C with shaking at 50 rpm for 16-hours. Plates were placed in a 96-well plate reader (Biotek Eon Microplate Reader) and agitated for 3 seconds with orbital shaking to resuspend cells that had settled out of culture. After the agitation, the optical density of each well was measure at 600 nm (OD600) wavelength light. The ratio of OD600 of the bacterial isolate in the presence of bacteriophage to the uninfected bacterial isolate culture was used as a metric to determine the efficiency of infection for a bacterial strain. A bacterial strain with a ratio of less than or equal to 0.4 (Table 19, italicized and bolded text) was considered to be sensitive to infection by the bacteriophage.

The liquid-based host range assay identified 192 and 153 bacterial strains sensitive to A511 and P100, respectively, of the 272 strains in the bacterial strain panel (Table 19). This data shows that A511 is capable of infecting approximately 70% and P100 is capable of infecting approximately 58% of the host range panel. In comparison to the liquid-based host range, the plate-based host range method identified 62 and 120 bacterial strains that demonstrated a plaquing-efficiency for A511 and P100, respectively. Of the strains identified in the plate-based host range methods, only 8 A511-sensitive bacterial strains and 3 P100-sensitive bacterial strains did not show clearance in the liquid-based clearance assay. Because the liquid-based assay is an endpoint assay and represents a kinetic interaction between bacteriophage infection and bacterial cell growth certain bacterial strains with increased cell growth rates may be able to saturate a culture even though the strain is susceptible to infection and this may explain the reason why a small number of strains identified in the plaque-based assay were not identified in the liquid assay.

The additional strains identified by the liquid-based host range assay were due to the ability to collect data on strains that demonstrated an ECK phenotype in the plate-based host range assay. The large number of strains that demonstrated this phenotype created a large amount of unknown information regarding the host range for A511 and P100. The liquid-based assay eliminated the ECK phenomenon, one of the large drawbacks of the plate-based host range method. Two factors contributed to the lack of ECK. First the concentration of phages used in the liquid-based assay is a set concentration that is lower than the concentrations of phage that demonstrated ECK in the plate-based host range assay. Second, the delocalized concentration of bacteriophage within the liquid infection and the low MOI decreases the number of interactions between the bacterial cells and bacteriophage. The limited interaction decreases the possibility of non-productive encounters and lowers super-infection, or infection by multiple bacteriophages of a cell. By eliminating ECK, the sensitivity for measuring susceptibility of a particular bacterial cell to a bacteriophage was increased substantially and provided a more accurate representation of the host range of a bacteriophage across the *Listeria* species.

The liquid-based host range assay showed substantial advances over the prior method of using a plate-based system for determining host range of a bacteriophage. Previous literature did not report the ability of growing these bacteriophages in a format other than a plate-based method. The liquid format is also useful because the speed with which the liquid-based host range assay can be performed increases the speed of determining the host range of a bacteriophage from 7-10 days for the panel as it was assembled to several hours of hands on labor. Additionally, the high-throughput nature of the scoring of host susceptibility allowed for multiple bacteriophage host ranges to be determined concurrently, a possibility that did not exist previously. The ability to process multiple bacteriophages concurrently allowed for a more direct comparison of bacteriophages by minimizing variation between bacterial culture physiology and media lots. Together, the increased speed and direct bacteriophage characterizations allowed for rapid processing of multiple phages and prioritization for bacteriophage engineering described herein. Moreover, the liquid-based host range assay allowed for a more accurate representation of the functional determination of a potential bacteriophage in a predicted product compared to a plate-based host range assay. The combination of the increased speed, ability for more direct comparison and ability to assess functionality of a bacteriophage in a more direct method to the final product makes the liquid-based host range assay significantly more useful than the plate-based host range method in most contexts.

The efficacy of a cocktail of a P100 and A511 bacteriophage can be determined by the ability of each of the bacteriophages to infect a particular strain. Infections of the host panel with a cocktail of P100 and A511 show the additive host range expected from the extrapolation of the individual host ranges. Based on observations regarding the bacteriophage concentration required for optimum luciferase production during the course of infection, the concentration of bacteriophage added was maintained at a constant total phage concentration of $1 \times 10^7$ whether a single bacteriophage or multiple phage cocktail was used for infections. The cocktail of A511 and P100 shows coverage of 74% of the panel constructed, while the individual bacteriophages show 70% and 55% coverage, respectively. (Table 19) This increased coverage of the panel arises from the face that while the phages have largely overlapping coverage the subset of strains susceptible to P100 infection is not full encompassed within the A511 strains. The ability to extrapolate function of a bacteriophage cocktail from the individual liquid-based host range provides as a powerful tool to identify and prioritize new bacteriophages for engineering to build a more complete cocktail.

The function of a bacteriophage cocktail of P100 and A511 on samples collected from environmental samples cannot be strictly inferred from the host panel assembled. The sites sampled in environmental testing represent diverse populations of bacteria and often have more than one species or subspecies of *Listeria* present at an individual location. Environmental sampling at food processing plants with geographic and source diversity identified 31 samples that have been confirmed positive for *Listeria* using a culture based method of detection at a third-party laboratory. Of these 31 positive samples, 10 samples contained multiple

*Listeria* species or subspecies. The A511 and P100 cocktail was capable of detecting 24 of the 31 (77%) of the positive samples. The correlation between the liquid-based host range results and the environmental samples collected allows for further iterations on the bacteriophage cocktail to be made in order to gain more complete coverage of the *Listeria* genus and validated the usefulness of the liquid-based host range method.

TABLE 19

| NP # | A511 Plate | P100 Plate | Avg A511 | Avg P100 | A511/P100 Cocktail |
|---|---|---|---|---|---|
| NP1900 |  | 0.00 | 0.09 | 1.03 | 0.29 |
| NP1901 | 0.75 | 0.17 | 0.15 | 0.10 | 0.10 |
| NP1902 |  |  | 0.10 | 1.04 | 0.30 |
| NP1903 | 0.75 | 0.03 | 0.09 | 0.11 | 0.10 |
| NP1904 |  |  | 0.09 | 0.11 | 0.11 |
| NP1905 |  |  | 0.16 | 0.12 | 0.12 |
| NP1906 |  |  | 0.10 | 1.08 | 0.79 |
| NP1907 |  | 0.00 | 0.09 | 1.05 | 0.30 |
| NP1908 | 0.45 | 0.17 | 0.19 | 0.10 | 0.11 |
| NP1909 |  | 0.00 | 0.09 | 1.00 | 0.10 |
| NP1912 |  | 0.00 | 0.10 | 0.93 | 0.28 |
| NP1959 | 0.28 | 0.20 | 0.09 | 0.09 | 0.10 |
| NP1960 | 0.00 | 0.00 | 0.09 | 0.91 | 0.15 |
| NP1961 |  | 0.20 | 0.11 | 0.10 | 0.12 |
| NP1962 |  | 0.00 | 0.09 | 0.91 | 0.34 |
| NP1963 | 0.12 | 0.90 | 0.09 | 0.09 | 0.12 |
| NP1964 | 0.80 | 1.40 | 0.09 | 0.09 | 0.10 |
| NP1965 | 0.20 | 0.30 | 0.09 | 0.09 | 0.10 |
| NP1966 |  | 0.20 | 0.09 | 0.10 | 0.11 |
| NP1967 | 1.40 | 0.50 | 0.10 | 0.09 | 0.10 |
| NP1915 | 0.10 |  | 0.77 | 0.10 | 0.11 |
| NP1997 | 0.05 | 0.00 | 0.09 | 0.11 | 0.11 |
| NP1998 | 0.10 |  | 0.09 | 0.10 | 0.11 |
| NP1999 | 0.10 | 0.70 | 0.09 | 0.14 | 0.11 |
| NP2000 | 0.10 | 0.00 | 0.09 | 0.10 | 0.11 |
| NP2001 | 0.05 | 1.00 | 0.10 | 0.11 | 0.11 |
| NP2002 |  |  | 0.10 | 0.98 | 0.28 |
| NP2003 |  | 0.00 | 0.16 | 1.03 | 0.09 |
| NP2004 |  | 0.00 | 0.13 | 1.00 | 0.10 |
| NP2005 |  | 0.00 | 0.31 | 0.89 | 0.13 |
| NP1916 |  | 0.00 | 0.41 | 0.90 | 1.01 |
| NP2006 |  | 0.00 | 0.12 | 0.77 | 0.09 |
| NP2007 | 0.06 | 10.00 | 0.09 | 0.09 | 0.11 |
| NP2008 | 0.10 | 1.00 | 0.09 | 0.09 | 0.11 |
| NP2009 | 0.25 | 0.90 | 0.09 | 0.11 | 0.11 |
| NP2010 |  | 0.00 | 0.29 | 0.76 | 0.09 |
| NP2011 |  | 0.00 | 0.45 | 0.78 | 1.00 |
| NP2012 | 0.00 | 0.00 | 0.57 | 1.04 | 1.04 |
| NP2013 | 0.00 | 0.00 | 0.49 | 1.00 | 1.04 |
| NP2014 |  | 0.00 | 0.39 | 0.84 | 0.10 |
| NP1869 | 0.10 | 1.71 | 0.13 | 0.21 | 0.13 |
| NP1840 |  |  | 1.02 | 1.17 | 1.05 |
| NP1839 | 1.00 | 1.00 | 0.24 | 0.35 | 0.14 |
| NP2024 | 4.00 | 0.50 | 0.10 | 0.10 | 0.11 |
| NP2025 | 1.20 | 0.33 | 0.09 | 0.09 | 0.11 |
| NP2026 | 1.10 | 0.33 | 0.56 | 0.57 | 0.26 |
| NP2027 | 0.00 | 0.27 | 0.10 | 0.12 | 0.12 |
| NP2028 | 1.00 | 0.33 | 0.09 | 0.09 | 0.12 |
| NP2029 |  | 0.21 | 0.98 | 0.12 |  |
| NP2030 | 0.00 | 1.33 | 0.10 | 0.09 | 0.12 |
| NP2031 | 0.10 | 0.27 | 0.09 | 0.09 | 0.11 |
| NP2032 | 1.00 | 0.33 | 0.08 | 0.09 | 0.12 |
| NP1879 | 0.20 | 0.50 | 1.05 | 0.13 | 0.20 |
| NP2033 | 1.00 | 0.67 | 0.10 | 0.11 | 0.10 |
| NP2034 | 0.90 | 3.33 | 0.10 | 0.11 | 0.11 |
| NP2035 | 2.00 | 0.30 | 0.10 | 0.11 | 0.11 |
| NP2036 | 1.00 | 0.33 | 0.09 | 0.09 | 0.12 |
| NP2037 | 1.00 | 0.33 | 0.10 | 0.11 | 0.11 |
| NP2038 |  | 1.00 | 1.04 | 0.11 | 0.23 |
| NP2039 |  | 0.33 | 0.99 | 0.10 | 0.24 |
| NP2040 |  | 0.33 | 0.89 | 0.10 | 0.23 |
| NP2041 | 1.50 | 0.33 | 0.10 | 0.12 | 0.12 |
| NP2042 |  | 0.17 | 0.15 | 0.09 | 0.13 |
| NP2043 |  | 1.33 | 0.09 | 0.09 | 0.10 |
| NP2044 |  | 0.00 | 0.09 | 0.09 | 0.26 |
| NP2045 |  | 3.33 | 0.20 | 0.20 | 0.11 |

TABLE 19-continued

| NP # | A511 Plate | P100 Plate | Avg A511 | Avg P100 | A511/P100 Cocktail |
|---|---|---|---|---|---|
| NP2046 | 0.00 | 0.07 | 0.09 | 0.09 | 0.11 |
| NP2047 |  | 0.17 | 0.10 | 0.10 | 0.13 |
| NP2048 |  | 0.33 | 0.13 | 0.10 | 0.17 |
| NP2049 |  | 0.33 | 0.10 | 0.09 | 0.21 |
| NP2050 |  | 0.27 | 0.10 | 0.09 | 0.12 |
| NP1880 | 0.00 | 0.00 | 1.01 | 1.07 | 1.07 |
| NP2051 |  | 0.33 | 0.90 | 0.09 | 0.19 |
| NP2052 | 1.00 | 0 07 | 0.09 | 0.09 | 0.10 |
| NP2053 | 0.30 | 0.33 | 0.09 | 0.09 | 0.12 |
| NP2054 | 0.30 | 0.07 | 0.09 | 0.09 | 0.16 |
| NP2055 | 2.00 | 0.43 | 0.09 | 0.09 | 0.10 |
| NP2056 | 1.20 | 0.10 | 0.09 | 0.09 | 0.12 |
| NP2057 |  | 0.33 | 0.97 | 0.09 | 0.28 |
| NP2058 |  | 0.10 | 0.97 | 0.10 | 0.25 |
| NP2059 | 0.09 | 0.17 | 0.12 | 0.13 | 0.14 |
| NP1881 | 0.00 | 0.00 | 0.17 | 1.05 | 0.20 |
| NP2060 | 0.00 |  | 0.44 | 0.95 | 0.98 |
| NP2061 |  |  | 0.12 | 0.89 | 0.12 |
| NP2062 |  |  | 0.12 | 0.90 | 0.13 |
| NP2063 |  |  | 0.96 | 1.03 | 1.25 |
| NP2064 |  | 0.01 | 0.09 | 0.09 | 0.25 |
| NP2065 |  |  | 0.11 | 0.97 | 0.09 |
| NP2066 |  |  | 0.49 | 1.02 | 0.96 |
| NP2067 | 0.00 | 0.00 | 1.06 | 1.08 | 0.93 |
| NP2068 |  |  | 1.12 | 1.11 | 1.05 |
| NP2069 |  |  | 0.19 | 1.04 | 0.17 |
| NP2070 |  | 0.27 | 0.45 | 0.10 | 0.11 |
| NP2071 | 0.00 | 0.00 | 1.14 | 1.14 | 1.21 |
| NP2072 | 0.60 | 0.33 | 0.10 | 0.11 | 0.12 |
| NP2073 |  |  | 0.63 | 1.12 | 1.07 |
| NP2074 | 0.10 | 0.33 | 0.18 | 0.11 | 0.16 |
| NP2075 |  | 0.03 | 0.12 | 0.91 | 0.79 |
| NP2076 | 1.20 | 0.27 | 0.09 | 0.10 | 0.11 |
| NP2077 | 0.00 | 0.17 | 0.14 | 0.10 | 0.11 |
| NP1882 | 0.95 | 0.58 | 0.93 | 0.11 | 0.12 |
| NP2078 |  |  | 0.11 | 0.77 | 0.17 |
| NP2079 |  |  | 1.04 | 1.07 | 1.04 |
| NP2080 | 0.00 | 0.00 | 1.04 | 1.05 | 1.02 |
| NP2081 | 0.00 | 0.00 | 1.00 | 0.98 | 1.01 |
| NP2082 | 0.00 | 0.00 | 1.07 | 1.06 | 1.02 |
| NP2083 |  |  | 0.13 | 0.36 | 0.89 |
| NP2084 |  |  | 0.14 | 1.00 | 0.17 |
| NP2085 | 0.00 | 0.00 | 1.01 | 1.00 | 0.95 |
| NP2086 |  |  | 0.19 | 1.06 | 0.17 |
| NP2087 | 0.00 | 0.00 | 0.96 | 0.96 | 1.16 |
| NP2088 | 0.20 | 0.60 | 0.11 | 0.11 | 0.15 |
| NP2089 | 0.00 | 0.00 | 0.90 | 1.00 | 1.06 |
| NP2090 | 0.50 | 0.40 | 0.12 | 0.12 | 0.17 |
| NP2091 | 0.01 | 0.01 | 0.10 | 0.16 | 0.49 |
| NP2092 | 0.50 | 1.00 | 0.09 | 0.09 | 0.10 |
| NP2093 |  | 1.00 | 0.25 | 0.09 | 0.10 |
| NP2094 |  | 1.00 | 0.09 | 0.09 | 0.10 |
| NP2095 | 1.00 | 0.20 | 0.14 | 0.18 | 0.22 |
| NP2096 |  | 0.30 | 0.13 | 0.09 | 0.10 |
| NP2097 | 0.00 | 0.70 | 0.12 | 0.10 | 0.11 |
| NP2098 |  | 0.00 | 0.12 | 0.09 | 0.13 |
| NP2099 | 0.00 | 0.20 | 0.12 | 0.09 | 0.11 |
| NP2100 | 0.00 | 0.00 | 0.97 | 1.00 | 0.99 |
| NP2101 |  | 0.00 | 0.91 | 1.02 | 1.04 |
| NP2102 |  | 0.00 | 0.98 | 1.02 | 1.01 |
| NP2103 | 0.00 | 0.00 | 1.02 | 1.01 | 0.98 |
| NP2104 |  | 0.00 | 0.98 | 1.02 | 1.03 |
| NP1883 | 0.00 | 0.00 | 0.40 | 0.94 | 1.00 |
| NP2105 | 0.00 | 0.00 | 1.05 | 1.03 | 1.02 |
| NP2106 |  |  | 0.79 | 1.04 | 1.01 |
| NP2107 | 0.00 | 0.00 | 1.07 | 1.12 | 1.03 |
| NP2108 | 0.00 | 0.00 | 1.05 | 1.11 | 1.01 |
| NP2109 |  |  | 0.10 | 1.09 | 0.10 |
| NP2110 | 0.00 | 0.00 | 0.92 | 0.84 | 1.06 |
| NP2111 |  |  | 0.71 | 0.92 | 1.12 |
| NP2112 | 0.00 | 0.00 | 1.00 | 0.92 | 1.05 |
| NP2113 | 2.00 | 0.30 | 0.09 | 0.09 | 0.10 |
| NP1884 | 0.00 |  | 0.10 | 1.09 | 0.20 |
| NP2114 |  |  | 0.09 | 0.48 | 0.09 |
| NP2115 |  |  | 0.09 | 0.97 | 0.09 |
| NP2116 |  |  | 0.09 | 1.03 | 0.09 |
| NP2117 |  |  | 0.10 | 0.88 | 0.10 |

TABLE 19-continued

| NP # | A511 Plate | P100 Plate | Avg A511 | Avg P100 | A511/P100 Cocktail |
|---|---|---|---|---|---|
| NP2118 | | | *0.10* | 1.01 | *0.10* |
| NP2119 | | | *0.09* | 0.86 | *0.09* |
| NP2120 | | 0.00 | *0.11* | 1.06 | *0.11* |
| NP2121 | | | *0.09* | 0.98 | *0.09* |
| NP2122 | | | *0.09* | 0.88 | *0.09* |
| NP1885 | *1.50* | *0.50* | 0.94 | *0.11* | *0.12* |
| NP2123 | *0.10* | *0.20* | *0.09* | *0.09* | *0.11* |
| NP2124 | *0.60* | *1.00* | *0.09* | *0.09* | *0.11* |
| NP2125 | | *2.00* | *0.09* | *0.09* | *0.10* |
| NP2126 | | *1.00* | 0.52 | *0.10* | *0.22* |
| NP2127 | | | 0.93 | 1.06 | 1.08 |
| NP2128 | *0.09* | *0.10* | *0.09* | *0.09* | *0.10* |
| NP2129 | *0.20* | *0.03* | *0.09* | *0.09* | *0.10* |
| NP2130 | *0.60* | *0.10* | *0.09* | *0.09* | *0.10* |
| NP2131 | 0.00 | *0.11* | *0.09* | *0.09* | *0.10* |
| NP1886 | 0.00 | 0.00 | 0.47 | 0.96 | 1.04 |
| NP2132 | 0.00 | 0.00 | 1.03 | 1.02 | 1.03 |
| NP1887 | | 0.00 | 1.02 | 0.99 | 1.00 |
| NP2133 | | *0.40* | 1.07 | *0.09* | *0.12* |
| NP2134 | | 0.00 | 1.06 | 1.12 | 1.16 |
| NP2135 | 0.00 | *0.30* | *0.12* | *0.08* | *0.18* |
| NP2136 | | *0.20* | 0.86 | *0.09* | *0.10* |
| NP2137 | | *0.20* | 0.85 | *0.09* | *0.10* |
| NP2138 | | 0.00 | 0.98 | 1.01 | 1.00 |
| NP2139 | *0.10* | *0.10* | *0.09* | *0.10* | *0.12* |
| NP2140 | | | 0.96 | 0.97 | 1.08 |
| NP2141 | | | *0.14* | *0.10* | *0.18* |
| NP2142 | | | 0.71 | 1.06 | 1.02 |
| NP2143 | | | 0.90 | 1.05 | 1.03 |
| NP2144 | 0.00 | 0.00 | *0.10* | *0.10* | *0.11* |
| NP2145 | 0.00 | 0.00 | *0.09* | *0.10* | *0.11* |
| NP2146 | *0.40* | *0.20* | 0.94 | 0.94 | 1.12 |
| NP2147 | | 0.00 | *0.09* | *0.09* | *0.15* |
| NP2148 | 0.00 | *0.30* | *0.10* | *0.10* | *0.10* |
| NP2149 | 0.00 | 0.00 | 1.12 | 1.18 | 1.01 |
| NP2150 | 0.00 | 0.00 | 0.73 | 1.12 | 1.11 |
| NP1888 | | | *0.09* | 0.97 | *0.19* |
| NP2151 | 0.00 | 0.00 | 1.13 | 1.07 | 1.04 |
| NP2152 | | *1.00* | *0.10* | *0.10* | *0.14* |
| NP2153 | | 0.00 | 0.81 | 1.01 | 1.05 |
| NP2154 | | 0.00 | 1.06 | 1.00 | 1.09 |
| NP2155 | 0.00 | 0.00 | 0.74 | 1.00 | 1.10 |
| NP2156 | *0.20* | *0.20* | *0.11* | *0.10* | *0.13* |
| NP2157 | *0.40* | *6.00* | *0.10* | *0.10* | *0.10* |
| NP2158 | 0.00 | *0.50* | *0.13* | *0.12* | *0.12* |
| NP2159 | 0.00 | 0.00 | 1.11 | 1.10 | 1.23 |
| NP1889 | *0.80* | *0.17* | 1.02 | *0.10* | *0.10* |
| NP2160 | *0.20* | 0.00 | *0.11* | *0.11* | *0.14* |
| NP2161 | *0.20* | *1.50* | *0.10* | *0.10* | *0.17* |
| NP2162 | *0.40* | *1.00* | *0.10* | *0.10* | *0.12* |
| NP2163 | *0.30* | *1.00* | *0.10* | *0.10* | *0.16* |
| NP2164 | *0.14* | *1.00* | 1.05 | 1.11 | 0.96 |
| NP2165 | | *1.10* | 0.44 | 0.95 | 1.16 |
| NP2166 | 0.00 | 0.00 | *0.09* | *0.09* | *0.13* |
| NP2167 | *0.12* | *1.60* | *0.09* | *0.11* | *0.16* |
| NP2168 | *0.80* | *1.30* | *0.11* | *0.11* | *0.14* |
| NP1890 | 0.00 | 0.00 | 0.89 | 1.02 | 1.04 |
| NP2169 | *0.04* | *1.00* | *0.10* | *0.10* | *0.14* |
| NP2170 | *0.30* | *0.70* | *0.10* | *0.10* | *0.13* |
| NP2171 | *0.60* | *0.60* | *0.09* | *0.10* | *0.11* |
| NP2172 | *0.22* | *0.10* | *0.09* | *0.10* | *0.11* |
| NP2173 | *0.40* | *0.10* | *0.10* | *0.10* | *0.11* |
| NP2174 | *0.20* | *3.00* | *0.09* | *0.09* | *0.11* |
| NP2175 | 0.00 | 0.00 | 1.08 | 1.05 | 1.05 |
| NP2176 | 0.00 | 0.00 | 1.07 | 1.06 | 1.08 |
| NP2177 | | | 1.08 | 1.06 | 0.91 |
| NP1878 | | | *0.11* | *0.12* | *0.12* |
| NP1911 | 0.00 | | *0.15* | 0.54 | *0.15* |
| NP1950 | *0.30* | *2.00* | *0.09* | *0.11* | *0.09* |
| NP1951 | *0.20* | *1.40* | *0.10* | *0.10* | *0.23* |
| NP1952 | *0.05* | *1.20* | *0.09* | *0.10* | *0.10* |
| NP1953 | | | *0.10* | *0.10* | *0.10* |
| NP1954 | *0.10* | *2.00* | *0.09* | *0.10* | *0.10* |
| NP1955 | | *1.30* | *0.14* | *0.09* | *0.10* |
| NP1956 | | 0.00 | *0.09* | 1.03 | *0.27* |
| NP1957 | 0.00 | *0.70* | *0.10* | *0.09* | *0.10* |
| NP1958 | *0.20* | *3.00* | *0.08* | *0.10* | *0.10* |
| NP1913 | | 0.00 | *0.09* | 0.78 | *0.15* |
| NP1968 | *0.40* | *2.00* | *0.10* | *0.10* | *0.09* |
| NP1969 | *1.00* | *2.00* | *0.09* | *0.10* | *0.09* |
| NP1970 | *0.08* | *0.50* | *0.10* | *0.10* | *0.08* |
| NP1971 | *0.40* | *0.60* | *0.12* | *0.10* | *0.09* |
| NP1972 | 0.00 | 0.00 | 1.11 | 1.22 | 0.92 |
| NP1973 | | 0.00 | *0.22* | 0.73 | *0.21* |
| NP1974 | | 0.00 | *0.23* | 0.70 | *0.31* |
| NP1975 | | | 0.95 | 1.03 | 1.12 |
| NP1976 | *0.50* | *1.00* | *0.10* | *0.10* | *0.11* |
| NP1891 | 0.00 | 0.00 | 0.99 | 1.03 | 0.95 |
| NP1892 | 0.00 | 0.00 | 1.01 | 1.04 | 0.96 |
| NP1893 | 0.00 | 0.00 | 1.00 | 1.04 | 0.97 |
| NP1894 | 0.00 | 0.00 | *0.10* | 0.99 | *0.20* |
| NP1895 | *3.00* | *0.67* | *0.16* | *0.11* | *0.12* |
| NP1896 | *1.00* | *0.33* | *0.10* | *0.16* | *0.12* |
| NP1897 | *1.00* | *0.25* | *0.09* | *0.10* | *0.10* |
| NP1898 | *5.00* | *16.70* | 0.99 | *0.09* | *0.10* |
| NP1899 | 0.00 | | *0.12* | 1.04 | *0.40* |
| NP1990 | | 0.00 | *0.10* | 1.07 | 0.59 |
| NP1991 | | 0.00 | *0.10* | 1.03 | *0.09* |
| NP1992 | | 0.00 | *0.10* | 1.07 | *0.10* |
| NP1993 | | 0.00 | *0.10* | 1.04 | *0.10* |
| NP1994 | | 0.00 | *0.09* | 0.99 | *0.16* |
| NP1995 | | 0.00 | *0.10* | 0.93 | *0.13* |
| NP1996 | *0.05* | *12.00* | *0.09* | *0.10* | *0.10* |
| NP1910 | *0.55* | | *0.09* | *0.09* | *0.11* |
| NP1945 | *0.10* | *0.60* | *0.14* | *0.10* | *0.10* |
| NP1946 | 0.00 | *1.90* | *0.12* | *0.10* | *0.17* |
| NP1947 | 0.00 | *0.70* | *0.14* | *0.10* | *0.12* |
| NP1948 | 0.00 | *0.20* | *0.09* | *0.14* | 0.47 |
| NP1949 | *0.10* | *20.00* | *0.10* | *0.10* | *0.11* |
| NP1977 | *0.06* | *2.00* | *0.09* | *0.09* | *0.11* |
| NP1978 | | 0.00 | 0.44 | 1.04 | 1.10 |
| NP1979 | 0.00 | 0.00 | 0.52 | 1.01 | 1.04 |
| NP1980 | | | *0.27* | 1.04 | *0.20* |
| NP1981 | | 0.00 | *0.39* | 0.84 | *0.39* |
| NP1982 | | 0.00 | *0.35* | 0.87 | *0.13* |
| NP1983 | | *0.20* | *0.11* | *0.10* | *0.16* |
| NP1984 | 0.00 | 0.00 | *0.27* | 0.95 | *0.21* |
| NP1985 | | 0.00 | 0.63 | 1.05 | 1.01 |
| NP1914 | | *0.25* | *0.09* | *0.10* | *0.11* |
| NP1986 | | *0.70* | *0.09* | *0.10* | *0.11* |
| NP1987 | | *0.60* | *0.09* | *0.10* | *0.11* |
| NP1988 | 0.00 | *0.40* | *0.10* | *0.10* | *0.11* |
| NP1989 | 0.00 | *1.00* | 0.83 | *0.09* | *0.21* |
| NP1917 | | 0.00 | *0.10* | 1.00 | *0.20* |
| NP2015 | 0.00 | 0.00 | *0.17* | *0.20* | *0.10* |
| NP2016 | 0.00 | 0.00 | *0.12* | *0.20* | *0.12* |
| NP2017 | | | *0.13* | *0.20* | *0.26* |
| NP2018 | | 0.00 | *0.10* | *0.25* | *0.25* |
| NP2019 | | | *0.10* | *0.24* | *0.24* |
| NP2020 | 0.00 | *0.20* | *0.12* | *0.27* | 0.83 |
| NP2021 | 0.00 | 0.00 | *0.26* | 1.06 | *0.39* |
| NP2022 | | 0.00 | *0.30* | 1.07 | *0.13* |
| NP2023 | | 0.00 | 0.44 | 0.98 | 1.03 |

Example 18: Host Range Characterization of Additional *Listeria* Phages

Construction of a *Listeria* host strain panel and development of a rapid liquid-based host range assay allowed for the rapid screening of additional bacteriophages to identify those bacteriophages that would increase the breadth of coverage of the *Listeria* genus. Twenty five additional bacteriophages were screened against the host panel in the liquid-based host range assay and analyzed for host susceptibility based on clearance versus an uninfected control. The data are presented in Table 20A-D. Strains were considered within host range if they demonstrated a ratio of 0.4 or less (italicized and bolded text). During the determination of the OD600 of the cultures there was no correction for the absorbance of the growth medium or culture plate, therefore, a ratio of 0.09 constituted a completely cleared culture by infection. Because of variations in the maximum OD600 obtained by different *Listeria* strains a conservative ratio of 0.4 was chosen to denote *Listeria* strains that were sensitive to a given bacteriophage. Strains that had a OD600 ratio of greater than 0.4 were considered to be outside of host range (Table 20A-D, plain text). From these twenty five bacteriophages assayed, seven (7) bacteriophages were selected to proceed into engineering based on the criteria that they provided useful host panel coverage, had genome sequence availability for development of phage targeting vectors and were capable of infecting *L. monocytogenes* strain EGD-e, the strain of *Listeria* most amenable to transformation.

The seven bacteriophages selected in addition to A511 and P100 were LP44, LP40, LP48, LP99, LP101, LP124, LP125, and LP143. No individual phage assayed covers more than 78% of the *Listeria* host strain panel. In combination, the bacteriophages cover approximately 92% of the host strain panel as assayed by liquid-based host range assay (Tables 20A-D). This combinatorial approach allows for the construction of a bacteriophage cocktail that provides the necessary coverage of the *Listeria* species to provide a reliable determination of the presence of *Listeria* in environmental sample collection.

After engineering the genome of the phages with two different genetic payloads, Firefly Luciferase and Nanoluciferase, the host range of these phages was retested to ensure that the genome modifications did not affect the fitness of the phages or compromise their ability to infect the target bacteria. To examine the result of combining bacteriophages in an infection the liquid-based host range assay was used to test the combinatorial effects of phage infection. For these infections the final concentration of phage was maintained at a constant $1\times10^5$ pfu consisting of equal amounts of each of the phage within the cocktail (i.e.—a two phage cocktail would consist of $5\times10^4$ pfu of each of the two component phages.

TABLE 20A

| NP # | LP14 | LP20 | LP30 | LP34 | LP39 | LP40 | LP44 |
|---|---|---|---|---|---|---|---|
| 1900 | 1.18 | *0.09* | 1.01 | 1.14 | 1.14 | 0.52 | *0.24* |
| 1901 | 1.11 | *0.18* | 1.00 | *0.12* | 1.14 | 0.98 | *0.09* |
| 1902 | 1.10 | *0.13* | 0.99 | *0.22* | 1.15 | 0.95 | *0.09* |
| 1903 | 1.10 | *0.11* | 1.01 | *0.13* | 1.13 | 0.95 | *0.09* |
| 1904 | 1.11 | *0.10* | 1.02 | *0.11* | 1.13 | 0.85 | *0.14* |
| 1905 | 1.12 | *0.10* | 1.01 | *0.19* | 1.12 | 0.87 | *0.13* |
| 1906 | 1.08 | *0.16* | 0.99 | *0.10* | 1.08 | 0.91 | *0.09* |
| 1907 | 1.14 | *0.10* | 1.02 | 1.11 | 1.12 | *0.22* | *0.25* |
| 1908 | 1.03 | *0.12* | 1.05 | *0.11* | 1.03 | 0.89 | *0.09* |
| 1909 | 1.08 | *0.09* | 0.95 | 1.05 | 1.07 | *0.21* | *0.16* |
| 1912 | 1.23 | *0.10* | 0.98 | 1.31 | 1.21 | *0.24* | *0.17* |
| 1959 | 1.02 | *0.22* | 1.04 | *0.10* | 0.99 | 0.97 | *0.22* |
| 1960 | *0.11* | *0.18* | 0.76 | *0.11* | 1.04 | 0.93 | *0.09* |
| 1961 | 0.94 | *0.09* | 0.88 | *0.12* | 1.25 | 0.87 | *0.10* |
| 1962 | 1.08 | *0.09* | 1.09 | 1.30 | 1.30 | *0.19* | *0.25* |
| 1963 | 0.97 | *0.09* | 1.02 | *0.13* | 1.22 | 0.78 | *0.23* |
| 1964 | 1.04 | *0.10* | 1.11 | *0.10* | 1.11 | 0.93 | *0.30* |
| 1965 | 1.04 | *0.11* | 0.97 | *0.10* | 1.13 | 0.87 | *0.23* |
| 1966 | 1.09 | *0.22* | 0.98 | *0.11* | 1.19 | 1.02 | *0.28* |
| 1967 | 1.00 | 0.42 | 1.16 | *0.11* | 1.16 | 0.95 | *0.18* |
| 1915 | 1.15 | *0.09* | 0.70 | *0.22* | 1.12 | 0.89 | *0.16* |
| 1997 | 1.08 | *0.09* | *0.11* | *0.10* | 1.06 | 0.93 | *0.18* |
| 1998 | 1.07 | *0.09* | *0.11* | *0.10* | 1.07 | 0.88 | *0.18* |
| 1999 | 1.06 | *0.09* | *0.16* | *0.10* | 1.05 | 0.91 | *0.25* |
| 2000 | 1.07 | *0.09* | *0.11* | *0.10* | 1.05 | 0.94 | *0.33* |
| 2001 | 1.08 | *0.10* | *0.14* | *0.11* | 1.06 | 0.89 | *0.19* |
| 2002 | 1.04 | 1.10 | 1.03 | *0.14* | 1.06 | 0.72 | *0.13* |
| 2003 | 1.05 | *0.09* | 0.73 | *0.10* | 1.05 | 0.80 | *0.22* |
| 2004 | 1.03 | *0.09* | *0.20* | *0.12* | 1.00 | 1.10 | *0.16* |

TABLE 20A-continued

| NP # | LP14 | LP20 | LP30 | LP34 | LP39 | LP40 | LP44 |
|---|---|---|---|---|---|---|---|
| 2005 | 1.05 | *0.10* | *0.16* | *0.11* | 1.04 | 0.98 | *0.21* |
| 1916 | 1.17 | 0.47 | 1.02 | *0.14* | 1.04 | 0.44 | *0.18* |
| 2006 | 1.08 | *0.25* | 1.04 | *0.11* | 0.90 | *0.31* | *0.23* |
| 2007 | *0.10* | *0.27* | *0.11* | *0.13* | 1.00 | 0.47 | *0.09* |
| 2008 | *0.10* | *0.16* | *0.11* | *0.09* | 1.01 | 0.45 | *0.10* |
| 2009 | 1.08 | 0.40 | *0.10* | *0.10* | 1.07 | 0.86 | *0.09* |
| 2010 | 1.01 | *0.18* | 1.16 | *0.10* | 0.91 | *0.26* | *0.20* |
| 2011 | 1.04 | *0.31* | 0.97 | *0.11* | 0.92 | 0.40 | *0.22* |
| 2012 | 1.06 | *0.34* | 0.99 | 1.02 | 1.07 | 0.61 | *0.32* |
| 2013 | 1.06 | *0.36* | 0.98 | 1.05 | 1.07 | 0.67 | *0.30* |
| 2014 | 1.04 | *0.33* | 0.98 | *0.11* | 0.96 | 0.42 | *0.27* |
| 1869 | 0.83 | *0.22* | 1.01 | *0.21* | *0.15* | *0.13* | *0.13* |
| 1840 | 1.04 | *0.38* | *0.14* | *0.24* | 1.09 | 0.41 | *0.32* |
| 1839 | 1.16 | 1.56 | 1.02 | 1.12 | *0.16* | *0.21* | 0.95 |
| 2024 | 1.00 | 1.16 | *0.20* | 0.95 | *0.10* | *0.08* | 1.02 |
| 2025 | 1.04 | 1.13 | *0.20* | 1.02 | *0.33* | *0.08* | 1.05 |
| 2026 | 1.05 | 1.35 | 0.52 | *0.17* | *0.21* | 0.44 | 1.05 |
| 2027 | 1.04 | 1.06 | 0.63 | 1.01 | *0.27* | *0.08* | 1.01 |
| 2028 | 0.98 | 1.12 | *0.16* | 0.99 | *0.19* | *0.10* | 0.99 |
| 2029 | 1.10 | 1.17 | 0.97 | 1.09 | *0.16* | *0.10* | 0.94 |
| 2030 | 1.03 | 1.22 | *0.25* | 0.90 | *0.12* | *0.09* | 0.84 |
| 2031 | 1.00 | 1.06 | 0.94 | 1.03 | *0.11* | *0.08* | 0.89 |
| 2032 | *0.26* | 1.12 | *0.15* | 1.04 | *0.10* | *0.08* | 0.96 |
| 1878 | 1.15 | 1.18 | 1.08 | 1.15 | *0.15* | *0.08* | 1.03 |
| 2033 | 1.01 | 1.21 | *0.18* | 0.98 | *0.20* | *0.09* | 1.01 |
| 2034 | 1.04 | 1.10 | *0.16* | 1.06 | *0.15* | *0.09* | 0.96 |
| 2035 | 1.02 | 1.19 | *0.14* | 1.02 | *0.16* | *0.09* | 0.97 |
| 2036 | 1.01 | 1.11 | *0.23* | 1.02 | *0.12* | *0.09* | 0.98 |
| 2037 | 0.99 | 1.09 | *0.17* | 1.05 | *0.13* | *0.09* | 0.92 |
| 2038 | 1.02 | 1.07 | 1.08 | 1.05 | *0.19* | *0.11* | 0.94 |
| 2039 | 1.06 | 1.02 | 1.03 | 1.03 | *0.22* | *0.10* | 0.93 |
| 2040 | 0.99 | 1.09 | 1.02 | 1.25 | *0.23* | *0.11* | 0.91 |
| 2041 | 1.13 | 1.10 | *0.20* | 1.15 | *0.12* | *0.11* | 1.01 |
| 2042 | 1.08 | 0.94 | *0.10* | 1.03 | 1.04 | 0.81 | *0.12* |
| 2043 | 1.05 | 1.09 | 0.83 | 1.08 | 1.05 | 0.65 | *0.11* |
| 2044 | 1.08 | 1.00 | *0.28* | 1.10 | 1.08 | 0.48 | *0.10* |
| 2045 | 1.03 | 0.45 | *0.10* | *0.19* | 1.04 | *0.26* | *0.09* |
| 2046 | 1.03 | 0.75 | *0.10* | *0.27* | 1.03 | *0.35* | *0.09* |
| 2047 | 1.00 | 1.12 | *0.10* | 1.07 | 1.00 | 0.44 | *0.09* |
| 2048 | 1.01 | *0.32* | *0.23* | *0.12* | 1.01 | *0.23* | *0.23* |
| 2049 | 1.07 | 0.97 | 1.06 | 1.14 | 1.12 | 0.58 | *0.12* |
| 2050 | 1.04 | 0.86 | 0.99 | 1.13 | 1.08 | 0.43 | *0.09* |
| 1880 | 1.15 | 1.05 | 1.08 | 0.43 | 1.15 | *0.09* | 1.03 |
| 2051 | 1.05 | 1.10 | 1.00 | 1.13 | *0.16* | *0.09* | 0.93 |
| 2052 | 1.06 | 1.15 | *0.18* | 1.08 | *0.15* | *0.10* | 0.94 |
| 2053 | 1.00 | 1.15 | *0.23* | 1.04 | 0.45 | *0.11* | 1.04 |
| 2054 | 1.11 | 1.14 | 0.77 | 1.17 | *0.18* | *0.11* | 0.96 |
| 2055 | 0.98 | 1.09 | *0.18* | 1.06 | *0.19* | *0.09* | 0.97 |
| 2056 | 1.21 | 1.07 | *0.25* | 1.21 | *0.12* | *0.10* | 0.99 |
| 2057 | 1.17 | 1.04 | 1.03 | 1.06 | *0.13* | *0.10* | 1.02 |
| 2058 | 1.16 | 1.14 | 1.01 | 1.12 | *0.16* | *0.10* | 0.95 |
| 2059 | 0.92 | 1.08 | *0.17* | 1.00 | *0.11* | *0.10* | 1.11 |
| 1881 | 1.15 | 1.24 | 1.13 | 1.09 | 1.13 | *0.08* | 1.01 |
| 2060 | 1.13 | 1.14 | 1.06 | 1.08 | *0.16* | *0.11* | 1.06 |
| 2061 | 1.15 | 1.32 | 1.08 | 1.09 | *0.20* | *0.10* | 1.04 |
| 2062 | 1.14 | 1.10 | 0.98 | 1.06 | *0.11* | *0.10* | 1.06 |
| 2063 | 1.06 | 1.06 | 1.02 | 1.11 | *0.21* | *0.10* | 1.08 |
| 2064 | 0.95 | 1.09 | 1.03 | 1.21 | *0.17* | *0.09* | 1.00 |
| 2065 | 0.98 | 1.12 | 1.04 | 1.01 | *0.13* | *0.11* | 1.04 |
| 2066 | 0.88 | 1.19 | 1.07 | 0.95 | *0.12* | *0.10* | 0.96 |
| 2067 | 0.89 | 1.09 | 0.99 | 0.94 | 0.91 | 0.90 | 1.00 |
| 2068 | 0.88 | 1.06 | 1.08 | 0.97 | 0.93 | *0.10* | 1.03 |
| 2069 | 0.90 | 1.07 | 1.13 | 1.07 | 0.96 | *0.12* | 1.05 |
| 2070 | 0.93 | 1.19 | 1.20 | 1.08 | *0.12* | *0.10* | 1.06 |
| 2071 | 0.92 | 1.18 | 1.09 | 1.03 | 1.09 | 0.95 | 1.01 |
| 2072 | 0.96 | 1.18 | *0.32* | 1.09 | *0.14* | *0.11* | 1.08 |
| 2073 | 1.04 | 1.21 | 1.04 | 1.09 | *0.29* | *0.11* | 1.06 |
| 2074 | 1.11 | 1.10 | 1.00 | 1.01 | *0.16* | *0.11* | 0.49 |
| 2075 | 1.01 | 1.30 | 1.03 | 1.20 | *0.17* | *0.11* | 1.04 |
| 2076 | 1.07 | 1.05 | *0.24* | 0.77 | *0.12* | *0.10* | 1.01 |
| 2077 | 1.13 | 1.11 | 1.08 | 1.17 | *0.13* | *0.09* | 1.02 |
| 1882 | 1.06 | 1.04 | 1.03 | 1.02 | *0.12* | *0.09* | 1.00 |
| 2078 | 1.08 | 1.05 | 1.06 | 1.11 | *0.14* | *0.09* | 1.03 |
| 2079 | 1.04 | 1.10 | 1.09 | 1.07 | 1.00 | *0.09* | 1.03 |
| 2080 | 1.05 | 1.05 | 1.08 | 1.09 | *0.16* | *0.09* | 1.06 |
| 2081 | 1.05 | 1.06 | 1.08 | 1.11 | 1.02 | 1.10 | 1.08 |
| 2082 | 1.02 | 1.08 | 1.06 | 1.07 | 0.98 | 1.17 | 1.06 |
| 2083 | 1.02 | 1.08 | 1.04 | 1.07 | *0.25* | *0.10* | 1.04 |

TABLE 20A-continued

| NP # | LP14 | LP20 | LP30 | LP34 | LP39 | LP40 | LP44 |
|---|---|---|---|---|---|---|---|
| 2084 | 0.97 | 1.09 | 1.06 | 1.01 | *0.14* | *0.09* | 1.05 |
| 2085 | 1.04 | 1.07 | 1.08 | 1.06 | *0.12* | *0.10* | 1.10 |
| 2086 | 1.06 | 0.97 | 1.07 | 0.96 | *0.12* | *0.11* | 1.08 |
| 2087 | 1.03 | 1.21 | 1.22 | 1.05 | 1.12 | 1.12 | 1.03 |
| 2088 | 1.02 | 1.00 | *0.22* | 0.72 | 0.81 | *0.35* | *0.10* |
| 2089 | 1.05 | 1.03 | 1.22 | 1.02 | 0.91 | 0.98 | 1.04 |
| 2090 | 1.13 | 1.04 | 0.72 | 0.99 | 1.07 | *0.37* | *0.11* |
| 2091 | 1.07 | 1.09 | 1.10 | 1.04 | *0.16* | *0.11* | 1.05 |
| 2092 | 0.89 | 1.01 | *0.18* | *0.11* | 0.99 | 0.58 | *0.10* |
| 2093 | 1.05 | 0.98 | 1.05 | 1.08 | 1.01 | 0.82 | *0.09* |
| 2094 | 1.08 | 1.00 | 0.87 | 1.03 | 0.95 | 0.78 | *0.09* |
| 2095 | 1.09 | 1.08 | *0.24* | 1.08 | 1.02 | *0.11* | 1.07 |
| 2096 | 1.09 | 1.10 | 1.08 | 1.05 | *0.24* | *0.09* | 1.06 |
| 2097 | 0.93 | 1.04 | 1.11 | 1.05 | *0.12* | *0.10* | 1.04 |
| 2098 | 1.13 | 1.05 | 1.07 | 0.94 | *0.18* | *0.10* | 1.06 |
| 2099 | 0.98 | 1.15 | 0.97 | 1.16 | *0.15* | *0.10* | 0.99 |
| 2100 | 1.06 | 1.06 | 1.13 | 1.05 | *0.12* | *0.10* | 1.04 |
| 2101 | 1.07 | 1.09 | 1.09 | 1.07 | 1.15 | 0.71 | 1.09 |
| 2102 | 1.06 | 1.08 | 1.10 | 1.04 | 1.09 | 0.70 | 1.04 |
| 2103 | 1.10 | 1.07 | 1.08 | 1.07 | *0.20* | *0.09* | 1.06 |
| 2104 | 1.06 | 1.09 | 1.10 | 1.05 | 1.16 | 0.75 | 1.07 |
| 1883 | 1.13 | 1.08 | 1.04 | 1.06 | 1.11 | 0.90 | 1.07 |
| 2105 | 1.08 | 1.12 | 1.07 | 1.06 | 1.07 | *0.10* | 1.04 |
| 2106 | 1.13 | 1.11 | 1.07 | 1.11 | *0.13* | *0.09* | 1.05 |
| 2107 | 1.06 | 1.09 | 1.07 | 1.00 | 1.00 | *0.10* | 1.05 |
| 2108 | 1.09 | 1.13 | 1.03 | 1.04 | 1.11 | 1.09 | 1.05 |
| 2109 | 1.22 | 1.23 | 1.06 | 1.04 | 1.10 | *0.13* | *0.09* |
| 2110 | 1.00 | 1.17 | 1.12 | 0.94 | 1.02 | 1.04 | 1.04 |
| 2111 | 1.00 | 1.25 | 0.98 | 1.11 | *0.24* | *0.10* | 1.00 |
| 2112 | 1.00 | 1.14 | 1.07 | 1.01 | 0.99 | 0.92 | 1.01 |
| 2113 | 0.63 | 1.16 | *0.18* | 1.03 | *0.14* | *0.09* | 1.03 |
| 1884 | 1.00 | 1.02 | 1.01 | 0.94 | 1.04 | 0.50 | *0.19* |
| 2114 | 1.03 | 1.13 | 1.07 | 0.48 | 1.02 | 0.54 | *0.09* |
| 2115 | 1.03 | 1.15 | 0.91 | 0.95 | 0.96 | 0.53 | *0.09* |
| 2116 | 1.02 | 1.11 | 1.03 | 0.92 | 1.03 | 0.70 | *0.10* |
| 2117 | 1.06 | 1.10 | 1.02 | 0.98 | 1.07 | 0.60 | *0.13* |
| 2118 | 1.03 | 1.11 | 0.96 | 0.96 | 1.05 | 0.69 | *0.11* |
| 2119 | 1.05 | 1.19 | 0.89 | 0.51 | 1.02 | *0.31* | *0.09* |
| 2120 | 1.07 | 1.12 | 1.01 | 1.08 | 1.05 | *0.12* | *0.10* |
| 2121 | 1.00 | 1.16 | 1.05 | 0.99 | 1.02 | 0.51 | *0.10* |
| 2122 | 1.11 | 1.12 | 0.97 | 0.99 | 1.00 | 0.55 | *0.09* |
| 1885 | 1.13 | 0.96 | 1.05 | 1.12 | *0.11* | *0.10* | 1.04 |
| 2123 | 1.05 | 1.13 | *0.18* | 1.04 | 1.17 | 0.44 | *0.09* |
| 2124 | 1.08 | 1.03 | *0.15* | *0.10* | 1.05 | *0.28* | *0.09* |
| 2125 | 1.04 | 1.02 | *0.09* | 0.95 | 1.06 | 0.74 | *0.10* |
| 2126 | 1.04 | 1.12 | 1.07 | 1.08 | *0.13* | *0.10* | 1.03 |
| 2127 | 1.02 | 1.14 | 1.09 | 1.10 | 0.98 | *0.10* | 1.04 |
| 2128 | 1.07 | 1.01 | *0.10* | 1.05 | 1.08 | 0.74 | *0.09* |
| 2129 | 1.06 | 1.04 | *0.10* | 1.08 | 1.07 | *0.32* | *0.09* |
| 2130 | 1.10 | 1.03 | *0.13* | 1.12 | 1.10 | *0.26* | *0.09* |
| 2131 | 1.07 | 1.08 | *0.09* | 1.07 | 1.03 | 0.79 | *0.10* |
| 1886 | 1.02 | 1.06 | 0.95 | 1.13 | *0.17* | *0.09* | 0.92 |
| 2132 | 1.05 | 1.07 | 1.10 | 1.04 | *0.14* | *0.09* | 1.06 |
| 1887 | 0.99 | 1.20 | 1.01 | 1.05 | *0.22* | *0.09* | 0.94 |
| 2133 | 1.09 | 1.12 | 1.13 | 1.20 | *0.12* | *0.11* | 1.11 |
| 2134 | 1.11 | 1.12 | 1.18 | 0.83 | 0.84 | 0.45 | 1.15 |
| 2135 | 1.01 | 1.15 | 1.02 | 1.02 | *0.24* | *0.09* | 1.00 |
| 2136 | 0.93 | 1.02 | 1.07 | 0.95 | *0.09* | *0.10* | 1.01 |
| 2137 | 1.04 | 1.06 | 1.08 | 1.03 | *0.13* | *0.09* | 1.04 |
| 2138 | 1.15 | 1.12 | 0.98 | 1.15 | 1.07 | 1.07 | 0.96 |
| 2139 | 1.06 | 1.09 | 1.14 | 1.09 | *0.12* | *0.09* | 1.11 |
| 2140 | 1.00 | 1.06 | 1.27 | 1.00 | 1.00 | *0.10* | 1.05 |
| 2141 | 0.99 | 1.21 | 1.25 | 1.11 | *0.13* | *0.10* | 1.17 |
| 2142 | 1.08 | 1.14 | 1.19 | 1.12 | *0.14* | *0.10* | 1.11 |
| 2143 | 1.09 | 1.13 | 1.21 | 1.12 | *0.13* | *0.10* | 1.14 |
| 2148 | 1.13 | 1.10 | *0.20* | 1.09 | *0.24* | *0.10* | 1.00 |
| 2149 | 1.07 | 1.12 | 0.95 | 1.08 | 1.05 | 0.97 | 0.95 |
| 2150 | 1.13 | 1.16 | 1.11 | 1.09 | *0.17* | *0.11* | 1.11 |
| 2164 | 1.05 | 1.13 | *0.27* | 1.05 | *0.21* | *0.11* | 1.08 |
| 2165 | 1.04 | 1.12 | *0.16* | 1.11 | *0.20* | *0.10* | 1.14 |
| 2166 | 0.98 | 1.14 | 1.17 | 0.92 | *0.16* | *0.11* | 1.16 |
| 2167 | 1.12 | 1.15 | *0.31* | 1.25 | *0.17* | *0.09* | 1.03 |
| 1888 | 1.18 | 1.17 | 1.07 | 1.16 | *0.11* | *0.09* | 0.98 |
| 2151 | 1.12 | 1.24 | 1.09 | 1.06 | *0.18* | *0.11* | 1.07 |
| 2152 | 1.13 | 1.09 | *0.22* | 1.08 | *0.12* | *0.11* | 1.21 |
| 2153 | 1.12 | 1.06 | 1.03 | 1.06 | *0.17* | *0.11* | 1.01 |
| 2154 | 1.07 | 1.21 | 1.08 | 1.09 | *0.13* | *0.11* | 1.03 |
| 2155 | 1.09 | 1.11 | 0.96 | 1.05 | *0.18* | *0.11* | 1.03 |
| 2156 | 1.11 | 1.12 | 1.11 | 0.98 | *0.21* | *0.09* | 1.34 |
| 2157 | 1.16 | 1.24 | *0.14* | 1.15 | *0.12* | *0.09* | 0.94 |
| 2158 | 0.94 | 1.05 | *0.29* | 0.90 | *0.12* | *0.10* | 1.07 |
| 2159 | 0.90 | 1.11 | 1.10 | 0.99 | *0.11* | *0.12* | 1.09 |
| 1889 | 1.18 | 1.19 | 1.03 | 1.15 | *0.19* | *0.09* | 0.99 |
| 2144 | 1.09 | 1.11 | 1.11 | 1.10 | *0.19* | *0.10* | 1.09 |
| 2145 | 1.10 | 1.10 | 1.17 | 1.13 | *0.12* | *0.10* | 1.12 |
| 2146 | 1.07 | 1.13 | *0.23* | 1.10 | *0.17* | *0.09* | 1.10 |
| 2147 | 0.97 | 1.10 | 1.13 | 0.98 | *0.18* | *0.12* | 1.05 |
| 2160 | 0.99 | 1.11 | *0.18* | 1.10 | *0.21* | *0.12* | 1.11 |
| 2161 | 1.05 | 1.13 | *0.18* | 1.16 | *0.25* | *0.11* | 1.14 |
| 2162 | 1.10 | 1.10 | *0.28* | 1.15 | *0.22* | *0.11* | 1.12 |
| 2163 | 1.04 | 1.16 | *0.27* | 1.08 | *0.30* | *0.11* | 1.19 |
| 2168 | 0.96 | 1.17 | *0.24* | 0.97 | *0.31* | *0.10* | 0.99 |
| 1890 | 1.15 | 1.14 | 1.06 | 1.13 | *0.19* | *0.09* | 1.00 |
| 2169 | 1.13 | 1.16 | 0.46 | 1.11 | *0.18* | *0.12* | 1.09 |
| 2170 | 1.08 | 1.07 | *0.16* | 1.10 | *0.19* | *0.10* | 1.07 |
| 2171 | 1.04 | 1.10 | *0.23* | 1.14 | *0.26* | *0.11* | 1.07 |
| 2172 | 1.06 | 1.10 | *0.20* | 1.19 | 1.04 | *0.11* | 1.10 |
| 2173 | 1.11 | 1.16 | *0.13* | 1.16 | 0.68 | *0.10* | 1.05 |
| 2174 | 1.09 | 1.07 | *0.23* | 1.12 | *0.10* | *0.11* | 1.05 |
| 2175 | 1.05 | 1.08 | 1.06 | 1.12 | *0.19* | *0.10* | 1.10 |
| 2176 | 1.17 | 1.10 | 1.08 | 1.11 | 1.09 | *0.10* | 1.08 |
| 2177 | 1.13 | 1.12 | 1.03 | 1.14 | 1.12 | 1.07 | 1.04 |
| 1879 | 1.28 | 1.07 | 1.04 | 0.68 | *0.13* | *0.08* | 1.14 |
| 1911 | 1.10 | *0.11* | 1.02 | 1.06 | 1.10 | *0.21* | *0.11* |
| 1950 | 1.08 | 1.06 | 1.12 | 1.09 | *0.10* | *0.09* | 1.09 |
| 1951 | 1.33 | 1.00 | 1.02 | 0.80 | 0.78 | L05 | 1.00 |
| 1952 | 0.95 | 1.02 | 1.02 | *0.10* | *0.12* | *0.10* | *0.11* |
| 1953 | *0.16* | *0.10* | 1.01 | *0.09* | 0.94 | 0.73 | *0.10* |
| 1954 | 1.03 | 1.10 | 1.00 | 1.08 | *0.11* | *0.09* | 1.02 |
| 1955 | 0.79 | *0.10* | 1.02 | *0.10* | 0.94 | 0.74 | *0.11* |
| 1956 | 1.09 | *0.10* | 1.02 | 1.17 | 1.14 | *0.14* | *0.10* |
| 1957 | 0.99 | 0.99 | 1.14 | 1.06 | *0.15* | *0.10* | 1.12 |
| 1958 | 1.00 | 1.05 | 1.08 | 1.03 | *0.10* | *0.09* | 1.04 |
| 1913 | 1.05 | *0.09* | 1.15 | 1.09 | 1.03 | *0.16* | *0.11* |
| 1968 | 1.09 | 1.14 | 1.07 | *0.11* | *0.14* | *0.10* | *0.11* |
| 1969 | 1.17 | 1.05 | 1.02 | 1.19 | 1.30 | *0.11* | 1.02 |
| 1970 | 1.14 | 1.17 | 1.08 | *0.11* | *0.10* | *0.09* | *0.14* |
| 1971 | 1.07 | 1.10 | 1.00 | 1.08 | *0.13* | *0.09* | 1.06 |
| 1972 | 1.26 | *0.09* | 0.96 | 1.07 | 1.11 | *0.15* | *0.10* |
| 1973 | 1.25 | *0.10* | 1.15 | 0.81 | 1.24 | *0.21* | *0.11* |
| 1974 | 1.16 | *0.10* | 1.05 | 0.94 | 1.10 | *0.14* | *0.10* |
| 1975 | 0.88 | 1.01 | 1.00 | 0.87 | 0.92 | *0.09* | 0.92 |
| 1976 | 0.92 | 1.02 | 0.97 | 0.97 | 0.82 | *0.09* | 1.00 |
| 1891 | 1.16 | 1.12 | 1.03 | 1.10 | 1.1.5 | 1.02 | 1.12 |
| 1892 | 1.12 | 1.14 | 1.06 | 1.12 | 1.12 | 1.00 | 0.99 |
| 1893 | 1.12 | 1.09 | 1.04 | 1.14 | *0.23* | *0.09* | 1.00 |
| 1894 | 1.16 | 1.02 | 1.05 | 1.15 | 1.16 | 1.04 | 1.12 |
| 1895 | 1.08 | 1.13 | 1.04 | 1.00 | *0.19* | *0.09* | 1.09 |
| 1896 | 1.09 | 1.05 | 1.02 | 1.02 | *0.18* | *0.10* | 1.03 |
| 1897 | 1.11 | 1.03 | 1.05 | *0.37* | *0.17* | *0.10* | 0.99 |
| 1898 | 0.91 | 0.94 | 1.10 | 1.04 | *0.23* | *0.09* | 0.96 |
| 1899 | 1.09 | 1.00 | 1.04 | 0.99 | 1.00 | 0.97 | 1.05 |
| 1990 | 1.00 | *0.09* | 1.05 | *0.30* | 1.00 | *0.09* | *0.09* |
| 1991 | 1.03 | *0.09* | 1.02 | *0.26* | 1.01 | *0.09* | *0.09* |
| 1992 | 1.02 | *0.09* | 1.03 | *0.38* | 1.10 | *0.09* | *0.09* |
| 1993 | 1.13 | *0.10* | 0.92 | *0.11* | *0.10* | *0.10* | *0.08* |
| 1994 | 1.06 | *0.10* | 1.08 | *0.09* | *0.12* | *0.09* | *0.09* |
| 1995 | 1.04 | *0.10* | 1.14 | *0.10* | *0.10* | *0.09* | *0.09* |
| 1996 | 1.04 | *0.09* | *0.09* | *0.09* | 1.01 | *0.09* | *0.09* |
| 1910 | *0.11* | *0.09* | *0.23* | *0.11* | 1.13 | 0.62 | *0.09* |
| 1945 | 1.14 | 1.10 | 1.05 | *0.15* | *0.20* | *0.08* | 0.90 |
| 1946 | *0.10* | *0.23* | 1.04 | *0.10* | 1.10 | 0.89 | *0.09* |
| 1947 | *0.10* | *0.29* | 0.95 | *0.15* | 1.04 | 0.72 | *0.10* |
| 1948 | *0.16* | *0.18* | 0.72 | *0.11* | 1.13 | 0.89 | *0.11* |
| 1949 | *0.17* | *0.09* | *0.22* | *0.11* | 1.09 | 0.53 | *0.09* |
| 1977 | *0.13* | 0.79 | 1.05 | *0.10* | 0.96 | 1.00 | *0.09* |
| 1978 | 0.95 | 0.75 | 1.03 | 0.96 | 1.00 | 0.80 | *0.37* |
| 1979 | 0.95 | 0.70 | 1.06 | 0.85 | 0.98 | 0.78 | *0.32* |
| 1980 | 1.01 | 0.92 | 1.09 | 1.01 | 1.04 | 0.78 | 0.82 |
| 1981 | 0.98 | 0.70 | 1.14 | 0.93 | 0.94 | 0.78 | *0.37* |
| 1982 | 1.05 | 0.90 | 1.09 | 1.03 | 1.11 | 0.94 | *0.34* |
| 1983 | 0.95 | 1.14 | 0.96 | 0.94 | *0.12* | *0.10* | *0.10* |
| 1984 | 1.05 | 0.79 | 1.03 | 1.05 | 1.04 | 0.88 | *0.27* |
| 1985 | *0.11* | 1.00 | 0.98 | *0.09* | 1.02 | 0.85 | *0.09* |
| 1914 | 1.19 | 1.05 | 1.03 | *0.11* | 1.12 | 0.86 | *0.11* |
| 1986 | 1.04 | 0.85 | 1.04 | *0.10* | 1.02 | 0.81 | *0.13* |

TABLE 20A-continued

| NP # | LP14 | LP20 | LP30 | LP34 | LP39 | LP40 | LP44 |
|---|---|---|---|---|---|---|---|
| 1987 | 1.04 | 0.83 | 1.03 | *0.09* | 1.02 | 0.85 | *0.12* |
| 1988 | 1.03 | 0.58 | 1.07 | *0.09* | 1.01 | 0.88 | *0.13* |
| 1989 | 1.01 | 1.07 | 1.01 | *0.11* | 0.22 | 0.08 | *0.15* |
| 1917 | 1.14 | 0.78 | 1.05 | 1.16 | 1.16 | 0.89 | 0.68 |
| 2015 | 0.99 | 0.46 | 1.08 | *0.10* | 1.04 | 0.89 | *0.10* |
| 2016 | 0.72 | 0.46 | 1.00 | *0.10* | 0.99 | 0.77 | *0.10* |
| 2017 | 1.12 | 0.43 | 0.93 | *0.12* | 1.24 | 0.80 | *0.10* |
| 2018 | 1.10 | *0.40* | 1.07 | *0.12* | 1.19 | 0.77 | *0.11* |
| 2019 | 1.09 | 0.53 | 1.11 | *0.11* | 1.10 | 0.74 | *0.11* |
| 2020 | 1.10 | 0.65 | 1.12 | *0.11* | 1.09 | 0.87 | 0.43 |
| 2021 | 1.08 | 0.50 | 1.10 | 1.09 | 1.08 | 0.79 | *0.36* |
| 2022 | 1.05 | 0.55 | 1.08 | 1.06 | 1.06 | 0.84 | *0.36* |
| 2023 | 1.03 | 1.07 | 1.05 | 1.09 | 1.04 | 0.98 | 0.51 |

TABLE 20B

| NP # | LP48 | LP49 | LP54 | LP-56 | LP95 | LP99 | LP101 |
|---|---|---|---|---|---|---|---|
| 1900 | 0.91 | 0.93 | *0.09* | 0.71 | 0.89 | *0.37* | *0.20* |
| 1901 | *0.13* | 0.95 | *0.13* | 1.01 | *0.09* | *0.09* | *0.10* |
| 1902 | 1.00 | 0.88 | *0.12* | 1.04 | 0.70 | *0.09* | *0.13* |
| 1903 | *0.13* | 0.88 | *0.10* | 1.02 | *0.10* | *0.10* | *0.10* |
| 1904 | *0.19* | 0.87 | *0.10* | 0.95 | *0.10* | *0.09* | 0.84 |
| 1905 | *0.18* | 0.94 | *0.10* | 1.01 | *0.11* | *0.09* | 0.90 |
| 1906 | 0.99 | 0.86 | *0.11* | 1.03 | 0.70 | *0.09* | *0.12* |
| 1907 | 0.94 | 0.79 | *0.10* | 0.77 | 0.98 | *0.39* | *0.15* |
| 1908 | *0.13* | 0.97 | *0.11* | 0.95 | *0.09* | *0.09* | *0.16* |
| 1909 | 0.91 | 0.82 | *0.09* | 0.72 | 0.97 | 0.40 | *0.17* |
| 1912 | 1.03 | 0.55 | *0.17* | 0.61 | 0.74 | *0.29* | *0.17* |
| 1959 | *0.14* | 1.01 | *0.22* | 0.93 | *0.09* | *0.08* | *0.10* |
| 1960 | 0.75 | 0.96 | *0.11* | 1.00 | *0.10* | *0.10* | *0.10* |
| 1961 | *0.18* | 0.97 | *0.09* | 0.89 | *0.09* | *0.09* | *0.10* |
| 1962 | 1.22 | 0.58 | *0.09* | 0.48 | 0.63 | *0.17* | *0.27* |
| 1963 | *0.12* | 0.89 | *0.09* | 0.93 | *0.08* | *0.08* | *0.09* |
| 1964 | *0.12* | 1.04 | *0.09* | 0.94 | *0.08* | *0.08* | *0.09* |
| 1965 | *0.12* | 0.92 | *0.09* | 1.02 | *0.09* | *0.08* | *0.09* |
| 1966 | *0.19* | 1.05 | *0.13* | 0.96 | *0.08* | *0.08* | 0.91 |
| 1967 | *0.17* | 1.08 | *0.18* | 1.00 | *0.09* | *0.08* | 0.49 |
| 1915 | *0.09* | 0.92 | *0.09* | 1.26 | *0.12* | *0.09* | *0.09* |
| 1997 | *0.10* | 0.95 | *0.09* | 0.99 | *0.10* | *0.09* | *0.09* |
| 1998 | *0.10* | 0.94 | *0.09* | 1.10 | *0.11* | *0.09* | *0.09* |
| 1999 | *0.11* | 0.94 | *0.09* | 1.11 | *0.10* | *0.09* | *0.10* |
| 2000 | *0.10* | 0.96 | *0.09* | 1.07 | *0.10* | *0.09* | *0.09* |
| 2001 | *0.10* | 0.97 | *0.10* | 1.04 | *0.10* | *0.09* | *0.09* |
| 2002 | *0.21* | 0.95 | 1.08 | 0.89 | *0.12* | *0.09* | *0.17* |
| 2003 | 0.86 | 0.94 | *0.09* | 1.04 | *0.22* | *0.09* | *0.09* |
| 2004 | 0.88 | 1.12 | *0.10* | 1.00 | 1.05 | *0.10* | *0.11* |
| 2005 | 0.92 | 0.90 | *0.10* | 1.07 | 1.08 | *0.12* | *0.11* |
| 1916 | 1.04 | 0.63 | 0.48 | 0.59 | 0.88 | 0.53 | 0.45 |
| 2006 | 0.94 | 0.72 | *0.13* | 0.86 | 0.95 | 0.46 | *0.22* |
| 2007 | *0.23* | 0.96 | *0.11* | 0.51 | *0.12* | *0.09* | *0.11* |
| 2008 | *0.25* | 0.89 | *0.11* | 0.65 | *0.12* | *0.10* | *0.11* |
| 2009 | *0.37* | 0.96 | *0.13* | 0.88 | *0.14* | *0.10* | *0.10* |
| 2010 | 0.82 | 0.72 | *0.12* | 0.86 | 1.24 | 0.59 | *0.20* |
| 2011 | 0.89 | 0.99 | *0.14* | 0.56 | 0.82 | 0.57 | *0.35* |
| 2012 | 0.85 | 0.96 | *0.20* | 0.87 | 0.96 | 0.41 | 0.41 |
| 2013 | 0.99 | 0.93 | *0.16* | 0.89 | 1.03 | 0.88 | *0.40* |
| 2014 | 0.95 | 0.83 | *0.14* | 0.59 | 0.70 | 0.63 | 0.44 |
| 1869 | *0.17* | *0.28* | *0.22* | 0.57 | *0.15* | *0.12* | *0.13* |
| 1840 | 1.00 | 0.99 | 0.85 | 0.85 | 1.05 | 0.48 | *0.26* |
| 1839 | *0.29* | *0.29* | 1.21 | 0.48 | 0.46 | *0.16* | *0.21* |
| 2024 | *0.09* | 0.54 | 1.10 | *0.10* | *0.10* | *0.11* | *0.08* |
| 2025 | *0.10* | 0.79 | 1.14 | *0.11* | *0.11* | *0.10* | *0.08* |
| 2026 | 0.46 | 0.50 | 1.32 | 0.60 | 0.60 | *0.32* | 0.45 |
| 2027 | *0.12* | *0.09* | 1.13 | *0.15* | *0.11* | *0.10* | *0.10* |
| 2028 | *0.10* | *0.10* | 1.07 | *0.10* | *0.09* | *0.09* | *0.11* |
| 2029 | 1.04 | 1.00 | 1.08 | *0.10* | *0.16* | *0.12* | *0.11* |
| 2030 | *0.09* | 0.49 | 1.21 | *0.10* | *0.09* | *0.10* | *0.09* |
| 2031 | *0.09* | 0.62 | 1.04 | *0.09* | *0.09* | *0.09* | *0.09* |
| 2032 | *0.10* | 0.69 | 1.11 | *0.10* | *0.09* | *0.09* | *0.09* |
| 1878 | *0.12* | 0.87 | 1.14 | 0.52 | *0.11* | *0.10* | *0.14* |
| 2033 | *0.10* | 0.72 | 1.10 | *0.10* | *0.10* | *0.11* | *0.09* |
| 2034 | *0.11* | 0.72 | 1.21 | *0.11* | *0.10* | *0.10* | *0.09* |
| 2035 | *0.10* | 0.73 | 1.09 | *0.11* | *0.10* | *0.09* | *0.09* |
| 2036 | *0.09* | 0.50 | 1.10 | *0.10* | *0.10* | *0.09* | *0.08* |

TABLE 20B-continued

| NP # | LP48 | LP49 | LP54 | LP-56 | LP95 | LP99 | LP101 |
|---|---|---|---|---|---|---|---|
| 2037 | *0.10* | 0.77 | 1.10 | *0.11* | *0.10* | *0.10* | *0.09* |
| 2038 | *0.08* | 1.03 | 1.12 | 0.88 | *0.10* | *0.10* | *0.21* |
| 2039 | *0.11* | 0.88 | 1.03 | *0.15* | *0.10* | *0.10* | *0.12* |
| 2040 | *0.11* | 1.11 | 1.18 | 1.11 | *0.11* | *0.10* | *0.31* |
| 2041 | *0.10* | 0.52 | 1.21 | *0.11* | *0.10* | *0.10* | *0.12* |
| 2042 | *0.09* | 0.96 | 1.08 | 0.91 | *0.09* | *0.10* | 0.46 |
| 2043 | *0.09* | 0.98 | 1.01 | 0.94 | *0.10* | *0.09* | *0.33* |
| 2044 | *0.09* | 0.81 | 1.00 | 0.85 | *0.10* | *0.10* | *0.31* |
| 2045 | *0.10* | 0.86 | *0.35* | 0.57 | *0.10* | *0.10* | *0.21* |
| 2046 | *0.09* | 0.90 | 0.72 | 0.90 | *0.11* | *0.10* | *0.26* |
| 2047 | *0.11* | 1.02 | 1.11 | 0.95 | *0.11* | *0.11* | *0.26* |
| 2048 | *0.20* | 0.60 | *0.33* | 0.57 | *0.19* | *0.11* | *0.19* |
| 2049 | *0.09* | 1.07 | 1.01 | 0.97 | *0.10* | *0.10* | *0.39* |
| 2050 | *0.09* | 1.05 | 0.75 | 0.90 | *0.10* | *0.10* | *0.34* |
| 1880 | 1.13 | 0.87 | 1.16 | 1.01 | 0.73 | *0.10* | 0.94 |
| 2051 | *0.11* | 0.83 | 1.11 | *0.27* | *0.10* | *0.10* | *0.17* |
| 2052 | *0.09* | 0.41 | 1.08 | *0.10* | *0.10* | *0.11* | *0.11* |
| 2053 | *0.10* | 0.78 | 1.17 | 1.08 | *0.10* | *0.11* | *0.31* |
| 2054 | *0.11* | *0.12* | 0.99 | *0.13* | *0.10* | *0.10* | *0.15* |
| 2055 | *0.09* | 0.60 | 1.04 | *0.10* | *0.09* | *0.09* | *0.09* |
| 2056 | *0.09* | *0.09* | 1.10 | *0.10* | *0.09* | *0.11* | *0.10* |
| 2057 | *0.10* | 0.94 | 1.09 | 0.56 | *0.10* | *0.10* | *0.21* |
| 2058 | *0.11* | 1.02 | 1.16 | 1.02 | *0.10* | *0.11* | *0.53* |
| 2059 | *0.10* | 0.51 | 1.08 | *0.11* | *0.10* | *0.10* | *0.10* |
| 1881 | 0.91 | 0.78 | 1.11 | 1.11 | 0.96 | *0.10* | 0.85 |
| 2060 | 1.05 | 1.16 | 1.12 | *0.12* | *0.13* | *0.10* | *0.13* |
| 2061 | 0.96 | 1.09 | 1.21 | *0.12* | *0.13* | *0.10* | *0.13* |
| 2062 | 1.05 | 1.03 | 1.14 | *0.12* | *0.13* | *0.11* | *0.13* |
| 2063 | 0.94 | 1.05 | 1.14 | *0.14* | 1.05 | 0.41 | *0.12* |
| 2064 | *0.22* | 0.42 | 1.13 | *0.10* | *0.09* | *0.09* | *0.09* |
| 2065 | 0.98 | 1.10 | 1.13 | *0.12* | *0.13* | *0.12* | *0.13* |
| 2066 | 1.04 | 1.03 | 1.19 | *0.13* | *0.15* | *0.13* | *0.12* |
| 2067 | 1.01 | 1.03 | 1.08 | 1.15 | 1.13 | 0.99 | 1.02 |
| 2068 | 0.90 | 1.06 | 1.16 | 1.18 | 1.17 | *0.11* | 0.96 |
| 2069 | 0.93 | 1.01 | 1.10 | 1.13 | *0.30* | *0.11* | 1.02 |
| 2070 | *0.09* | 0.93 | 1.26 | *0.12* | *0.11* | *0.10* | *0.10* |
| 2071 | 0.85 | 1.01 | 1.19 | 1.21 | 1.12 | 1.09 | 1.03 |
| 2072 | *0.10* | 0.57 | 1.14 | *0.13* | *0.11* | *0.11* | *0.11* |
| 2073 | 0.95 | 0.46 | 1.15 | 1.06 | 1.06 | *0.09* | 0.99 |
| 2074 | *0.08* | 0.69 | 0.99 | *0.11* | *0.10* | *0.12* | *0.11* |
| 2075 | 1.05 | 1.12 | 1.29 | *0.13* | *0.13* | *0.10* | *0.13* |
| 2076 | *0.10* | 0.87 | 1.11 | 1.11 | *0.11* | *0.09* | 0.99 |
| 2077 | *0.09* | 0.75 | 1.14 | *0.12* | *0.11* | *0.09* | *0.09* |
| 1882 | *0.10* | 0.48 | 1.07 | *0.11* | *0.10* | *0.09* | *0.09* |
| 2078 | 1.04 | 1.09 | 1.08 | *0.13* | *0.16* | *0.09* | *0.11* |
| 2079 | 1.07 | 0.89 | 1.14 | 1.17 | 1.16 | *0.14* | 0.89 |
| 2080 | 1.04 | 1.01 | 1.14 | *0.12* | 1.05 | 0.94 | *0.11* |
| 2081 | 1.04 | 0.96 | 1.15 | 1.13 | 1.12 | 0.99 | 0.91 |
| 2082 | 1.09 | 0.98 | 1.13 | 1.11 | 1.10 | 1.08 | 0.95 |
| 2083 | 1.07 | 0.94 | 1.05 | *0.11* | *0.12* | *0.10* | *0.10* |
| 2084 | 1.10 | 0.95 | 1.10 | *0.11* | *0.12* | *0.09* | *0.11* |
| 2085 | 1.07 | 1.03 | 1.14 | *0.12* | 1.07 | 0.98 | *0.11* |
| 2086 | 1.04 | 0.99 | 1.10 | *0.11* | *0.12* | *0.10* | *0.12* |
| 2087 | 1.01 | 0.95 | 1.20 | 0.98 | 1.00 | 1.08 | 1.17 |
| 2088 | *0.20* | 0.97 | 0.92 | 0.76 | *0.12* | *0.11* | *0.28* |
| 2089 | 1.10 | 0.92 | 1.08 | 1.16 | 1.11 | 0.95 | 0.98 |
| 2090 | *0.19* | 0.84 | 1.01 | 0.58 | *0.12* | *0.12* | *0.31* |
| 2091 | 1.05 | 0.90 | 1.15 | *0.12* | *0.13* | *0.10* | *0.10* |
| 2092 | *0.10* | 0.92 | 1.08 | 0.92 | *0.10* | *0.09* | *0.35* |
| 2093 | *0.09* | 0.96 | 1.07 | 1.03 | *0.11* | *0.09* | 0.49 |
| 2094 | *0.10* | 0.91 | 1.13 | 1.06 | *0.11* | *0.09* | 0.42 |
| 2095 | *0.13* | 1.02 | 1.09 | *0.14* | *0.12* | *0.13* | *0.10* |
| 2096 | *0.10* | 0.94 | 1.15 | *0.12* | *0.11* | *0.09* | *0.09* |
| 2097 | *0.10* | *0.38* | 1.19 | *0.11* | *0.10* | *0.09* | *0.10* |
| 2098 | *0.09* | 0.82 | 1.14 | *0.10* | *0.10* | *0.10* | *0.11* |
| 2099 | *0.10* | 0.76 | 1.17 | *0.11* | *0.11* | *0.09* | *0.11* |
| 2100 | 1.04 | 0.99 | 1.10 | *0.13* | 1.15 | 0.96 | *0.11* |
| 2101 | 1.05 | 0.96 | 1.18 | 1.22 | 1.22 | 0.96 | 0.85 |
| 2102 | 1.07 | 1.05 | 1.08 | 1.27 | 1.16 | 0.92 | 1.10 |
| 2103 | 1.05 | 1.01 | 1.16 | *0.15* | 1.11 | 0.96 | *0.10* |
| 2104 | 1.10 | 0.83 | 1.09 | 1.25 | 1.22 | 0.96 | 0.92 |
| 1883 | 0.96 | 0.91 | 1.08 | 1.04 | 1.06 | 1.10 | 0.88 |
| 2105 | 1.04 | 1.08 | 1.19 | 1.16 | 1.11 | 0.96 | 1.00 |
| 2106 | 1.12 | 1.10 | 1.08 | *0.14* | 1.06 | *0.10* | *0.10* |
| 2107 | 1.07 | 1.01 | 1.11 | 1.05 | 1.01 | 0.97 | 0.93 |
| 2108 | 1.07 | 1.00 | 1.10 | 1.05 | 1.10 | 0.97 | 1.00 |
| 2109 | 1.05 | 0.94 | 1.23 | 0.65 | 1.09 | *0.10* | *0.11* |
| 2110 | 1.05 | 1.03 | 1.11 | 1.00 | 1.01 | 0.91 | 1.10 |

TABLE 20B-continued

| NP # | LP48 | LP49 | LP54 | LP-56 | LP95 | LP99 | LP101 |
|---|---|---|---|---|---|---|---|
| 2111 | 0.94 | 0.95 | 1.28 | *0.11* | 0.35 | *0.09* | *0.10* |
| 2112 | 1.01 | 1.00 | 1.19 | 1.15 | 1.09 | 0.93 | 0.97 |
| 2113 | *0.09* | 0.96 | 1.17 | *0.10* | *0.10* | *0.09* | *0.09* |
| 1884 | 0.98 | 0.88 | 0.99 | 0.90 | 1.02 | *0.09* | *0.34* |
| 2114 | 1.02 | 0.97 | 1.14 | 1.01 | 1.05 | *0.09* | *0.36* |
| 2115 | 1.04 | 1.07 | 1.17 | 1.09 | 1.04 | *0.09* | *0.36* |
| 2116 | 1.02 | 1.00 | 1.19 | 1.06 | 1.04 | *0.09* | 0.50 |
| 2117 | 1.08 | 1.08 | 1.16 | 1.00 | 0.87 | *0.09* | *0.32* |
| 2118 | 1.02 | 0.99 | 1.22 | 1.00 | 1.03 | *0.09* | *0.38* |
| 2119 | 1.03 | 1.01 | 1.24 | 0.58 | 0.55 | *0.10* | *0.20* |
| 2120 | 0.97 | 1.01 | 1.16 | 0.66 | 0.99 | *0.10* | *0.11* |
| 2121 | 0.95 | 1.01 | 1.17 | 1.07 | 1.09 | *0.09* | *0.32* |
| 2122 | 0.99 | 1.00 | 1.14 | 0.95 | 1.01 | *0.09* | *0.34* |
| 1885 | *0.09* | 0.72 | 0.94 | *0.10* | *0.10* | *0.09* | *0.09* |
| 2123 | *0.09* | 1.03 | 1.08 | 0.95 | *0.09* | *0.09* | *0.31* |
| 2124 | *0.10* | 1.02 | 1.05 | 0.84 | *0.10* | *0.09* | *0.22* |
| 2125 | *0.10* | 0.97 | 0.99 | 0.86 | *0.09* | *0.09* | *0.32* |
| 2126 | *0.11* | 0.95 | 1.14 | *0.26* | *0.10* | *0.10* | *0.16* |
| 2127 | 1.08 | 0.94 | 1.17 | 1.02 | 0.96 | *0.10* | 1.16 |
| 2128 | *0.10* | 0.96 | 0.97 | 1.04 | *0.11* | *0.09* | *0.29* |
| 2129 | *0.10* | 0.95 | 0.98 | 0.95 | *0.10* | *0.09* | *0.30* |
| 2130 | *0.10* | 1.01 | 1.12 | 0.91 | *0.11* | *0.09* | *0.25* |
| 2131 | *0.10* | 1.10 | 1.05 | 1.03 | *0.11* | *0.09* | *0.37* |
| 1886 | 1.06 | 0.97 | 1.00 | *0.11* | 0.97 | 1.06 | *0.10* |
| 2132 | 1.20 | 0.94 | 1.09 | *0.13* | 1.18 | 0.98 | *0.10* |
| 1887 | 1.12 | 0.91 | 1.08 | *0.11* | *0.31* | *0.11* | *0.09* |
| 2133 | *0.11* | 0.65 | 1.15 | *0.12* | *0.10* | *0.11* | *0.11* |
| 2134 | 1.10 | 0.91 | 1.1 | 1.00 | 1.08 | 0.85 | 1.13 |
| 2135 | *0.09* | 0.75 | 1.11 | *0.11* | *0.10* | *0.09* | *0.10* |
| 2136 | *0.09* | 0.91 | 1.15 | *0.11* | *0.10* | *0.09* | *0.10* |
| 2137 | *0.10* | 0.79 | 1.13 | *0.11* | *0.10* | *0.10* | *0.10* |
| 2138 | 0.99 | 0.92 | 1.12 | 1.11 | 1.10 | 0.97 | 1.05 |
| 2139 | *0.10* | 0.56 | 1.09 | *0.14* | *0.11* | *0.10* | *0.10* |
| 2140 | 0.94 | 0.84 | 1.04 | 1.09 | 1.07 | *0.10* | 0.97 |
| 2141 | *0.09* | 0.47 | 1.13 | *0.11* | *0.10* | *0.10* | *0.11* |
| 2142 | 0.98 | 1.00 | 1.19 | *0.12* | 0.85 | *0.10* | *0.11* |
| 2143 | 0.99 | 1.05 | 1.17 | *0.15* | 0.99 | *0.11* | *0.11* |
| 2148 | *0.10* | 0.82 | 1.06 | *0.11* | *0.09* | *0.09* | *0.10* |
| 2149 | 1.06 | 0.99 | 1.04 | 1.01 | 1.02 | 0.95 | 1.00 |
| 2150 | 1.09 | 1.01 | 1.11 | *0.12* | *0.25* | *0.09* | *0.12* |
| 2164 | *0.10* | 0.51 | 1.17 | *0.11* | *0.09* | *0.11* | *0.11* |
| 2165 | *0.10* | 0.77 | 1.21 | *0.10* | *0.09* | *0.10* | *0.11* |
| 2166 | 0.95 | 1.02 | 1.06 | *0.11* | 1.01 | 1.10 | *0.12* |
| 2167 | *0.09* | 0.87 | 1.02 | *0.11* | *0.10* | 0.08 | *0.10* |
| 1888 | 0.98 | 0.95 | 1.12 | *0.11* | *0.18* | *0.12* | *0.09* |
| 2151 | 1.08 | 1.12 | 1.22 | *0.12* | *0.20* | *0.11* | *0.12* |
| 2152 | *0.10* | 1.03 | 1.14 | *0.11* | *0.10* | *0.09* | *0.11* |
| 2153 | 1.06 | 0.90 | 1.02 | *0.11* | *0.15* | *0.12* | *0.11* |
| 2154 | 1.07 | 1.16 | 1.17 | *0.13* | *0.20* | *0.09* | *0.12* |
| 2155 | 1.14 | 1.09 | 1.21 | *0.11* | *0.15* | *0.12* | *0.11* |
| 2156 | *0.10* | 0.87 | 0.95 | *0.11* | *0.10* | *0.10* | *0.10* |
| 2157 | *0.10* | 0.96 | 1.10 | *0.10* | *0.09* | *0.09* | *0.10* |
| 2158 | *0.09* | 0.98 | 1.06 | *0.11* | *0.10* | *0.09* | *0.11* |
| 2159 | 1.16 | 1.20 | 1.13 | *0.13* | *0.25* | *0.11* | *0.13* |
| 1889 | *0.10* | 0.63 | 1.08 | *0.10* | *0.09* | *0.11* | *0.10* |
| 2144 | 1.06 | 0.84 | 1.13 | *0.11* | 1.07 | 1.21 | *0.10* |
| 2145 | 0.77 | 0.90 | 1.14 | 1.04 | 0.94 | *0.10* | 0.94 |
| 2146 | *0.10* | 0.88 | 1.13 | *0.12* | *0.10* | *0.09* | *0.11* |
| 2147 | *0.12* | 1.03 | 1.11 | *0.14* | *0.10* | *0.10* | *0.13* |
| 2160 | *0.11* | 1.14 | 0.55 | *0.12* | *0.10* | *0.10* | *0.13* |
| 2161 | *0.10* | 1.06 | 1.17 | *0.11* | *0.10* | *0.10* | *0.11* |
| 2162 | *0.11* | 1.05 | 1.17 | *0.11* | *0.10* | *0.10* | *0.11* |
| 2163 | *0.11* | 1.00 | 1.17 | *0.11* | *0.10* | *0.10* | *0.12* |
| 2168 | *0.10* | 1.03 | 1.10 | *0.11* | *0.10* | 0.08 | *0.11* |
| 1890 | 0.90 | 0.87 | 1.10 | 0.81 | 1.00 | 1.06 | 0.19 |
| 2169 | *0.11* | 1.15 | 1.12 | *0.11* | *0.11* | 0.51 | *0.13* |
| 2170 | *0.10* | 1.01 | 1.16 | *0.38* | *0.11* | *0.09* | *0.18* |
| 2171 | *0.10* | 0.98 | 1.12 | 0.57 | *0.10* | *0.10* | *0.15* |
| 2172 | *0.11* | 0.95 | 1.16 | 1.20 | *0.11* | *0.09* | 1.07 |
| 2173 | *0.11* | 1.11 | 1.26 | 1.11 | *0.10* | *0.09* | 0.98 |
| 2174 | *0.09* | 0.88 | 1.15 | *0.11* | *0.10* | *0.30* | *0.10* |
| 2175 | 1.13 | 1.02 | 1.14 | *0.25* | 1.13 | 0.97 | *0.21* |
| 2176 | 1.09 | 1.05 | 1.15 | 1.09 | 0.75 | *0.09* | 1.05 |
| 2177 | 1.00 | 1.09 | 1.14 | 1.11 | 1.04 | 0.98 | 0.97 |
| 1879 | *0.11* | 0.66 | 1.03 | *0.10* | *0.10* | *0.10* | *0.09* |
| 1911 | 0.99 | 0.68 | *0.11* | *0.37* | 0.50 | *0.13* | *0.14* |
| 1950 | *0.10* | 1.00 | 0.98 | *0.09* | *0.09* | 0.08 | *0.09* |
| 1951 | 1.24 | 1.02 | 0.98 | 0.98 | 0.98 | 0.91 | 1.07 |
| 1952 | *0.10* | 0.97 | 1.00 | *0.09* | *0.09* | *0.09* | *0.10* |
| 1953 | 1.01 | 1.12 | *0.09* | 0.92 | 0.88 | 0.91 | *0.12* |
| 1954 | *0.09* | 0.92 | 1.05 | *0.10* | *0.10* | *0.09* | *0.09* |
| 1955 | 1.07 | 1.08 | *0.10* | 0.78 | 0.83 | 0.77 | *0.12* |
| 1956 | 1.09 | 0.62 | *0.10* | *0.38* | 0.56 | *0.11* | *0.12* |
| 1957 | *0.09* | 1.02 | 1.00 | *0.10* | *0.10* | *0.09* | *0.09* |
| 1958 | *0.09* | 0.98 | 1.07 | *0.09* | *0.09* | *0.09* | *0.09* |
| 1913 | 1.04 | 0.72 | *0.11* | *0.23* | *0.39* | *0.12* | *0.11* |
| 1968 | *0.09* | 0.96 | 1.02 | *0.09* | 0.08 | *0.09* | *0.10* |
| 1969 | *0.10* | 1.03 | 1.04 | 0.96 | 0.08 | *0.09* | 1.05 |
| 1970 | *0.09* | 0.88 | 1.05 | *0.09* | *0.09* | 0.08 | *0.09* |
| 1971 | *0.09* | 0.92 | 1.10 | *0.09* | *0.09* | 0.08 | *0.09* |
| 1972 | 1.01 | *0.39* | *0.09* | *0.23* | *0.36* | *0.09* | *0.12* |
| 1973 | 1.20 | 0.70 | *0.09* | 0.45 | *0.40* | *0.10* | *0.19* |
| 1974 | 1.08 | 0.76 | *0.10* | *0.24* | *0.35* | *0.11* | *0.11* |
| 1975 | *0.09* | 0.87 | 1.00 | 1.14 | *0.10* | *0.12* | 0.65 |
| 1976 | *0.09* | 0.87 | 0.97 | 1.03 | *0.09* | 0.08 | 0.92 |
| 1891 | 1.03 | 0.99 | 1.07 | 1.14 | 0.95 | 1.02 | 0.88 |
| 1892 | 0.95 | 0.96 | 1.07 | 1.08 | 0.99 | 1.04 | 0.88 |
| 1893 | 0.90 | 0.90 | 1.06 | *0.11* | 1.00 | 1.04 | *0.09* |
| 1894 | 0.94 | 0.99 | 1.02 | 1.09 | 1.09 | 1.03 | 0.89 |
| 1895 | *0.11* | *0.28* | 1.02 | *0.13* | *0.14* | *0.10* | *0.10* |
| 1896 | *0.10* | *0.25* | 1.00 | *0.11* | *0.10* | *0.11* | *0.10* |
| 1897 | *0.09* | *0.32* | 0.98 | *0.09* | *0.09* | *0.09* | *0.10* |
| 1898 | *0.09* | *0.38* | 0.90 | *0.11* | *0.09* | 0.08 | *0.09* |
| 1899 | 1.00 | 0.96 | 0.98 | 1.04 | 0.94 | 1.05 | 0.96 |
| 1990 | 0.74 | 0.63 | *0.09* | *0.15* | 0.90 | *0.10* | *0.09* |
| 1991 | 0.80 | *0.32* | *0.10* | *0.15* | 0.88 | *0.10* | *0.09* |
| 1992 | 0.80 | *0.37* | *0.10* | *0.17* | 1.05 | *0.10* | *0.09* |
| 1993 | 0.94 | *0.22* | *0.09* | *0.12* | 1.14 | *0.10* | *0.10* |
| 1994 | 0.93 | *0.19* | *0.10* | *0.16* | 1.08 | *0.10* | *0.09* |
| 1995 | 0.94 | *0.27* | *0.10* | *0.14* | 1.18 | *0.10* | *0.09* |
| 1996 | 0.88 | 0.82 | *0.09* | 0.48 | *0.30* | *0.09* | *0.09* |
| 1910 | *0.24* | 0.92 | *0.09* | 1.08 | *0.12* | *0.09* | *0.09* |
| 1945 | *0.09* | *0.15* | 0.73 | *0.14* | *0.12* | *0.09* | *0.09* |
| 1946 | *0.11* | 0.98 | *0.13* | 1.24 | *0.11* | *0.09* | 0.08 |
| 1947 | *0.10* | 0.83 | *0.12* | 1.16 | *0.11* | *0.09* | 0.08 |
| 1948 | 0.92 | 0.94 | *0.30* | 1.21 | 1.28 | 0.97 | *0.09* |
| 1949 | *0.33* | 0.89 | *0.09* | 0.88 | *0.10* | *0.09* | *0.09* |
| 1977 | 0.87 | 0.91 | 0.66 | 1.05 | *0.27* | *0.19* | *0.12* |
| 1978 | 0.90 | 0.88 | 0.43 | 1.10 | 1.15 | 1.10 | 0.79 |
| 1979 | 0.95 | 0.83 | 0.49 | 0.95 | 1.00 | 0.96 | 0.80 |
| 1980 | 1.02 | 0.77 | 0.80 | 1.09 | 1.05 | 1.00 | 0.80 |
| 1981 | 1.03 | 0.85 | 0.49 | 1.03 | 1.06 | 0.92 | 0.78 |
| 1982 | 0.98 | 0.96 | 0.64 | 1.19 | 1.11 | 0.97 | 0.90 |
| 1983 | *0.10* | *0.16* | 1.09 | *0.13* | *0.11* | *0.09* | *0.11* |
| 1984 | 0.97 | 0.94 | 0.48 | 1.08 | 1.10 | 0.83 | 0.81 |
| 1985 | 0.88 | 0.88 | 0.83 | 1.15 | 1.11 | 0.93 | 0.08 |
| 1914 | *0.25* | 0.93 | 1.05 | 1.18 | *0.14* | *0.10* | *0.23* |
| 1986 | *0.27* | 0.94 | 0.53 | 1.18 | *0.15* | *0.10* | *0.28* |
| 1987 | *0.26* | 0.94 | 0.59 | 1.13 | *0.14* | *0.10* | *0.31* |
| 1988 | *0.28* | 0.87 | 0.42 | 0.95 | *0.12* | *0.10* | *0.31* |
| 1989 | *0.10* | *0.28* | 1.05 | *0.14* | *0.11* | *0.09* | *0.09* |
| 1917 | 0.95 | 0.92 | 0.50 | 0.86 | 1.01 | 0.70 | 0.80 |
| 2015 | 0.86 | 0.95 | *0.39* | 0.88 | 0.80 | *0.21* | *0.16* |
| 2016 | 0.89 | 0.97 | *0.32* | 1.00 | 0.83 | *0.22* | *0.24* |
| 2017 | 0.97 | 0.77 | *0.29* | 0.97 | 0.85 | *0.23* | *0.19* |
| 2018 | 0.88 | 0.87 | *0.36* | 1.14 | 0.73 | *0.21* | *0.13* |
| 2019 | 1.09 | 0.79 | 0.44 | 1.10 | 0.72 | *0.19* | *0.12* |
| 2020 | 0.84 | 0.88 | 0.59 | 0.95 | *0.22* | *0.15* | 0.78 |
| 2021 | 0.94 | 0.95 | *0.34* | 1.06 | 0.93 | 0.45 | 0.69 |
| 2022 | 0.92 | 0.93 | *0.37* | 1.08 | 1.03 | 0.57 | 0.72 |
| 2023 | 1.04 | 1.05 | 0.99 | 1.15 | 1.10 | *0.18* | 0.97 |

TABLE 20C

| NP # | LP103 | LP106 | LP109 | LP114 | LP124 | LP125 |
|---|---|---|---|---|---|---|
| 1900 | 1.25 | 1.16 | 1.06 | 0.97 | 0.66 | 1.18 |
| 1901 | *0.10* | *0.16* | *0.12* | *0.09* | *0.10* | 1.14 |
| 1902 | 1.14 | 1.20 | *0.13* | *0.10* | *0.36* | 1.17 |
| 1903 | *0.10* | *0.28* | *0.12* | *0.10* | *0.11* | 1.12 |
| 1904 | *0.12* | *0.22* | 0.77 | *0.11* | *0.11* | 1.09 |
| 1905 | *0.11* | *0.23* | 0.95 | *0.11* | *0.11* | 1.14 |
| 1906 | 1.17 | 0.98 | *0.12* | *0.10* | 0.76 | 1.08 |

TABLE 20C-continued

| NP # | LP103 | LP106 | LP109 | LP114 | LP124 | LP125 |
|---|---|---|---|---|---|---|
| 1907 | 1.22 | 1.16 | 1.02 | 0.96 | 0.76 | 1.07 |
| 1908 | *0.10* | *0.11* | *0.12* | *0.09* | *0.10* | 0.73 |
| 1909 | 1.26 | 1.05 | 0.95 | 0.88 | 0.73 | 1.00 |
| 1912 | 1.08 | 1.27 | 1.15 | 1.08 | 0.71 | 1.13 |
| 1959 | *0.09* | *0.10* | *0.09* | 1.00 | *0.09* | 1.06 |
| 1960 | *0.20* | *0.38* | *0.09* | *0.08* | *0.13* | 0.94 |
| 1961 | *0.16* | *0.16* | *0.08* | 0.95 | *0.12* | 1.00 |
| 1962 | 0.91 | 1.21 | 1.01 | 1.15 | *0.25* | 1.06 |
| 1963 | *0.08* | *0.10* | *0.09* | 1.00 | *0.09* | 1.00 |
| 1964 | *0.08* | *0.11* | *0.09* | 1.08 | *0.09* | 1.06 |
| 1965 | *0.08* | *0.10* | *0.08* | 1.03 | *0.09* | 1.01 |
| 1966 | *0.10* | *0.12* | *0.08* | 0.97 | *0.10* | 1.06 |
| 1967 | *0.09* | *0.13* | *0.10* | 1.14 | *0.10* | 1.03 |
| 1915 | *0.09* | *0.23* | *0.09* | *0.12* | *0.10* | *0.10* |
| 1997 | *0.09* | *0.10* | *0.09* | 1.03 | *0.09* | *0.10* |
| 1998 | *0.09* | *0.11* | *0.09* | 1.03 | *0.10* | *0.10* |
| 1999 | *0.09* | *0.10* | *0.09* | 1.00 | *0.09* | *0.11* |
| 2000 | *0.09* | *0.10* | *0.09* | 1.02 | *0.09* | *0.09* |
| 2001 | *0.09* | *0.23* | *0.09* | 1.02 | *0.10* | *0.10* |
| 2002 | *0.10* | *0.12* | *0.09* | 0.97 | *0.10* | 0.77 |
| 2003 | 0.97 | 1.04 | *0.09* | 1.10 | *0.09* | 1.10 |
| 2004 | 1.06 | 1.06 | *0.09* | 0.96 | *0.09* | 1.06 |
| 2005 | 1.12 | 1.17 | *0.09* | 1.10 | *0.10* | 1.02 |
| 1916 | 1.08 | 1.04 | 1.14 | 1.11 | 0.73 | 1.07 |
| 2006 | 0.97 | 0.99 | 0.77 | 1.00 | 0.59 | 1.18 |
| 2007 | *0.14* | *0.23* | *0.10* | *0.10* | *0.11* | 1.11 |
| 2008 | *0.18* | *0.20* | *0.10* | *0.10* | *0.11* | 1.08 |
| 2009 | *0.28* | 0.45 | *0.09* | *0.09* | *0.14* | 1.05 |
| 2010 | 1.24 | 0.84 | 0.74 | 0.98 | 0.57 | 1.13 |
| 2011 | 0.94 | 0.86 | 0.88 | 1.02 | 0.59 | 1.14 |
| 2012 | 1.06 | 1.04 | 0.94 | 1.01 | 0.91 | 1.03 |
| 2013 | 1.06 | 1.04 | 0.92 | 0.98 | 0.89 | 1.03 |
| 2014 | 1.01 | 0.89 | 0.78 | 1.01 | 0.63 | 1.08 |
| 1869 | *0.13* | *0.14* | *0.13* | *0.13* | *0.22* | 0.62 |
| 1840 | 1.19 | 1.08 | *0.16* | *0.13* | 1.02 | 1.10 |
| 1839 | *0.17* | *0.15* | 1.07 | 1.23 | *0.21* | *0.17* |
| 2024 | *0.09* | *0.10* | 1.00 | 1.09 | *0.10* | *0.09* |
| 2025 | *0.09* | *0.18* | 1.04 | 1.14 | *0.09* | *0.09* |
| 2026 | *0.30* | *0.16* | 0.97 | 1.05 | *0.26* | *0.32* |
| 2027 | *0.10* | *0.20* | 1.09 | 1.11 | *0.09* | *0.09* |
| 2028 | *0.09* | *0.15* | 0.97 | 0.95 | *0.09* | *0.09* |
| 2029 | 0.47 | *0.29* | 1.11 | 0.99 | *0.15* | *0.11* |
| 2030 | *0.09* | *0.24* | 0.90 | 0.96 | *0.10* | *0.10* |
| 2031 | *0.08* | *0.11* | 0.92 | 0.91 | *0.10* | *0.10* |
| 2032 | *0.09* | *0.19* | 1.05 | 0.93 | *0.09* | *0.10* |
| 1878 | *0.10* | *0.11* | 0.95 | 0.98 | *0.11* | *0.11* |
| 2033 | *0.10* | *0.10* | 1.15 | 0.97 | *0.10* | *0.10* |
| 2034 | *0.09* | *0.15* | 0.95 | 0.99 | *0.10* | *0.12* |
| 2035 | *0.09* | *0.12* | 1.08 | 0.93 | *0.10* | *0.11* |
| 2036 | *0.09* | *0.15* | 1.14 | 0.95 | *0.09* | *0.11* |
| 2037 | *0.09* | *0.10* | 1.09 | 0.94 | *0.10* | *0.10* |
| 2038 | *0.09* | *0.28* | 0.96 | 0.91 | *0.09* | *0.10* |
| 2039 | *0.09* | *0.23* | 1.07 | 0.94 | *0.09* | *0.10* |
| 2040 | *0.09* | *0.12* | 0.90 | 1.07 | *0.10* | *0.11* |
| 2041 | *0.10* | *0.16* | 1.14 | 0.99 | *0.10* | *0.10* |
| 2042 | *0.09* | *0.16* | 0.91 | 0.98 | *0.10* | *0.10* |
| 2043 | *0.09* | *0.10* | 0.89 | 0.99 | *0.09* | *0.09* |
| 2044 | *0.09* | *0.14* | 1.01 | 1.03 | *0.09* | *0.10* |
| 2045 | *0.10* | *0.11* | 0.75 | 0.93 | *0.13* | *0.10* |
| 2046 | *0.09* | *0.10* | 0.94 | 1.08 | *0.10* | *0.09* |
| 2047 | *0.11* | *0.11* | 0.96 | 0.91 | *0.11* | *0.12* |
| 2048 | *0.10* | *0.10* | *0.30* | 0.95 | *0.13* | *0.12* |
| 2049 | *0.09* | *0.15* | 1.03 | 0.93 | *0.09* | *0.09* |
| 2050 | *0.10* | *0.13* | 0.98 | 0.90 | *0.10* | *0.10* |
| 1880 | 1.26 | 1.16 | 0.98 | 1.03 | 1.07 | 1.12 |
| 2051 | *0.10* | *0.11* | 0.98 | 0.91 | *0.10* | *0.10* |
| 2052 | *0.10* | *0.24* | 0.98 | 0.86 | *0.10* | *0.10* |
| 2053 | *0.11* | *0.34* | 1.12 | 1.07 | *0.10* | *0.10* |
| 2054 | *0.10* | *0.13* | 1.07 | 1.10 | *0.11* | *0.11* |
| 2055 | *0.09* | *0.23* | 1.02 | 1.15 | *0.09* | *0.09* |
| 2056 | *0.10* | *0.17* | 1.03 | 0.99 | *0.09* | *0.10* |
| 2057 | *0.10* | *0.11* | 1.03 | 0.98 | *0.09* | *0.10* |
| 2058 | *0.11* | *0.13* | 1.00 | 0.96 | *0.10* | *0.10* |
| 2059 | *0.10* | *0.16* | 1.10 | 1.09 | *0.10* | *0.22* |
| 1881 | 1.23 | 1.16 | 0.93 | 0.97 | 1.06 | 1.20 |
| 2060 | 0.51 | *0.19* | 1.07 | 1.04 | *0.14* | *0.11* |
| 2061 | *0.25* | *0.23* | 1.08 | 1.03 | *0.14* | *0.26* |
| 2062 | *0.28* | *0.18* | 1.06 | 1.25 | *0.13* | *0.12* |
| 2063 | 0.99 | 0.87 | 1.05 | 1.16 | 1.06 | 0.96 |
| 2064 | *0.14* | *0.30* | 1.05 | 1.24 | *0.09* | *0.09* |
| 2065 | 0.42 | *0.15* | 1.07 | 1.02 | *0.14* | *0.11* |
| 2066 | *0.38* | *0.11* | 1.00 | 1.11 | *0.17* | *0.10* |
| 2067 | 1.14 | 1.08 | 0.96 | 1.10 | 1.10 | 0.94 |
| 2068 | 0.98 | 1.17 | 1.03 | 1.12 | 1.17 | 0.97 |
| 2069 | 0.70 | *0.25* | 1.08 | 1.33 | *0.36* | *0.11* |
| 2070 | *0.09* | *0.20* | 1.12 | 1.21 | *0.11* | *0.11* |
| 2071 | 0.93 | 0.92 | 1.06 | 0.94 | 1.05 | 0.97 |
| 2072 | *0.11* | *0.16* | 1.07 | 0.96 | *0.11* | *0.10* |
| 2073 | 0.90 | *0.20* | 1.14 | 0.89 | 1.09 | *0.31* |
| 2074 | *0.11* | *0.12* | 1.13 | 0.57 | *0.09* | *0.11* |
| 2075 | *0.23* | *0.24* | 1.13 | 1.14 | *0.15* | *0.13* |
| 2076 | *0.08* | *0.21* | 0.96 | 1.04 | *0.09* | *0.10* |
| 2077 | *0.09* | *0.11* | 0.97 | 1.01 | *0.10* | *0.10* |
| 1882 | *0.09* | *0.10* | 0.99 | 0.97 | *0.10* | *0.10* |
| 2078 | *0.19* | *0.16* | 1.10 | 1.02 | *0.15* | *0.13* |
| 2079 | 0.94 | 1.03 | 1.02 | 1.08 | 1.11 | 1.07 |
| 2080 | 0.93 | 1.03 | 1.04 | 1.06 | 1.03 | 1.07 |
| 2081 | 0.96 | 1.02 | 0.94 | 0.99 | 1.02 | 1.02 |
| 2082 | 1.03 | 0.99 | 1.01 | 1.07 | 1.09 | 0.98 |
| 2083 | *0.15* | *0.12* | 1.05 | 1.09 | *0.13* | *0.09* |
| 2084 | *0.16* | *0.10* | 1.05 | 1.04 | *0.13* | *0.14* |
| 2085 | 1.00 | 1.09 | 1.09 | 1.20 | 1.10 | 0.97 |
| 2086 | *0.17* | *0.14* | 1.12 | 1.19 | *0.11* | *0.21* |
| 2087 | 1.16 | 1.11 | 1.13 | 1.18 | 1.08 | *0.11* |
| 2088 | *0.12* | *0.16* | 0.96 | 1.07 | *0.13* | *0.17* |
| 2089 | 1.03 | 0.95 | 0.97 | 1.09 | 1.12 | 1.01 |
| 2090 | *0.12* | *0.14* | 1.10 | 1.04 | *0.12* | *0.12* |
| 2091 | *0.13* | *0.23* | 1.02 | 1.06 | *0.15* | *0.10* |
| 2092 | *0.08* | *0.10* | 1.04 | 1.07 | *0.09* | *0.10* |
| 2093 | *0.08* | *0.09* | 0.94 | 1.05 | *0.09* | *0.10* |
| 2094 | *0.08* | *0.09* | 1.01 | 1.05 | *0.09* | *0.09* |
| 2095 | *0.11* | 0.86 | 1.05 | 1.05 | *0.11* | *0.10* |
| 2096 | *0.09* | *0.09* | 1.05 | 1.19 | *0.09* | *0.09* |
| 2097 | *0.09* | *0.13* | 1.09 | 1.07 | *0.09* | *0.09* |
| 2098 | *0.09* | *0.12* | 1.12 | 1.13 | *0.09* | *0.10* |
| 2099 | *0.09* | *0.28* | 1.12 | 1.07 | *0.10* | *0.09* |
| 2100 | 1.07 | 1.07 | 1.08 | 1.08 | 1.10 | 1.09 |
| 2101 | 0.97 | 1.07 | 1.02 | 1.14 | 1.06 | 1.10 |
| 2102 | 0.97 | 0.97 | 0.96 | 1.07 | 1.11 | 1.02 |
| 2103 | 1.00 | 1.04 | 1.11 | 1.07 | 1.12 | 0.99 |
| 2104 | 0.99 | 1.03 | 0.95 | 1.15 | 1.14 | 1.08 |
| 1883 | 1.22 | 1.13 | 1.00 | 0.96 | 1.02 | 1.06 |
| 2105 | 1.02 | 1.06 | 0.99 | 1.15 | 1.18 | 0.94 |
| 2106 | 1.00 | 0.67 | 1.14 | 1.15 | 1.00 | *0.12* |
| 2107 | 0.98 | 1.02 | 1.02 | 1.25 | 1.11 | 0.92 |
| 2108 | 1.12 | 1.03 | 0.96 | 1.15 | 1.05 | 1.10 |
| 2109 | 0.92 | 1.04 | 1.06 | 1.06 | 1.10 | 0.93 |
| 2110 | 0.97 | 1.14 | 1.17 | 1.15 | 1.11 | 0.94 |
| 2111 | 1.05 | *0.37* | 1.05 | 1.12 | *0.34* | *0.12* |
| 2112 | 1.02 | 0.99 | 1.13 | 1.14 | 1.12 | 1.15 |
| 2113 | *0.08* | *0.09* | 1.07 | 1.10 | *0.10* | *0.10* |
| 1884 | 1.12 | 1.01 | 1.12 | 0.93 | 0.98 | 1.05 |
| 2114 | 0.97 | 0.92 | 1.01 | 1.20 | 1.06 | 1.09 |
| 2115 | 0.98 | 0.99 | 1.12 | 1.18 | 1.08 | 1.09 |
| 2116 | 1.13 | 0.87 | 1.00 | 1.15 | 1.10 | 1.14 |
| 2117 | 1.03 | 1.01 | 0.96 | 1.12 | 1.03 | 1.04 |
| 2118 | 1.06 | 1.05 | 1.03 | 1.11 | 1.13 | 1.01 |
| 2119 | 1.11 | 1.00 | 1.07 | 1.10 | 1.15 | 0.97 |
| 2120 | 0.99 | 1.05 | 1.02 | 1.18 | 1.04 | 0.95 |
| 2121 | 0.97 | 0.96 | 1.02 | 1.09 | 1.11 | 1.03 |
| 2122 | 0.86 | 1.09 | 1.21 | 1.13 | 1.12 | 0.92 |
| 1885 | *0.10* | *0.16* | 1.06 | 0.96 | *0.09* | *0.09* |
| 2123 | *0.09* | *0.12* | 1.01 | 0.98 | *0.09* | *0.09* |
| 2124 | *0.09* | *0.10* | 1.03 | 1.17 | *0.09* | *0.10* |
| 2125 | *0.09* | *0.09* | 1.03 | *0.15* | *0.09* | *0.10* |
| 2126 | *0.09* | *0.15* | 1.04 | 1.13 | *0.10* | *0.09* |
| 2127 | 1.03 | 1.03 | 1.03 | 1.14 | 1.01 | 0.97 |
| 2128 | *0.09* | *0.09* | 1.00 | *0.14* | *0.09* | *0.09* |
| 2129 | *0.09* | *0.14* | 1.01 | *0.17* | *0.09* | *0.11* |
| 2130 | *0.09* | *0.19* | 1.00 | 1.16 | *0.10* | *0.11* |
| 2131 | *0.09* | *0.13* | 1.02 | *0.14* | *0.09* | *0.10* |
| 1886 | 0.98 | 1.14 | 0.94 | 1.13 | 1.00 | 1.05 |
| 2132 | 0.92 | 1.05 | 1.04 | 1.10 | 1.01 | 1.04 |
| 1887 | 1.14 | *0.12* | 0.93 | 0.92 | *0.36* | *0.10* |
| 2133 | *0.10* | *0.18* | 1.02 | 1.03 | *0.10* | *0.09* |
| 2134 | 0.88 | 0.85 | 1.01 | 1.26 | 1.11 | 0.89 |

TABLE 20C-continued

| NP # | LP103 | LP106 | LP109 | LP114 | LP124 | LP125 |
|---|---|---|---|---|---|---|
| 2135 | *0.09* | *0.16* | 1.05 | 1.15 | *0.09* | *0.09* |
| 2136 | *0.09* | *0.13* | *0.11* | 1.02 | *0.09* | *0.08* |
| 2137 | *0.09* | *0.16* | 1.21 | 1.20 | *0.10* | *0.09* |
| 2138 | 0.97 | 1.14 | 1.04 | 1.20 | 1.03 | 0.97 |
| 2139 | *0.10* | *0.27* | 1.03 | 1.17 | *0.10* | *0.09* |
| 2140 | 0.86 | *0.18* | 1.08 | 1.09 | 0.54 | *0.17* |
| 2141 | *0.09* | *0.16* | 1.18 | 1.25 | *0.10* | *0.09* |
| 2142 | 1.00 | *0.13* | 1.05 | 1.19 | 1.03 | *0.10* |
| 2143 | 1.06 | 0.50 | 1.03 | 1.32 | 0.98 | *0.15* |
| 2148 | *0.09* | *0.23* | 1.13 | 1.09 | *0.10* | *0.10* |
| 2149 | 0.92 | 1.07 | 1.08 | 1.00 | 0.96 | 1.06 |
| 2150 | 0.78 | *0.32* | 0.99 | 1.11 | 0.60 | *0.19* |
| 2164 | *0.10* | *0.20* | 1.07 | 1.20 | *0.10* | *0.09* |
| 2165 | *0.10* | *0.15* | 0.97 | 1.27 | *0.10* | *0.08* |
| 2166 | 1.12 | 0.93 | 1.03 | 1.37 | 1.06 | 1.03 |
| 2167 | *0.08* | *0.11* | 1.04 | 1.09 | *0.10* | *0.10* |
| 1888 | 1.13 | *0.12* | 1.02 | 0.97 | *0.19* | *0.11* |
| 2151 | 0.92 | *0.15* | 1.15 | 1.09 | 0.54 | *0.11* |
| 2152 | *0.09* | *0.11* | 1.11 | 1.18 | *0.10* | *0.11* |
| 2153 | 0.44 | *0.23* | 1.22 | 1.07 | *0.14* | *0.10* |
| 2154 | 0.90 | *0.25* | 1.39 | 1.12 | *0.22* | *0.11* |
| 2155 | 0.44 | *0.13* | 1.20 | 1.05 | *0.15* | *0.12* |
| 2156 | *0.10* | *0.12* | 1.16 | 1.06 | *0.09* | *0.09* |
| 2157 | *0.09* | *0.11* | 1.17 | 1.20 | *0.09* | *0.09* |
| 2158 | *0.09* | *0.14* | 1.22 | 1.17 | *0.09* | *0.09* |
| 2159 | 1.05 | *0.20* | 1.00 | 1.09 | *0.21* | *0.13* |
| 1889 | *0.10* | *0.18* | 0.99 | 0.97 | *0.10* | *0.11* |
| 2144 | 1.18 | 1.14 | 1.22 | 1.21 | 1.11 | 0.99 |
| 2145 | *0.11* | 0.85 | 1.02 | 1.26 | 0.71 | *0.10* |
| 2146 | *0.09* | *0.14* | 1.15 | 1.16 | *0.10* | *0.09* |
| 2147 | *0.11* | *0.23* | 1.10 | 1.15 | *0.10* | *0.11* |
| 2160 | *0.11* | *0.18* | 1.05 | 1.08 | *0.10* | *0.09* |
| 2161 | *0.10* | *0.28* | 1.05 | 1.15 | *0.10* | *0.10* |
| 2162 | *0.10* | *0.23* | 1.03 | 1.20 | *0.10* | *0.09* |
| 2163 | *0.10* | *0.19* | 1.07 | 1.22 | *0.10* | *0.10* |
| 2168 | *0.08* | 0.41 | 1.05 | 1.06 | *0.10* | *0.09* |
| 1890 | 1.20 | 1.10 | 1.00 | 0.97 | 1.04 | 1.13 |
| 2169 | 0.50 | *0.11* | 1.64 | 1.19 | *0.10* | *0.10* |
| 2170 | *0.08* | *0.16* | 1.09 | 1.08 | *0.10* | *0.09* |
| 2171 | *0.10* | *0.30* | 1.13 | 1.12 | *0.10* | *0.09* |
| 2172 | *0.10* | *0.13* | 1.12 | 1.06 | *0.10* | *0.09* |
| 2173 | *0.09* | *0.11* | 1.06 | 1.04 | *0.11* | *0.09* |
| 2174 | *0.31* | *0.13* | 1.04 | 1.02 | *0.09* | *0.09* |
| 2175 | 0.90 | 1.21 | 1.04 | 1.15 | 1.14 | 0.89 |
| 2176 | 0.84 | 0.43 | 1.15 | 1.13 | 0.65 | *0.14* |
| 2177 | 1.00 | 1.14 | 1.02 | 1.03 | 1.12 | 0.95 |
| 1879 | *0.10* | 0.43 | 0.99 | 1.01 | *0.10* | *0.12* |
| 1911 | 1.18 | 1.03 | 1.06 | 1.09 | *0.27* | 1.13 |
| 1950 | *0.08* | *0.15* | 1.01 | 1.18 | *0.09* | *0.08* |
| 1951 | 0.89 | 0.91 | 1.00 | 1.02 | 1.07 | *0.09* |
| 1952 | *0.09* | *0.12* | *0.38* | *0.17* | *0.09* | *0.09* |
| 1953 | 1.11 | 1.00 | *0.14* | *0.09* | 0.76 | 0.97 |
| 1954 | *0.09* | *0.14* | 0.92 | 0.98 | *0.09* | *0.09* |
| 1955 | 1.09 | *0.10* | *0.14* | *0.09* | 0.74 | 1.01 |
| 1956 | 1.10 | 0.95 | 0.90 | 1.02 | *0.16* | 0.98 |
| 1957 | *0.09* | *0.23* | 1.18 | 1.04 | *0.09* | *0.09* |
| 1958 | *0.09* | *0.14* | 1.03 | 1.07 | *0.09* | *0.09* |
| 1913 | 1.23 | 0.98 | 0.91 | 1.07 | 0.45 | 1.00 |
| 1968 | *0.09* | *0.14* | *0.26* | *0.15* | *0.09* | *0.10* |
| 1969 | *0.09* | *0.14* | 1.16 | 1.02 | *0.10* | *0.10* |
| 1970 | *0.08* | *0.15* | *0.12* | *0.17* | *0.09* | |
| 1971 | 0.07 | *0.13* | 1.16 | 0.98 | *0.09* | *0.09* |
| 1972 | 0.89 | *0.34* | 0.93 | 0.94 | *0.13* | 1.00 |
| 1973 | 1.14 | *0.30* | 0.65 | 1.02 | *0.17* | 1.01 |
| 1974 | 0.98 | 0.86 | 0.76 | 0.82 | *0.15* | 1.05 |
| 1975 | *0.11* | *0.13* | 0.95 | 0.85 | *0.09* | *0.10* |
| 1976 | *0.08* | *0.27* | 0.83 | 0.85 | *0.09* | *0.10* |
| 1891 | 1.07 | 1.13 | 1.02 | 1.06 | 1.04 | 1.12 |
| 1892 | 1.12 | 1.13 | 1.17 | 1.02 | 1.03 | 1.06 |
| 1893 | 1.11 | 1.11 | 1.19 | 0.96 | 1.02 | 1.12 |
| 1894 | 1.13 | 1.14 | 1.04 | 1.01 | 1.05 | 1.03 |
| 1895 | *0.10* | *0.15* | 1.09 | 1.00 | *0.11* | *0.11* |
| 1896 | *0.11* | *0.14* | 1.13 | 1.03 | *0.11* | *0.10* |
| 1897 | *0.08* | *0.12* | 1.01 | 1.04 | *0.09* | *0.09* |
| 1898 | *0.08* | *0.23* | 0.97 | 1.00 | *0.08* | *0.10* |
| 1899 | 1.14 | 1.03 | 1.00 | 0.99 | 0.97 | 1.20 |
| 1990 | 0.94 | 1.01 | 0.95 | 0.90 | 0.46 | 1.00 |
| 1991 | 0.96 | 0.97 | 0.99 | 0.91 | 0.40 | 1.03 |
| 1992 | 0.92 | 1.08 | 0.82 | 0.94 | *0.36* | 1.03 |
| 1993 | 1.02 | 1.11 | 0.86 | 1.01 | *0.11* | 0.95 |
| 1994 | 1.13 | 0.98 | 1.05 | 0.98 | *0.10* | 1.08 |
| 1995 | 1.10 | 1.03 | 0.84 | 0.97 | *0.10* | 1.09 |
| 1996 | 0.76 | *0.14* | *0.09* | *0.09* | *0.20* | 1.07 |
| 1910 | *0.14* | *0.36* | *0.09* | *0.09* | *0.09* | 1.14 |
| 1945 | *0.09* | *0.19* | 0.97 | 1.04 | *0.09* | *0.10* |
| 1946 | *0.10* | *0.13* | *0.09* | *0.09* | *0.09* | 1.14 |
| 1947 | *0.09* | *0.10* | *0.10* | *0.10* | *0.10* | 1.14 |
| 1948 | 1.09 | 1.19 | *0.09* | *0.09* | 0.59 | 1.07 |
| 1949 | *0.15* | 0.70 | *0.09* | *0.09* | *0.11* | 1.07 |
| 1977 | 0.89 | 0.56 | 0.69 | *0.09* | *0.34* | 1.04 |
| 1978 | 1.12 | 1.15 | 0.99 | 0.90 | 1.03 | 1.06 |
| 1979 | 1.11 | 1.09 | 1.01 | 0.85 | 0.99 | 1.05 |
| 1980 | 1.00 | 1.18 | 0.94 | 1.01 | 1.01 | 1.08 |
| 1981 | 0.95 | 1.09 | 1.08 | 1.12 | 0.96 | 0.98 |
| 1982 | 1.07 | 1.19 | 1.08 | 1.10 | 1.08 | 1.02 |
| 1983 | *0.09* | *0.14* | 0.88 | *0.11* | *0.09* | *0.10* |
| 1984 | 1.05 | 1.07 | 0.83 | 1.02 | 0.98 | 1.03 |
| 1985 | 1.04 | 1.04 | *0.34* | *0.09* | 1.02 | 1.03 |
| 1914 | *0.17* | *0.16* | *0.09* | *0.12* | *0.16* | 1.16 |
| 1986 | *0.16* | *0.11* | *0.09* | *0.12* | *0.14* | 1.03 |
| 1987 | *0.15* | *0.12* | *0.09* | *0.11* | *0.12* | 1.06 |
| 1988 | *0.16* | *0.11* | *0.09* | *0.12* | *0.12* | 1.01 |
| 1989 | *0.09* | *0.15* | *0.12* | *0.31* | *0.10* | *0.09* |
| 1917 | 1.17 | 1.15 | 1.02 | 1.03 | 1.03 | 1.04 |
| 2015 | 0.98 | 0.98 | *0.12* | *0.10* | 0.83 | 1.02 |
| 2016 | 1.00 | 0.96 | *0.13* | *0.10* | 0.83 | 1.05 |
| 2017 | 0.97 | 1.11 | *0.14* | *0.10* | 0.81 | 0.98 |
| 2018 | 1.01 | 1.25 | *0.15* | *0.11* | 0.85 | 0.98 |
| 2019 | 1.05 | 1.05 | *0.13* | *0.11* | 0.94 | 0.98 |
| 2020 | 0.69 | 0.78 | 1.09 | 1.21 | *0.30* | 0.99 |
| 2021 | 1.05 | 1.10 | 1.05 | 1.19 | 0.96 | 1.06 |
| 2022 | 1.10 | 1.06 | 1.06 | 1.14 | 0.96 | 0.98 |
| 2023 | 1.10 | 1.03 | 1.01 | 0.99 | 1.11 | 0.95 |

TABLE 20D

| NP # | LP128 | LP129 | LP141 | LP143 | LP177 |
|---|---|---|---|---|---|
| 1900 | 0.54 | 1.01 | 1.10 | *0.30* | 0.79 |
| 1901 | *0.10* | *0.09* | *0.10* | *0.10* | *0.09* |
| 1902 | *0.10* | *0.09* | *0.10* | *0.36* | 0.55 |
| 1903 | *0.10* | *0.09* | *0.11* | *0.10* | *0.10* |
| 1904 | *0.10* | *0.10* | *0.11* | *0.11* | *0.10* |
| 1905 | *0.10* | *0.10* | *0.11* | *0.10* | *0.10* |
| 1906 | *0.09* | *0.10* | *0.10* | *0.20* | 0.48 |
| 1907 | 0.55 | 1.11 | 1.02 | *0.28* | 0.64 |
| 1908 | *0.09* | *0.09* | *0.11* | *0.11* | *0.09* |
| 1909 | 0.53 | 1.26 | 1.11 | *0.17* | 0.76 |
| 1912 | 0.56 | 0.75 | 1.10 | 0.62 | 0.61 |
| 1959 | 0.60 | 0.96 | 0.84 | *0.09* | *0.09* |
| 1960 | *0.09* | *0.09* | *0.10* | *0.11* | *0.10* |
| 1961 | 0.48 | 0.96 | 0.95 | *0.12* | *0.09* |
| 1962 | 0.44 | 0.62 | 0.85 | *0.12* | 0.52 |
| 1963 | 0.61 | 0.91 | 0.86 | *0.09* | *0.08* |
| 1964 | 0.72 | 0.97 | 0.95 | *0.09* | *0.08* |
| 1965 | 0.47 | 0.92 | 0.93 | *0.09* | *0.08* |
| 1966 | 0.63 | 0.79 | 0.98 | *0.09* | *0.08* |
| 1967 | 0.45 | 0.95 | 0.89 | *0.09* | *0.09* |
| 1915 | 0.67 | 0.75 | 1.04 | *0.09* | *0.12* |
| 1997 | 0.64 | 0.84 | 1.07 | *0.09* | *0.10* |
| 1998 | 0.76 | 0.95 | 0.74 | *0.09* | *0.11* |
| 1999 | 0.98 | 0.90 | 0.95 | *0.09* | *0.10* |
| 2000 | 0.77 | 1.02 | 0.94 | *0.09* | *0.10* |
| 2001 | 0.59 | 0.85 | 0.97 | *0.10* | *0.11* |
| 2002 | 0.59 | 1.07 | 1.14 | *0.11* | *0.11* |
| 2003 | 0.57 | 1.00 | 1.04 | *0.10* | 1.01 |
| 2004 | 0.54 | *0.36* | 1.16 | *0.10* | *0.23* |
| 2005 | 0.45 | 0.99 | 1.18 | *0.11* | 1.08 |
| 1916 | *0.16* | 0.65 | *0.16* | 0.68 | 0.72 |
| 2006 | *0.20* | 0.53 | *0.29* | *0.39* | 0.78 |
| 2007 | *0.11* | *0.09* | *0.10* | *0.11* | *0.13* |
| 2008 | *0.11* | *0.09* | *0.10* | *0.11* | *0.13* |
| 2009 | *0.10* | *0.09* | *0.28* | *0.12* | *0.13* |

TABLE 20D-continued

| NP # | LP128 | LP129 | LP141 | LP143 | LP177 |
|---|---|---|---|---|---|
| 2010 | *0.20* | 0.79 | 0.66 | *0.30* | 0.90 |
| 2011 | *0.14* | 0.65 | 0.46 | 0.44 | 0.56 |
| 2012 | 0.79 | 1.11 | 1.14 | 0.43 | 0.81 |
| 2013 | 0.86 | 1.02 | 1.10 | 0.44 | 0.89 |
| 2014 | *0.13* | 0.84 | *0.25* | 0.43 | 0.51 |
| 1869 | *0.15* | *0.12* | *0.13* | *0.22* | *0.14* |
| 1840 | *0.10* | *0.10* | *0.11* | 1.06 | 1.10 |
| 1839 | 1.21 | 0.98 | 1.28 | *0.18* | *0.47* |
| 2024 | 1.06 | 1.09 | 1.07 | *0.10* | *0.10* |
| 2025 | 1.13 | 1.18 | 1.07 | *0.09* | *0.11* |
| 2026 | 1.10 | 0.72 | 1.02 | *0.28* | 0.61 |
| 2027 | 1.09 | 1.09 | 1.06 | *0.10* | *0.11* |
| 2028 | 1.02 | 1.01 | 1.02 | *0.10* | *0.09* |
| 2029 | 1.04 | 1.11 | 1.12 | *0.20* | *0.14* |
| 2030 | 1.01 | 1.01 | 1.06 | *0.10* | *0.09* |
| 2031 | 1.00 | 1.02 | 1.01 | *0.10* | *0.09* |
| 2032 | 1.01 | 0.99 | 1.13 | *0.10* | *0.09* |
| 1878 | 1.14 | 1.22 | 1.20 | *0.11* | *0.11* |
| 2033 | 1.10 | 1.02 | 1.03 | *0.10* | *0.10* |
| 2034 | 1.09 | 0.98 | 1.01 | *0.10* | *0.10* |
| 2035 | 1.10 | 0.96 | 1.00 | *0.10* | *0.10* |
| 2036 | 1.07 | 0.95 | 1.09 | *0.09* | *0.09* |
| 2037 | 1.10 | 1.04 | 1.16 | *0.10* | *0.10* |
| 2038 | 1.09 | 0.98 | 1.00 | *0.09* | *0.10* |
| 2039 | 1.13 | 0.93 | 1.10 | *0.09* | *0.10* |
| 2040 | 1.27 | 0.96 | 1.02 | *0.10* | *0.11* |
| 2041 | 1.09 | 1.03 | 1.09 | *0.10* | *0.10* |
| 2042 | *0.24* | 1.07 | 1.09 | *0.10* | *0.09* |
| 2043 | *0.23* | 1.12 | 1.10 | *0.09* | *0.10* |
| 2044 | *0.29* | 1.24 | 1.17 | *0.09* | *0.11* |
| 2045 | *0.19* | 0.85 | 1.18 | *0.14* | *0.10* |
| 2046 | *0.18* | 1.09 | 1.20 | *0.10* | *0.10* |
| 2047 | *0.25* | 1.01 | 1.24 | *0.11* | *0.11* |
| 2048 | *0.23* | 0.44 | 0.95 | *0.14* | *0.19* |
| 2049 | *0.28* | 1.04 | 1.05 | *0.09* | *0.10* |
| 2050 | *0.20* | 1.07 | 1.05 | *0.10* | *0.10* |
| 1880 | 1.02 | 1.10 | 1.17 | 1.06 | 0.84 |
| 2051 | 1.11 | 1.03 | 0.98 | *0.10* | *0.10* |
| 2052 | 1.12 | 1.05 | 1.24 | *0.10* | *0.10* |
| 2053 | 1.07 | 1.11 | 1.21 | *0.10* | *0.10* |
| 2054 | 1.03 | 0.98 | 1.11 | *0.12* | *0.09* |
| 2055 | 1.02 | 1.02 | 1.17 | *0.09* | *0.09* |
| 2056 | 1.03 | 1.08 | 1.34 | *0.10* | *0.09* |
| 2057 | 1.00 | 1.05 | 1.13 | *0.10* | *0.10* |
| 2058 | 1.02 | 1.18 | 1.07 | *0.10* | *0.10* |
| 2059 | 1.09 | 1.00 | 1.05 | *0.10* | *0.10* |
| 1881 | 1.13 | 1.20 | 1.00 | 1.07 | 1.02 |
| 2060 | 1.07 | 0.97 | 1.10 | *0.30* | *0.11* |
| 2061 | 1.07 | 1.02 | 0.97 | *0.18* | *0.11* |
| 2062 | 1.09 | 0.99 | 0.93 | *0.18* | *0.12* |
| 2063 | 0.95 | 0.93 | 0.92 | 1.17 | 1.06 |
| 2064 | 0.99 | 0.82 | 1.00 | *0.09* | *0.09* |
| 2065 | 1.03 | 1.06 | 1.07 | *0.16* | *0.11* |
| 2066 | 1.00 | 0.99 | 1.04 | *0.18* | *0.13* |
| 2067 | 1.15 | 1.01 | 1.08 | 1.05 | 1.21 |
| 2068 | 1.14 | 1.07 | 1.02 | 1.27 | 1.21 |
| 2069 | 1.13 | 0.92 | 1.04 | 0.52 | *0.25* |
| 2070 | 1.13 | 1.02 | 0.93 | *0.11* | *0.11* |
| 2071 | 1.17 | 1.22 | 1.03 | 1.18 | 1.17 |
| 2072 | 1.11 | 1.32 | 1.03 | *0.10* | *0.12* |
| 2073 | 1.06 | 0.98 | 0.92 | 1.26 | 1.04 |
| 2074 | 1.08 | 1.03 | 1.48 | *0.09* | *0.10* |
| 2075 | 0.99 | 1.07 | 1.05 | *0.18* | *0.12* |
| 2076 | 1.06 | 0.97 | 1.02 | *0.10* | *0.10* |
| 2077 | 1.16 | 1.06 | 1.04 | *0.09* | *0.11* |
| 1882 | 1.07 | 1.22 | 0.99 | *0.10* | *0.10* |
| 2078 | 1.07 | 0.94 | 0.97 | *0.14* | *0.14* |
| 2079 | 1.21 | 0.84 | 0.98 | 1.09 | 1.14 |
| 2080 | 1.08 | 0.84 | 0.96 | 1.13 | 1.09 |
| 2081 | 1.26 | 0.99 | 1.03 | 1.06 | 1.23 |
| 2082 | 1.11 | 1.05 | 1.04 | 1.07 | 1.14 |
| 2083 | 1.05 | 1.18 | 1.02 | *0.13* | *0.12* |
| 2084 | 1.07 | 1.03 | 0.99 | *0.13* | *0.12* |
| 2085 | 1.09 | 1.02 | 0.99 | 1.17 | 1.12 |
| 2086 | 1.09 | 1.14 | 1.06 | *0.11* | *0.12* |
| 2087 | 0.92 | 1.02 | 0.95 | 1.22 | 1.00 |
| 2088 | *0.32* | 0.89 | 0.99 | *0.14* | *0.12* |
| 2089 | 1.09 | 1.01 | 0.97 | 1.09 | 1.14 |
| 2090 | *0.36* | 0.81 | 1.00 | *0.12* | *0.11* |
| 2091 | 1.11 | 1.00 | 1.02 | *0.11* | *0.12* |
| 2092 | *0.33* | 1.00 | 1.05 | *0.09* | *0.11* |
| 2093 | *0.37* | 1.08 | 1.03 | *0.09* | *0.11* |
| 2094 | 0.41 | 1.03 | 1.00 | *0.09* | *0.11* |
| 2095 | 1.17 | 1.01 | 1.08 | *0.11* | *0.12* |
| 2096 | 1.18 | 1.01 | 1.11 | *0.09* | *0.11* |
| 2097 | 1.12 | 0.98 | 0.98 | *0.10* | *0.10* |
| 2098 | 1.03 | 0.95 | 0.92 | *0.09* | *0.09* |
| 2099 | 1.16 | 0.91 | 0.99 | *0.10* | *0.11* |
| 2100 | 1.29 | 1.03 | 1.03 | 1.04 | 1.12 |
| 2101 | 1.29 | 1.04 | 1.00 | 1.07 | 1.18 |
| 2102 | 1.31 | 0.99 | 0.98 | 1.05 | 1.19 |
| 2103 | 1.18 | 0.99 | 0.99 | 1.05 | 1.12 |
| 2104 | 1.25 | 1.00 | 1.01 | 1.03 | 1.22 |
| 1883 | 1.04 | 1.11 | 0.90 | 1.16 | 1.06 |
| 2105 | 1.15 | 1.10 | 1.03 | 1.17 | 1.11 |
| 2106 | 1.25 | 1.09 | 1.16 | 0.92 | 1.01 |
| 2107 | 1.16 | 0.97 | 1.01 | 1.16 | 1.13 |
| 2108 | 1.12 | 1.00 | 1.03 | 1.10 | 1.09 |
| 2109 | *0.21* | 0.99 | 1.05 | 1.25 | 1.07 |
| 2110 | 1.03 | 1.05 | 0.96 | 1.17 | 1.00 |
| 2111 | 1.02 | 0.95 | 0.83 | 0.77 | *0.35* |
| 2112 | 1.12 | 1.00 | 0.99 | 1.19 | 1.10 |
| 2113 | 1.08 | 0.99 | 1.00 | *0.10* | *0.10* |
| 1884 | *0.19* | 1.05 | 0.84 | 0.98 | 0.97 |
| 2114 | *0.27* | 0.92 | 0.98 | 1.10 | 1.07 |
| 2115 | *0.26* | 0.95 | 0.97 | 1.10 | 1.02 |
| 2116 | *0.26* | 0.98 | 0.99 | 1.11 | 1.12 |
| 2117 | *0.40* | 1.03 | 1.00 | 1.11 | 0.84 |
| 2118 | *0.21* | 1.01 | 1.00 | 1.16 | 0.99 |
| 2119 | *0.15* | 1.04 | 1.11 | 1.10 | 0.47 |
| 2120 | *0.22* | 0.95 | 1.02 | 1.13 | 1.08 |
| 2121 | *0.21* | 0.97 | 1.17 | 1.17 | 1.04 |
| 2122 | *0.15* | 1.07 | 0.98 | 1.19 | 0.88 |
| 1885 | 1.01 | 1.09 | 1.02 | *0.09* | *0.09* |
| 2123 | *0.10* | *0.14* | 1.04 | *0.09* | *0.09* |
| 2124 | *0.16* | 0.86 | 1.09 | *0.09* | *0.10* |
| 2125 | *0.10* | *0.13* | *0.32* | *0.09* | *0.09* |
| 2126 | 1.14 | 1.10 | 1.20 | *0.10* | *0.11* |
| 2127 | 1.08 | 0.97 | 1.06 | 1.09 | 1.03 |
| 2128 | *0.11* | *0.12* | *0.31* | *0.09* | *0.11* |
| 2129 | *0.11* | *0.13* | 0.49 | *0.09* | *0.10* |
| 2130 | *0.25* | 0.85 | 1.15 | *0.10* | *0.11* |
| 2131 | *0.12* | *0.12* | *0.32* | *0.09* | *0.11* |
| 1886 | 1.01 | 0.98 | 0.95 | 1.01 | 0.99 |
| 2132 | 1.25 | 0.96 | 1.11 | 1.03 | 1.17 |
| 1887 | 1.08 | 1.04 | 0.99 | 1.17 | *0.12* |
| 2133 | 1.10 | 1.00 | 1.10 | *0.10* | *0.10* |
| 2134 | 1.00 | 0.94 | 1.03 | 1.24 | 1.07 |
| 2135 | 1.02 | 1.14 | 1.00 | *0.09* | *0.09* |
| 2136 | 1.05 | 1.10 | 0.97 | *0.09* | *0.10* |
| 2137 | 1.07 | 1.13 | 0.97 | *0.09* | *0.10* |
| 2138 | 1.09 | 1.03 | 0.84 | 1.08 | 1.09 |
| 2139 | 1.10 | 1.03 | 1.11 | *0.09* | *0.10* |
| 2140 | 1.08 | 1.00 | 0.93 | 0.88 | 1.08 |
| 2141 | 1.03 | 0.96 | 0.96 | *0.11* | *0.10* |
| 2142 | 1.08 | 1.05 | 1.18 | 0.83 | 0.96 |
| 2143 | 1.11 | 1.07 | 1.00 | 1.03 | 1.07 |
| 2148 | 1.08 | 1.08 | 1.00 | *0.09* | *0.10* |
| 2149 | 1.02 | 1.18 | 0.96 | 1.06 | 1.17 |
| 2150 | 1.10 | 1.00 | 0.86 | 0.71 | *0.31* |
| 2164 | 1.06 | 1.06 | 0.98 | *0.10* | *0.09* |
| 2165 | 1.04 | 1.03 | 0.97 | *0.10* | *0.09* |
| 2166 | 1.02 | 1.15 | 1.24 | 1.09 | 0.97 |
| 2167 | 1.07 | 0.80 | 0.92 | *0.10* | *0.10* |
| 1888 | 1.08 | 1.14 | 1.09 | *0.22* | *0.19* |
| 2151 | 1.15 | 0.94 | 0.90 | *0.36* | *0.28* |
| 2152 | 1.10 | 0.97 | 1.05 | *0.10* | *0.10* |
| 2153 | 1.09 | 1.03 | 0.95 | *0.16* | *0.15* |
| 2154 | 1.11 | 0.95 | 0.85 | *0.29* | *0.30* |
| 2155 | 1.06 | 1.07 | 1.18 | *0.19* | *0.17* |
| 2156 | 0.99 | 0.95 | 1.02 | *0.09* | *0.10* |
| 2157 | 1.01 | 1.07 | 0.99 | *0.09* | *0.09* |
| 2158 | 0.97 | 0.81 | 0.91 | *0.09* | *0.10* |
| 2159 | 1.06 | 0.93 | 1.09 | 0.40 | *0.35* |
| 1889 | 1.03 | 1.09 | 1.09 | *0.10* | *0.09* |
| 2144 | 1.10 | 1.11 | 1.04 | 1.07 | 1.08 |

TABLE 20D-continued

| NP # | LP128 | LP129 | LP141 | LP143 | LP177 |
|---|---|---|---|---|---|
| 2145 | 1.03 | 1.07 | 1.06 | 0.64 | 0.94 |
| 2146 | 1.05 | 1.04 | 1.05 | *0.10* | *0.10* |
| 2147 | 1.06 | 0.98 | 0.99 | *0.10* | *0.10* |
| 2160 | 1.01 | 0.89 | 1.05 | *0.10* | *0.10* |
| 2161 | 1.06 | 0.95 | 1.08 | *0.10* | *0.10* |
| 2162 | 1.02 | 0.96 | 1.05 | *0.10* | 0.09 |
| 2163 | 0.98 | 0.92 | 0.97 | *0.10* | *0.10* |
| 2168 | 1.13 | 0.93 | 0.93 | *0.10* | *0.10* |
| 1890 | 1.06 | 1.12 | 1.07 | 1.03 | 1.01 |
| 2169 | 1.12 | 0.90 | 1.11 | *0.10* | *0.10* |
| 2170 | 1.12 | 0.82 | 0.94 | *0.10* | *0.11* |
| 2171 | 1.10 | 0.86 | 0.91 | *0.11* | *0.11* |
| 2172 | 1.15 | 0.83 | 1.07 | *0.10* | *0.12* |
| 2173 | 1.03 | 0.84 | 0.95 | *0.11* | *0.10* |
| 2174 | 1.09 | 3.35 | 3.43 | *0.10* | *0.10* |
| 2175 | 1.14 | 0.91 | 0.97 | 1.11 | 1.11 |
| 2176 | 0.98 | 0.95 | 0.97 | 0.58 | 0.89 |
| 2177 | 1.02 | 1.01 | 1.08 | 1.18 | 1.05 |
| 1879 | 0.99 | 1.30 | 1.20 | *0.10* | 0.09 |
| 1911 | *0.18* | 0.94 | 1.23 | *0.14* | *0.30* |
| 1950 | 0.91 | 1.08 | 1.07 | 0.09 | 0.09 |
| 1951 | 0.98 | 0.89 | 0.98 | 1.00 | 0.98 |
| 1952 | *0.10* | *0.11* | 0.98 | 0.09 | 0.09 |
| 1953 | *0.10* | 0.09 | *0.11* | *0.27* | 0.79 |
| 1954 | 1.02 | 1.06 | 1.05 | 0.09 | *0.10* |
| 1955 | *0.09* | *0.09* | *0.11* | *0.27* | 0.81 |
| 1956 | *0.19* | 0.96 | 1.00 | *0.10* | *0.28* |
| 1957 | 1.09 | 0.92 | 0.96 | 0.09 | 0.09 |
| 1958 | 1.02 | 0.99 | 0.92 | 0.09 | 0.09 |
| 1913 | *0.17* | 0.97 | 1.18 | *0.35* | *0.20* |
| 1968 | *0.09* | *0.11* | 0.99 | 0.09 | 0.08 |
| 1969 | 0.92 | 0.99 | 0.86 | *0.10* | 0.08 |
| 1970 | *0.11* | *0.20* | 0.97 | 0.09 | 0.08 |
| 1971 | 0.98 | 0.84 | 0.87 | *0.08* | 0.09 |
| 1972 | *0.17* | *0.21* | 0.95 | *0.11* | *0.20* |
| 1973 | *0.24* | 0.79 | 0.95 | *0.11* | *0.27* |
| 1974 | *0.18* | 0.81 | 0.95 | *0.11* | *0.20* |
| 1975 | 1.14 | 1.26 | 1.27 | 0.09 | *0.19* |
| 1976 | 1.03 | 1.00 | 0.89 | 0.09 | 0.09 |
| 1891 | 1.07 | 1.06 | 1.02 | 1.06 | 1.14 |
| 1892 | 1.15 | 1.13 | 1.00 | 1.04 | 1.11 |
| 1893 | 1.09 | 1.11 | 0.95 | 1.13 | 1.09 |
| 1894 | 1.15 | 1.05 | 0.92 | 1.02 | 1.14 |
| 1895 | 1.11 | 1.08 | 0.95 | *0.11* | *0.11* |
| 1896 | 0.99 | 0.95 | 0.91 | 0.09 | *0.10* |
| 1897 | 0.98 | 1.01 | 0.97 | *0.09* | *0.09* |
| 1898 | 1.07 | 0.96 | 0.85 | *0.08* | *0.09* |
| 1899 | 0.99 | 0.99 | 1.07 | 1.00 | 1.03 |
| 1990 | *0.12* | *0.27* | 1.11 | 0.09 | *0.20* |
| 1991 | *0.12* | *0.31* | 1.12 | *0.10* | *0.19* |
| 1992 | *0.13* | *0.28* | 1.07 | 0.09 | *0.22* |
| 1993 | *0.11* | *0.21* | 1.16 | *0.10* | 0.58 |
| 1994 | *0.11* | *0.28* | 1.08 | 0.09 | 1.16 |
| 1995 | *0.13* | *0.22* | 1.05 | *0.10* | 0.71 |
| 1996 | *0.11* | *0.09* | *0.10* | 0.09 | *0.33* |
| 1910 | *0.11* | *0.09* | *0.10* | 0.09 | *0.12* |
| 1945 | *0.35* | 0.81 | 0.99 | 0.09 | *0.12* |
| 1946 | *0.11* | *0.09* | *0.09* | 0.09 | *0.11* |
| 1947 | *0.11* | *0.09* | *0.09* | 0.09 | *0.11* |
| 1948 | *0.11* | *0.09* | *0.09* | *0.31* | 1.04 |
| 1949 | *0.09* | *0.09* | *0.09* | *0.10* | *0.10* |
| 1977 | *0.09* | *0.10* | *0.10* | *0.31* | *0.26* |
| 1978 | 1.10 | 1.10 | 1.17 | 1.00 | 1.06 |
| 1979 | 0.95 | 1.10 | 0.97 | 0.87 | 0.85 |
| 1980 | 1.08 | 1.06 | 0.98 | 0.99 | 0.98 |
| 1981 | 1.01 | 0.97 | 0.93 | 0.87 | 0.93 |
| 1982 | 0.97 | 1.06 | 0.93 | 1.10 | 1.13 |
| 1983 | *0.11* | 1.02 | 0.91 | *0.10* | *0.11* |
| 1984 | 0.95 | 1.05 | 1.04 | 0.94 | 1.00 |
| 1985 | *0.10* | *0.08* | *0.09* | 1.00 | 1.01 |
| 1914 | *0.11* | *0.10* | *0.11* | *0.15* | *0.14* |
| 1986 | *0.11* | *0.09* | *0.13* | *0.14* | *0.15* |
| 1987 | *0.11* | *0.09* | *0.12* | *0.14* | *0.14* |
| 1988 | *0.10* | *0.09* | *0.11* | *0.13* | *0.12* |
| 1989 | *0.13* | 0.98 | 1.04 | *0.10* | *0.11* |
| 1917 | 0.81 | 1.20 | 0.90 | 1.05 | 0.71 |
| 2015 | *0.10* | *0.11* | *0.22* | 0.67 | 0.55 |
| 2016 | *0.11* | *0.11* | *0.21* | 0.61 | 0.58 |
| 2017 | 0.10 | 0.11 | 0.22 | 0.58 | 0.56 |
| 2018 | 0.11 | 0.10 | 0.27 | 0.66 | 0.70 |
| 2019 | 0.11 | 0.10 | 0.24 | 0.74 | 0.59 |
| 2020 | 0.30 | 1.11 | 0.13 | 0.25 | 0.22 |
| 2021 | 0.78 | 1.09 | 1.18 | 0.82 | 0.88 |
| 2022 | 0.82 | 1.16 | 1.11 | 0.79 | 0.96 |
| 2023 | 1.04 | 1.04 | 1.09 | 1.03 | 1.08 |

Example 19: Cloning and Genetically Modifying Phage T3

A. Phage Capture

Phage T3 was cloned and manipulated in the following manner. T3 was grown using E. coli DH10B as a host, grown in Luria Broth (LB)+2 mM calcium chloride. The phage lysate was concentrated via incubation with 10% polyethylene glycol-8000 overnight at 4° C., followed by centrifugation. The pellet was resuspended in SM buffer (Sambrook et al., Molecular Cloning: A Laboratory Manual, 3d ed., Cold Spring Harbor Laboratory Press, Cold Spring Harbor, N.Y. (2001)). DNA was prepared from the concentrated T3 lysate using the Norgen Phage DNA kit (Cat#46700). The genomic sequence of T3 (NCBI accession #NC_003298) was used to design oligos to capture T3 into the pYES1L vector (Invitrogen®). Oligos used were duplexes of:

[SEQ ID NO: 78]
CCTAGTGTACCAGTATGATAGTACATCTCTATGTGTCCCTCCTCGCCGCA
GTTAATTAAAGTCAGTGAGCGAGGAAGCGC
and its complement, and duplexes of:

[SEQ ID NO: 79]
GAACGACCGAGCGCAGCGGCGGCCGCGCTGATACCGCCGCTCTCATAGTT
CAAGAACCCAAAGTACCCCCCCCATAGCCC
and its complement.

The oligos were transformed into competent MaV203 yeast cells (Invitrogen®) together with purified T3 DNA and yeast artificial chromosome pYES1L Transformed cells were plated on synthetic complete media without tryptophan, selecting for the TRP marker on pYES1L. Colonies that grew on synthetic complete trp-minus were screened by PCR to show successful capture of the T3 genome.

B. YAC to Plaque

Selected MaV203 cells that contained the pYES1L-T3 phage-YAC were grown up and g lass-bead lysates were prepared (Invitrogen® High-Order Genetic Assembly kit) and electroporated into TOP10 E. coli. The transformations were mixed with LB+2 mM calcium chloride top agar, and plated on an LB+2 mM calcium chloride agar plate. Incubations overnight revealed plaques, corresponding to the captured phage. Captured phages typically yielded $1 \times 10^2$ to $1 \times 10^4$ plaques per transformation.

C. Luciferase Insertion into Cloned T3 Phage

Expression cassettes were designed for insertion into different locations of the T3 genome. The cassettes contain an intact luciferase open reading frame inserted to take the place of an endogenous T3 gene such that luciferase expression is driven by the endogenous T3 promoter, followed by the URA3 gene with its own promoter, and optionally a direct repeat of the 3' end of the luciferase gene. Insertions were made into the T3 0.7 and 4.3 genes. In T3::0.7 luc a cassette containing luciferase and URA3 is swapped into the T3 0.7 gene. In T3::0.7DRluc a cassette containing luciferase, URA3, and a direct repeat of the 3' end of the luciferase gene is swapped into the T3 0.7 gene. In T3::4.3DRluc a cassette containing luciferase, URA3, and a direct repeat of the 3' end of the luciferase gene is swapped into the T3 4.3 gene. In T3::0.7IceuILuc a cassette containing luciferase, URA3, and a ICeu I homing endonuclease site is swapped into the T3 0.7 gene.

For insertion, the cassettes were amplified as two or three PCR products, one containing the luciferase and flanking homology to a first site in the phage, the second containing the URA3 gene with flanking homology to the other two PCR products, and the third containing a fragment of luciferase, and homology to a different site on the phage chromosome. The constructs were designed to replace the targeted gene without deleting other adjacent sequences. The internal fragment containing URA3 was amplified using primers:

[SEQ ID NO: 80]
CCTCATAAAGGCCAAGAAGGGCGGAAAGTCCAAATTGTAAACGGATTCAC
CACTCCAAGA and

[SEQ ID NO: 81]
ATAATCATAGGTCCTCTGACACATAATTCGCCTCTCTGATTCAACGACAG
GAGCACGATC.

The 3' end of the full luciferase fragment was amplified by:

[SEQ ID NO: 82]
AAGAATTGATTGGCTCCAATTCTTGGAGTGGTGAATCCGTTTACAATTTG

GACTTTCCGC.

The 5' end of the shorter luciferase fragment was amplified by:

[SEQ ID NO: 83]
TCCTGGCCACGGGTGCGCATGATCGTGCTCCTGTCGTTGAATCAGAGAGG

CGAATTATGT.

For inserting this duplication cassette at the T3 0.7 gene, the 5' end of the full luciferase fragment was amplified with:

[SEQ ID NO: 84]
AATTTACTCTTTACTCTTACAGATAACAGGACACTGAACGATGGAAGACG

CCAAAAACAT, and the 3' end of the shorter luciferase fragment with:

[SEQ ID NO: 85]
ATTCAGGCCACCTCATGATGACCTGTAAGAAAAGACTCTATTACAATTTG

GACTTTCCGC.

For insertions at the 4.3 gene site, the 5' end of the full luciferase fragment was amplified with:

[SEQ ID NO: 86]
CTCACTAACGGGAACAACCTCAAACCATAGGAGACACATCATGGAAGACG

CCAAAAACAT, and the 3' end of the shorter luciferase fragment with

[SEQ ID NO: 87]
TGTTTGCGTGCTTGATTGATTTACTCATGTTGTGCTCCTATTACAATTTG

GACTTTCCGC.

In each case (0.7 and 4.3 gene sites), 3 PCR products were created, and co-transformed into yeast containing the T3-YAC described above. Recombination was selected by growing cells in the absence of uracil. Colonies that grew in the absence of uracil were screened by PCR for presence of the cassette. Colonies positive by PCR were subjected to the YAC-to-plaque technique (described above) to recover viable phages. These phages were subsequently screened by PCR to confirm the presence of the cassette.

D. Expression of Luciferase in Recombinant Phage

An overnight culture of *E. coli* cells was diluted 1/100 and grown into mid-log phase in LB+1 mM calcium chloride (approximately 2 and a half hours). Cells were diluted and infected with a vast excess of phages ($1 \times 10^7$ phages per infection) in a total of 100 µl. Infections were allowed to proceed, non-shaking at 37 degrees C. After 90 minutes, 100 µl of Promega® Steady-Glo luciferase detection reagent was added to 20 uL of infection, and infections were immediately read on a Promega® GloMax 20/20. Cells infected with the different engineered phage showed some variation of expression levels, but cells infected with T3::0.7Luc, T3::DRLuc, T3::4.3DRLuc, and T3::0.7IceuILuc all expressed detectable levels of luciferase.

Example 20: Cloning and Genetically Modifying Phage T7

A. Phage Capture

T7 luc was created in a slightly different manner than the engineered T3 phage of Example 19.

T7 dspB (T. K. Lu and J. J. Collins, "Dispersing Biofilms with Engineered Enzymatic Bacteriophage," Proceedings of the National Academy of Sciences, vol. 104, no. 27, pp. 11197-11202, Jul. 3, 2007, incorporated herein by reference) was captured in pYES1L by transforming genomic DNA of T7 dspB, YAC pYES1L, a duplex of:

[SEQ ID NO: 88]
TTGTCTTTGGGTGTTACCTTGAGTGTCTCTCTGTGTCCCTCCTCGCCGCA
GTTAATTAAAGTCAGTGAGCGAGGAAGCGC
and its complement, and a duplex of:

[SEQ ID NO: 89]
CCCGAACGACCGAGCGCAGCGGCGGCCGCGCTGATACCGCCGCCGCCGGC
GTCTCACAGTGTACGGACCTAAAGTTCCCCCATAGGGGGT
and its complement, into MaV203 yeast cells (Invitrogen®). Those oligonucleotides bridge the ends of the T7 genomic sequence (NC_001604) and the YAC vector.

B. YAC to Plaque

Cloned T7 phages were shown to be able to YAC-to-plaque, as above.

Selected MaV203 cells that contained the pYES1L-T7 dspB phage-YAC were grown up and glass-bead lysates were prepared (Invitrogen® High-Order Genetic Assembly kit) and electroporated into TOP10 *E. coli*. The transformations were plated and overnight incubations revealed plaques, corresponding to the captured phage.

C. Luciferase Insertion into Cloned T7 Phage

The T7-dspB YAC was purified by glass-bead lysate, and cut with EcoRI and HindIII. Luciferase was amplified with the primers

[SEQ ID NO: 89]
TAGAAATAATTTTGTTTAACTTTAAGAAGGAGATATACATATGGAAGACG
CCAAAAACAT
and

[SEQ ID NO: 90]
CCAAGGGGTTAACTAGTTACTCGAGTGCGGCCGCAAGCTTTTACAATTTG
GACTTTCCGC.

Duplexed

[SEQ ID NO: 91]
ACATTTTCTGGCGTCAGTCCACCAGCTAACATAAAATGTAAGCTTTCGGG
GCTCTCTTGCCTTCCAACCCAGTCAGAAAT and its complement was also used to repair the HindIII cut YAC backbone. The cut phage-YAC, luciferase PCR product and duplexed repair oligos were co-transformed into MaV203 yeast cells (Invitrogen®), and selected on media lacking tryptophan, resulting in a single TRP+ colony. Engineered phage-YAC were confirmed by PCR and converted into phage particles via the YAC-to-plaque technique, as described above.

D. Expression of Luciferase in *E. coli* Infected with Recombinant Phage

An overnight culture of *E. coli* cells was diluted 1/100 and grown into mid-log phase in LB+1 mM calcium chloride (approximately 2 and a half hours). Cells were diluted and infected with a vast excess of phages ($1 \times 10^7$ phages per infection) in a total of 100 μl. Infections were allowed to proceed, non-shaking at 37 degrees C. After 90 minutes, 100 μl of Promega® Steady-Glo luciferase detection reagent was added to 20 uL of infection, and infections were immediately read on a Promega® GloMax 20/20. Cells infected with the T7::Luc phage expressed of detectable levels of luciferase.

The recombinant phages described herein were deposited on May 16, 2013 with the American Type Culture Collection (ATCC®). The address of ATCC® is: American Type Culture Collection (ATCC®), Patent Depository, 10801 University Boulevard, Manassas, Va. 20110-2209 USA. The deposits were made under the terms of the Budapest Treaty on the International Recognition of the Deposit of Microorganisms for the Purposes of Patent Procedure. The ATCC Patent Deposit Designations for the deposits are provided in Table 21.

TABLE 21

| PHAGE | ATCC® Patent Deposit Designation |
| --- | --- |
| LP48::ffluc | PTA-120333 |
| LP125::ffluc | PTA-120334 |
| LP40::nluc | PTA-120335 |
| A511::nluc | PTA-120336 |
| P100::ffluc | PTA-120337 |
| LP124::nluc | PTA-120338 |
| LP101::ffluc | PTA-120339 |
| LP99::ffluc | PTA-120340 |
| LP143::ffluc | PTA-120341 |
| A511::ffluc | PTA-120342 |
| P100::nluc | PTA-120343 |
| LP124:ffluc | PTA-120344 |
| LP125::nluc | PTA-120345 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A composition comprising:
   at least one recombinant phage capable of infecting at least one *Listeria* or *Salmonella* microbe obtained from an environmental sample, wherein the at least one recombinant phage comprises a heterologous nucleic acid sequence encoding a marker, and wherein the at least one recombinant phage is selected from the group consisting of LP48::ffluc, LP99::ffluc, LP101::ffluc, LP124::ffluc, LP125::ffluc, LP143::ffluc, A511::ffluc, P100::ffluc, LP40::nluc, LP124::nluc, LP125::nluc, A511::nluc, and P100::nluc; and
   at least one aqueous solution suitable for propagation of the at least one recombinant phage in the at least one *Listeria* or *Salmonella* microbe, said solution comprising:
   a) at least one nutrient;
   b) at least one selective agent suitable to inhibit growth of at least one non-target microbe in said environmental sample;
   c) at least one vitamin;
   d) at least one divalent metal;
   e) at least one buffering agent capable of maintaining the composition at pH 7.0-7.5; and
   f) at least one agent suitable to neutralize a sanitizer present in said environmental sample, wherein said agent suitable to neutralize a sanitizer is selected from the group consisting of non-ionic detergents, oxygen scavengers and emulsifiers.

2. The composition of claim 1, wherein the at least one recombinant phage is present in the composition at a concentration of $1\times10^6$ to $1\times10^{11}$ pfu/ml.

3. The composition of claim 2, wherein the at least one recombinant phage is present in the composition at a concentration of $1\times10^7$ to $1\times10^8$ pfu/ml.

4. The composition of claim 3, wherein the at least one recombinant phage is present in the composition at a concentration of $1.5\times10^7$ pfu/ml.

5. The composition of claim 4, wherein the at least one recombinant phage comprises 3 recombinant phages and each recombinant phage is present in the composition at a concentration of $1.5\times10^7$ pfu/ml.

6. The composition of claim 1, wherein the at least one nutrient comprises Brain Heart Infusion medium.

7. The composition of claim 1, wherein the at least one selective agent is selected from the group consisting of LiCl, acriflavine, nalidixic acid, and cycloheximide.

8. The composition of claim 1, wherein the at least one vitamin comprises yeast extract.

9. The composition of claim 1, wherein the at least one divalent metal comprises $CaCl_2$.

10. The composition of claim 1, wherein the at least one buffering agent comprises HEPES buffer.

11. The composition of claim 1, wherein the at least one aqueous solution comprises 1× Brain Heart Infusion medium; 0.5% LiCl; 0.002% nalidixic acid; 0.2% yeast extract; 2 mM $CaCl_2$, 40 mM HEPES, pH 7.4; 1 mM sodium metabisulfite; 0.1% sodium thiosulfate; 0.5% Polysorbate 80; and 0.1% lecithin.

12. The composition of claim 1, wherein the *Listeria* microbe is selected from the group consisting of *Listeria innocua, Listeria monocytogenes, Listeria seeligeri, Listeria ivanovii, Listeria grayi, Listeria marthii, Listeria rocourti, Listeria welshimeri, Listeria floridensis, Listeria aquatic, Listeria cornellensis, Listeria riparia*, and *Listeria grandensis*.

13. A kit comprising:
    the composition of claim 1; and
    a solid substrate capable of supporting adhesion by the at least one *Listeria* or *Salmonella* microbe.

14. A method of determining the presence or absence of a target microbe in an environmental sample, comprising:
    collecting an environmental sample;
    contacting the environmental sample with the composition of claim 1
    and
    assaying the phage-exposed environmental sample to detect the presence or absence of the marker to determine the presence or absence of the target microbe;
    wherein the time from contacting the environmental sample with the recombinant phage to detecting the presence or absence of the target microbe is between 1 minute and 6 hours.

15. The method of claim 14, wherein the time from contacting the environmental sample with the recombinant phage to detecting the presence or absence of the target microbe is between 1 minute and 4 hours.

16. The method of claim 15, wherein the time from contacting the environmental sample with the recombinant phage to detecting the presence or absence of the target microbe is between 1 minute and 1 hours.

17. The method of claim 14, wherein assaying the phage-exposed environmental sample to detect the presence or absence of the marker to determine the presence or absence of the target microbe comprises a lower limit of detection of 100 target microbe cells 30 minutes after contacting the environmental sample with the recombinant phage.

18. The method of claim 14, wherein assaying the phage-exposed environmental sample to detect the presence or absence of the marker to determine the presence or absence of the target microbe comprises a lower limit of detection of 10 target microbe cells 60 minutes after contacting the environmental sample with the recombinant phage.

19. The method of claim 14, wherein assaying the phage-exposed environmental sample to detect the presence or absence of the marker to determine the presence or absence of the target microbe comprises a lower limit of detection of a single target microbe cell 180 minutes after contacting the environmental sample with the recombinant phage.

20. The composition of claim 5, wherein the three recombinant phages comprise LP40::nluc, LP124::nluc, and A511::nluc.

21. The composition of claim 1, wherein the at least one aqueous solution suitable for propagation of the at least one recombinant phage in the at least one *Listeria* or *Salmonella* microbe, further comprises g) at least one agent to prevent the decomposition of luciferin.

22. The composition of claim 21, wherein the at least one agent to prevent the decomposition of luciferin is selected from sodium thiosulfate, polysorbate 80, HEPES, and lecithin.

* * * * *